US010941158B2

(12) United States Patent
Ghosh et al.

(10) Patent No.: US 10,941,158 B2
(45) Date of Patent: *Mar. 9, 2021

(54) PYRAZOLE ACC INHIBITORS AND USES THEREOF

(71) Applicant: Gilead Apollo, LLC, Foster City, CA (US)

(72) Inventors: Shomir Ghosh, Brookline, MA (US); Jeremy Robert Greenwood, Brooklyn, NY (US); Geraldine C. Harriman, Charlestown, RI (US); Silvana Marcel Leit de Moradei, Burlington, MA (US)

(73) Assignee: Gilead Apollo, LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,360

(22) Filed: Jan. 3, 2019

(65) Prior Publication Data
US 2019/0375759 A1 Dec. 12, 2019

Related U.S. Application Data

(63) Continuation of application No. 15/358,627, filed on Nov. 22, 2016, now abandoned.

(60) Provisional application No. 62/259,973, filed on Nov. 25, 2015.

(51) Int. Cl.
C07D 495/04 (2006.01)
C07D 487/04 (2006.01)
C12N 9/00 (2006.01)
A01N 43/90 (2006.01)

(52) U.S. Cl.
CPC .......... *C07D 495/04* (2013.01); *A01N 43/90* (2013.01); *C12N 9/93* (2013.01); *C12Y 604/01002* (2013.01)

(58) Field of Classification Search
None
See application file for complete search history.

(56) References Cited

U.S. PATENT DOCUMENTS

| 4,670,560 | A | ‡ | 6/1987 | Press | C07D 495/04 544/25 |
|---|---|---|---|---|---|
| 6,180,635 | B1 | ‡ | 1/2001 | Cheshire | C07D 495/04 514/26 |
| 6,197,780 | B1 | ‡ | 3/2001 | Munter | A61K 31/505 514/27 |
| 8,623,880 | B2 | | 1/2014 | Chaudhari et al. | |
| 8,969,557 | B2 | ‡ | 3/2015 | Harriman et al. | C07D 495/04 544/278 |
| 9,346,822 | B2 | | 5/2016 | Cho et al. | |
| 9,453,026 | B2 | ‡ | 9/2016 | Harriman | A61K 31/519 |
| 9,957,277 | B2 | | 5/2018 | Ernst et al. | |
| 9,988,399 | B2 | | 6/2018 | Greenwood et al. | |
| 10,208,044 | B2 | | 2/2019 | Greenwood et al. | |
| 10,208,053 | B2 | | 2/2019 | Strohbach et al. | |
| 2003/0187254 | A1 | ‡ | 10/2003 | Perry | C07D 401/04 540/57 |
| 2003/0191142 | A1 | ‡ | 10/2003 | Cheshire | C07D 495/04 514/26 |
| 2005/0124636 | A1 | ‡ | 6/2005 | Sharma | C07D 495/04 514/26 |
| 2006/0039943 | A1 | ‡ | 2/2006 | Applebaum | A01N 35/10 424/40 |
| 2007/0208040 | A1 | ‡ | 9/2007 | Elzein | C07D 495/04 514/26 |
| 2008/0287465 | A1 | ‡ | 11/2008 | Tumey | C07D 491/048 514/26 |
| 2013/0123231 | A1 | ‡ | 5/2013 | Harriman | A01N 43/90 514/21 |
| 2016/0075661 | A1 | ‡ | 3/2016 | Oberholzer | C07D 231/38 514/40 |
| 2016/0108060 | A1 | ‡ | 4/2016 | Greenwood | C07D 471/04 514/26 |
| 2016/0108061 | A1 | ‡ | 4/2016 | Greenwood | C07D 487/04 |
| 2016/0185783 | A1 | ‡ | 6/2016 | Greenwood | C07D 413/14 504/24 |
| 2016/0185799 | A1 | ‡ | 6/2016 | Greenwood | C07D 487/04 514/22 |
| 2016/0297834 | A1 | ‡ | 10/2016 | Harriman | A61K 31/519 |
| 2017/0145028 | A1 | ‡ | 5/2017 | Ghosh | A01N 43/90 |
| 2017/0166582 | A1 | | 6/2017 | Ghosh et al. | |
| 2017/0166583 | A1 | ‡ | 6/2017 | Ghosh | C07D 495/04 |
| 2017/0166584 | A1 | ‡ | 6/2017 | Ghosh | A01N 43/90 |
| 2017/0166585 | A1 | ‡ | 6/2017 | Bennett | C07D 495/04 |
| 2017/0267690 | A1 | ‡ | 9/2017 | Alexander | C07D 309/12 |
| 2018/0354973 | A1 | | 12/2018 | Bradner et al. | |
| 2019/0016732 | A1 | | 1/2019 | Bhat et al. | |

(Continued)

FOREIGN PATENT DOCUMENTS

CN 1106663 A ‡ 8/1995
CN 1301162 A ‡ 6/2001

(Continued)

OTHER PUBLICATIONS

International Search Report and Written Opinion for PCT/US2016/063386 dated Jan. 26, 2017 (11 pages).‡
Abe, et al., "Reactions of 2-Amino-,2-Alkylamino-, and 2-Piperidino-1-aza-azulenes with Aryl and Chlorosulfonyl Isocyanates", Journal of Heterocyclic Chemistry, 1996, 33(4), 1323-1331.‡
Cambridge Medchem Consulting. "Tuning the Basicity of Amines" (https://www.cambridgemedchemconsulting.com/resources/tuningbases.html) Updated Apr. 4, 2011.‡
Caplus record for US 2007/020840 A1 by Elzein et al. (retrieved Nov. 2013).‡
Cho et al., "Thieno[2,3-d]pyrimidine-3-acetic acids. A new class of nonpeptide endothelin receptor antagonists," Chemical & Pharmaceutical Bulletin, vol. 46, No Month Listed 1998 (pp. 1724-1737).‡
Corbett, "Review of recent acetyl-CoA carboxylase inhibitor patents: mid-2007-2008," Expert Opinion on Therapeutic Patents, vol. 19, No. 7, No Month Listed 2009 (pp. 943-956).‡

(Continued)

*Primary Examiner* — Erin E Hirt
(74) *Attorney, Agent, or Firm* — Sheppard Mullin Richter & Hampton LLP

(57) ABSTRACT

The present invention provides pyrazole compounds useful as inhibitors of Acetyl CoA Carboxylase (ACC), compositions thereof, and methods of using the same.

1 Claim, No Drawings

(56) References Cited

U.S. PATENT DOCUMENTS

| | | | |
|---|---|---|---|
| 2019/0040078 A1 | 2/2019 | Bennett et al. | |
| 2019/0241582 A1 | 8/2019 | Ghosh et al. | |
| 2019/0330224 A1 | 10/2019 | Ghosh et al. | |
| 2020/0010478 A1 | 1/2020 | Ghosh et al. | |
| 2020/0017519 A1 | 1/2020 | Ghosh et al. | |
| 2020/0102323 A1 | 4/2020 | Bhat et al. | |

FOREIGN PATENT DOCUMENTS

| | | | |
|---|---|---|---|
| CN | 101198614 A | | 6/2008 |
| EP | 0640606 A1 | ‡ | 3/1995 |
| EP | 02351743 A1 | ‡ | 8/2011 |
| JP | 62-289583 A | ‡ | 12/1987 |
| JP | 02-225485 A | ‡ | 9/1990 |
| JP | 08-073467 A | ‡ | 3/1996 |
| JP | 09-110873 A | ‡ | 4/1997 |
| JP | 2002-500666 A | ‡ | 1/2002 |
| JP | 2002-541258 | ‡ | 12/2002 |
| JP | 2002-541258 A | | 12/2002 |
| JP | 2004-51 8732 A | ‡ | 6/2004 |
| JP | 2004-518732 A | | 6/2004 |
| JP | 2007-302703 A | ‡ | 11/2007 |
| JP | 2009-528389 A | ‡ | 8/2009 |
| WO | WO 97/007119 A1 | ‡ | 2/1997 |
| WO | WO 1997/007119 A1 | | 2/1997 |
| WO | WO 97/040846 A1 | ‡ | 11/1997 |
| WO | WO 1997/040846 A1 | | 11/1997 |
| WO | WO 98/54190 A1 | ‡ | 12/1998 |
| WO | WO 1998/54190 A1 | | 12/1998 |
| WO | WO 00/61583 A1 | ‡ | 10/2000 |
| WO | WO 2000/61583 A1 | | 10/2000 |
| WO | WO 02/064598 A1 | ‡ | 8/2002 |
| WO | WO 2002/064598 A1 | | 8/2002 |
| WO | WO 2004/014916 A1 | ‡ | 2/2004 |
| WO | WO 2006/014647 A | ‡ | 2/2006 |
| WO | WO 2006/014647 A2 | | 2/2006 |
| WO | WO 2007/103776 A2 | ‡ | 9/2007 |
| WO | WO 2008/143262 A1 | ‡ | 11/2008 |
| WO | WO 2011/080277 A1 | ‡ | 7/2011 |
| WO | WO 2011/143553 | ‡ | 11/2011 |
| WO | WO 2013/071169 | | 5/2013 |
| WO | WO 2014/182943 | | 11/2014 |
| WO | WO 2014/182950 | | 11/2014 |
| WO | WO 2015/003879 | | 1/2015 |
| WO | WO 2015/007451 | ‡ | 1/2015 |

OTHER PUBLICATIONS

Database Chemcats [Online], Chemical Abstracts Services, Columbus, Ohio, USA, XP002765978, retrieved from STN Database accession No. AX101218917, Oct. 5, 2016, Aldlab Chemicals Building Blocks.‡
Database Chemcats [Online], Chemical Abstracts Services, Columbus, Ohio, USA, XP002765979, retrieved from STN Database accession No. K01.513.094, Apr. 7, 2016, Aurora Screening Library.‡
Database Chemcats [Online], Chemical Abstracts Services, Columbus, Ohio, USA, XP002765980, retrieved from STN Database accession No. A05.862.801, Oct. 20, 2016, Aurora Building Blocks.‡
Database Chemcats [Online], Chemical Abstracts Services, Columbus, Ohio, USA, XP002765981, retrieved from STN Database accession No. A29.986.104, Oct. 20, 2016, Aurora Building Blocks.‡
Extended European Search Report dated Feb. 26, 2015 for EP Application No. 12848361.7. (3 pages).‡
Fernandez et al., "Bayesian-regularized Genetic Neural Networks Applied to the Modeling on Non- Peptide Antagonists for the Human Luteinizing Hormone-releasing Hormone Receptor", Journal of Molecular Graphics and Modelling, 2006, 25(4), 410-422.‡
International Search Report and Written Opinion dated Feb. 1, 2017 for PCT/US2016/063424. (11 pages).‡
International Search Report and Written Opinion dated Feb. 4, 2013 for PCT/US2012/064528. (14 pages).‡

International Search Report and Written Opinion for PCT/US2016/058867 dated Feb. 2, 2017, 18 pages.‡
International Search Report and Written Opinion for PCT/US2016/063410 dated Jan. 25, 2017, 11 pages.‡
International Search Report and Written Opinion for PCT/US2016/063388 dated Jan. 20, 2017, 10 pages.‡
Lange, et al. Bioisosteric replacements of the pyrazole moiety of rimonabant: synthesis, biological properties, and molecular modeling investigations of thiazoles, triazoles, and imidazoles as potent and selective CB1 cannabinoid receptor antagonits. J Med Chem. Mar. 24, 2005;48(6):1823-38.‡
Malamas et al., "Quinazolineacetic Acids and Related Analogues as Aldose Reductase Inhibitors", Journal of Medicinal Chemistry, 1991, 34(4), 1492-1503.‡
Registry (STN) [online], May 8, 2009, retrieval date Apr. 22, 2016, CAS registration Nos. 1144464-32-3, 1089988-38-4, 1089987-08-5, 1089986-32-2, 1089984-45-1, 1089983-19-6, 1089981-89-4, 1089978-89-1, 1089978-06-2, 1089978-06-2, 1089978-05-1, 1089977-32-1 and the like.‡
Sasaki et al., "Discovery of a Thieno[2,3-d] pyrimidine-2,4-dione Bearing a p-Methoxyureidophenyl Moiety at the 6-Position: A Highly Potent and Orally Bioavailable Non-Peptide Antagonist for the Human Luteinizing Hormone-Releasing Hormone Receptor", Journal of Medicinal Chemistry, 2003, 46(1), 113-.‡
Vlasov et al., "The Synthesis of Novel 3-Substituted 1-Alkyl-5-Methyl-6-(3-Aryl-1,2,4-Oxadiazole-5-Yl)Thieno[2,3-D]Pyrimidine-2,4(1 H3H)-Diones and Their Antimicrobial Activity", Journal of Organic and Pharmaceutical Chemistry, 2011, 9(3):51-55. with English translation, 6 pages.‡
You et al., "Section II Lead Optimization", Medicinal Chemistry, 2nd version, Chemical Industry Press, pp. 25-29, 2008.‡
International Search Report and Written Opinion for PCT/US2016/063424 dated Feb. 1, 2017, 11 ages.
International Search Report and Written Opinion for PCT/US2012/064528 dated Feb. 4, 2013, 14 pages
Lange, et al. Bioisosteric replacements of the pyrazole moiety of rimonabant: synthesis, biological properties, and molecular modeling investigations of thiazoles, triazoles, and imidazoles as potent and selective CB1 cannabinoid receptor antagonists. J Med Chem. Mar. 24, 2005;48(6):1823-38.
Sasaki et al., "Discovery of a Thieno[2,3-d] pyrimidine-2,4-dione Bearing a p-Methoxyureidophenyl Moiety at the 6-Position: A Highly Potent and Orally Bioavailable Non-Peptide Antagonist for the Human Luteinizing Hormone-Releasing Hormone Receptor", Journal of Medicinal Chemistry, 2003, 46(1), 113-124.
Vlasov et al., "The Synthesis of Novel 3-Substituted 1-Alkyl-5-Methyl-6-(3-Aryl-1,2,4-Oxadiazole-5-Yl)Thieno[2,3-D]Pyrimidine-2,4(1H3H)-Diones and Their Antimicrobial Activity", Journal of Organic and Pharmaceutical Chemistry, 2011, 9(3):51-55, with English translation, 6 pages.
Extended European Search Report dated Mar. 20, 2018 for EP Application No. 17209455.9 (5 pages).
Extended European Search Report dated Dec. 10, 2019 for EP Application No. 19190936.5. (6 pages).
Database Registry [online] RN 1089878-77-2, Dec. 25, 2008.
Database Registry [online] RN 1089896-86-5, Dec. 25, 2008.
Database Registry [online] RN 1089952-27-1, Dec. 25, 2008.
Database Registry [online] RN 1222836-90-9, May 13, 2010.
El-Barbary, et al. Synthesis of 5'-amino- and 5'-azido-2',5'-dideoxy nucleosides from thieno[2,3-d]pyrimidine-2,4(1H,3H)-dione. Monatshefte für Chemie. 1995; 126(5):593-600.
Jourdan, et al. Synthesis of Cyclic and Acyclic Nucleoside Analogues Having a Thiophene or Dihydrothiophene Ring Fused to the d Side of an Uracyl, J. Heterocyclic Chem, 1995, 32, p. 953-957.
Renault, et al. Synthesis and Antiviral Evaluation of Furopyramidine Diones: Cyclic and Acyclic Nucleoside Analogues, Heterocycles, 1995, 41(5):937-945.
Sunkara, et al. A Carbocyclic 7-Deazapurine-pyramidine hybrid nucleoside, Collect. Czech. Chem. Commune, 2006, vol. 71, No. 8, p. 1161-1168.

(56) References Cited

OTHER PUBLICATIONS

Wei, et al., Advances in Antimicrobial Agents Targeted Acetyl CoA Carboxylase. World Pesticides, Jun. 30, 2014; vol. 36, No. 3; 16-19. (In Chinese with English Translation).

‡ imported from a related application

PYRAZOLE ACC INHIBITORS AND USES THEREOF

CROSS REFERENCE TO RELATED APPLICATIONS

This application is a continuation of U.S. application Ser. No. 15/358,627, filed Nov. 22, 2016, which claims the benefit under 35 U.S.C. § 119(e) to U.S. Provisional Application No. 62/259,973, filed on Nov. 25, 2015, the entireties of which are incorporated herein by reference.

BACKGROUND OF THE INVENTION

Obesity is a health crisis of epic proportions. The health burden of obesity, measured by quality-adjusted life-years lost per adult, has surpassed that of smoking to become the most serious, preventable cause of death. In the US, about 34% of adults have obesity, up from 31% in 1999 and about 15% in the years 1960 through 1980. Obesity increases the rate of mortality from all causes for both men and women at all ages and in all racial and ethnic groups. Obesity also leads to social stigmatization and discrimination, which decreases quality of life dramatically. The chronic diseases that result from obesity cost the US economy more than $150 billion in weight-related medical bills each year. Furthermore, about half of the obese population, and 25% of the general population, have metabolic syndrome, a condition associated with abdominal obesity, hypertension, increased plasma triglycerides, decreased HDL cholesterol, and insulin resistance, which increases the risk for type-2 diabetes (T2DM), stroke and coronary heart disease. [Harwood, *Expert Opin. Ther. Targets* 9: 267, 2005].

Diet and exercise, even when used in conjunction with the current pharmacotherapy, do not provide sustainable weight loss needed for long-term health benefit. Currently, only a few anti-obesity drugs are approved in the US, the fat absorption inhibitor orlistat (Xenical®), the 5-HT$_2$c antagonist lorcaserin (Belviq®), and the combination therapy phentermine/topiramate (Qsymia®). Unfortunately, poor efficacy and unappealing gastrointestinal side effects limit the use of orlistat. Surgery can be effective but is limited to patients with extremely high body-bass indices (BMI) and the low throughput of surgery limits the impact of this modality to about 200 k patients per year. The majority of obesity drugs in clinical development are designed to reduce caloric intake through central action in the CNS (e.g., anorectics and satiety agents). However, the FDA has taken an unfavorable position against CNS-active agents, due to their modest efficacy and observed/potential side-effect profiles.

The continuing and increasing problem of obesity, and the current lack of safe and effective drugs for treating it, highlight the overwhelming need for new drugs to treat this condition and its underlying causes.

Another ongoing problem is the lack of antifungal drugs with activity against a broad range of fungal pathogens. Often, a given antifungal drug will have activity against one fungal species but lack activity against other, even closely related, species, such as *Candida albicans, Candida krusei,* and *Candida parapsilosis*.

SUMMARY OF THE INVENTION

It has now been found that compounds of this invention, and pharmaceutically acceptable compositions thereof, are effective as inhibitors of Acetyl-CoA carboxylase (ACC). Such compounds have the general formula I:

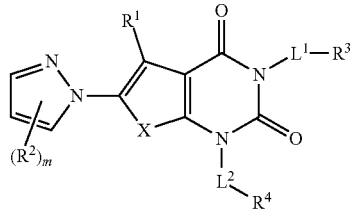

or a pharmaceutically acceptable salt or agriculturally acceptable salt thereof, wherein each variable is as defined and described herein.

Compounds of the present invention, and pharmaceutically acceptable compositions thereof, are useful for treating a variety of diseases, disorders or conditions, associated with regulation of the production or oxidation of fatty acids. Such diseases, disorders, or conditions include those described herein.

Compounds of the present invention, and agriculturally acceptable compositions thereof, are useful for control of fungal pathogens in agriculture.

Compounds provided by this invention are also useful for the study of ACC enzymes in biological and pathological phenomena; the study of intracellular signal transduction pathways occurring in lipogenic tissues; and the comparative evaluation of new ACC inhibitors or other regulators of fatty acid levels in vitro or in vivo.

DETAILED DESCRIPTION OF CERTAIN EMBODIMENTS

1. General Description of Compounds of the Invention

In certain embodiments, the present invention provides a compound of formula I:

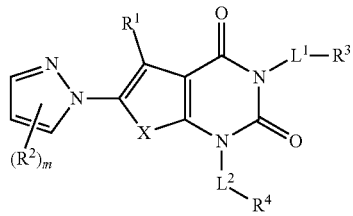

or a pharmaceutically acceptable salt or agriculturally acceptable salt thereof, wherein:

X is —O—, —S—, or —NR—;

$R^1$ is hydrogen, $C_{1-4}$ aliphatic optionally substituted with 1-4 halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R;

each $R^2$, $R^6$, $R^7$, $R^8$, and $R^{10}$ is independently oxo, halogen, —CN, —R$^a$, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R;

each R is hydrogen or $R^a$;

each $R^a$ is independently an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^1$ is a covalent bond, a 1-6 membered straight or branched bivalent hydrocarbon chain, cyclopropylenyl, cyclobutylenyl, or oxetanylenyl;

$L^2$ is a covalent bond or a 1-6 membered straight or branched bivalent hydrocarbon chain, wherein $L^2$ is substituted by n instances of $R^9$;

$R^3$ is —OR, —C(O)OR, —N(R)C(O)OR, —OC(O)N(R)$_2$, —C(O)N(R)OR, —C(O)NH$_2$, —C(O)NHR$^a$, —C(O)N(R$^a$)$_2$, or —C(O)Hy;

Hy is a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, wherein Hy is substituted by p instances of $R^6$;

$R^4$ is selected from a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, and an 8-10 membered bicyclic heteroaryl ring having 1-4 heteroatoms independently selected from nitrogen, oxygen, or sulfur, wherein $R^4$ is substituted by q instances of $R^7$;

each $R^5$ is independently selected from hydrogen, $C_{1-4}$ aliphatic, a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur, wherein each $R^5$ is substituted with r instances of $R^8$;

each $R^9$ is independently $R^{10}$ or —OR$^5$;

m is 0, 1, 2, or 3;

n is 0, 1, or 2;

p is 0, 1, 2, 3, or 4;

q is 0, 1, 2, 3, 4, or 5; and r is 0, 1, 2, 3, or 4.

2. Compounds and Definitions

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R)C(O)R$; $-N(R)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R$; $-OC(O)(CH_2)_{0-4}SR-$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R$; $-C(O)CH_2C(O)R^\circ$; $-C(NOR^\circ)R^\circ$; $-(CH_2)_{0-4}SSR$;

—(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$; wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The phrase "candidal onychomycosis" as used herein refers to a fungal yeast infection of the fingernails and/or toenails caused by a *Candida* spp., including for example, *Candida albicans* and *Candida parapsilosis*.

As used herein, the term "dermatomycosis" refers to a fungal infection of the skin caused by a dermatophyte.

As used herein, the phrase "fungal infection" refers to any superficial fungal infection, including for example, one or more of a superficial fungal infection of the skin, onychomycosis, and a fungal infection of a hair follicle, each of which is as defined herein. Such fungal infections can include superficial fungal infections of the skin, including for example, one or more of Tinea cruris, Tinea corporis, interdigital Tinea pedis, moccasin-type Tinea pedis, Tinea manuum, Tinea versicolor (pityriasis), Tinea nigra, cutaneous candidiasis, Tinea faciei, and white and black piedra; fungal infections of the hair follicle including one or more of Tinea capitis, Tinea Favose (favus), and Tinea barbae; and onychomycosis, a fungal infection of one or more of the nail bed, matrix, and nail plate, caused by, for example, dermatophytes, yeasts, and non-dermatophyte molds.

As used herein, the phrase "fungal infection of the hair follicle" refers to a fungal infection of at least the tubular infolding of the epidermis (skin) containing the root of a hair of any one or more of the scalp, eyebrows, eyelashes, and bearded area of an individual. The phrase "fungal infection of the hair follicle" also refers to a fungal infection of the tubular infolding of the epidermis (skin) containing the root of a hair of any one or more of the scalp, eyebrows, eyelashes, and bearded area, along with a fungal infection of the hair shaft, of an individual. Such fungal infections can include, for example, one or more of Tinea capitis, Tinea favosa, and Tinea Barbae. The term "hair follicle" refers to a tubular infolding of the epidermis (skin) containing the root of a hair. The follicle is lined by cells derived from the epidermal layer of the skin. Tinea capitis (or severe highly-inflammatory cases sometimes termed Kerion) is a superficial fungal infection (dermatophytosis) of the skin of the scalp, eyebrows, and eyelashes, that attacks the hair follicles and shaft. The disease is primarily caused by dermatophytes in the *Trichophyton* and *Microsporum* genera, including for example, *Microsporum audouini, Microsporum canis, Microsporum distortum, Microsporum gpseum, Trichophyton megninii, Trichophylon mentagrophytes, Trichophyton rubrum, Trichophyton schoenleinii, Trichophyton tonsurans,* and *Trichophyton verrucosum.* The clinical presentation is typically a single or multiple patches of hair loss, sometimes with a 'black dot' pattern (often with broken-off hairs), that may be accompanied by inflammation, scaling, pustules, and itching. Tinea favosa can be considered a variety of Tinea capitis because it involves the scalp; however, it may also involve glabrous skin and nails. Tinea favosa is primarily caused by dermatophytes in the *Trichophyton* and *Microsporum* genera, including for example, *Microsporum gypseum* and *Trichophyton schoenleinii*. Tinea barbae is a superficial dermatophytosis that is limited to the bearded areas of the face, neck, chin, cheeks, and/or lips and occurs almost exclusively in older adolescent and adult males. The clinical presentation of Tinea barbae includes inflammatory, deep, kerion-like plaques and non-inflammatory superficial patches resembling Tinea corporis or bacterial folliculitis. The mechanism that causes Tinea barbae is similar to that of Tinea capitis, and is frequently the result of a *Trichophyton rubrum* (*T. rubrum*) infection but may also be the result of *Trichophyton mentagrophytes* var *gramdlosum* and *Trichophyton verrucosum*. Finally *Microsporum canis* and *Trichophyton mentagrophytes* var *erinacei* have been known to cause Tinea barbae but are relatively rare.

As used herein, the term "infection" refers to the invasion, development and/or multiplication of a microorganism within or on another organism. An infection may be localized to a specific region of an organism or systemic.

The term "onychomycosis" as used herein refers to a fungal infection of the nail bed, matrix, and/or nail plate. Onychomycosis is caused by three main classes of fungi: dermatophytes, yeasts (candidal onychomycosis), and non-dermatophyte molds. Dermatophytes are the most common cause of onychomycosis. Onychomycosis caused by non-dermatophyte molds is becoming more common worldwide. Onychomycosis due to *Candida* is less common. Dermatophytes that can cause onychomycosis include one or more of *Trichophyton rubrum, Irichophyton interdigitale, Epidermophylon floccosum, Trichophyton violaceum, Microsporum gypseum, Trichophyton tonsurans, Trichophyton soudanense,* and *Trichophyton verrucosum,* and such disease is often also referred to as Tinea ungium. Candidal onychomycosis include cutaneous candidisis and mucocutaneous candidiasis that are caused by one or more *Candida* species, including for example, *Candida albicans* and *Candida parapsilosis*. Non-dermatophyte molds that can cause onychomycosis can include one or more of, for example, *Scopulariopsis brevicaulis, Fusarium* spp., *Aspergillus* spp., *Alternaria, Acremonium, Scytalidinum dimidiatum,* and *Scytalidinium hyalinum*. There are four classic types of onychomycosis including the following: distal and lateral subungal onychomycosis (DLSO) that is the most common form of onychomycosis, and is usually caused by *Trichophyton rubrum* and/or *Trichophyton interdigitale*, which invades the nail bed and the underside of the nail plate; white superficial onychomycosis (WSO) is caused by fungal (e.g., *T. mentagrophytes*) invasion of the superficial layers of the nail plate to form "white islands" on the plate, non-dermatophyte molds cause deep white superficial onychomycosis; proximal subungal onychomycosis (PSO) is fungal penetration of the newly formed nail plate through the proximal nail fold and it is the least common form of onychomycosis in healthy people, but is found more commonly when the patient is immunocompromised; endonyx onychomycosis (EO), and candidal onychomycosis (CO) which is *Candida* species invasion of the fingernails.

As used herein, the term "superficial fungal infection of the skin" refers to a fungal infection present on the outer layer of skin, including Tinea cruris (jock itch), Tinea corporis (ringworm), Tinea pedis, interdigital Tinea pedis, moccasin-type Tinea pedis, Tinea manuum, Tinea *versicolor* (piyriasis), Tinea nigra, cutaneous candidiasis, Tinea faciei (facial ringworm), and white and black *piedra*. Tinea corporis (body ringworm), Tinea cruris (jock itch), and Tinea faciei (facial ringworm), can be caused by *Epidermophyton floccosum, Microsporum canis, Trichophyton mentagrophytes, T. rubrum, T. tonsurans, T. verrucosum,* and/or *T.* violaceum. *Tinea pedis* (athlete's foot) or *Tinea manuum* (fungal infection of the hand), are caused by *Epidermophyton floccosum, Microsporum canis, Trichophyton mentagrophytes, T. rubrum, T. tonsurans, T. verrucosum,* and/or *T. violaceum*. Cutaneous candidiasis can be caused by *C. albicans*.

3. Description of Exemplary Embodiments

In certain embodiments, the present invention provides a compound of formula I:

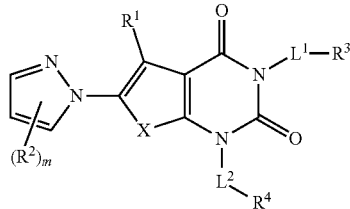

or a pharmaceutically acceptable salt or agriculturally acceptable salt thereof, wherein:

X is —O—, —S—, or —NR—;

$R^1$ is hydrogen, $C_{1-4}$ aliphatic optionally substituted with 1-4 halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R;

each $R^2$, $R^6$, $R^7$, and $R^1$ is independently oxo, halogen, —CN, —$R^a$, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R;

each R is independently hydrogen or $R^a$;

each $R^a$ is independently an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^1$ is a covalent bond, a 1-6 membered straight or branched bivalent hydrocarbon chain, cyclopropylenyl, cyclobutylenyl, or oxetanylenyl;

$L^2$ is a covalent bond or a 1-6 membered straight or branched bivalent hydrocarbon chain, wherein $L^2$ is substituted by n instances of $R^9$; $R^3$ is —OR, —C(O)OR, —N(R)C(O)OR, —OC(O)N(R)$_2$, —C(O)N(R)OR, —C(O)NH$_2$, —C(O)NHR$^a$, —C(O)N(R$^a$)$_2$, or —C(O)Hy;

Hy is a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, wherein Hy is substituted by p instances of $R^6$;

$R^4$ is selected from a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, and an 8-10 membered bicyclic heteroaryl ring having 1-4 heteroatoms independently selected from nitrogen, oxygen, or sulfur, wherein $R^4$ is substituted by q instances of $R^7$;

each $R^5$ is independently selected from hydrogen, $C_{1-4}$ aliphatic, a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur, wherein each $R^5$ is substituted with r instances of $R^8$;

each $R^9$ is independently oxo or —OR$^5$;

m is 0, 1, 2, or 3;

n is 0, 1, or 2;

p is 0, 1, 2, 3, or 4;

q is 0, 1, 2, 3, 4, or 5; and r is 0, 1, 2, 3, or 4.

As defined generally above, X is —O—, —S—, or —N(R)—. In some embodiments, X is —O—. In some embodiments, X is —S—. In some embodiments, X is —N(R)—.

As defined generally above, $R^1$ is hydrogen, $C_{1-4}$ aliphatic optionally substituted with 1-4 halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, $R^1$ is hydrogen. In some embodiments, $R^1$ is $C_{1-4}$ aliphatic optionally substituted with 1-4 halogen. In some embodiments, $R^1$ is —OR. In some embodiments, $R^1$ is —SR. In some embodiments, $R^1$ is —N(R)$_2$. In some embodiments, $R^1$ is —N(R)C(O)R. In some embodiments, $R^1$ is —C(O)N(R)$_2$. In some embodiments, $R^1$ is —N(R)C(O)N(R)$_2$. In some embodiments, $R^1$ is —N(R)C(O)OR. In some embodiments, $R^1$ is —OC(O)N(R)$_2$. In some embodiments, $R^1$ is —N(R)S(O)$_2$R. In some embodiments, $R^1$ is —S(O)$_2$N(R)$_2$. In some embodiments, $R^1$ is —C(O)R. In some embodiments, $R^1$ is —C(O)OR. In some embodiments, $R^1$ is —OC(O)R. In some embodiments, $R^1$ is —S(O)R. In some embodiments, $R^1$ is —S(O)$_2$R.

In some embodiments, $R^1$ is methyl.

As defined generally above, $R^2$ is oxo, halogen, —CN, —$R^a$, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, $R^2$ is oxo. In some embodiments, $R^2$ is halogen. In some embodiments, $R^2$ is —CN. In some embodiments, $R^2$ is —Re. In some embodiments, $R^2$ is —OR. In some embodiments, $R^2$ is —SR. In some embodiments, $R^2$ is —N(R)$_2$. In some embodiments, $R^2$ is —N(R)C(O)R. In some embodiments, $R^2$ is —C(O)N(R)$_2$. In some embodiments, $R^2$ is —N(R)C(O)N(R)$_2$. In some embodiments, $R^2$ is —N(R)C(O)OR. In some embodiments, $R^2$ is —OC(O)N(R)$_2$. In some embodiments, R$^2$ is —N(R)S(O)$_2$R. In some embodiments, R$^2$ is —S(O)$_2$N(R)$_2$. In some embodiments, R$^2$ is —C(O)R. In some embodiments, R$^2$ is —C(O)OR. In some embodiments, R$^2$ is —OC(O)R. In some embodiments, R$^2$ is —S(O)R. In some embodiments, R$^2$ is —S(O)$_2$R. In some embodiments, R$^2$ is C$_{1-4}$ aliphatic optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^2$ is selected from those depicted in Table 1, below.

As defined generally above, R$^6$ is oxo, halogen, —CN, —R$^a$, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^6$ is oxo. In some embodiments, R$^6$ is halogen. In some embodiments, R$^6$ is —CN. In some embodiments, R$^6$ is —R$^a$. In some embodiments, R$^6$ is —OR. In some embodiments, R$^6$ is —SR. In some embodiments, R$^6$ is —N(R)$_2$. In some embodiments, R$^6$ is —N(R)C(O)R. In some embodiments, R$^6$ is —C(O)N(R)$_2$. In some embodiments, R$^6$ is —N(R)C(O)N(R)$_2$. In some embodiments, R$^6$ is —N(R)C(O)OR. In some embodiments, R$^6$ is —OC(O)N(R)$_2$. In some embodiments, R$^6$ is —N(R)S(O)$_2$R. In some embodiments, R$^6$ is —S(O)$_2$N(R)$_2$. In some embodiments, R$^6$ is —C(O)R. In some embodiments, R$^6$ is —C(O)OR. In some embodiments, R$^6$ is —OC(O)R. In some embodiments, R$^6$ is —S(O)R. In some embodiments, R$^6$ is —S(O)$_2$R. In some embodiments, R$^6$ is C$_{1-4}$ aliphatic optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^6$ is hydroxyl.

In some embodiments, R$^6$ is selected from those depicted in Table 1, below.

As defined generally above, R$^7$ is oxo, halogen, —CN, —R$^a$, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^7$ is oxo. In some embodiments, R$^7$ is halogen. In some embodiments, R$^7$ is —CN. In some embodiments, R$^7$ is —R$^3$. In some embodiments, R$^7$ is —OR. In some embodiments, R$^7$ is —SR. In some embodiments, R$^7$ is —N(R)$_2$. In some embodiments, R$^7$ is —N(R)C(O)R. In some embodiments, R$^7$ is —C(O)N(R)$_2$. In some embodiments, R$^7$ is —N(R)C(O)N(R)$_2$. In some embodiments, R$^7$ is —N(R)C(O)OR. In some embodiments, R$^7$ is —OC(O)N(R)$_2$. In some embodiments, R$^7$ is —N(R)S(O)$_2$R. In some embodiments, R$^7$ is —S(O)$_2$N(R)$_2$. In some embodiments, R$^7$ is —C(O)R. In some embodiments, R$^7$ is —C(O)OR. In some embodiments, R$^7$ is —OC(O)R. In some embodiments, R$^7$ is —S(O)R. In some embodiments, R$^7$ is —S(O)$_2$R. In some embodiments, R$^7$ is C$_{1-4}$ aliphatic optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^8$ is fluoro. In some embodiments, R$^7$ is methoxyl.

In some embodiments, R$^7$ is selected from those depicted in Table 1, below.

As defined generally above, R$^8$ is oxo, halogen, —CN, —R$^a$, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^8$ is oxo. In some embodiments, R$^8$ is halogen. In some embodiments, R$^8$ is —CN. In some embodiments, R$^8$ is —R$^a$. In some embodiments, R$^8$ is —OR. In some embodiments, R$^8$ is —SR. In some embodiments, R$^8$ is —N(R)$_2$. In some embodiments, R$^8$ is —N(R)C(O)R. In some embodiments, R$^8$ is —C(O)N(R)$_2$. In some embodiments, R$^8$ is —N(R)C(O)N(R)$_2$. In some embodiments, R$^8$ is —N(R)C(O)OR. In some embodiments, R$^8$ is —OC(O)N(R)$_2$. In some embodiments, R$^8$ is —N(R)S(O)$_2$R. In some embodiments, R$^8$ is —S(O)$_2$N(R)$_2$. In some embodiments, R$^8$ is —C(O)R. In some embodiments, R$^8$ is —C(O)OR. In some embodiments, R$^8$ is —OC(O)R. In some embodiments, R$^8$ is —S(O)R. In some embodiments, R$^8$ is —S(O)$_2$R. In some embodiments, R$^8$ is C$_{1-4}$ aliphatic optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —S(O)$_2$N(R)$_2$, —C(O)R, —C(O)OR, —OC(O)R, —S(O)R, or —S(O)$_2$R.

In some embodiments, R$^8$ is hydroxyl. In some embodiments, R$^8$ is oxo. In some embodiments, R$^8$ is methoxyl.

In some embodiments, R$^8$ is selected from those depicted in Table 1, below.

As defined generally above, L$^1$ is a covalent bond, a 1-6 membered straight or branched bivalent hydrocarbon chain, cyclopropylenyl, cyclobutylenyl, or oxetanylenyl.

In some embodiments, L$^1$ is a covalent bond. In some embodiments, L is a 1-6 membered straight or branched bivalent hydrocarbon chain. In some embodiments, L$^1$ is cyclopropylenyl. In some embodiments, L$^1$ is cyclobutylenyl. In some embodiments, L$^1$ is a oxetanylenyl.

In some embodiments, L$^1$ is —C(CH$_3$)$_2$—. In some embodiments, L$^1$ is —CH$_2$—. In some embodiments, L is —CH(CH$_3$)—. In some embodiments, L$^1$ is —CH(CH$_3$)— with (S) configuration at the chiral center. In some embodiments, L$^1$ is —CH(CH$_3$)— with an (R) configuration at the chiral center.

In some embodiments, L$^1$ is selected from those depicted in Table 1, below.

As defined generally above, L$^2$ is a covalent bond or a 1-6 membered straight or branched bivalent hydrocarbon chain; wherein L$^2$ is substituted by n instances of —OR$^5$.

In some embodiments, L$^2$ is a covalent bond. In some embodiments, L$^2$ is a 1-6 membered straight or branched bivalent hydrocarbon chain; wherein L$^2$ is substituted by n instances of R$^9$.

In some embodiments, L$^2$ is a 2-membered straight bivalent hydrocarbon chain; wherein L$^2$ is substituted by n instances of R$^9$. In some embodiments, L$^2$ is ethylene, substituted with 1-2 instances of R$^9$.

As defined generally above, each R$^9$ is independently R$^{10}$ or —OR$^5$. In some embodiments, each R$^9$ is independently oxo or —OR$^5$. In some embodiments, at least one R$^9$ is oxo. In some embodiments, at least one R$^9$ is —OR$^5$. In some embodiments, R$^9$ is R$^{10}$. In some embodiments, R$^{10}$ is optionally substituted C$_1$-C$_6$ aliphatic.

In some embodiments, L$^2$ is —CH$_2$CH(OR$^5$)—. In some embodiments, L2 is —CH$_2$C(O)—.

In some embodiments, $L^2(R^9)_n$, taken together, is:

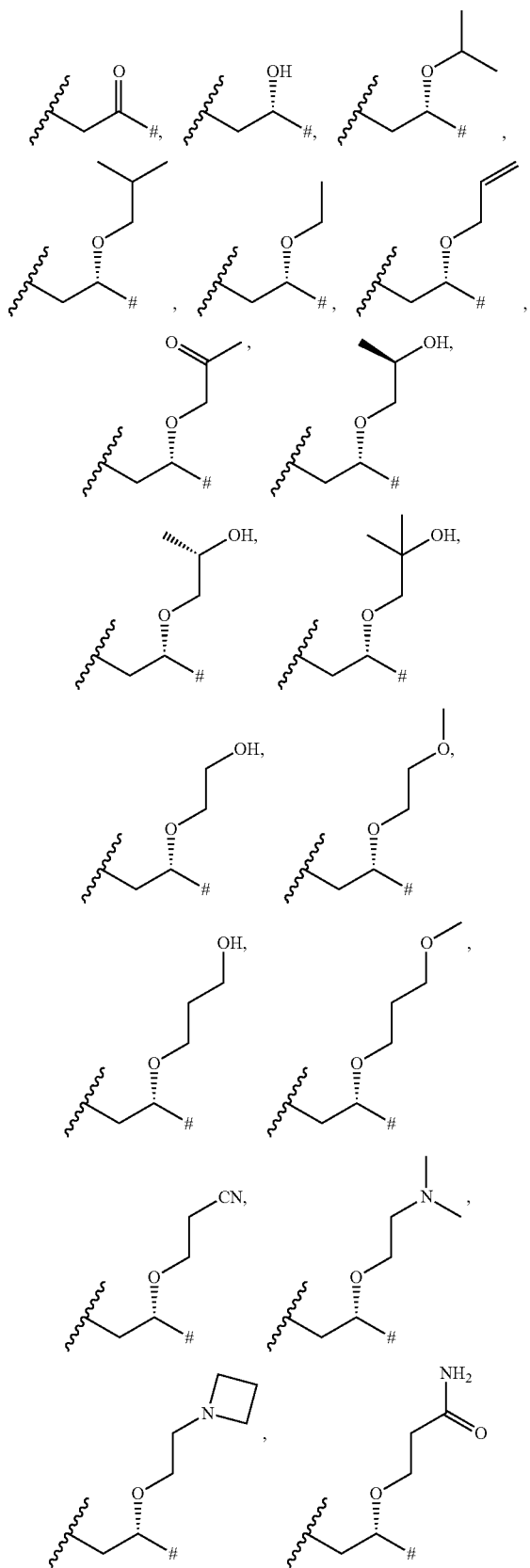
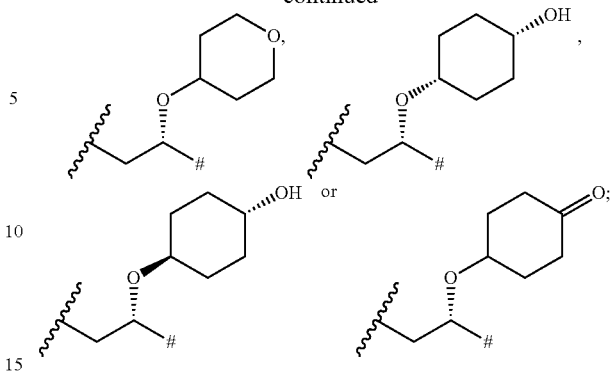

wherein # is the point of attachment to $R^4$.

In some embodiments, $L^2$ is selected from those depicted in Table 1, below.

As defined generally above, $R^3$ is —OR, —C(O)OR, —N(R)C(O)OR, —OC(O)N(R)$_2$, —C(O)N(R)OR, —C(O)NH$_2$, —C(O)NHR$^a$, —C(O)NR$^a_2$, or —C(O)Hy.

In some embodiments, $R^3$ is —C(O)NHR$^a$, —C(O)NR$^a_2$, or —C(O)Hy.

In some embodiments, $R^3$ is —OR. In some embodiments, $R^3$ is —C(O)OR. In some embodiments, $R^3$ is —C(O)N(R)OR. In some embodiments, $R^3$ is —C(O)NH$_2$. In some embodiments, $R^3$ is —C(O)NHR$^a$. In some embodiments, $R^3$ is —C(O)N(R$^a$)$_2$. In some embodiments, $R^3$ is —C(O)Hy.

In some embodiments, $R^3$ is —C(O)NH$_2$. In some embodiments, $R^3$ is —C(O)NHR$^a$, where $R^a$ is optionally substituted $C_{1-6}$ alkyl. In some embodiments, $R^3$ is:

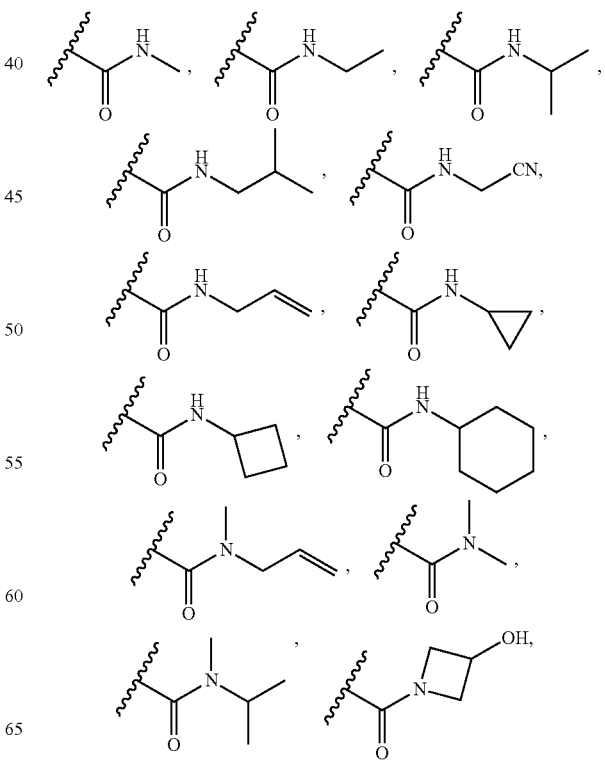

-continued

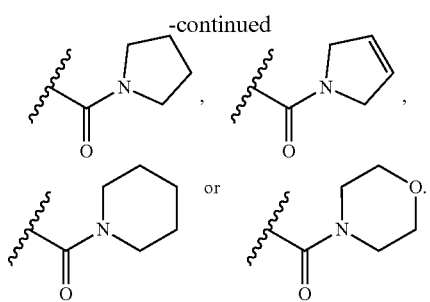

In some embodiments, R³ is:

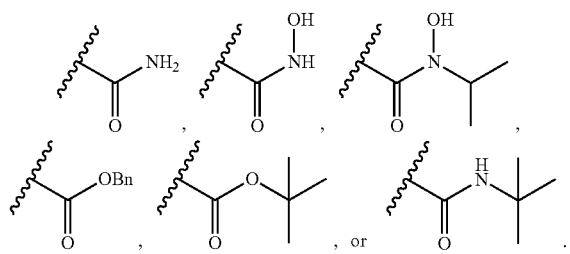

In some embodiments, R³ is selected from those depicted in Table 1, below.

In some embodiments, -L¹-R³, taken together, is:

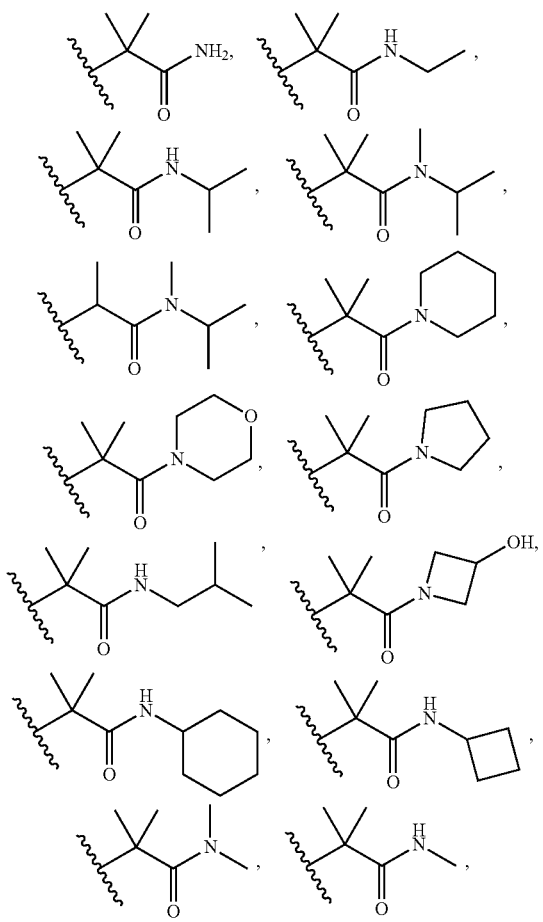

-continued

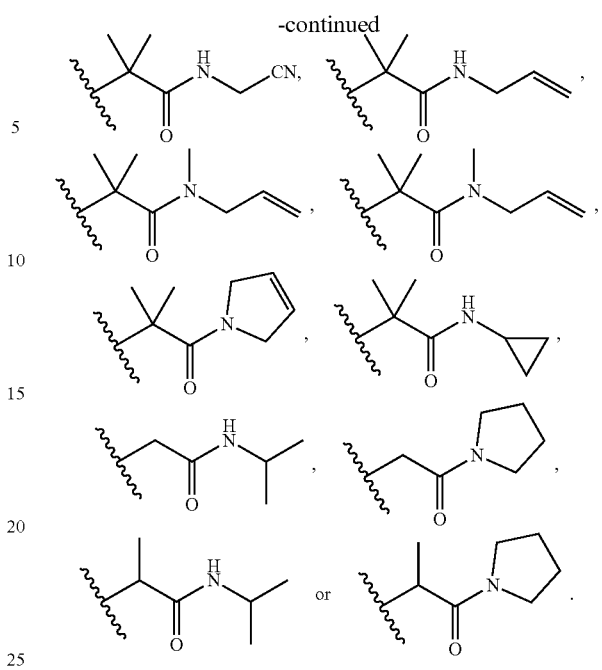

In some embodiments, -L¹-R³, taken together, is:

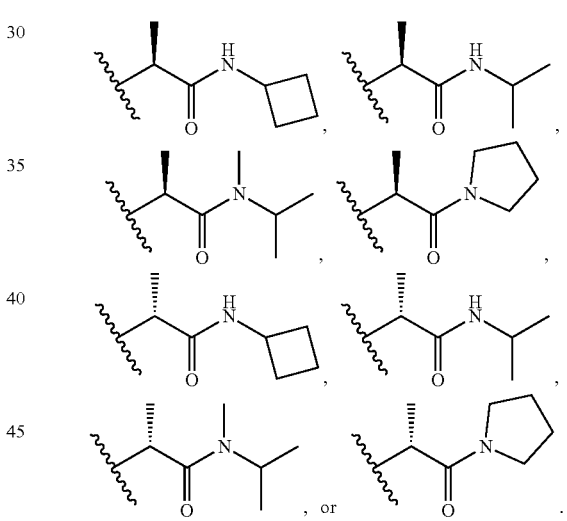

In some embodiments, L¹-R³ is selected from those depicted in Table 1, below.

As defined generally above, Hy is a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; wherein Hy is substituted by p instances of R⁶.

In some embodiments, Hy is a 3-8 membered saturated or partially unsaturated monocyclic heterocyclic ring having 1-2 heteroatoms independently selected from nitrogen, oxygen, or sulfur; wherein Hy is substituted by p instances of R⁶. In some embodiments, Hy is a 5-6 membered monocyclic heteroaromatic ring having 1-4 heteroatoms independently selected from nitrogen, oxygen, or sulfur; wherein Hy is substituted by p instances of R⁶. In some embodiments, Hy is an 8-10 membered bicyclic heteroaromatic ring having 1-5 heteroatoms independently selected from nitrogen, oxygen, or sulfur; wherein Hy is substituted by p instances of R⁶.

In some embodiments, Hy is

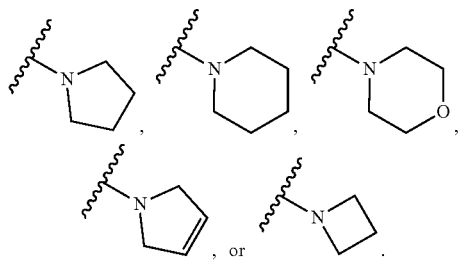

, or

In some embodiments, Hy is

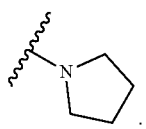

In some embodiments, Hy is

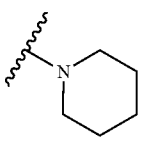

In some embodiments, Hy is

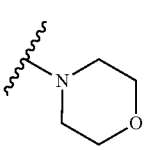

In some embodiments, Hy is

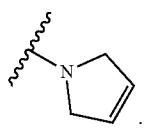

In some embodiments, Hy is

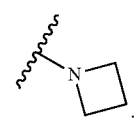

In some embodiments, Hy(R⁶)$_p$, taken together, is

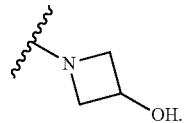 [SMILES: *N1CC(O)C1]

In some embodiments, Hy is selected from those depicted in Table 1, below.

As defined generally above, R⁴ is a ring selected from a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, and an 8-10 membered bicyclic heteroaryl ring having 1-4 heteroatoms independently selected from nitrogen, oxygen, or sulfur, wherein R⁴ is substituted by q instances of R⁷.

In some embodiments, R⁴ is a ring selected from a 3-8 membered monocyclic saturated or partially unsaturated carbocyclic ring; wherein R⁴ is substituted by q instances of R⁷. In some embodiments, R⁴ is a 4-8 membered monocyclic saturated or partially unsaturated heterocyclic ring having 1-2 heteroatoms independently selected from nitrogen, oxygen, or sulfur; wherein R⁴ is substituted by q instances of R⁷. In some embodiments, R⁴ is phenyl; wherein R⁴ is substituted by q instances of R⁷. In some embodiments, R⁴ is an 8-10 membered bicyclic aryl ring; wherein R⁴ is substituted by q instances of R⁷. In some embodiments, R⁴ is a 5-6 membered monocyclic heteroaryl ring having 1-4 heteroatoms independently selected from nitrogen, oxygen, or sulfur; wherein R⁴ is substituted by q instances of R⁷. In some embodiments, R⁴ is an 8-10 membered bicyclic heteroaryl ring having 1-4 heteroatoms independently selected from nitrogen, oxygen, or sulfur; wherein R⁴ is substituted by q instances of R⁷.

In some embodiments, R⁴(R⁷)$_q$, taken together, is

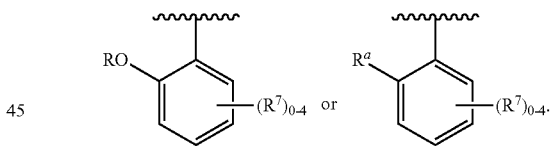

In some embodiments, R⁴(R⁷)$_q$, taken together, is

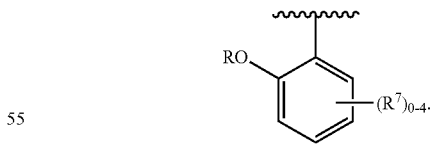

In some embodiments, R⁴(R⁷)$_q$, taken together, is

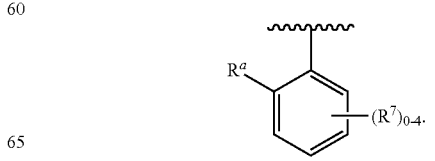

In some embodiments, R⁴(R⁷)_q, taken together, is

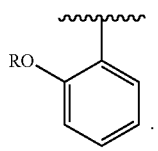

In some embodiments, R⁴(R⁷)_q, taken together, is

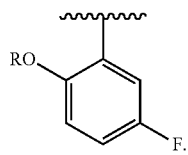

In some embodiments, R⁴(R⁷)_q, taken together, is

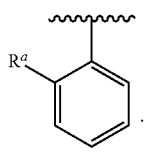

In some embodiments, R⁴(R⁷)_q, taken together, is

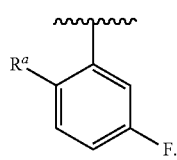

In some embodiments, R⁴(R⁷)_q, taken together, is

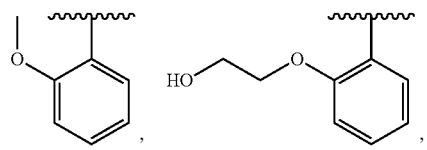

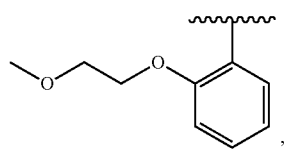

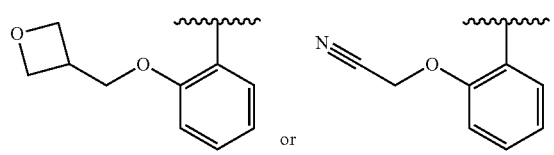

or

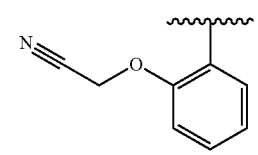

In some embodiments, R⁴(R⁷)_q, taken together, is

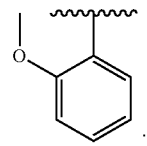

In some embodiments, R⁴(R⁷)_q, taken together, is

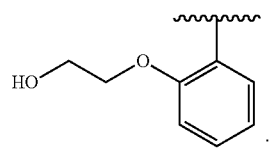 [SMILES: *c1ccccc1OCCO]

In some embodiments, R⁴(R⁷)_q, taken together, is

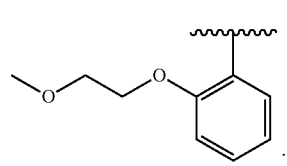 [SMILES: *c1ccccc1OCCOC]

In some embodiments, R⁴(R⁷)_q, taken together, is

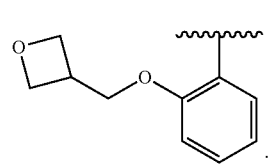 [SMILES: *c1ccccc1OCC1COC1]

In some embodiments, R⁴(R⁷)_q, taken together, is

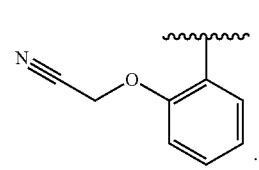 [SMILES: *c1ccccc1OCC#N]

In some embodiments, R⁴(R⁷)_q, taken together, is

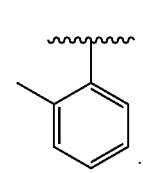

In some embodiments, R⁴(R⁷)_q, taken together, is

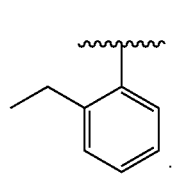 [SMILES: *c1ccccc1CC]

In some embodiments, $R^4(R^7)_q$, taken together, is

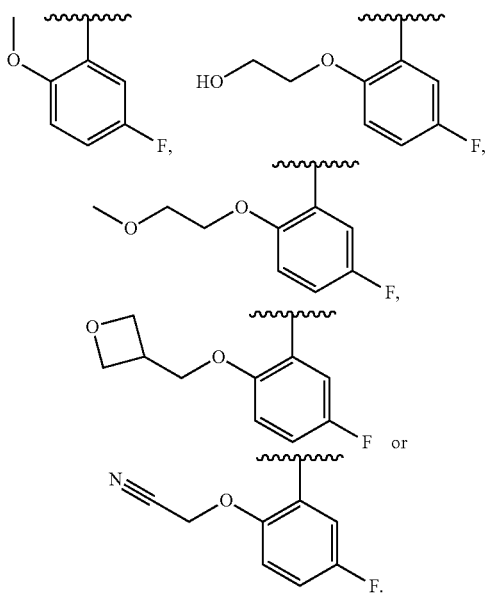

In some embodiments, $R^4(R^7)_q$, taken together, is

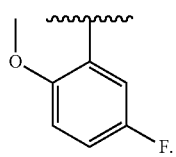 [SMILES: *c1cc(F)ccc1OC]

In some embodiments, $R^4(R^7)_q$, taken together, is

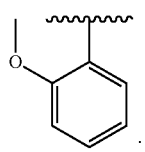

In some embodiments, $R^4(R^7)_q$, taken together, is

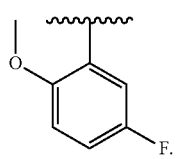 [SMILES: *c1cc(F)ccc1OC]

In some embodiments, $R^4(R^7)_q$, taken together, is

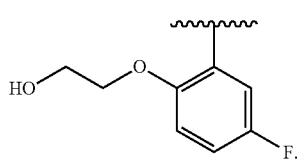 [SMILES: *c1cc(F)ccc1OCCO]

In some embodiments, $R^4(R^7)_q$, taken together, is

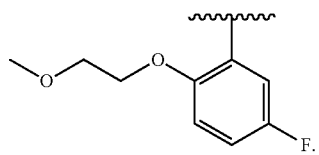 [SMILES: *c1cc(F)ccc1OCCOC]

In some embodiments, $R^4(R^7)_q$, taken together, is

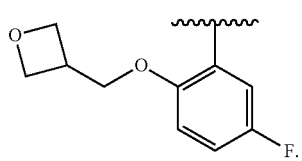 [SMILES: *c1cc(F)ccc1OCC1COC1]

In some embodiments, $R^4(R^7)_q$, taken together, is

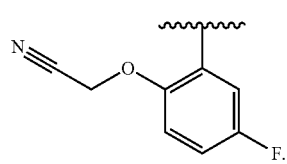 [SMILES: *c1cc(F)ccc1OCC#N]

In some embodiments, $R^4(R^7)_q$, taken together, is

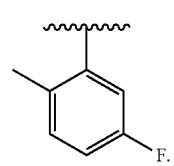 [SMILES: *c1cc(F)ccc1C]

In some embodiments, $R^4(R^7)_q$, taken together, is

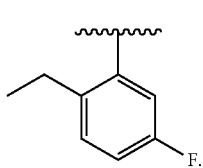 [SMILES: *c1cc(F)ccc1CC]

In some embodiments, $R^4$ is selected from those depicted in Table 1, below.

In some embodiments, $-L^2-R^4$ is selected from the following:

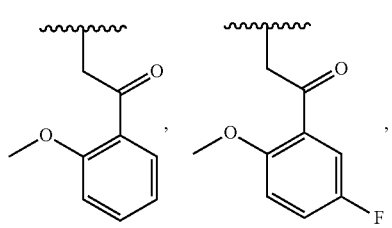

-continued

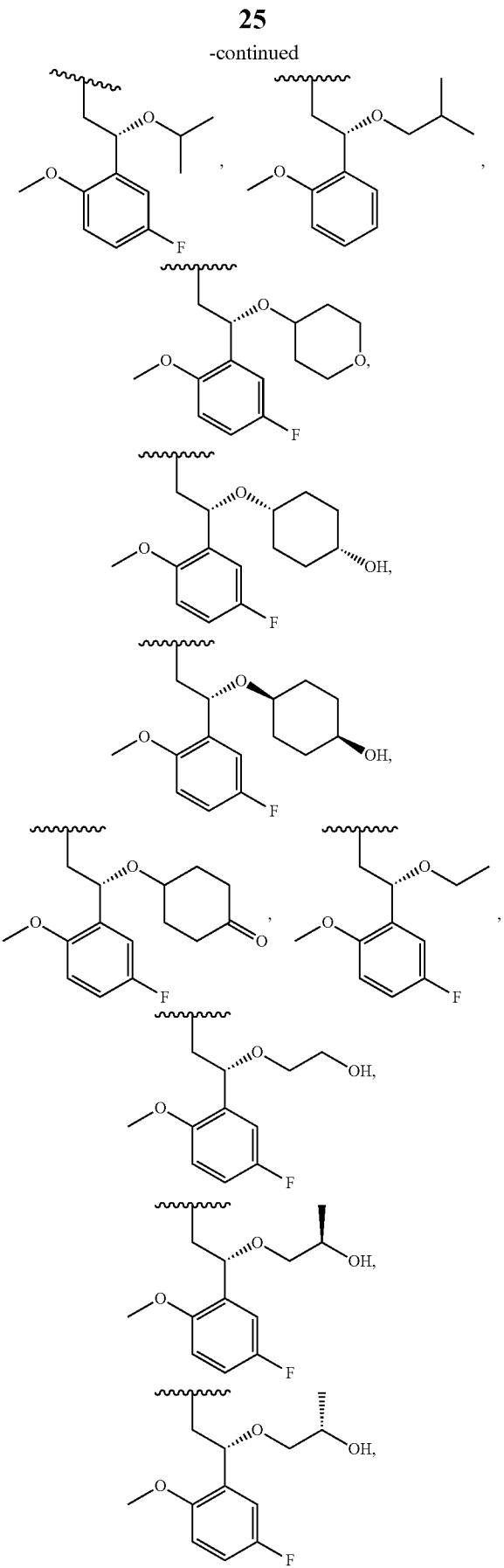

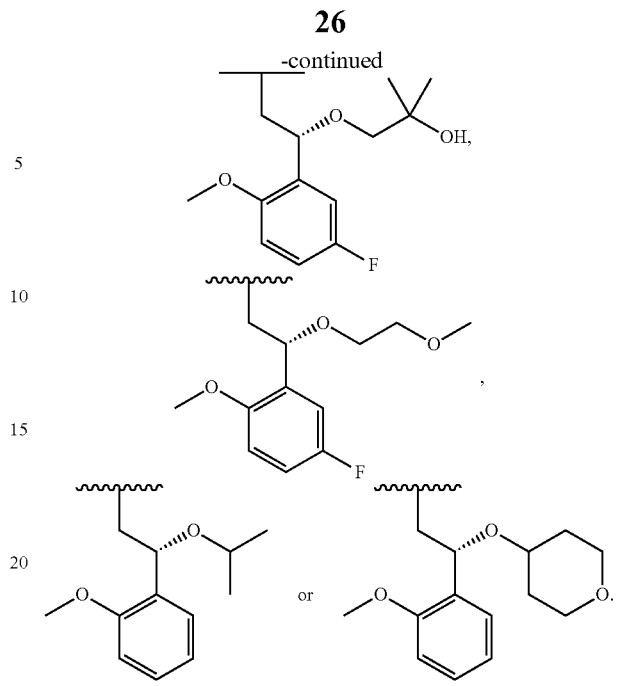

In some embodiments, $L^2$-$R^4$ is selected from those depicted in Table 1, below.

As defined generally above, each $R^5$ is independently hydrogen, $C_{1-4}$ aliphatic, a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur, wherein each $R^5$ is substituted with r instances of $R^8$.

In some embodiments, $R^5$ is hydrogen. In some embodiments, $R^5$ is a $C_{1-4}$ aliphatic; wherein each $R^5$ is substituted with r instances of $R^8$. In some embodiments, $R^5$ is a 3-8 membered monocyclic saturated or partially unsaturated carbocyclic ring, wherein each $R^5$ is substituted with r instances of $R^8$. In some embodiments, $R^5$ is a 4-8 membered monocyclic saturated or partially unsaturated heterocyclic ring having 1-2 heteroatoms independently selected from nitrogen, oxygen, or sulfur, wherein each $R^5$ is substituted with r instances of $R^8$. In some embodiments, $R^5$ is phenyl, wherein each $R^5$ is substituted with r instances of $R^8$. In some embodiments, $R^5$ is an 8-10 membered bicyclic aryl ring, wherein each $R^5$ is substituted with r instances of $R^8$. In some embodiments, $R^5$ is a 5-6 membered monocyclic heteroaryl ring having 1-4 heteroatoms independently selected from nitrogen, oxygen, or sulfur, wherein each $R^5$ is substituted with r instances of $R^8$. In some embodiments, $R^5$ is an 8-10 membered bicyclic heteroaryl ring having 1-4 heteroatoms independently selected from nitrogen, oxygen, or sulfur, wherein each $R^5$ is substituted with r instances of $R^8$.

In some embodiments, $R^5$ is isopropyl. In some embodiments, $R^5$ is 4-tetrahydropyranyl. In some embodiments, $R^5$ is isobutyl. In some embodiments, $R^5$ is cyclohexyl wherein $R^8$ is oxo. In some embodiments, $R^5$ is cyclohexyl wherein $R^8$ is hydroxyl. In some embodiments, $R^5$ is ethyl.

In some embodiments, R⁵ is selected from the following:

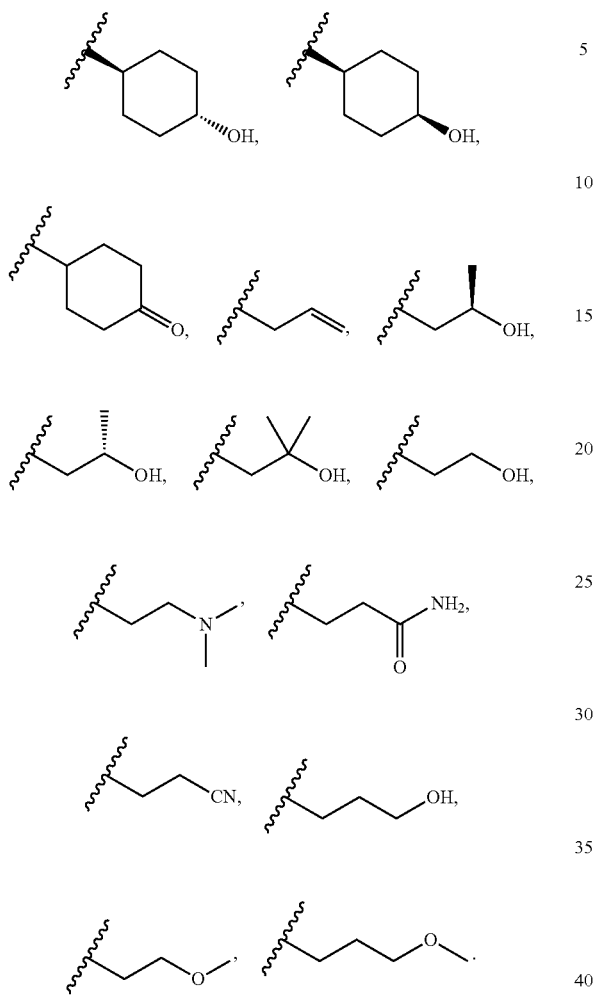

In some embodiments, R⁵ is selected from those depicted in Table 1, below.

As defined generally above, m is 0-3. In some embodiments, m is 0. In some embodiments, m is 1. In some embodiments, m is 2. In some embodiments, m is 3.

As defined generally above, n is 0-2. In some embodiments, n is 0. In some embodiments, n is 1-2. In some embodiments, n is 1. In some embodiments, n is 2.

As defined generally above, p is 0-4. In some embodiments, p is 0. In some embodiments, p is 1. In some embodiments, p is 2. In some embodiments, p is 3. In some embodiments, p is 4.

As defined generally above, q is 0-5. In some embodiments, q is 0. In some embodiments, q is 1. In some embodiments, q is 2. In some embodiments, q is 3. In some embodiments, q is 4. In some embodiments, q is 5.

As defined generally above, r is 0-4. In some embodiments, r is 0. In some embodiments, r is 1. In some embodiments, r is 2. In some embodiments, r is 3. In some embodiments, r is 4.

In some embodiments, the present invention provides a compound of formulae II-a or II-b:

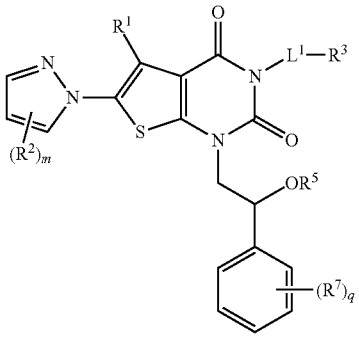

II-a

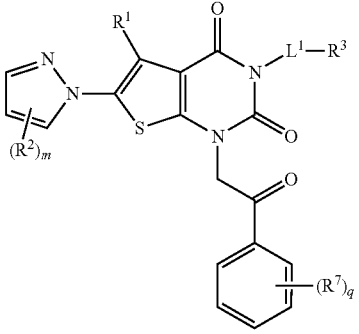

II-b or a pharmaceutically acceptable salt or agriculturally acceptable salt thereof, wherein each of R¹, R², R³, R⁵, R⁷, m, q, and L¹, is as defined above and described in embodiments herein, both singly and in combination.

In some embodiments, the present invention provides a compound of formulae II-a-i:

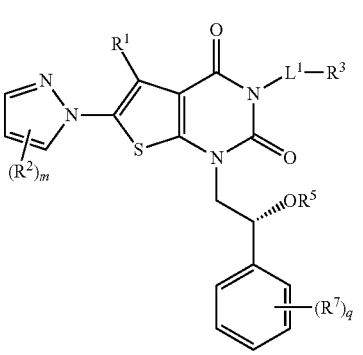

II-a-i or a pharmaceutically acceptable salt or agriculturally acceptable salt thereof, wherein each of R¹, R², R³, R⁵, R⁷, m, q, and L¹ is as defined above and described in embodiments herein, both singly and in combination In some embodiments, the present invention provides a compound of formulae III-a, III-b, III-c, or III-d:

III-a
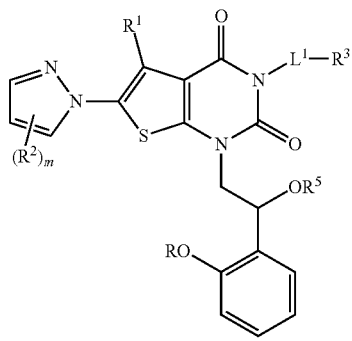

III-b
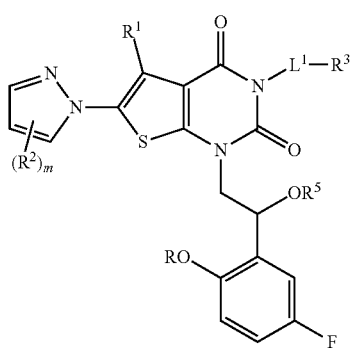

III-c
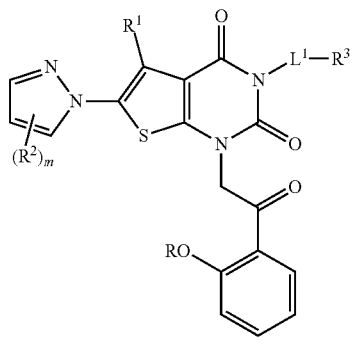

III-d
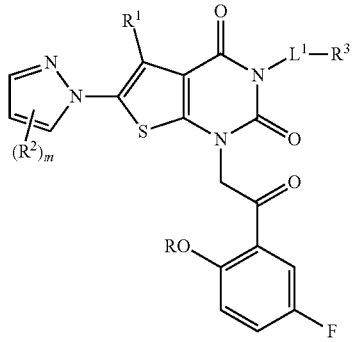

or a pharmaceutically acceptable salt or agriculturally acceptable salt thereof, wherein each of R, $R^1$, $R^2$, $R^3$, $R^5$, $R^7$, m, and $L^1$ is as defined above and described in embodiments herein, both singly and in combination.

In some embodiments, the present invention provides a compound of formulae III-a-i, or III-b-i:

III-a-i
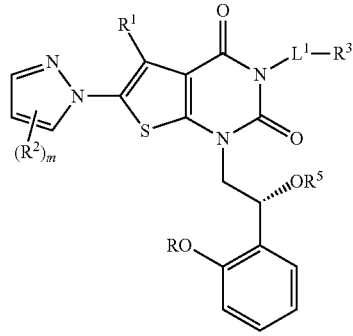

III-b-i
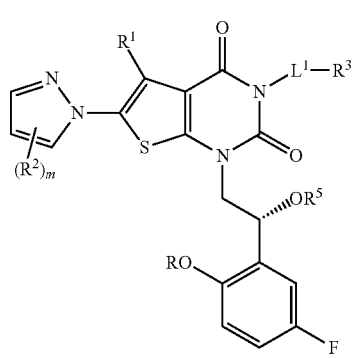

or a pharmaceutically acceptable salt or agriculturally acceptable salt thereof, wherein each of R, $R^1$, $R^2$, $R^3$, $R^5$, $R^7$, m, and $L^1$ is as defined above and described in embodiments herein, both singly and in combination.

In some embodiments, the present invention provides a compound of formula IV-a, IV-b, or IV-c:

IV-a
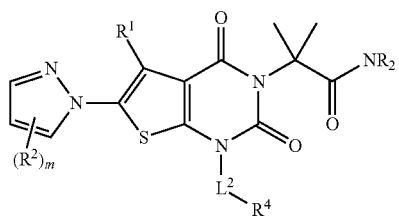

IV-b
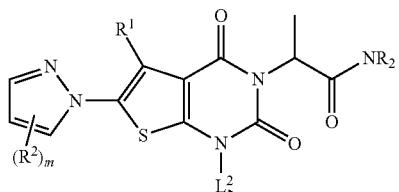

IV-c
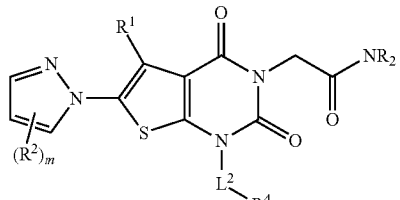

or a pharmaceutically acceptable salt or agriculturally acceptable salt thereof, wherein each of R, $R^1$, $R^2$, $R^4$, m, and $L^2$ is as defined above and described in embodiments herein, both singly and in combination.

In some embodiments, the present invention provides a compound of formula IV-a, IV-b, IV-c, IV-d, IV-e, or IV-f:

IV-a
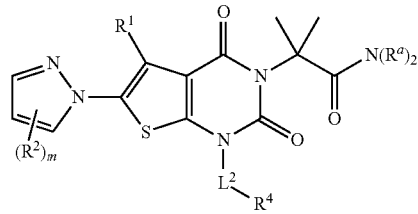

IV-b
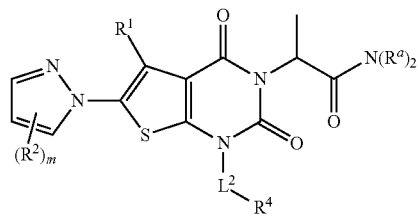

IV-c
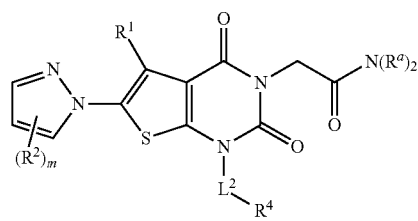

IV-d
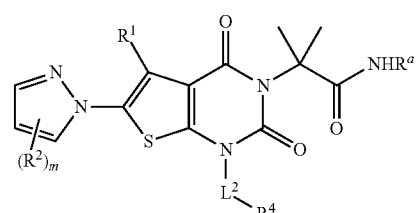

IV-e
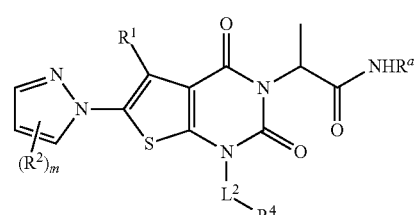

IV-f
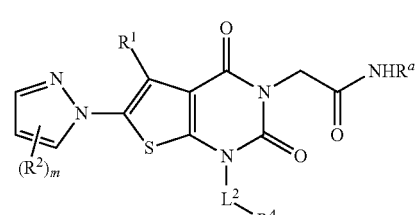

or a pharmaceutically acceptable salt or agriculturally acceptable salt thereof, wherein each of $R^a$, $R^1$, $R^2$, $R^4$, m, and $L^2$ is as defined above and described in embodiments herein, both singly and in combination.

In some embodiments, the present invention provides a compound of formula IV-b-i, or IV-b-ii:

IV-b-i
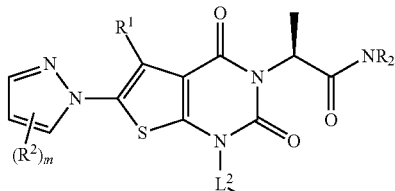

IV-b-ii
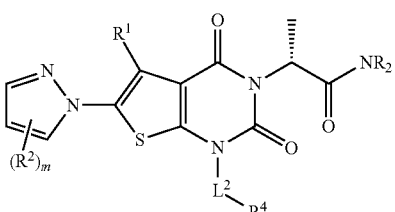

or a pharmaceutically acceptable salt or agriculturally acceptable salt thereof, wherein each of R, $R^1$, $R^2$, $R^4$, m, and $L^2$ is as defined above and described in embodiments herein, both singly and in combination.

In some embodiments, the present invention provides a compound of formula IV-b-i, IV-b-ii, IV-e-i, or IV-e-ii:

IV-b-i
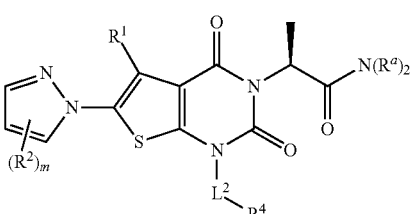

IV-b-ii
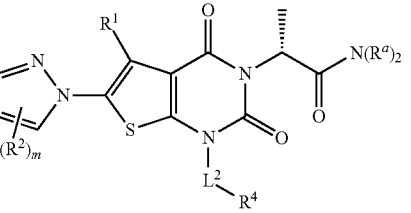

IV-e-i
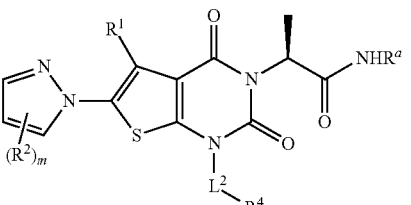

IV-e-ii
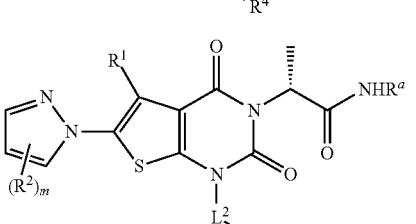

or a pharmaceutically acceptable salt or agriculturally acceptable salt thereof, wherein each of $R^a$, $R^1$, $R^2$, $R^4$, m, and $L^2$ is as defined above and described in embodiments herein, both singly and in combination.

In some embodiments, the present invention provides a compound of formula V-a, V-b, V-c, V-d, V-e, or V-f:

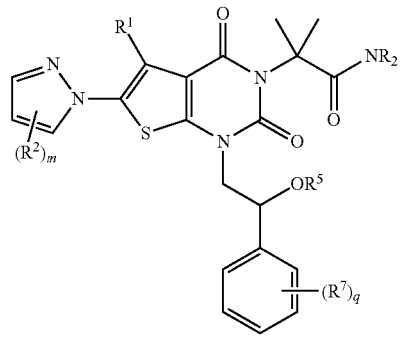

V-a

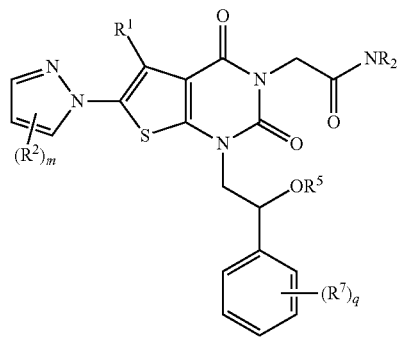

V-b

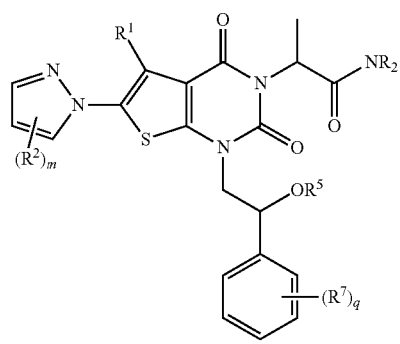

V-c

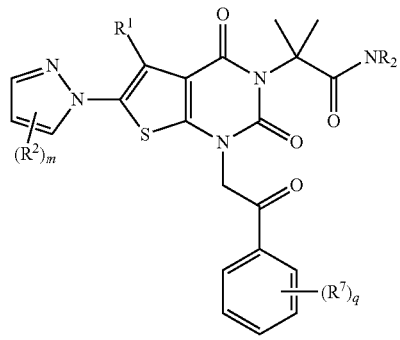

V-d

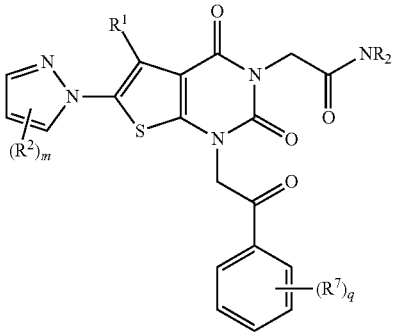

V-e

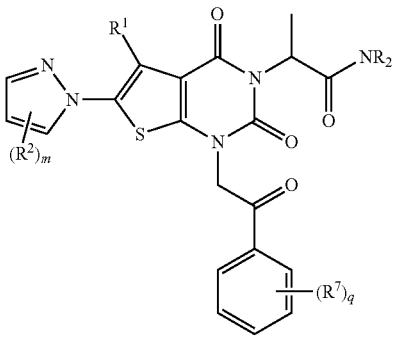

V-f or a pharmaceutically acceptable salt or agriculturally acceptable salt thereof, wherein each of R, $R^1$, $R^2$, $R^1$, $R^7$, m, and q is as defined above and described in embodiments herein, both singly and in combination.

In some embodiments, the present invention provides a compound of formula V-a, V-b, V-c, V-d, V-e, V-f, V-g, V-h, V-i, V-j, V-k, or V-l:

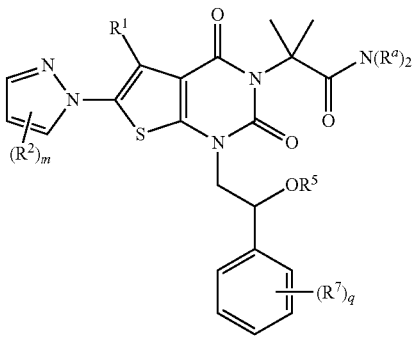

V-a

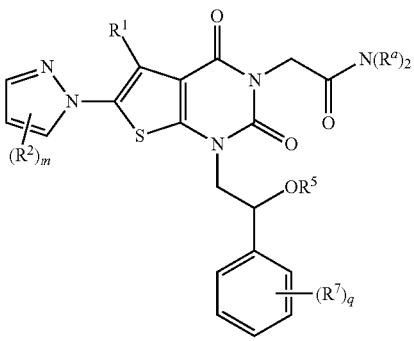

V-b

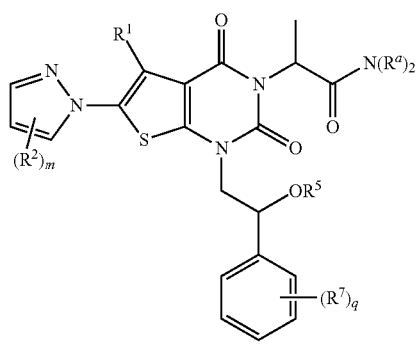 V-c
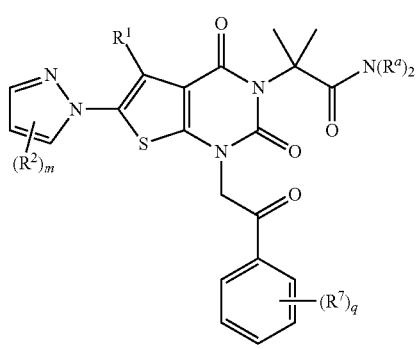 V-d
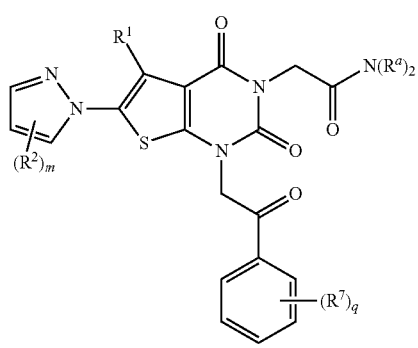 V-e
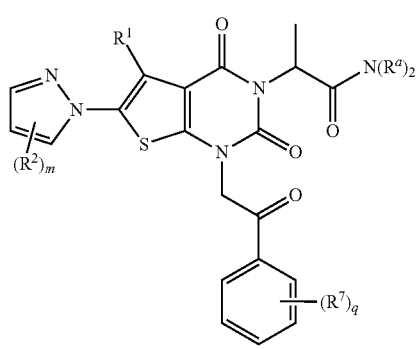 V-f
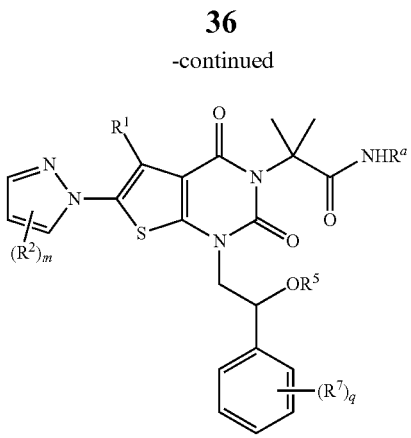 V-g
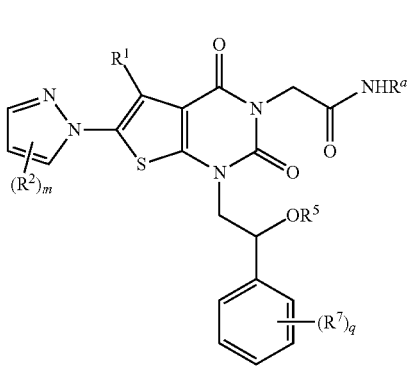 V-h
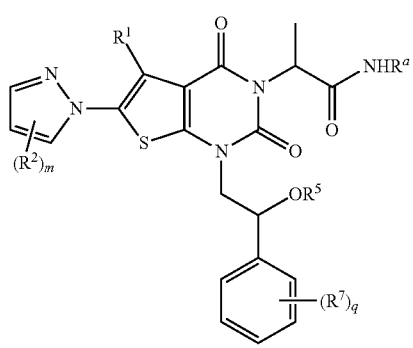 V-i
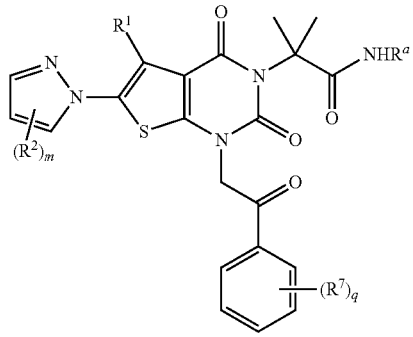 V-j

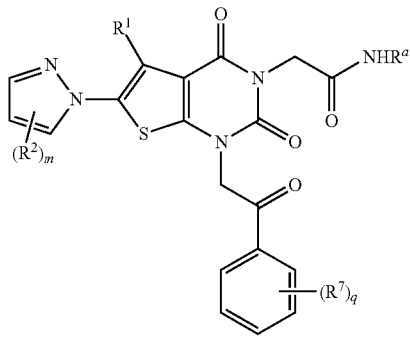

V-k

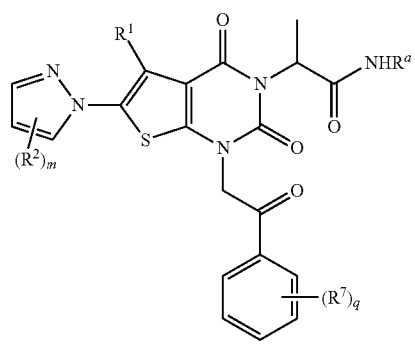

V-l

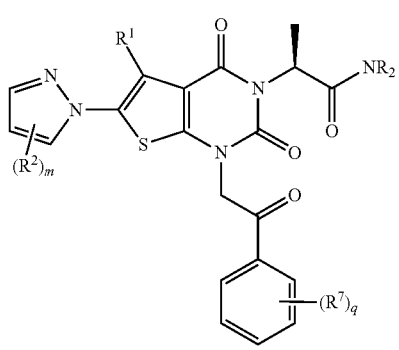

V-f-i

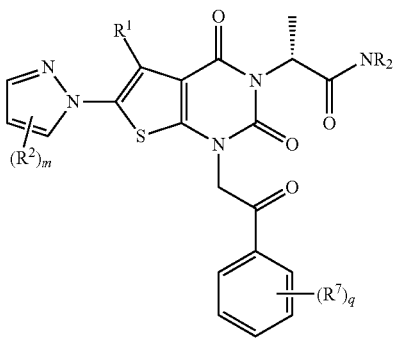

V-f-ii or a pharmaceutically acceptable salt or agriculturally acceptable salt thereof, wherein each of $R^a$, $R^1$, $R^2$, $R^1$, $R^7$, m, and q is as defined above and described in embodiments herein, both singly and in combination.

In some embodiments, the present invention provides a compound of formula V-c-i, V-c-ii, V-f-i, or V-f-ii:

or a pharmaceutically acceptable salt or agriculturally acceptable salt thereof, wherein each of R, $R^1$, $R^2$, $R^5$, $R^7$, m, and q is as defined above and described in embodiments herein, both singly and in combination.

In some embodiments, the present invention provides a compound of formula V-c-i, V-c-ii, V-f-i, V-f-ii, V-i-i, V-i-ii, V-l-i, or V-l-i:

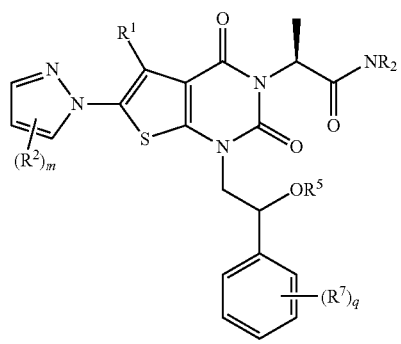

V-c-i

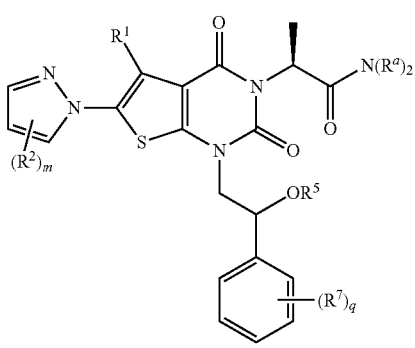

V-c-i

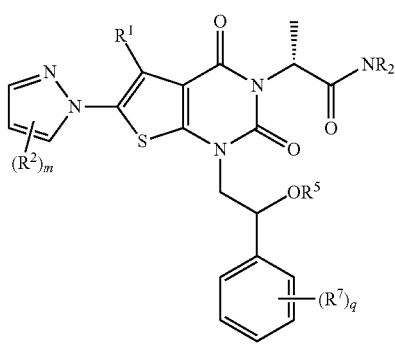

V-c-ii

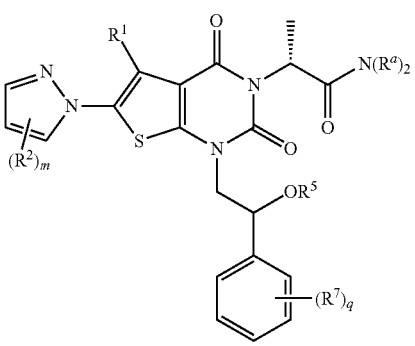

V-c-ii

V-f-i
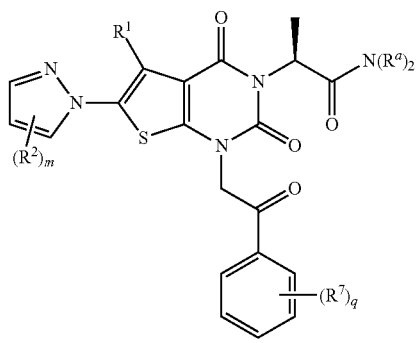
V-f-ii
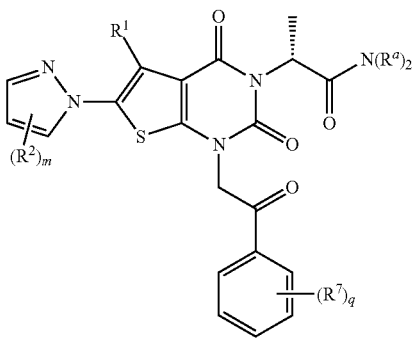
V-i-i
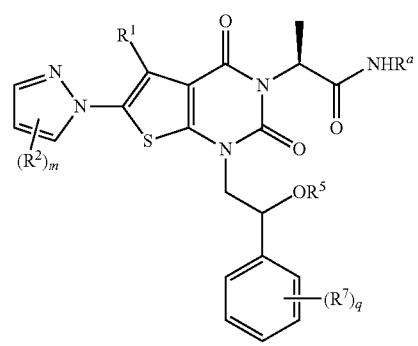
V-i-ii
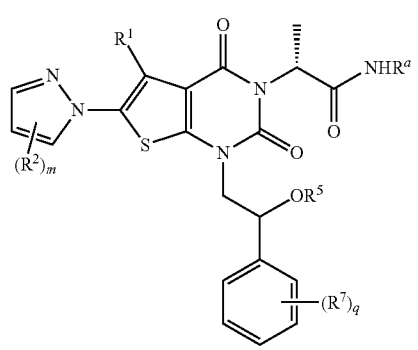
V-l-i
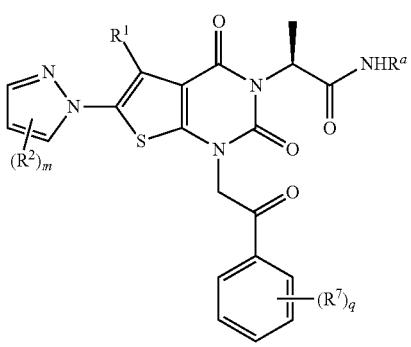
V-l-ii
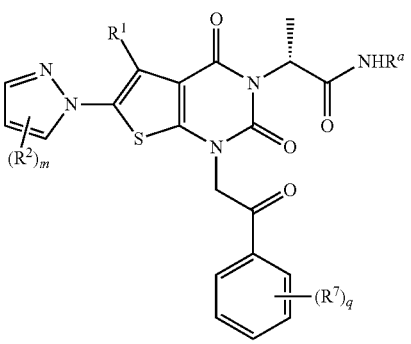
or a pharmaceutically acceptable salt or agriculturally acceptable salt thereof, wherein each of $R^a$, $R^1$, $R^2$, $R^1$, $R^7$, m, and q is as defined above and described in embodiments herein, both singly and in combination.
In certain embodiments, the present invention provides a compound of formula VI-a, VI-b, or VI-c:
VI-a
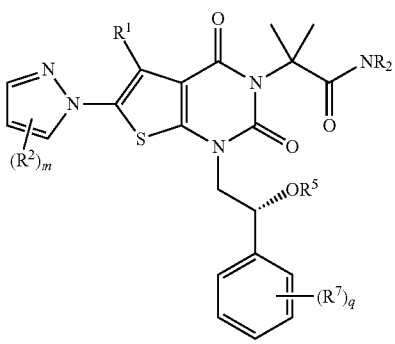
VI-b
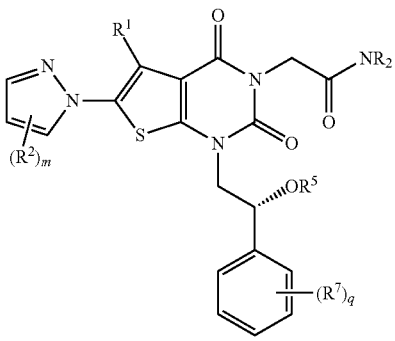

VI-c

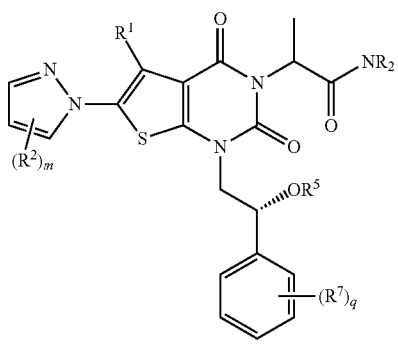

or a pharmaceutically acceptable salt or agriculturally acceptable salt thereof, wherein each of R, R¹, R², R⁵, R⁷, m, and q is as defined above and described in embodiments herein, both singly and in combination.

In certain embodiments, the present invention provides a compound of formula VI-a, VI-b, VI-c, VI-d, VI-e, or VI-f:

VI-a

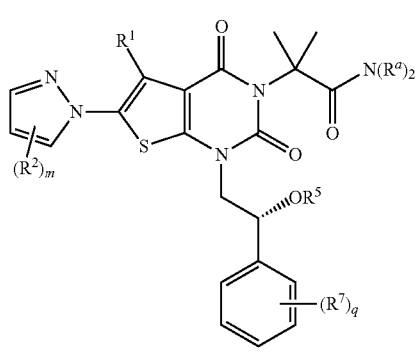

VI-b

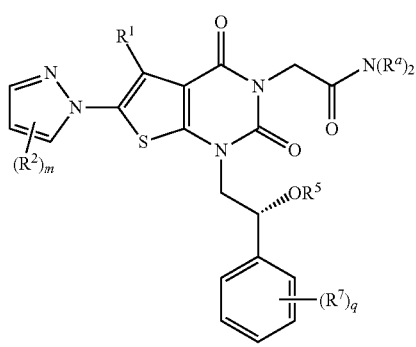

VI-c

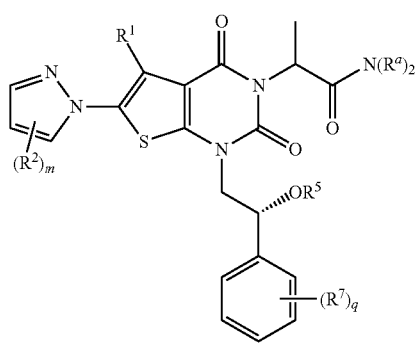

VI-d

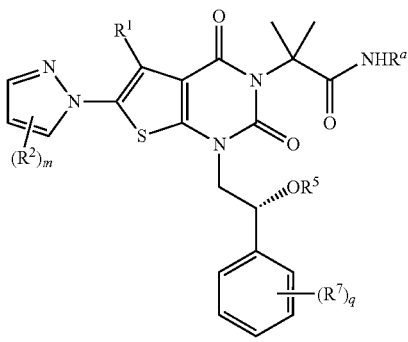

VI-e

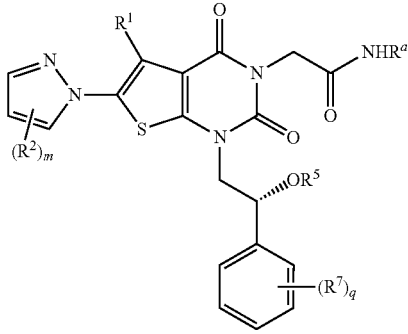

VI-f

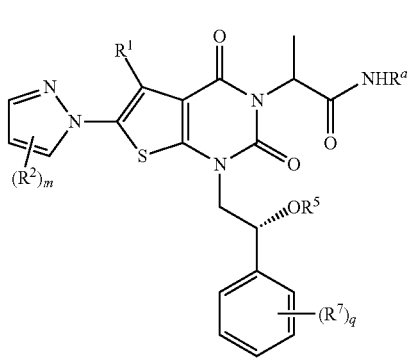

or a pharmaceutically acceptable salt or agriculturally acceptable salt thereof, wherein each of $R^a$, $R^1$, $R^2$, $R^5$, $R^7$, m, and q is as defined above and described in embodiments herein, both singly and in combination.

In certain embodiments, the present invention provides a compound of formula VI-c-i, or VI-c-ii:

VI-c-i

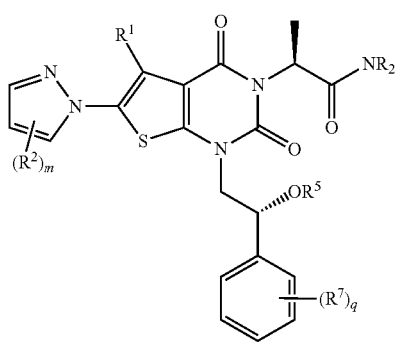

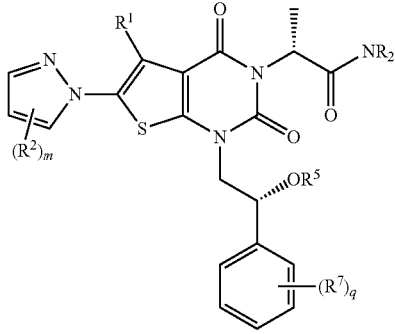

VI-c-ii

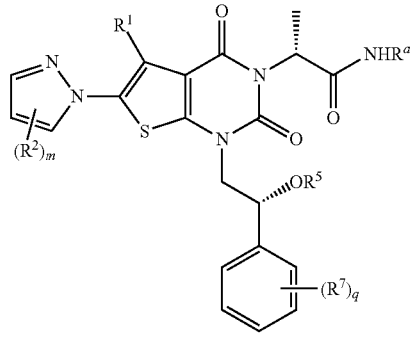

VI-f-i or a pharmaceutically acceptable salt or agriculturally acceptable salt thereof, wherein each of R, $R^1$, $R^2$, $R^5$, $R^7$, m, and q is as defined above and described in embodiments herein, both singly and in combination.

In certain embodiments, the present invention provides a compound of formula VI-c-i, VI-c-ii, VI-f-i, or VI-f-ii:

or a pharmaceutically acceptable salt or agriculturally acceptable salt thereof, wherein each of $R^a$, $R^1$, $R^2$, $R^5$, $R^7$, m, and q is as defined above and described in embodiments herein, both singly and in combination.

In certain embodiments, the present invention provides a compound of formula VII-a, VII-b, or VII-c:

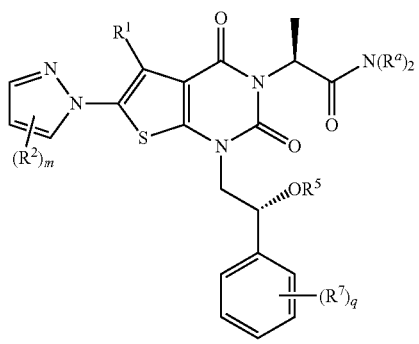

VI-c-i

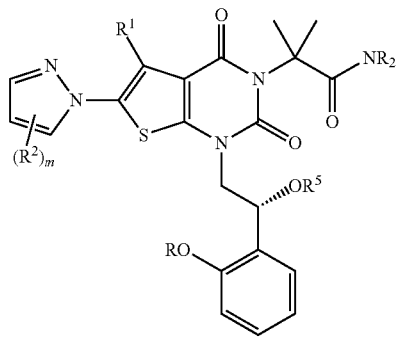

VII-a

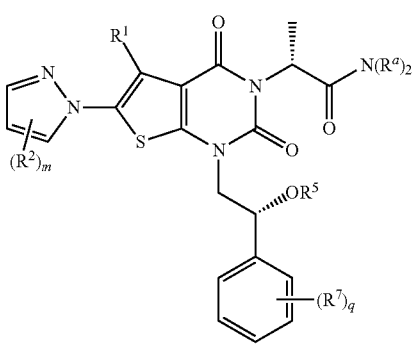

VI-c-ii

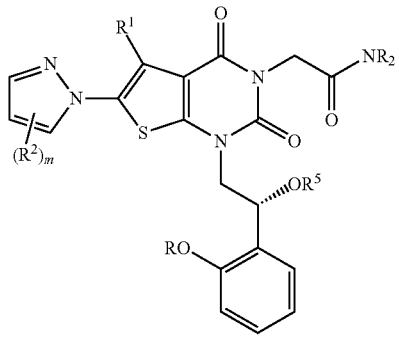

VII-b

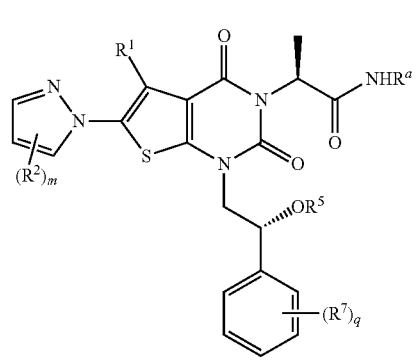

VI-f-i

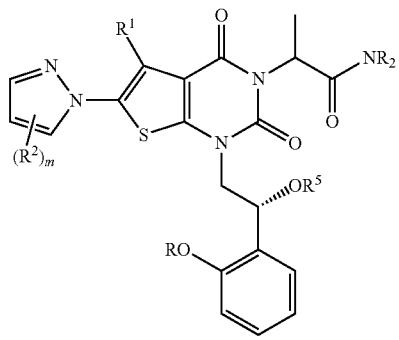

VII-c or a pharmaceutically acceptable salt or agriculturally acceptable salt thereof, wherein each of R, $R^1$, $R^2$, $R^5$, m is as defined above and described in embodiments herein, both singly and in combination.

In certain embodiments, the present invention provides a compound of formula VII-a, VII-b, VII-c, VII-d, VII-e, or VII-f:

VII-a
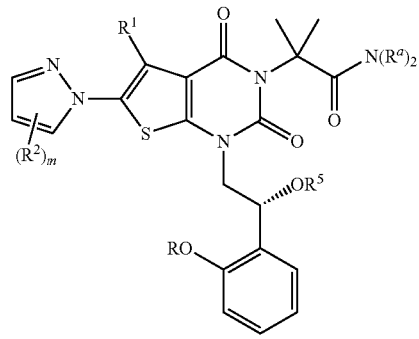

VII-b
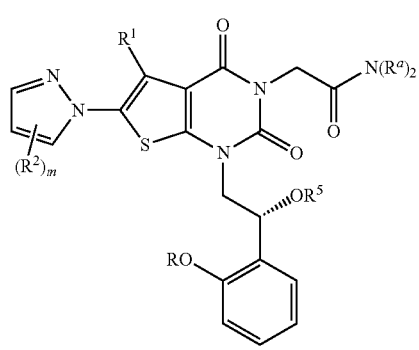

VII-c
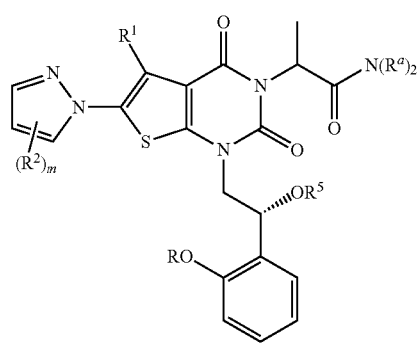

VII-d
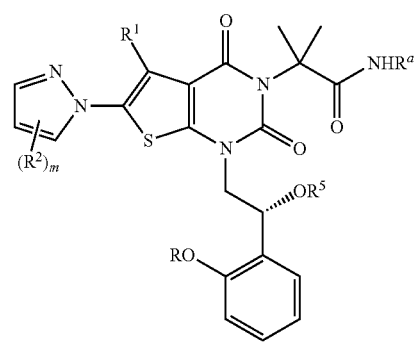

VII-e
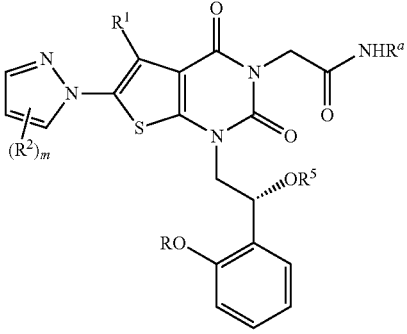

VII-f
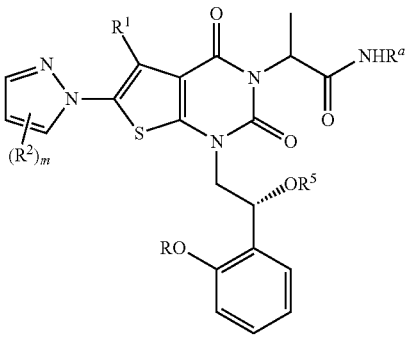

or a pharmaceutically acceptable salt or agriculturally acceptable salt thereof, wherein each of R, $R^a$, $R^1$, $R^2$, $R^5$, m is as defined above and described in embodiments herein, both singly and in combination.

In certain embodiments, the present invention provides a compound of formula VII-c-i, or VII-c-ii:

VII-c-i
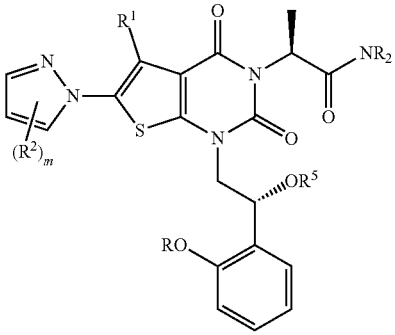

VII-c-ii
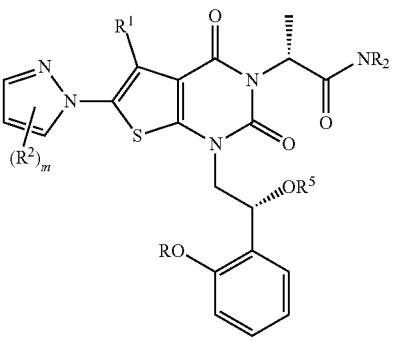

or a pharmaceutically acceptable salt or agriculturally acceptable salt thereof, wherein each of R, $R^1$, $R^2$, $R^5$, m is as defined above and described in embodiments herein, both singly and in combination.

In certain embodiments, the present invention provides a compound of formula VII-c-i, VII-c-ii, VII-f-i, or VII-f-ii:

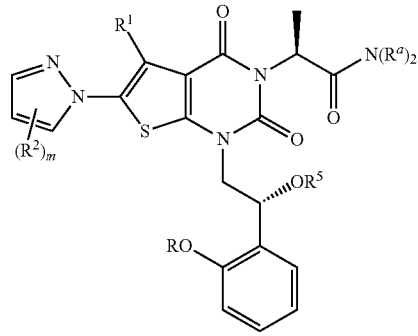

VII-c-i

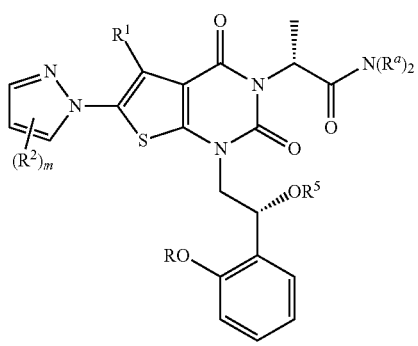

VII-c-ii

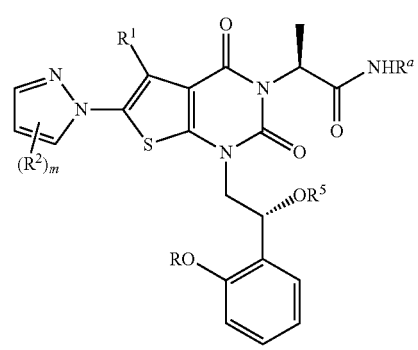

VII-f-i

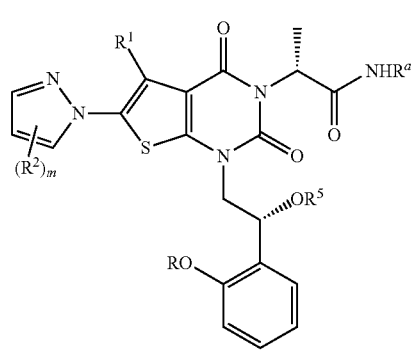

VII-f-ii or a pharmaceutically acceptable salt or agriculturally acceptable salt thereof, wherein each of R, $R^a$, $R^1$, $R^2$, $R^5$, and m is as defined above and described in embodiments herein, both singly and in combination.

In certain embodiments, the present invention provides a compound of formula VIII-a, VIII-b, or VIII-c:

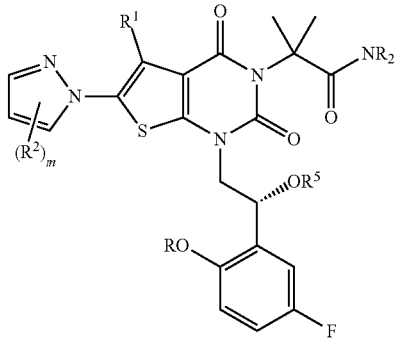

VIII-a

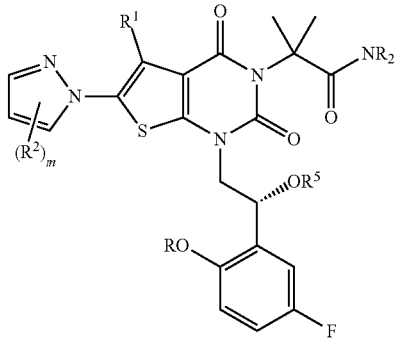

VIII-b

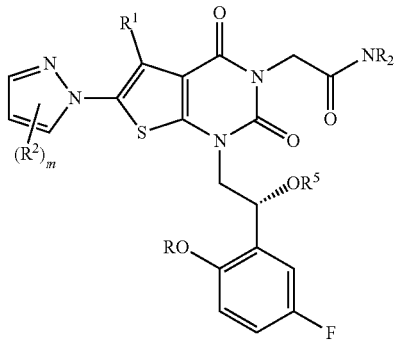

VIII-c or a pharmaceutically acceptable salt or agriculturally acceptable salt thereof, wherein each of R, $R^1$, $R^2$, $R^5$, and m is as defined above and described in embodiments herein, both singly and in combination.

In certain embodiments, the present invention provides a compound of formula VIII-a, VIII-b, VIII-c, VIII-d, VIII-e, or VIII-f:

VIII-a
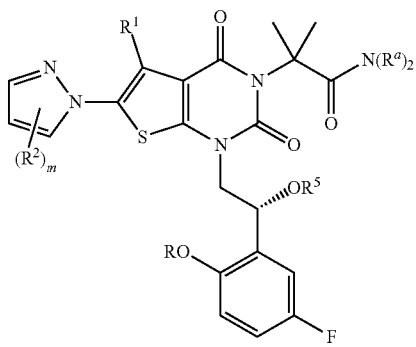

VIII-b
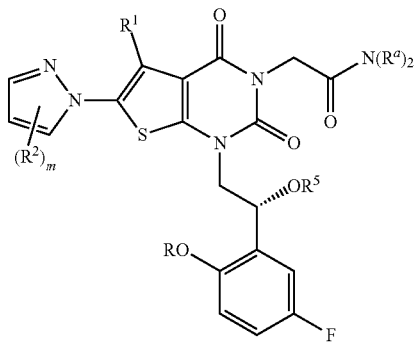

VIII-c
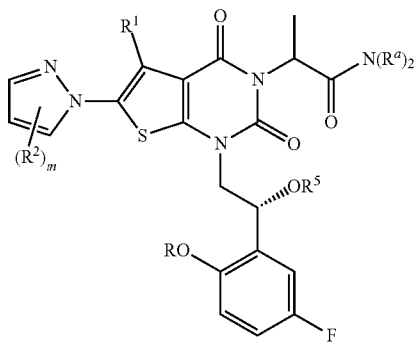

VIII-d
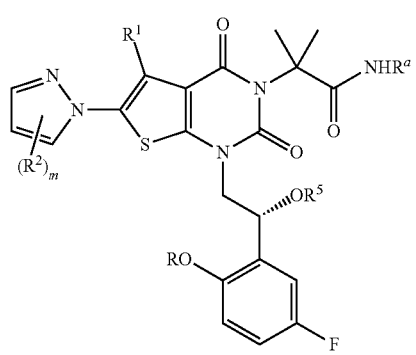

VIII-e
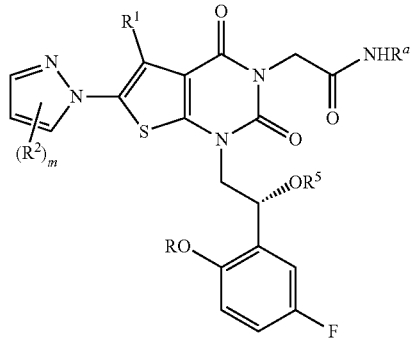

VIII-f
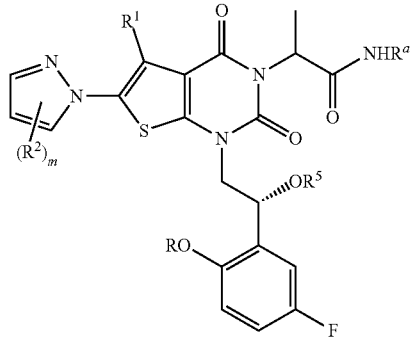

or a pharmaceutically acceptable salt or agriculturally acceptable salt thereof, wherein each of R, $R^a$, $R^1$, $R^2$, $R^5$, and m is as defined above and described in embodiments herein, both singly and in combination.

In certain embodiments, the present invention provides a compound of formula VIII-c-i, or VIII-c-ii:

VIII-c-i
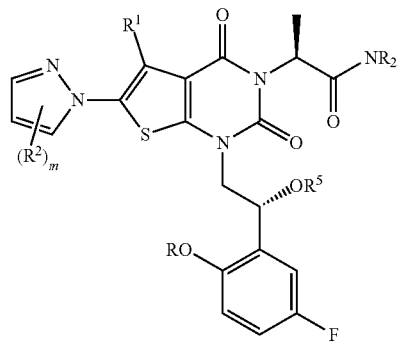

VIII-c-ii
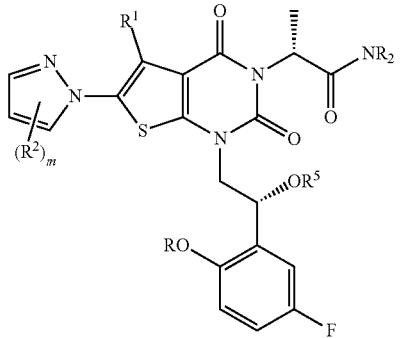

or a pharmaceutically acceptable salt or agriculturally acceptable salt thereof, wherein each of R, $R^1$, $R^2$, $R^5$, and m is as defined above and described in embodiments herein, both singly and in combination.

In certain embodiments, the present invention provides a compound of formula VIII-c-i, VIII-c-ii, VIII-f-i, or VIII-f-ii:

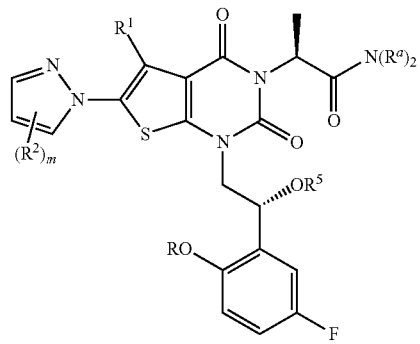

VIII-c-i

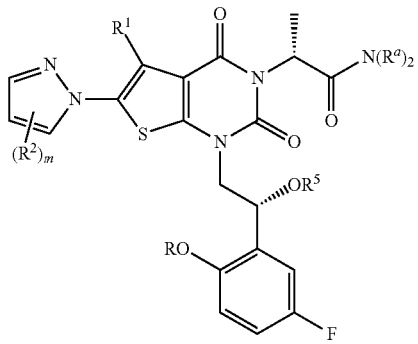

VIII-c-ii

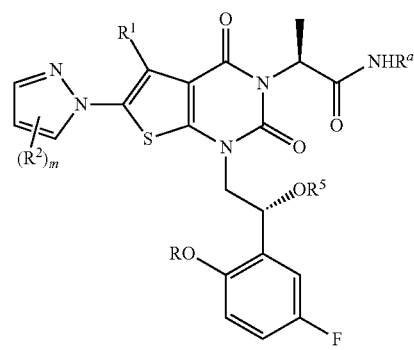

VIII-f-i

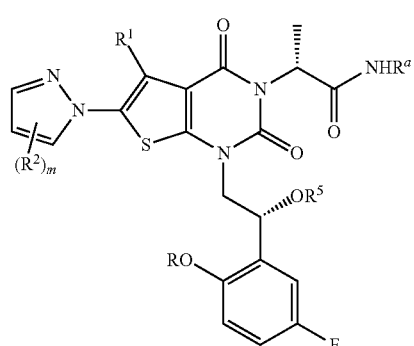

VIII-f-ii or a pharmaceutically acceptable salt or agriculturally acceptable salt thereof, wherein each of R, $R^a$, $R^1$, $R^2$, $R^5$, and m is as defined above and described in embodiments herein, both singly and in combination.

In some embodiments, the present invention provides a compound of formula IX-a, IX-b, or IX-c:

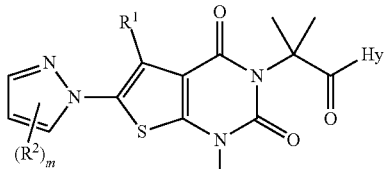

IX-a

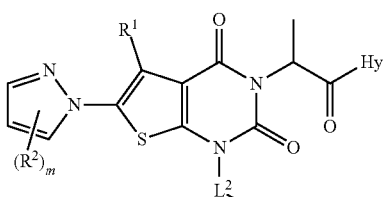

IX-b

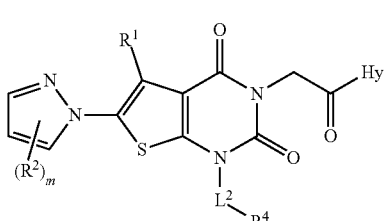

IX-c or a pharmaceutically acceptable salt or agriculturally acceptable salt thereof, wherein each of R, $R^1$, $R^2$, $R^4$, Hy, m, and $L^2$ is as defined above and described in embodiments herein, both singly and in combination.

In some embodiments, the present invention provides a compound of formula IX-b-i, or IX-b-ii:

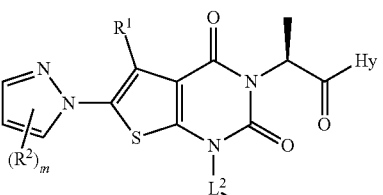

IX-b-i

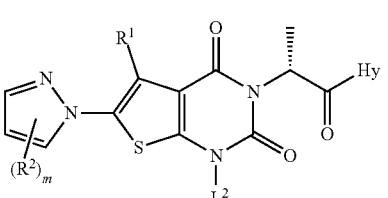

IX-b-ii or a pharmaceutically acceptable salt or agriculturally acceptable salt thereof, wherein each of R, $R^1$, $R^2$, $R^4$, m, and $L^2$ is as defined above and described in embodiments herein, both singly and in combination.

In some embodiments, the present invention provides a compound of formula X-a, X-b, X-c, X-d, X-e, or X-f:

X-a
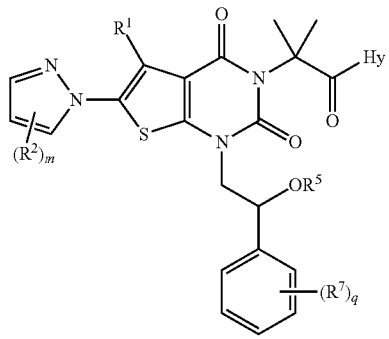
X-b
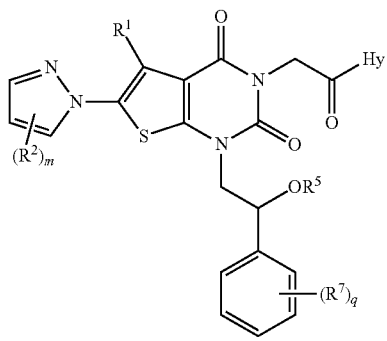
X-c
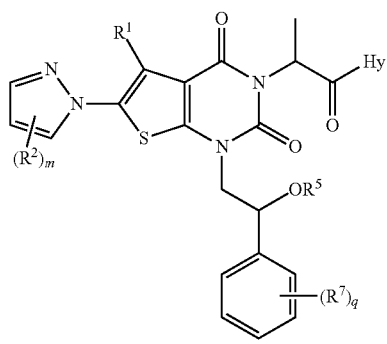
X-d
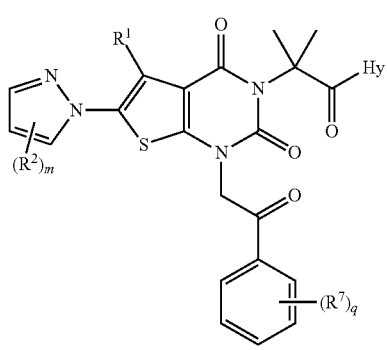
X-e
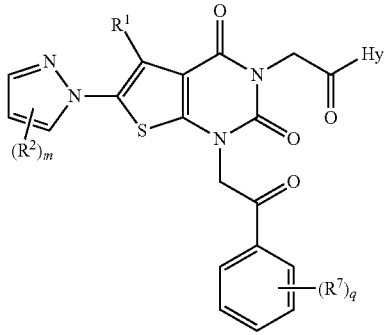
X-f
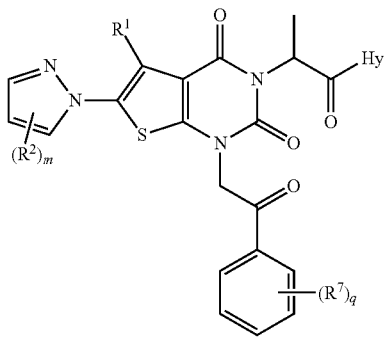
or a pharmaceutically acceptable salt or agriculturally acceptable salt thereof, wherein each of $R^1$, $R^2$, $R^1$, $R^6$, $R^7$, $R^8$, Hy, m, and q is as defined above and described in embodiments herein, both singly and in combination.
In some embodiments, the present invention provides a compound of formula X-c-i, or X-c-ii:
X-c-i
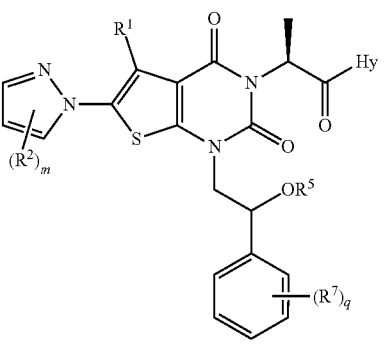
X-c-ii
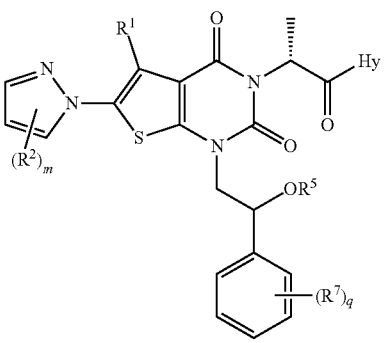

or a pharmaceutically acceptable salt or agriculturally acceptable salt thereof, wherein each of $R^1$, $R^2$, $R^5$, $R^7$, Hy, m, and q is as defined above and described in embodiments herein, both singly and in combination.

In certain embodiments, the present invention provides a compound of formula XI-a, XI-b, or XI-c:

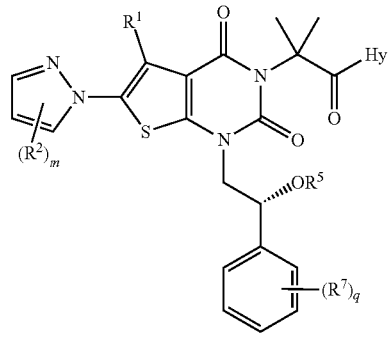

XI-a

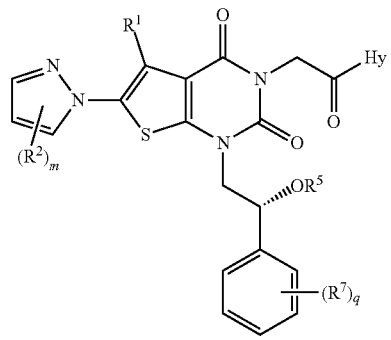

XI-b

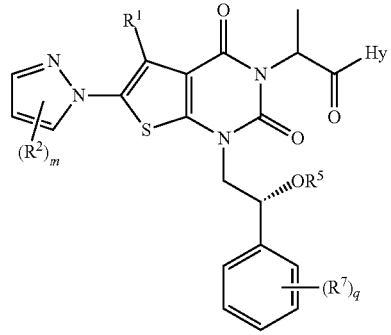

XI-c or a pharmaceutically acceptable salt or agriculturally acceptable salt thereof, wherein each of $R^1$, $R^2$, $R^5$, $R^7$, Hy, m, and q is as defined above and described in embodiments herein, both singly and in combination.

In certain embodiments, the present invention provides a compound of formula XI-c-i, or XI-c-ii:

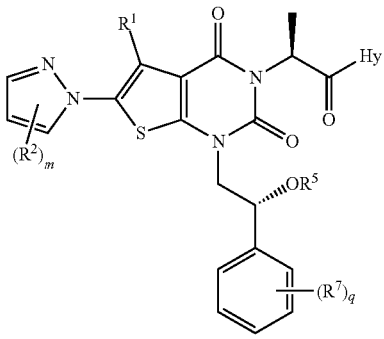

XI-c-i

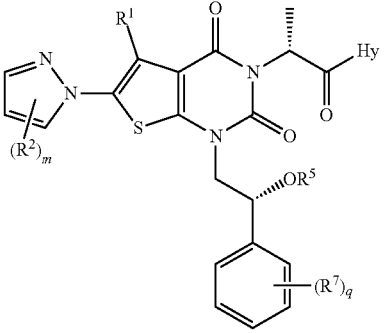

XI-c-ii or a pharmaceutically acceptable salt or agriculturally acceptable salt thereof, wherein each of $R^1$, $R^2$, $R^5$, $R^7$, Hy, m, and q is as defined above and described in embodiments herein, both singly and in combination.

In certain embodiments, the present invention provides a compound of formula XII-a, XII-b, or XII-c:

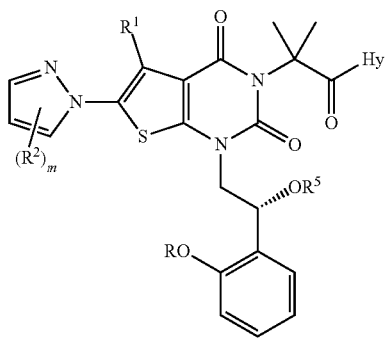

XII-a

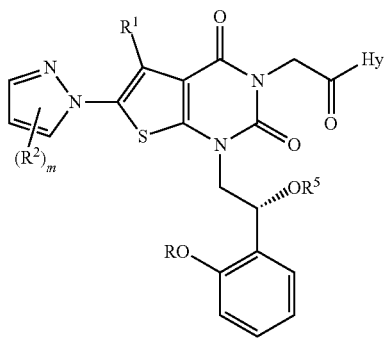

XII-b

XII-c

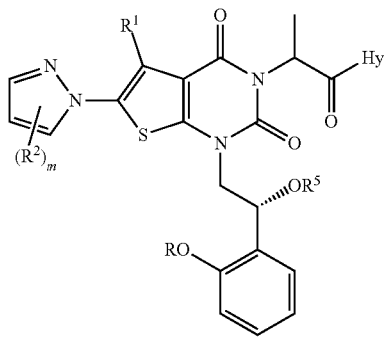

or a pharmaceutically acceptable salt or agriculturally acceptable salt thereof, wherein each of $R^1$, $R^2$, $R^5$, $R^6$, $R^8$, m, p, r, and R is as defined above and described in embodiments herein, both singly and in combination.

In certain embodiments, the present invention provides a compound of formula XII-c-i, or XII-c-ii:

XII-c-i

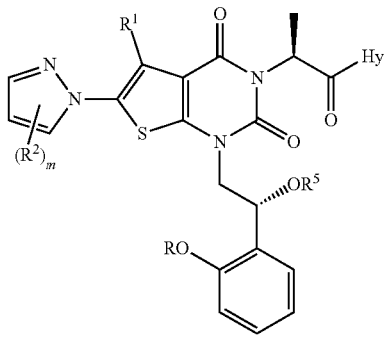

XII-c-ii

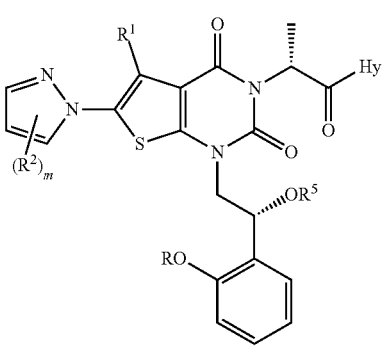

or a pharmaceutically acceptable salt or agriculturally acceptable salt thereof, wherein each of R, $R^1$, $R^2$, $R^5$, Hy, and m is as defined above and described in embodiments herein, both singly and in combination.

In certain embodiments, the present invention provides a compound of formula XIII-a, XII-b, and XIII-c:

XIII-a

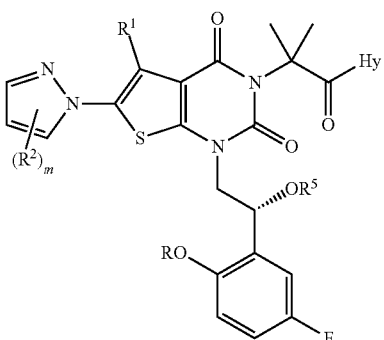

XIII-b

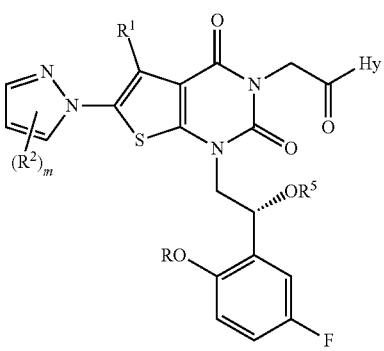

XIII-c

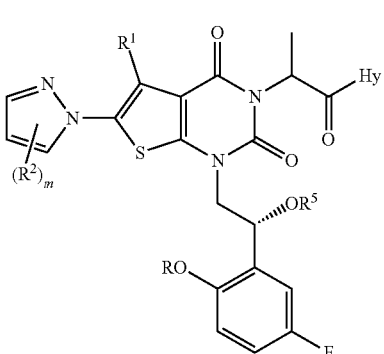

or a pharmaceutically acceptable salt or agriculturally acceptable salt thereof, wherein each of R, $R^1$, $R^2$, $R^5$, $R^6$, $R^8$, Hy, and m is as defined above and described in embodiments herein, both singly and in combination.

In certain embodiments, the present invention provides a compound of formula XIII-c-i, or XIII-c-ii:

XIII-c-i

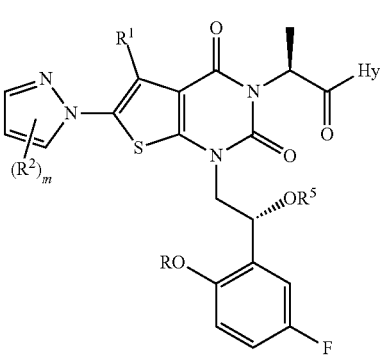

-continued

XIII-c-ii

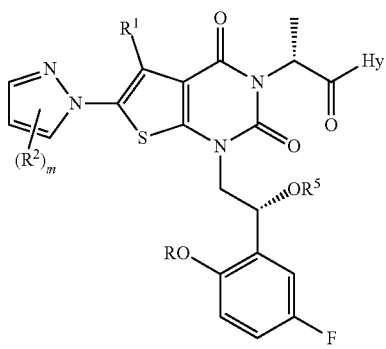

or a pharmaceutically acceptable salt or agriculturally acceptable salt thereof, wherein each of R, R¹, R², R⁵, Hy, and m is as defined above and described in embodiments herein, both singly and in combination.

Exemplary compounds of formula I are set forth in Table 1, below:

TABLE 1

Exemplary Compounds of Formula I

I-1
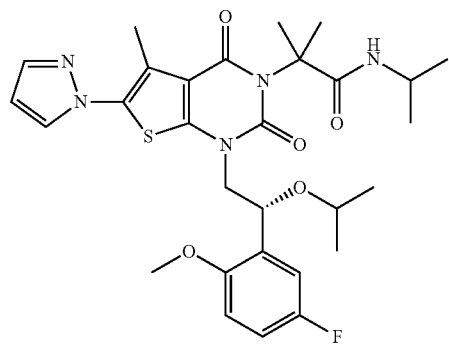 [SMILES: COc1ccc(F)cc1[C@H](Cn1c(=O)n(C(C)(C)C(=O)NC(C)C)c(=O)c2c(C)c(-n3cccn3)sc21)OC(C)C]

I-2
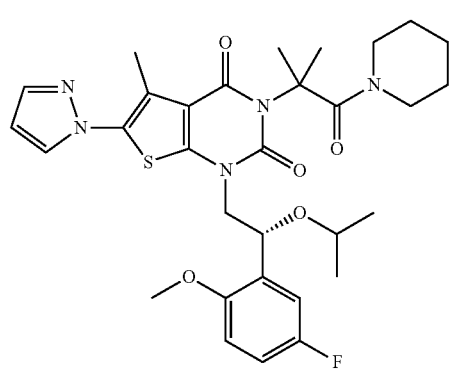 [SMILES: COc1ccc(F)cc1[C@H](Cn1c(=O)n(C(C)(C)C(=O)N2CCCCC2)c(=O)c2c(C)c(-n3cccn3)sc21)OC(C)C]

TABLE 1-continued

Exemplary Compounds of Formula I

I-3
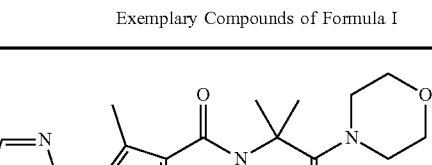
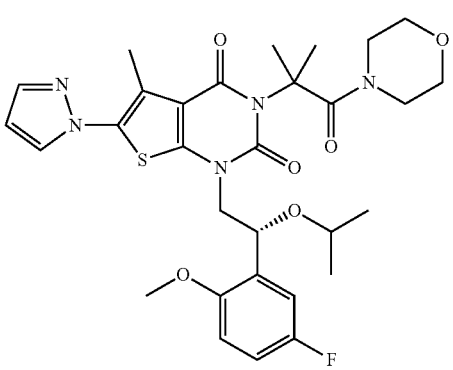 [SMILES: COc1ccc(F)cc1[C@H](Cn1c(=O)n(C(C)(C)C(=O)N2CCOCC2)c(=O)c2c(C)c(-n3cccn3)sc21)OC(C)C]

I-4
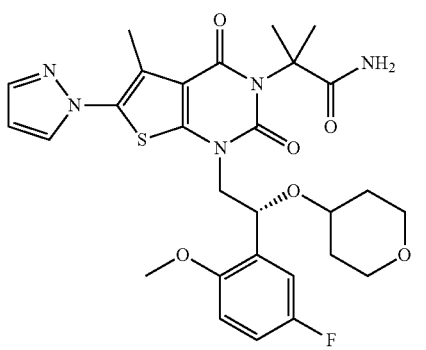 [SMILES: COc1ccc(F)cc1[C@H](Cn1c(=O)n(C(C)(C)C(N)=O)c(=O)c2c(C)c(-n3cccn3)sc21)OC1CCOCC1]

I-5
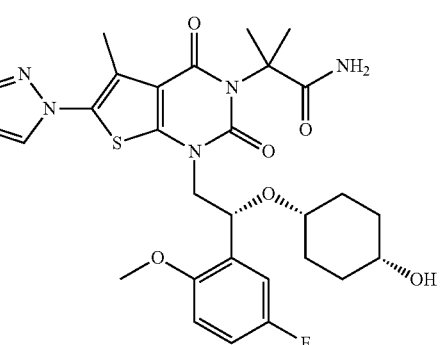
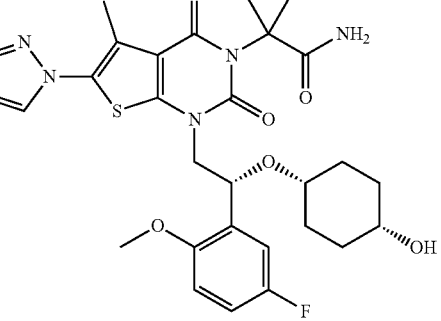

I-6
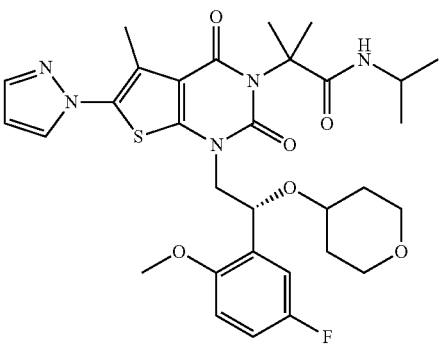 [SMILES: COc1ccc(F)cc1[C@H](Cn1c(=O)n(C(C)(C)C(=O)NC(C)C)c(=O)c2c(C)c(-n3cccn3)sc21)OC1CCOCC1]

TABLE 1-continued
Exemplary Compounds of Formula I
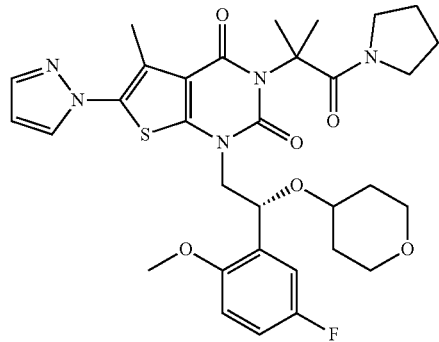 [SMILES: COc1ccc(F)cc1[C@H](Cn1c(=O)n(C(C)(C)C(=O)N2CCCC2)c(=O)c2c(C)c(-n3cccn3)sc21)OC1CCOCC1] I-7
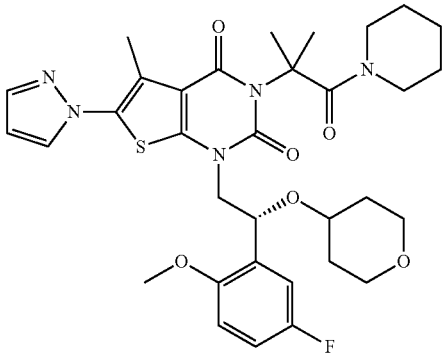 [SMILES: COc1ccc(F)cc1[C@H](Cn1c(=O)n(C(C)(C)C(=O)N2CCCCC2)c(=O)c2c(C)c(-n3cccn3)sc21)OC1CCOCC1] I-8
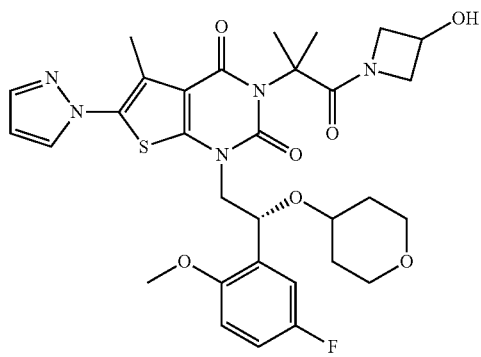 [SMILES: COc1ccc(F)cc1[C@H](Cn1c(=O)n(C(C)(C)C(=O)N2CC(O)C2)c(=O)c2c(C)c(-n3cccn3)sc21)OC1CCOCC1] I-9
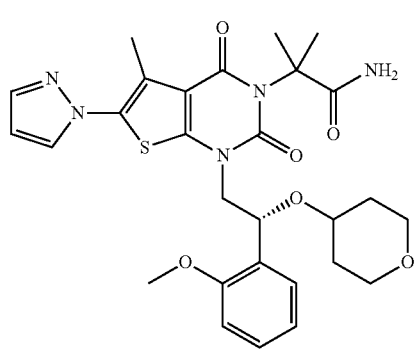 [SMILES: COc1ccccc1[C@H](Cn1c(=O)n(C(C)(C)C(N)=O)c(=O)c2c(C)c(-n3cccn3)sc21)OC1CCOCC1] I-10
TABLE 1-continued
Exemplary Compounds of Formula I
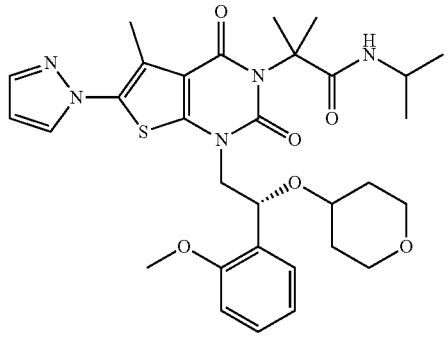 [SMILES: COc1ccccc1[C@H](Cn1c(=O)n(C(C)(C)C(=O)NC(C)C)c(=O)c2c(C)c(-n3cccn3)sc21)OC1CCOCC1] I-11
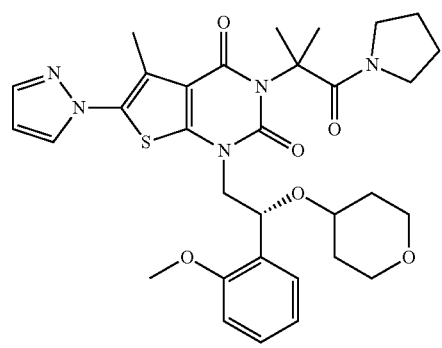 [SMILES: COc1ccccc1[C@H](Cn1c(=O)n(C(C)(C)C(=O)N2CCCC2)c(=O)c2c(C)c(-n3cccn3)sc21)OC1CCOCC1] I-12
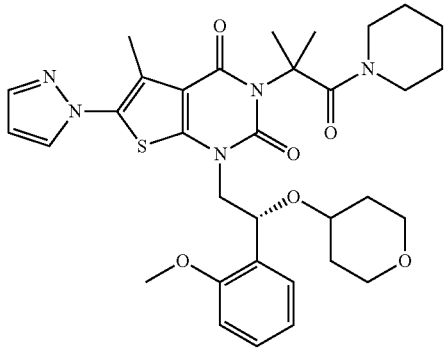 [SMILES: COc1ccccc1[C@H](Cn1c(=O)n(C(C)(C)C(=O)N2CCCCC2)c(=O)c2c(C)c(-n3cccn3)sc21)OC1CCOCC1] I-13
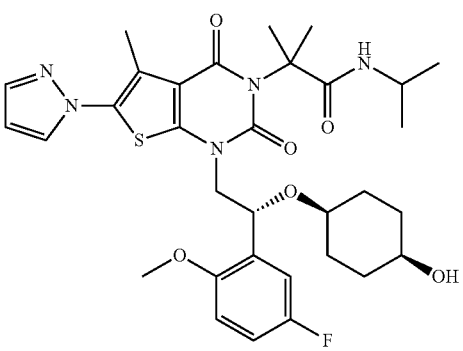 [SMILES: COc1ccc(F)cc1[C@H](Cn1c(=O)n(C(C)(C)C(=O)NC(C)C)c(=O)c2c(C)c(-n3cccn3)sc21)O[C@H]1CC[C@@H](O)CC1] I-14

TABLE 1-continued
Exemplary Compounds of Formula I
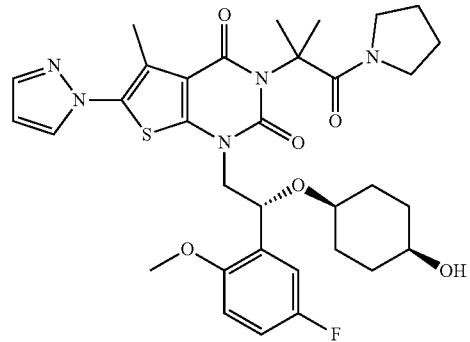 [SMILES: COc1ccc(F)cc1[C@H](Cn1c(=O)n(C(C)(C)C(=O)N2CCCC2)c(=O)c2c(C)c(-n3cccn3)sc21)O[C@H]1CC[C@@H](O)CC1]
I-15
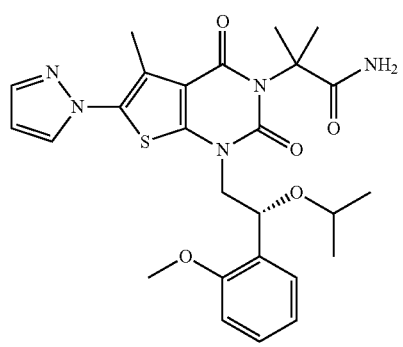 [SMILES: COc1ccccc1[C@H](Cn1c(=O)n(C(C)(C)C(N)=O)c(=O)c2c(C)c(-n3cccn3)sc21)OC(C)C]
I-16
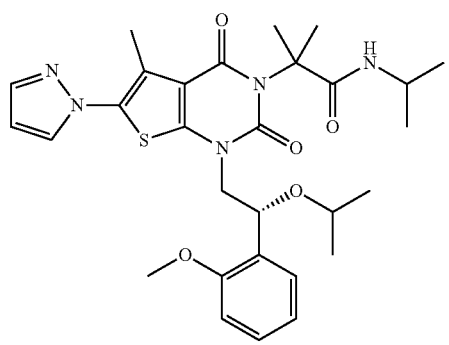 [SMILES: COc1ccccc1[C@H](Cn1c(=O)n(C(C)(C)C(=O)NC(C)C)c(=O)c2c(C)c(-n3cccn3)sc21)OC(C)C]
I-17
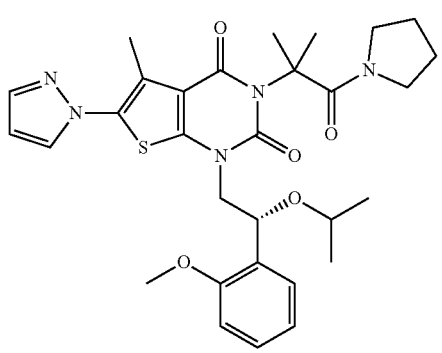 [SMILES: COc1ccccc1[C@H](Cn1c(=O)n(C(C)(C)C(=O)N2CCCC2)c(=O)c2c(C)c(-n3cccn3)sc21)OC(C)C]
I-18
TABLE 1-continued
Exemplary Compounds of Formula I
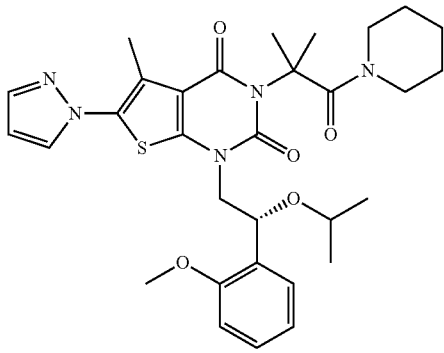 [SMILES: COc1ccccc1[C@H](Cn1c(=O)n(C(C)(C)C(=O)N2CCCCC2)c(=O)c2c(C)c(-n3cccn3)sc21)OC(C)C]
I-19
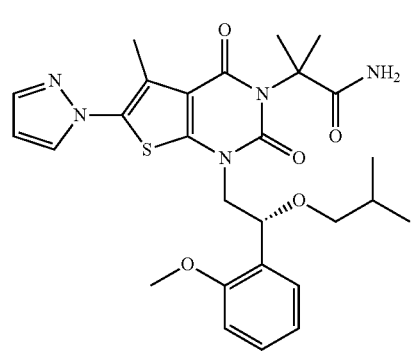 [SMILES: COc1ccccc1[C@H](Cn1c(=O)n(C(C)(C)C(N)=O)c(=O)c2c(C)c(-n3cccn3)sc21)OCC(C)C]
I-20
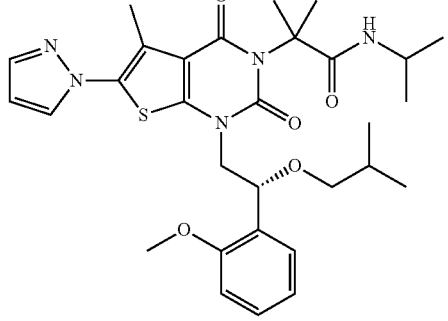
I-21
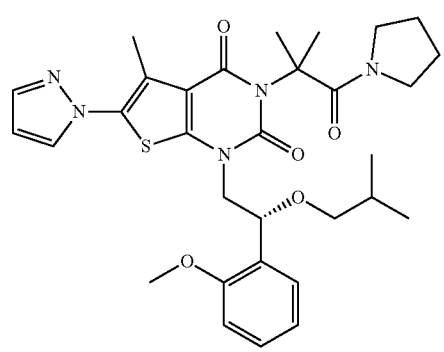 [SMILES: COc1ccccc1[C@H](Cn1c(=O)n(C(C)(C)C(=O)N2CCCC2)c(=O)c2c(C)c(-n3cccn3)sc21)OCC(C)C]
I-22

TABLE 1-continued
Exemplary Compounds of Formula I
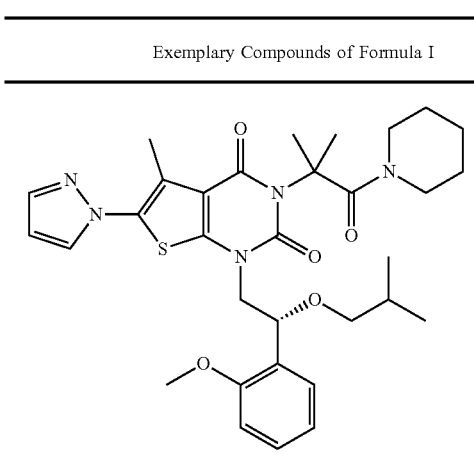
I-23
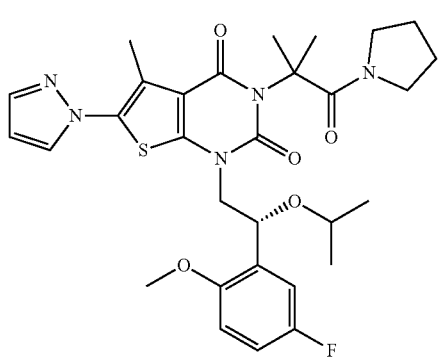 [SMILES: COc1ccc(F)cc1[C@H](Cn1c(=O)n(C(C)(C)C(=O)N2CCCC2)c(=O)c2c(C)c(-n3cccn3)sc21)OC(C)C]
I-24
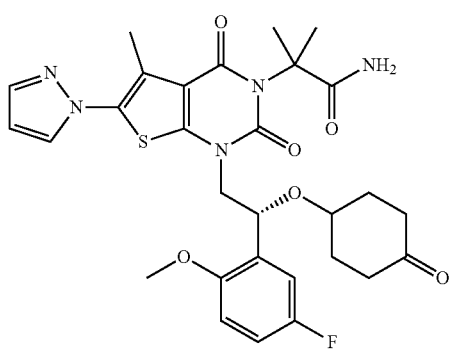 [SMILES: COc1ccc(F)cc1[C@H](Cn1c(=O)n(C(C)(C)C(N)=O)c(=O)c2c(C)c(-n3cccn3)sc21)OC1CCC(=O)CC1]
I-25
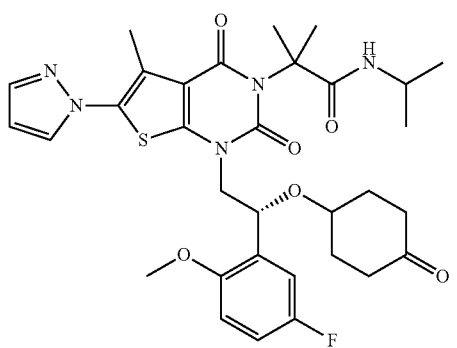 [SMILES: COc1ccc(F)cc1[C@H](Cn1c(=O)n(C(C)(C)C(=O)NC(C)C)c(=O)c2c(C)c(-n3cccn3)sc21)OC1CCC(=O)CC1]
I-26
TABLE 1-continued
Exemplary Compounds of Formula I
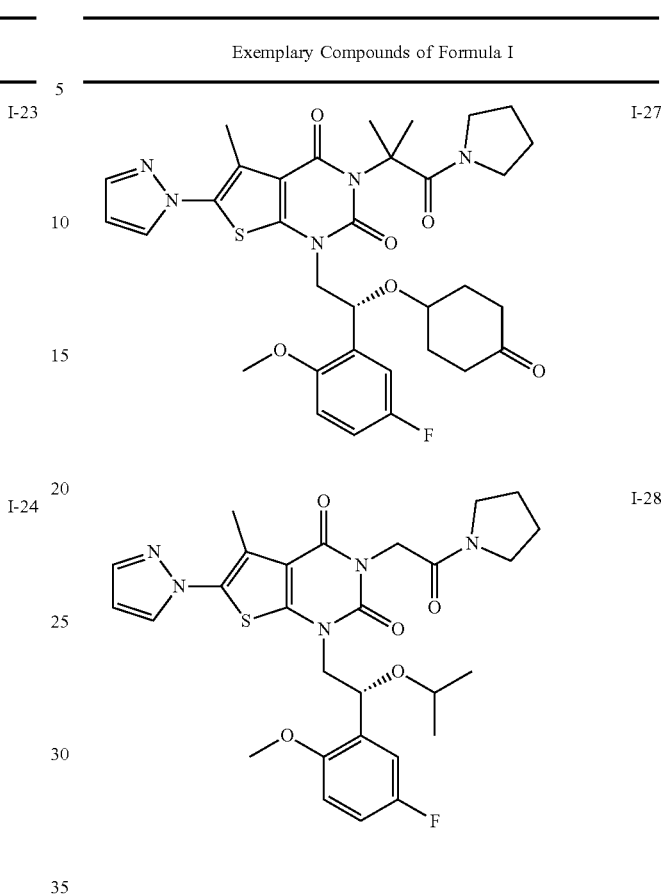
I-27
I-28
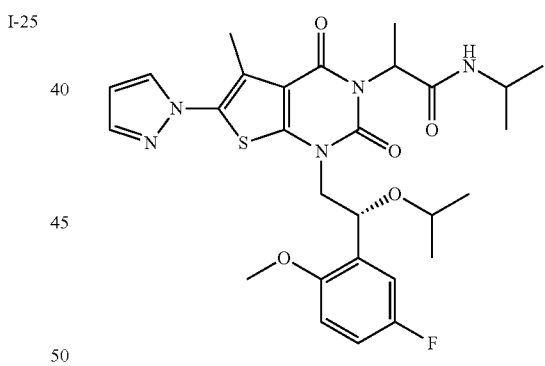
I-29
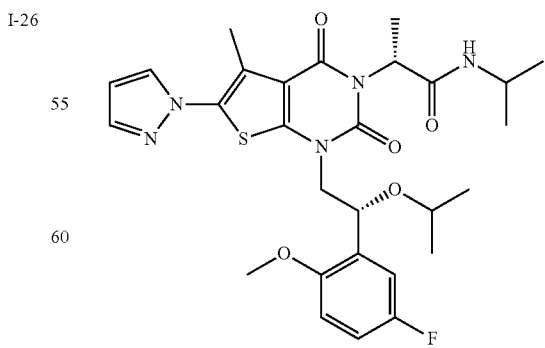
I-30

TABLE 1-continued
Exemplary Compounds of Formula I
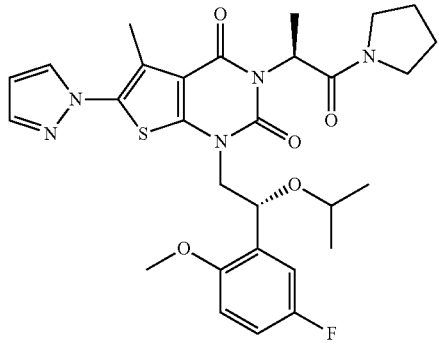 [SMILES: COc1ccc(F)cc1[C@H](Cn1c(=O)n([C@@H](C)C(=O)N2CCCC2)c(=O)c2c(C)c(-n3cccn3)sc21)OC(C)C] I-31
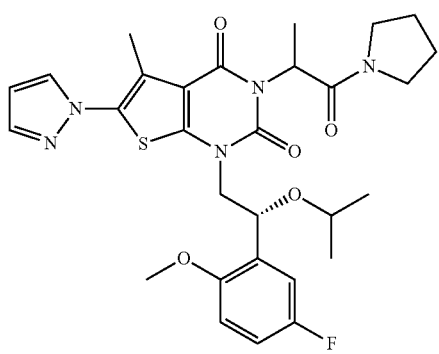 [SMILES: COc1ccc(F)cc1[C@H](Cn1c(=O)n(C(C)C(=O)N2CCCC2)c(=O)c2c(C)c(-n3cccn3)sc21)OC(C)C] I-32
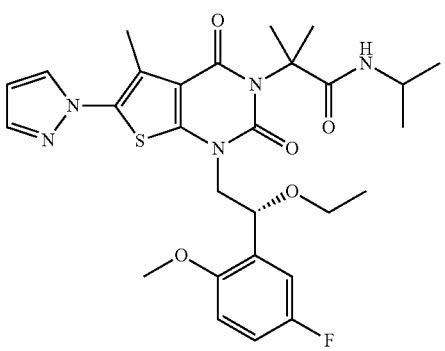 [SMILES: CCO[C@@H](Cn1c(=O)n(C(C)(C)C(=O)NC(C)C)c(=O)c2c(C)c(-n3cccn3)sc21)c1cc(F)ccc1OC] I-33
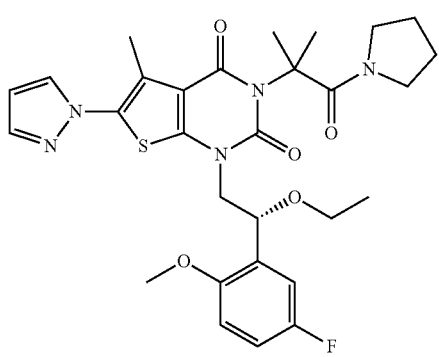 [SMILES: CCO[C@@H](Cn1c(=O)n(C(C)(C)C(=O)N2CCCC2)c(=O)c2c(C)c(-n3cccn3)sc21)c1cc(F)ccc1OC] I-34
TABLE 1-continued
Exemplary Compounds of Formula I
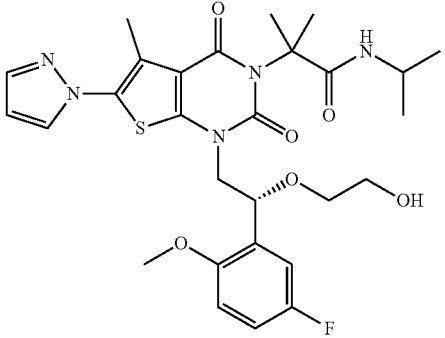 I-35
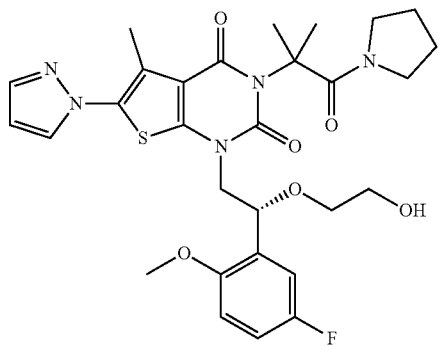 [SMILES: COc1ccc(F)cc1[C@H](Cn1c(=O)n(C(C)(C)C(=O)N2CCCC2)c(=O)c2c(C)c(-n3cccn3)sc21)OCCO] I-36
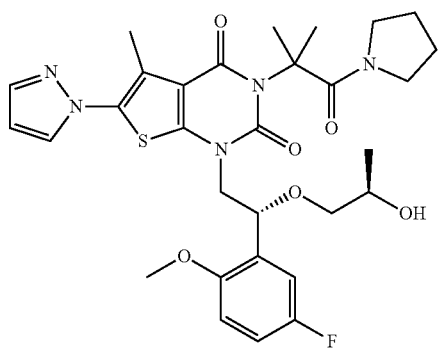 [SMILES: COc1ccc(F)cc1[C@H](Cn1c(=O)n(C(C)(C)C(=O)N2CCCC2)c(=O)c2c(C)c(-n3cccn3)sc21)OC[C@@H](C)O] I-37
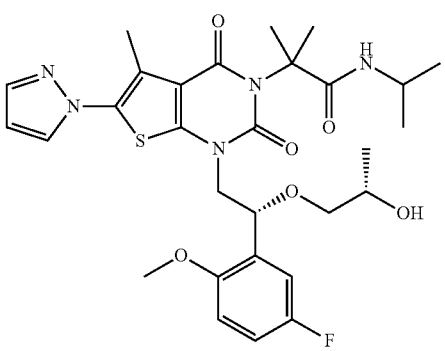 [SMILES: COc1ccc(F)cc1[C@H](Cn1c(=O)n(C(C)(C)C(=O)NC(C)C)c(=O)c2c(C)c(-n3cccn3)sc21)OC[C@H](C)O] I-38

TABLE 1-continued
Exemplary Compounds of Formula I
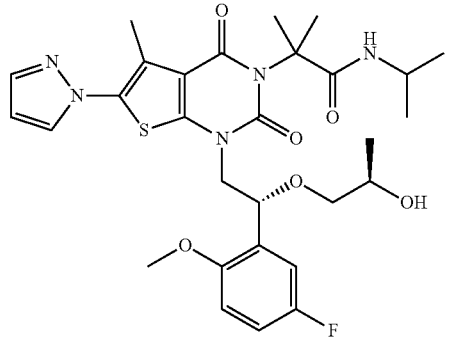 [SMILES: COc1ccc(F)cc1[C@H](Cn1c(=O)n(C(C)(C)C(=O)NC(C)C)c(=O)c2c(C)c(-n3cccn3)sc21)OC[C@@H](C)O]
I-39
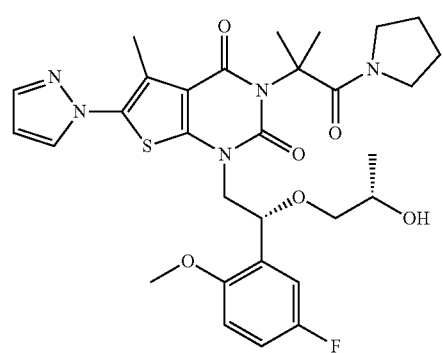 [SMILES: COc1ccc(F)cc1[C@H](Cn1c(=O)n(C(C)(C)C(=O)N2CCCC2)c(=O)c2c(C)c(-n3cccn3)sc21)OC[C@H](C)O]
I-40
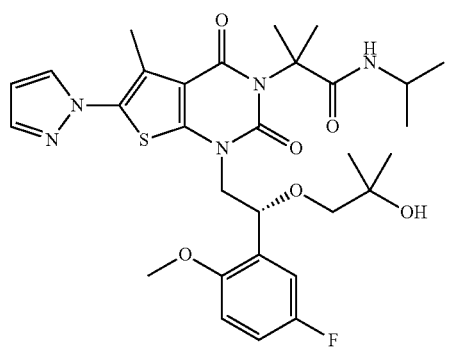 [SMILES: COc1ccc(F)cc1[C@H](Cn1c(=O)n(C(C)(C)C(=O)NC(C)C)c(=O)c2c(C)c(-n3cccn3)sc21)OCC(C)(C)O]
I-41
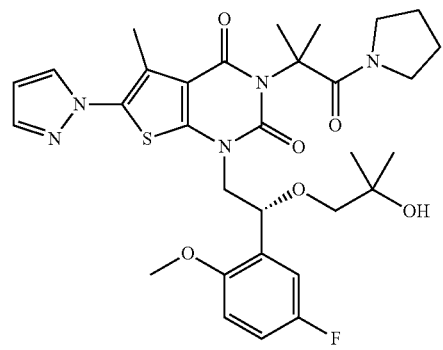 [SMILES: COc1ccc(F)cc1[C@H](Cn1c(=O)n(C(C)(C)C(=O)N2CCCC2)c(=O)c2c(C)c(-n3cccn3)sc21)OCC(C)(C)O]
I-42
TABLE 1-continued
Exemplary Compounds of Formula I
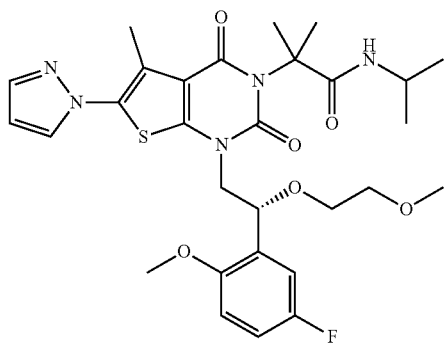 [SMILES: COCCO[C@@H](Cn1c(=O)n(C(C)(C)C(=O)NC(C)C)c(=O)c2c(C)c(-n3cccn3)sc21)c1cc(F)ccc1OC]
I-43
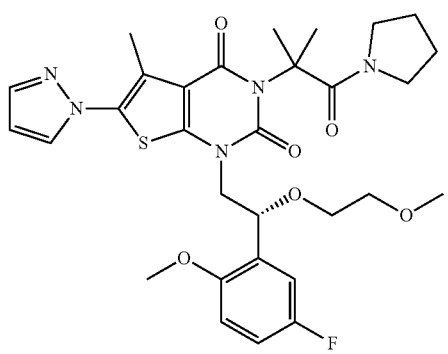 [SMILES: COCCO[C@@H](Cn1c(=O)n(C(C)(C)C(=O)N2CCCC2)c(=O)c2c(C)c(-n3cccn3)sc21)c1cc(F)ccc1OC]
I-44
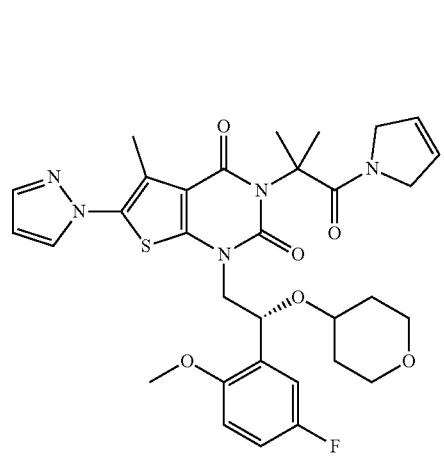 [SMILES: COc1ccc(F)cc1[C@H](Cn1c(=O)n(C(C)(C)C(=O)N2CC=CC2)c(=O)c2c(C)c(-n3cccn3)sc21)OC1CCOCC1]
I-45
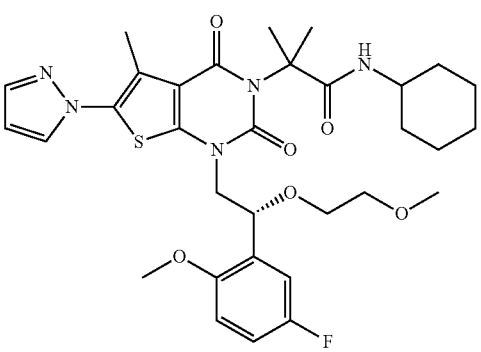 [SMILES: COCCO[C@@H](Cn1c(=O)n(C(C)(C)C(=O)NC2CCCCC2)c(=O)c2c(C)c(-n3cccn3)sc21)c1cc(F)ccc1OC]
I-46

TABLE 1-continued
Exemplary Compounds of Formula I
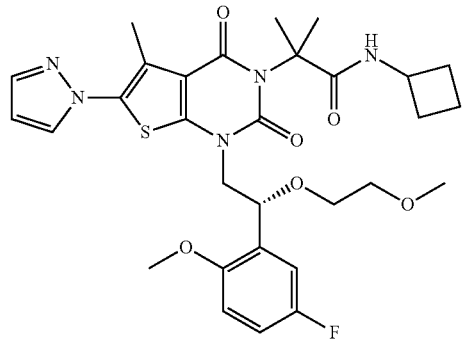 [SMILES: COCCO[C@@H](Cn1c(=O)n(C(C)(C)C(=O)NC2CCC2)c(=O)c2c(C)c(-n3cccn3)sc21)c1cc(F)ccc1OC]
I-47
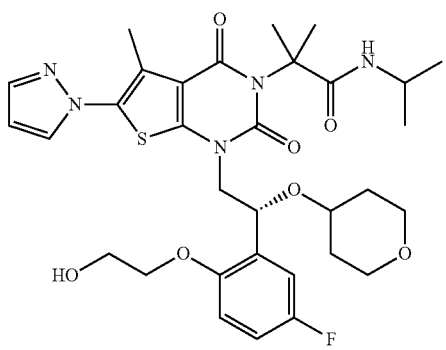 [SMILES: Cc1c(-n2cccn2)sc2c1c(=O)n(C(C)(C)C(=O)NC(C)C)c(=O)n2C[C@H](OC1CCOCC1)c1cc(F)ccc1OCCO]
I-48
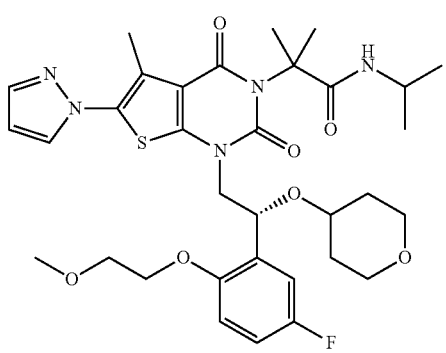 [SMILES: COCCOc1ccc(F)cc1[C@H](Cn1c(=O)n(C(C)(C)C(=O)NC(C)C)c(=O)c2c(C)c(-n3cccn3)sc21)OC1CCOCC1]
I-49
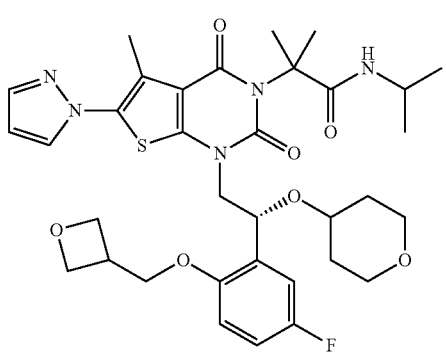 [SMILES: Cc1c(-n2cccn2)sc2c1c(=O)n(C(C)(C)C(=O)NC(C)C)c(=O)n2C[C@H](OC1CCOCC1)c1cc(F)ccc1OCC1COC1]
I-50
TABLE 1-continued
Exemplary Compounds of Formula I
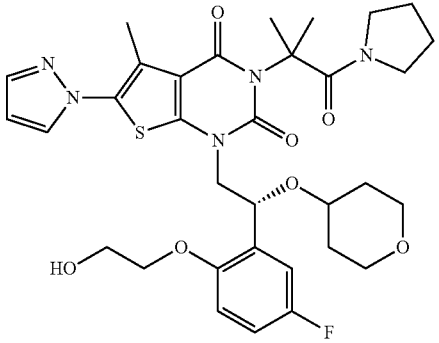 [SMILES: Cc1c(-n2cccn2)sc2c1c(=O)n(C(C)(C)C(=O)N1CCCC1)c(=O)n2C[C@H](OC1CCOCC1)c1cc(F)ccc1OCCO]
I-51
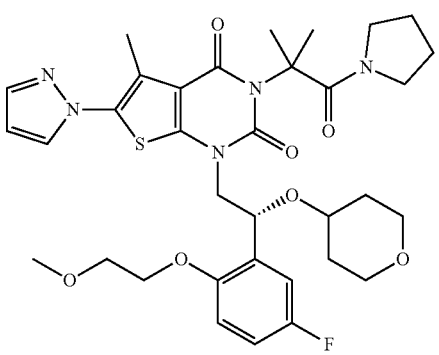 [SMILES: COCCOc1ccc(F)cc1[C@H](Cn1c(=O)n(C(C)(C)C(=O)N2CCCC2)c(=O)c2c(C)c(-n3cccn3)sc21)OC1CCOCC1]
I-52
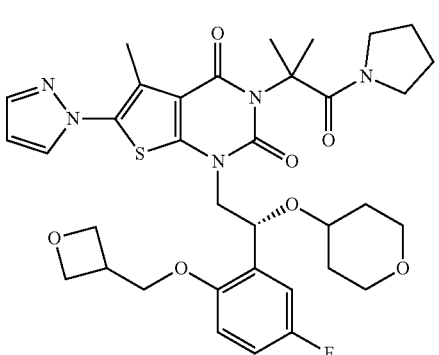
I-53
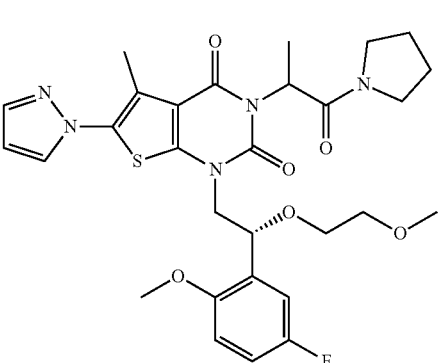
I-54

TABLE 1-continued
Exemplary Compounds of Formula I
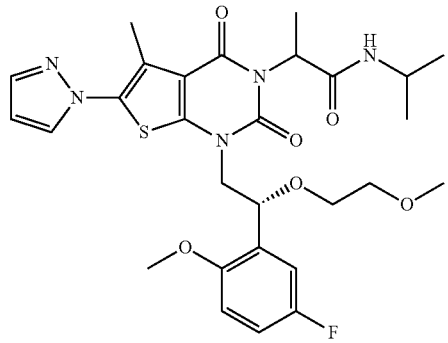 [SMILES: COCCO[C@@H](Cn1c(=O)n(C(C)C(=O)NC(C)C)c(=O)c2c(C)c(-n3cccn3)sc21)c1cc(F)ccc1OC]
I-55
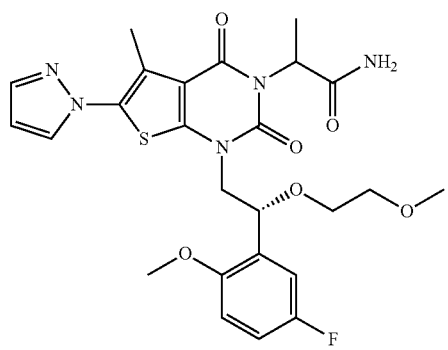 [SMILES: COCCO[C@@H](Cn1c(=O)n(C(C)C(N)=O)c(=O)c2c(C)c(-n3cccn3)sc21)c1cc(F)ccc1OC]
I-56
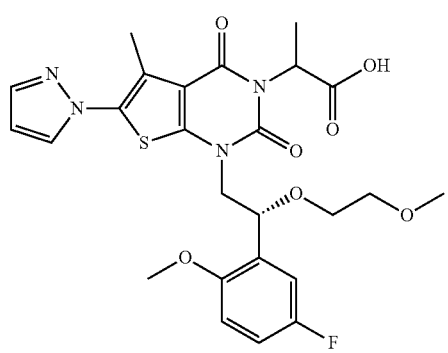 [SMILES: COCCO[C@@H](Cn1c(=O)n(C(C)C(=O)O)c(=O)c2c(C)c(-n3cccn3)sc21)c1cc(F)ccc1OC]
I-57
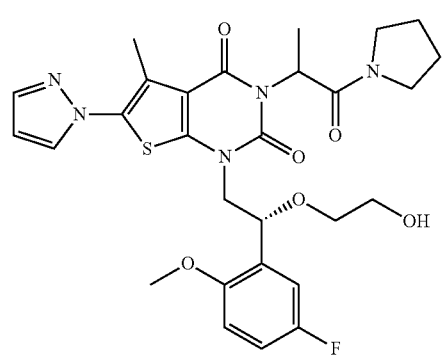 [SMILES: COc1ccc(F)cc1[C@H](Cn1c(=O)n(C(C)C(=O)N2CCCC2)c(=O)c2c(C)c(-n3cccn3)sc21)OCCO]
I-58
TABLE 1-continued
Exemplary Compounds of Formula I
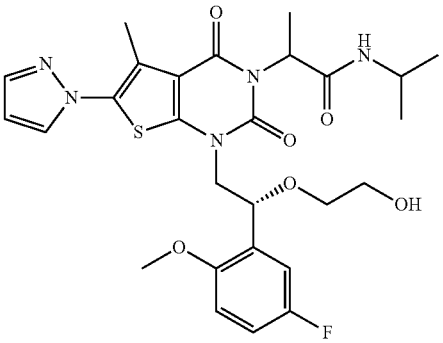 [SMILES: COc1ccc(F)cc1[C@H](Cn1c(=O)n(C(C)C(=O)NC(C)C)c(=O)c2c(C)c(-n3cccn3)sc21)OCCO]
I-59
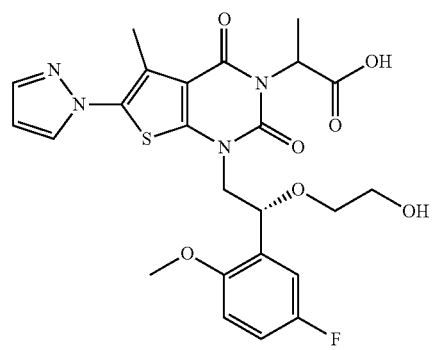 [SMILES: COc1ccc(F)cc1[C@H](Cn1c(=O)n(C(C)C(=O)O)c(=O)c2c(C)c(-n3cccn3)sc21)OCCO]
I-60
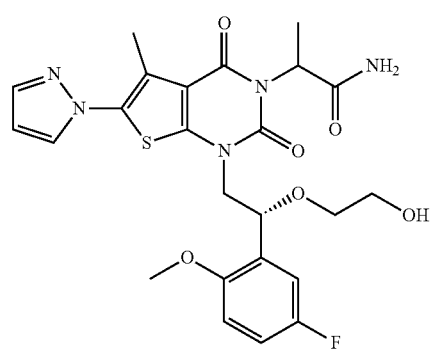 [SMILES: COc1ccc(F)cc1[C@H](Cn1c(=O)n(C(C)C(N)=O)c(=O)c2c(C)c(-n3cccn3)sc21)OCCO]
I-61
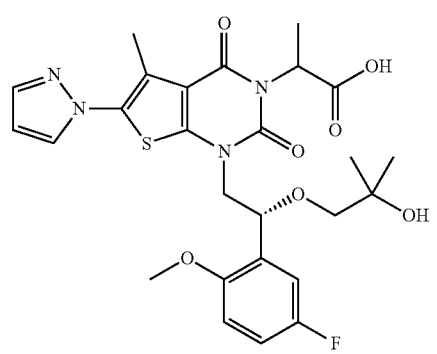 [SMILES: COc1ccc(F)cc1[C@H](Cn1c(=O)n(C(C)C(=O)O)c(=O)c2c(C)c(-n3cccn3)sc21)OCC(C)(C)O]
I-62

TABLE 1-continued
Exemplary Compounds of Formula I
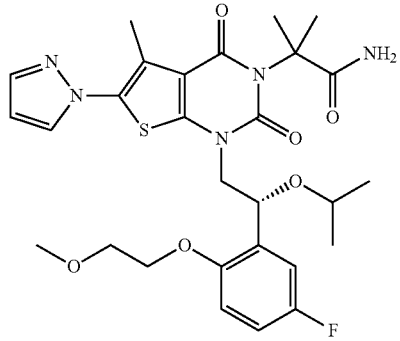 [SMILES: COCCOc1ccc(F)cc1[C@H](Cn1c(=O)n(C(C)(C)C(N)=O)c(=O)c2c(C)c(-n3cccn3)sc21)OC(C)C] I-63
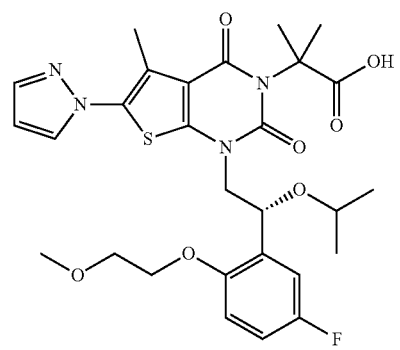 [SMILES: COCCOc1ccc(F)cc1[C@H](Cn1c(=O)n(C(C)(C)C(=O)O)c(=O)c2c(C)c(-n3cccn3)sc21)OC(C)C] I-64
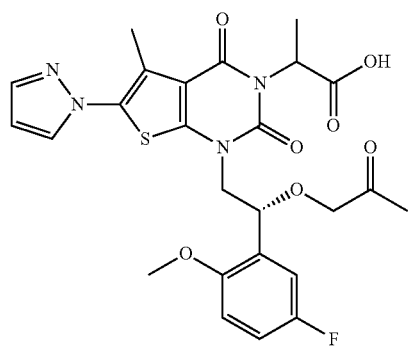 [SMILES: COc1ccc(F)cc1[C@H](Cn1c(=O)n(C(C)C(=O)O)c(=O)c2c(C)c(-n3cccn3)sc21)OCC(C)=O] I-65
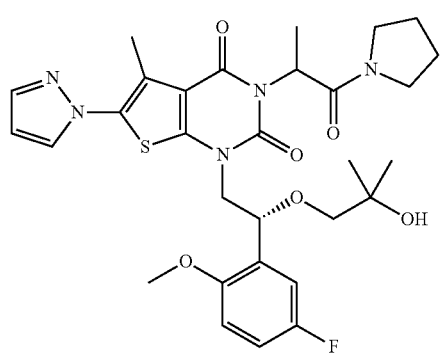 [SMILES: COc1ccc(F)cc1[C@H](Cn1c(=O)n(C(C)C(=O)N2CCCC2)c(=O)c2c(C)c(-n3cccn3)sc21)OCC(C)(C)O] I-66
TABLE 1-continued
Exemplary Compounds of Formula I
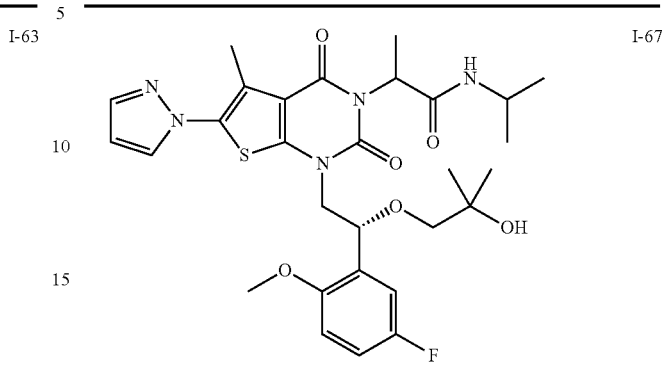 I-67
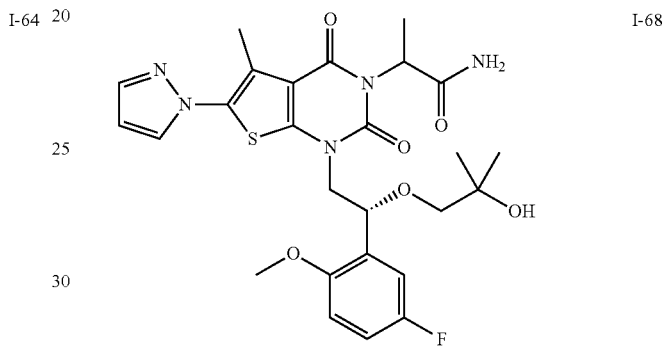 I-68
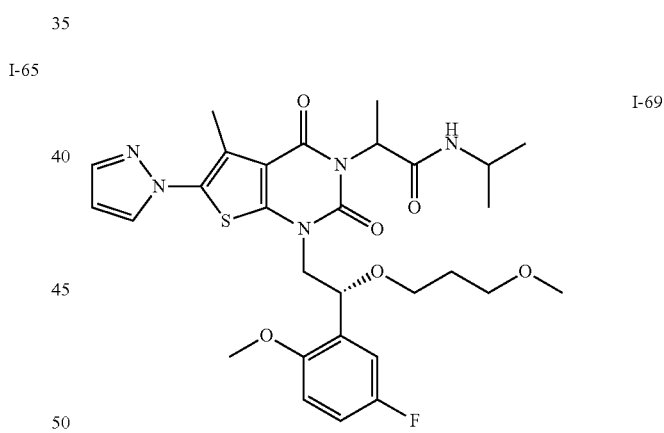 I-69
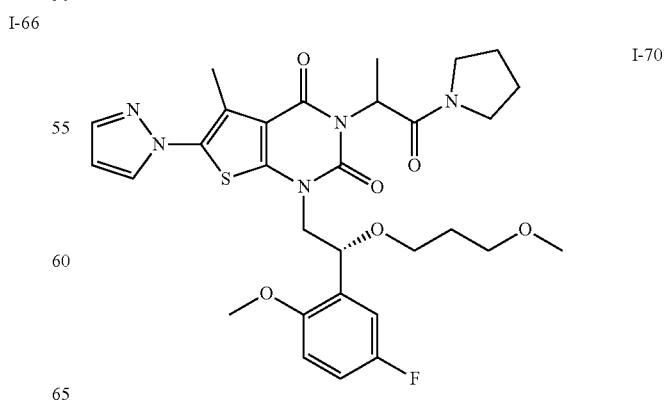 I-70

TABLE 1-continued
Exemplary Compounds of Formula I
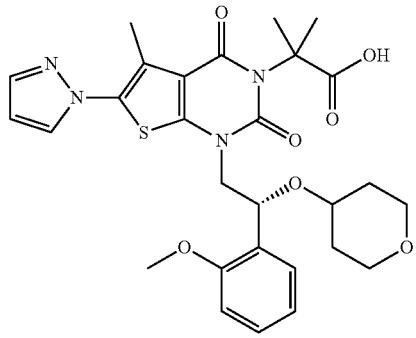 [SMILES: COc1ccccc1[C@H](Cn1c(=O)n(C(C)(C)C(=O)O)c(=O)c2c(C)c(-n3cccn3)sc21)OC1CCOCC1]
I-71
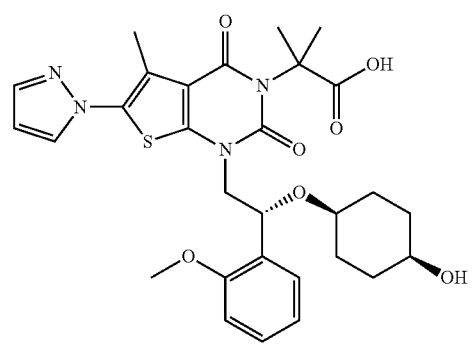 [SMILES: COc1ccccc1[C@H](Cn1c(=O)n(C(C)(C)C(=O)O)c(=O)c2c(C)c(-n3cccn3)sc21)O[C@H]1CC[C@@H](O)CC1]
I-72
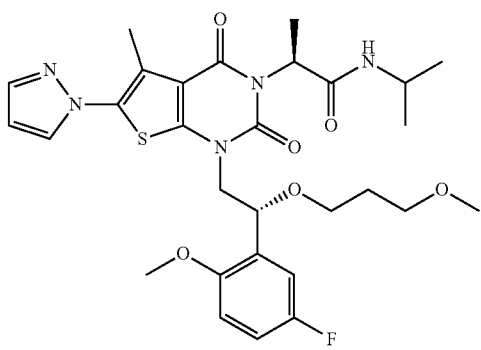 [SMILES: COCCCO[C@@H](Cn1c(=O)n([C@@H](C)C(=O)NC(C)C)c(=O)c2c(C)c(-n3cccn3)sc21)c1cc(F)ccc1OC]
I-73
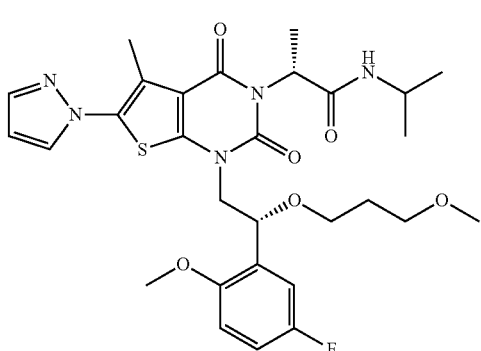
I-74
TABLE 1-continued
Exemplary Compounds of Formula I
I-75
I-76
I-77
I-78

TABLE 1-continued
Exemplary Compounds of Formula I
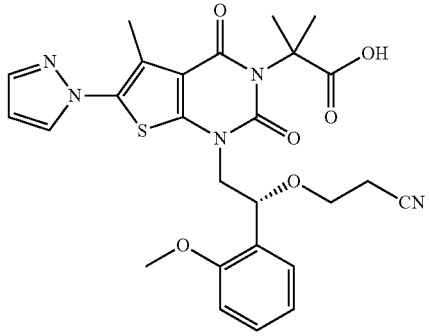 [SMILES: COc1ccccc1[C@H](Cn1c(=O)n(C(C)(C)C(=O)O)c(=O)c2c(C)c(-n3cccn3)sc21)OCCC#N] I-79
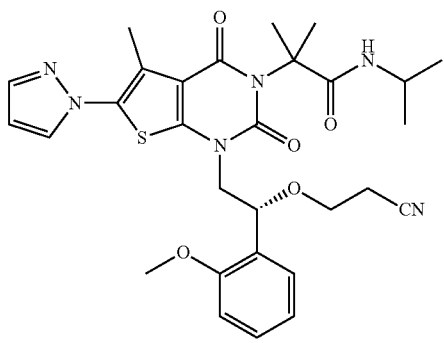 [SMILES: COc1ccccc1[C@H](Cn1c(=O)n(C(C)(C)C(=O)NC(C)C)c(=O)c2c(C)c(-n3cccn3)sc21)OCCC#N] I-80
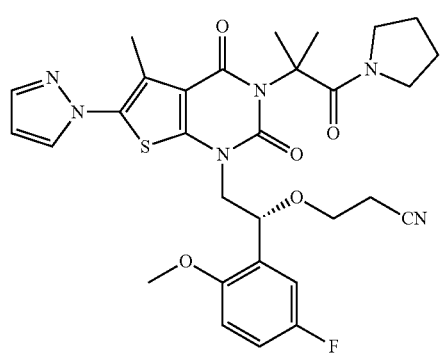 [SMILES: COc1ccc(F)cc1[C@H](Cn1c(=O)n(C(C)(C)C(=O)N2CCCC2)c(=O)c2c(C)c(-n3cccn3)sc21)OCCC#N] I-81
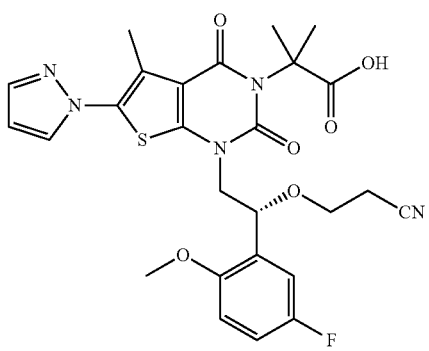 [SMILES: COc1ccc(F)cc1[C@H](Cn1c(=O)n(C(C)(C)C(=O)O)c(=O)c2c(C)c(-n3cccn3)sc21)OCCC#N] I-82
TABLE 1-continued
Exemplary Compounds of Formula I
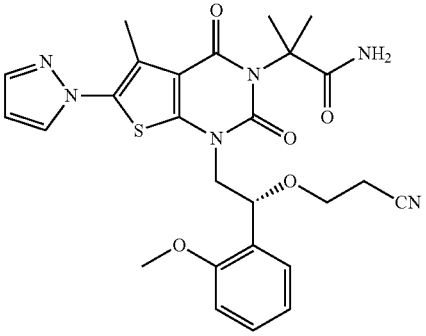 [SMILES: COc1ccccc1[C@H](Cn1c(=O)n(C(C)(C)C(N)=O)c(=O)c2c(C)c(-n3cccn3)sc21)OCCC#N] I-83
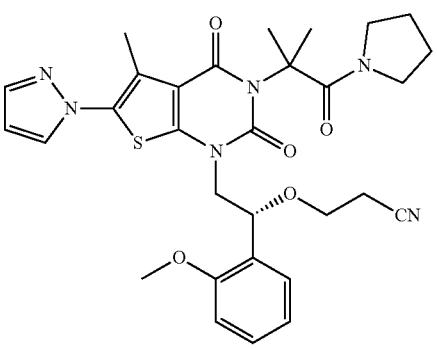 [SMILES: COc1ccccc1[C@H](Cn1c(=O)n(C(C)(C)C(=O)N2CCCC2)c(=O)c2c(C)c(-n3cccn3)sc21)OCCC#N] I-84
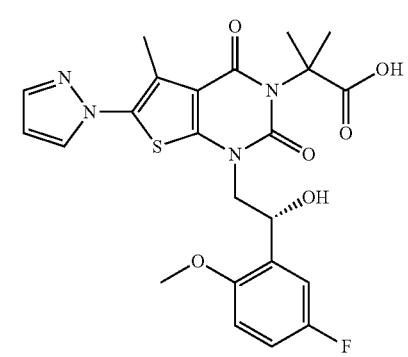 [SMILES: COc1ccc(F)cc1[C@@H](O)Cn1c(=O)n(C(C)(C)C(=O)O)c(=O)c2c(C)c(-n3cccn3)sc21] I-85
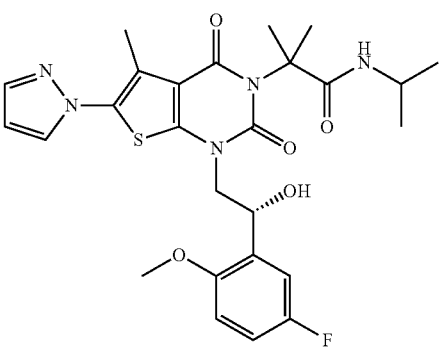 [SMILES: COc1ccc(F)cc1[C@@H](O)Cn1c(=O)n(C(C)(C)C(=O)NC(C)C)c(=O)c2c(C)c(-n3cccn3)sc21] I-86

TABLE 1-continued
Exemplary Compounds of Formula I
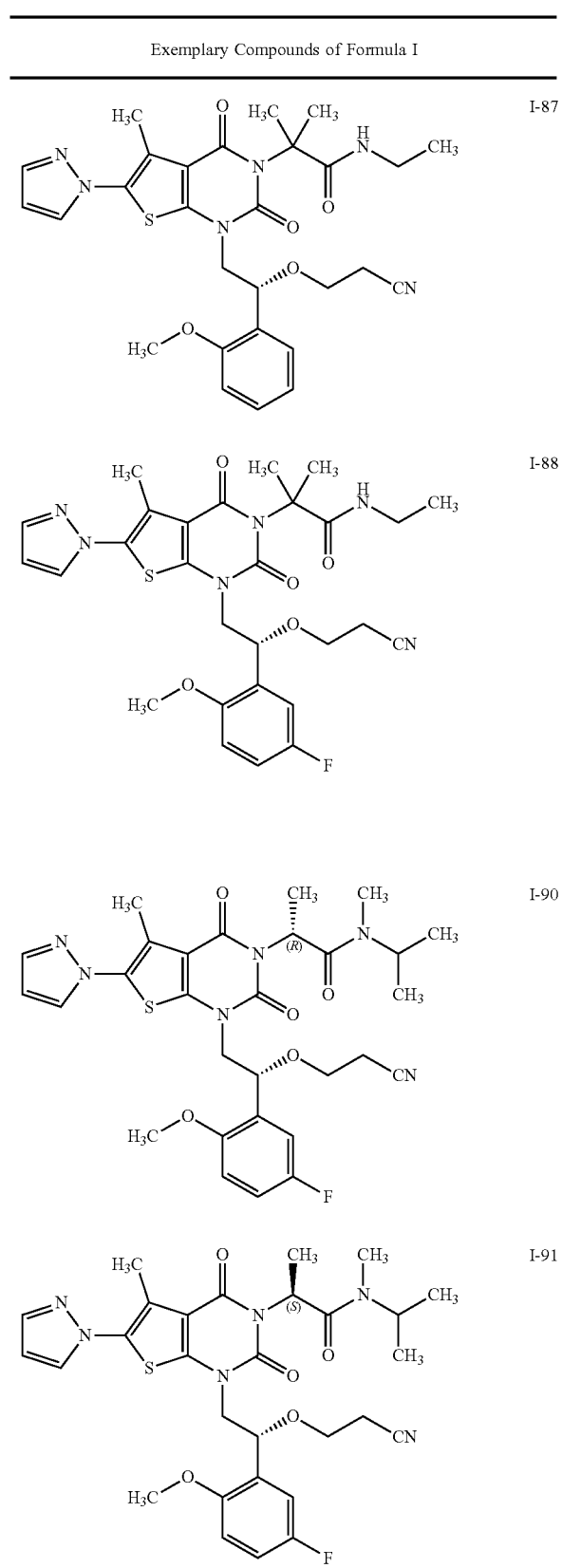
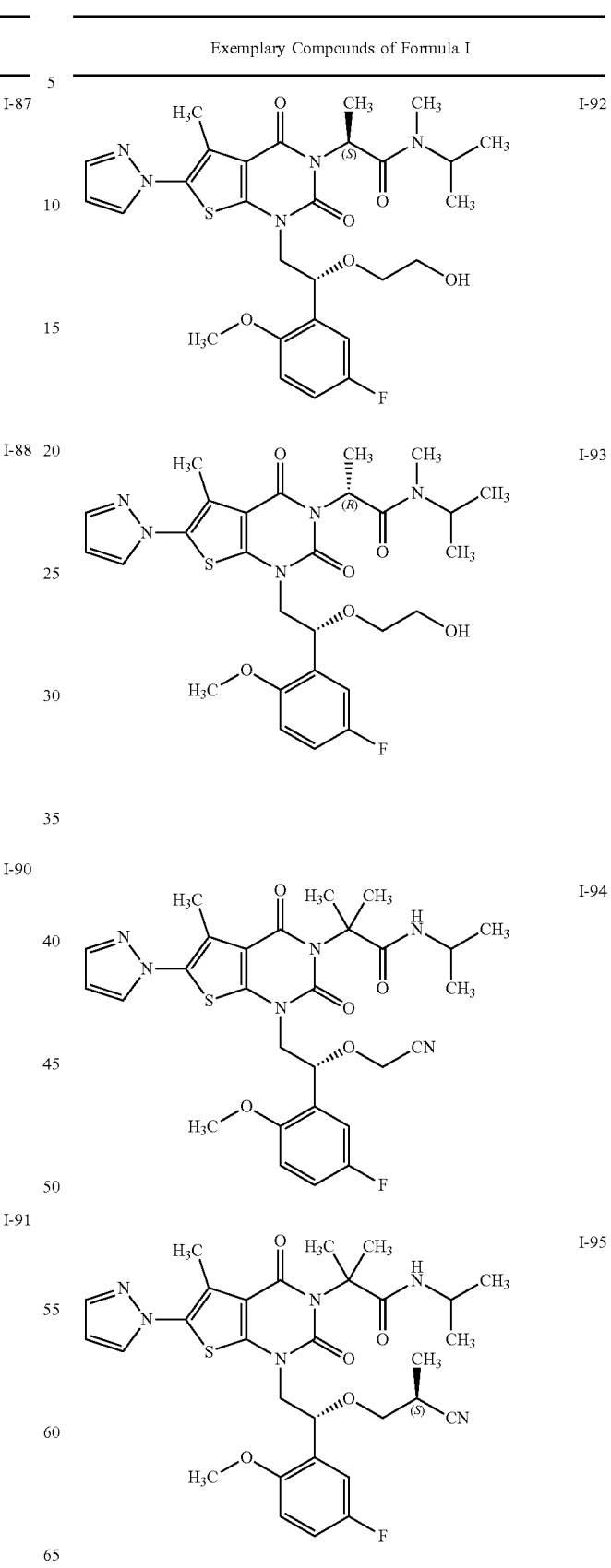

TABLE 1-continued
Exemplary Compounds of Formula I
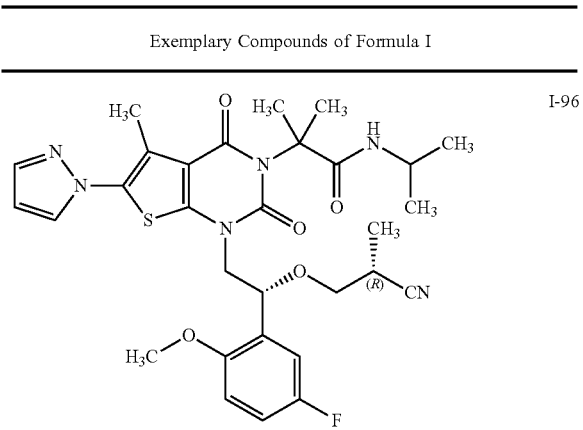 I-96
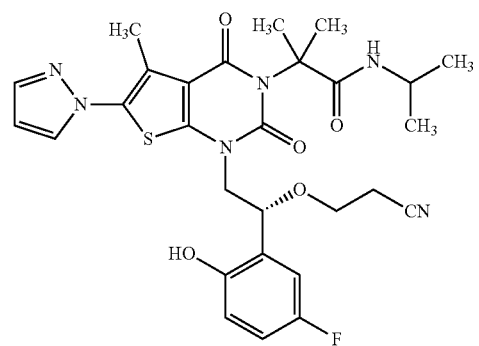 [SMILES: Cc1c(-n2cccn2)sc2c1c(=O)n(C(C)(C)C(=O)NC(C)C)c(=O)n2C[C@H](OCCC#N)c1cc(F)ccc1O] I-97
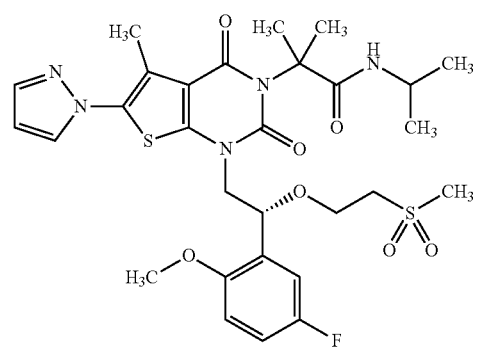 [SMILES: COc1ccc(F)cc1[C@H](Cn1c(=O)n(C(C)(C)C(=O)NC(C)C)c(=O)c2c(C)c(-n3cccn3)sc21)OCCS(C)(=O)=O] I-98
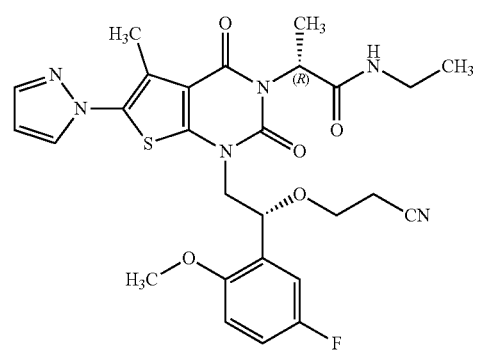 I-99
TABLE 1-continued
Exemplary Compounds of Formula I
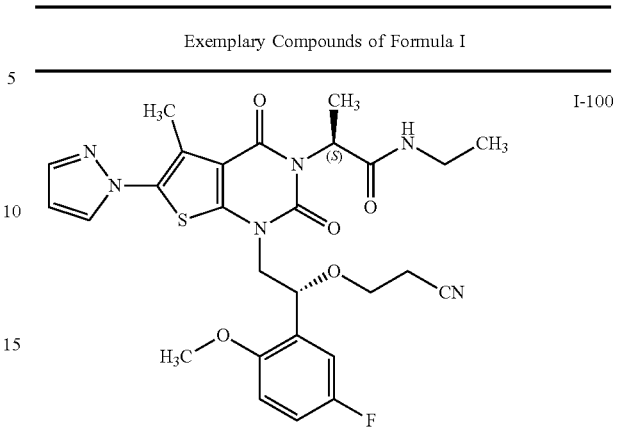 I-100
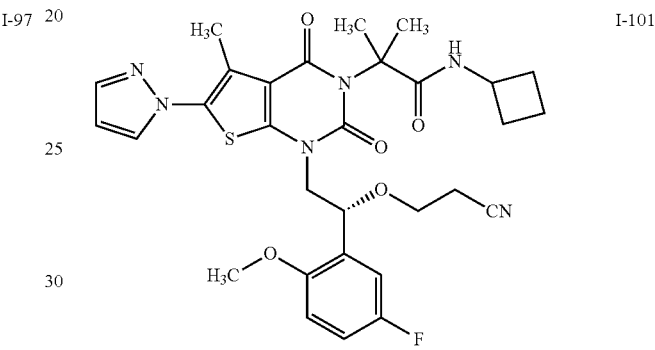 I-101
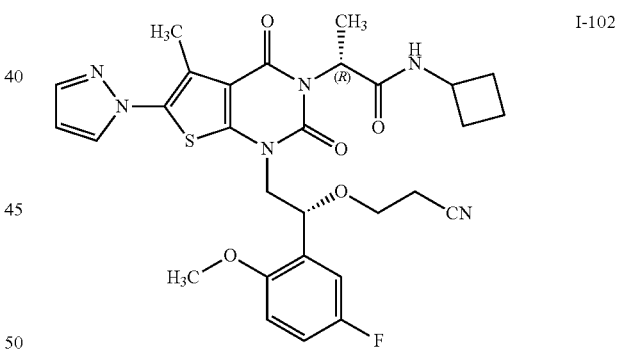 I-102
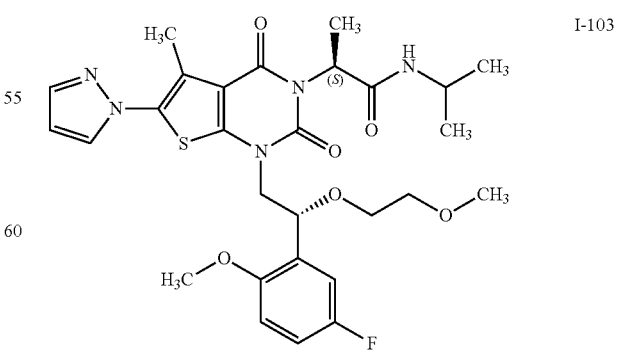 I-103

TABLE 1-continued

Exemplary Compounds of Formula I

[Structure I-104]

[Structure I-105]

[Structure I-107]

[Structure I-108]

[Structure I-109]

[Structure I-110]

In certain embodiments, the present invention provides any compound selected from those depicted in Table 1, above, or a pharmaceutically acceptable salt or agriculturally acceptable salt thereof.

In certain embodiments, the present invention provides a compound as described above, wherein the compound is present as a pharmaceutically acceptable salt. In certain embodiments, the present invention provides a compound as described above, wherein the compound is present as an agriculturally acceptable salt.

4. General Methods for Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, compounds of the present invention of formula I are generally prepared according to Scheme I set forth below:

Scheme I

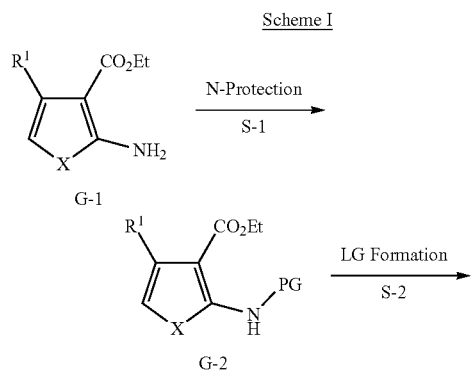

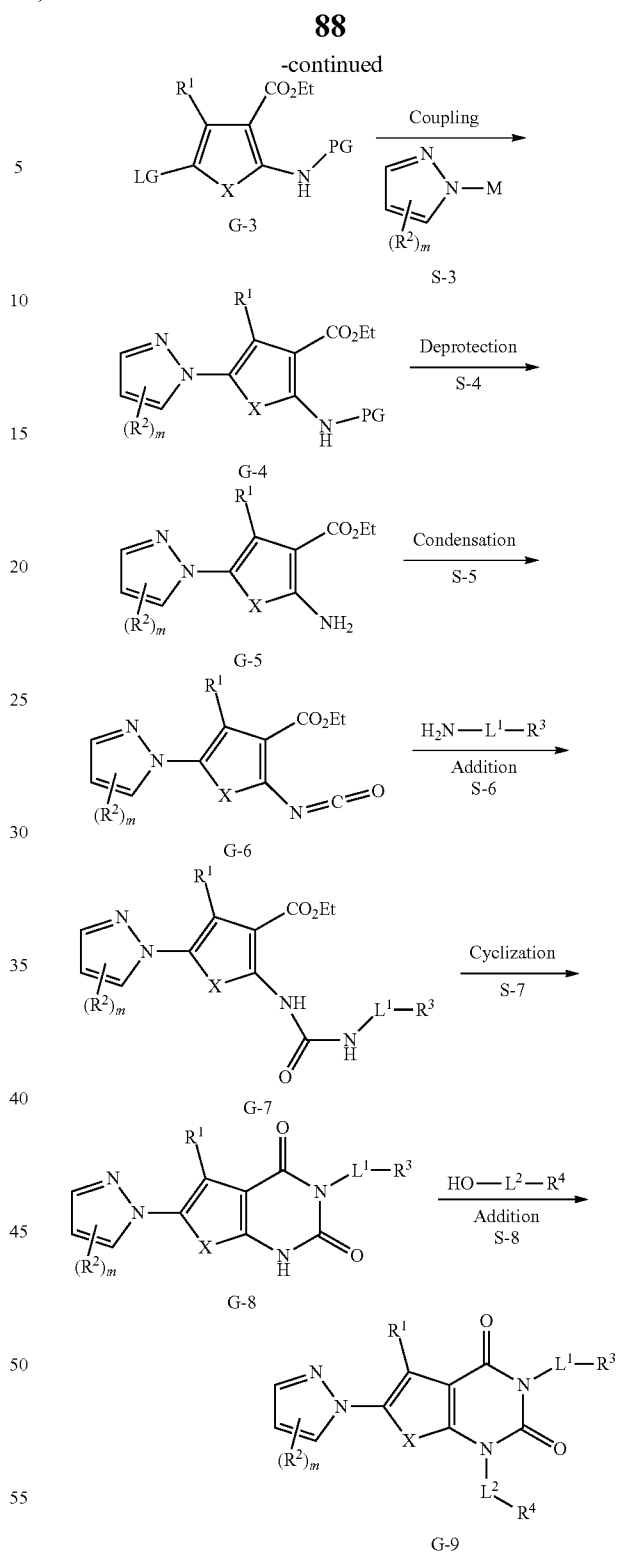

In Scheme I above, each of PG, LG, $R^1$, $R^2$, $R^3$, $R^4$, $L^1$, $L^2$, and X is as defined above and below and in classes and subclasses as described herein.

In one aspect, the present invention provides methods for preparing compounds of formula G-9 according to the steps depicted in Scheme I, above. In some embodiments, step S-1 comprises protecting the amine of a compound of formula G-1, thereby forming a compound of formula G-2. In some embodiments, the PG is acetyl. In some embodiments, the acetyl protection is accomplished through the use of acetic anhydride. In some embodiments, a catalyst is added to promote the reaction. In some embodiments, the catalyst is MgClO$_4$.

In some embodiments, step S-2 comprises the formation of a LG to within compound of formula G-2, thereby forming a compound of formula G-3. In some embodiments, LG is a sulfonate. In some embodiments, LG is a halogen. In some embodiments, LG is chlorine. In some embodiments, LG is bromine. In some embodiments, a bromine-containing compound, G-3, is produced through the use of N-bromosuccinimide.

In some embodiments, step S-3 comprises the coupling of

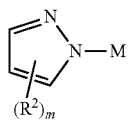

with a compound of formula G-3, thereby forming a compound of formula G-4. In some embodiments, the coupling is a Stille cross coupling. In some embodiments, M is a metal complex. In some embodiments, M is SnR$_3$, where R is as defined above and described within. In some embodiments, M is Sn(C$_4$H$_9$)$_3$. In some embodiments, an additional metal catalyst is added to facilitate the coupling. In some embodiments, the metal catalyst comprises Pd. In some embodiments, the metal catalyst is Pd(PPh$_3$)$_4$. In some embodiments, the coupling is copper-catalyzed. In some embodiments, the metal catalyst is CuSO$_4$. In some embodiments, a base is added. In some embodiments, the base is Cs$_2$CO$_3$. In some embodiments, the solvent is DMF.

In some embodiments, step S-4 comprises deprotection of the amine of a compound of formula G-4, thereby forming a compound of formula G-5. In some embodiments, the PG is acetyl. In some embodiments, deprotection is achieved through use of hydrazine. In some embodiments, water is added to the reaction mixture. In some embodiments, ethanol is added to the reaction mixture.

In some embodiments, step S-5 comprises contacting a compound of formula G-5 with a reagent, thereby forming a compound of formula G-6. In some embodiments, the reagent is bis(trichloromethyl)carbonate. In some embodiments, step S-5 further comprises a base. In some embodiments, the base is triethylamine. In some embodiments, the solvent is CH$_2$Cl$_2$.

In some embodiments, step S-6 comprises contacting a compound of formula G-6 with a reagent, thereby forming a compound of formula G-7. In some embodiments, the reagent is H$_2$N-L$^1$-R$^3$, wherein L and R$^3$ is as defined above and described within.

In some embodiments, step S-7 comprises cyclization of a compound of formula G-7, thereby forming a compound of formula G-8. In some embodiments, a base is added to catalyze the cyclization. In some embodiments, the base is Cs$_2$CO$_3$. In some embodiments, the solvent is t-BuOH.

In some embodiments, step S-8 comprises contacting a compound of formula G-8 with a reagent, thereby forming a compound of formula G-9. In some embodiments, the reagent is HO-L$^2$-R$^4$. In some embodiments, the addition of L$^2$-R$^4$ is accomplished through the use of additional reagents. In some embodiments, the additional reagents are diisopropyl azodicarboxylate and triphenylphosine. In some embodiments, the solvent is THF.

One of skill in the art will appreciate that compounds of formula G-9 may contain one or more stereocenters, and may be present as an racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

In certain embodiments, compounds of the present invention of formula II are generally prepared according to Scheme II set forth below.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See e.g. "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit ACC, in a biological sample or in a patient. In certain embodiments, the amount of compound in compositions of this invention is such that is effective to measurably inhibit ACC, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ACC.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Compositions Thereof
Pharmaceutical Uses

Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle [Harwood, 2005].

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation [Tong and Harwood, *J. Cellular Biochem.* 99: 1476, 2006]. This compartmentalization of malonyl-CoA results from a combination of synthesis proximity [Abu-Elheiga et al., PNAS (USA) 102: 12011, 2005] and the rapid action of malonyl-CoA decarboxylase [Cheng et al., *J. Med. Chem.* 49:1517, 2006].

Simultaneous inhibition of the enzymatic activities of ACC1 and ACC2 offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of direct inhibition of ACC activity as an important therapeutic target for treating obesity, diabetes, insulin resistance, and the metabolic syndrome.

Abu-Elheiga et al. [*Proc. Natl. Acad. Sci.* USA 100: 10207-10212, 2003] demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. [*J. Clin. Invest.* 116: 817, 2006], using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. [*J. Biol. Chem.* 278: 37099, 2003] demonstrated that the isozyme-nonselective ACC inhibitor, CP-640186, which equally inhibits ACC1 and ACC2 ($IC_{50}$=~60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. [*Diabetes* 55:A288, 2006] demonstrated stimulation of insulin sensitivity in insulin-resistant rat muscle tissue by CP-640186 within 30 min of compound administration, and studies by Furler et al. [*Diabetes* 55:A333, 2006] used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, ACC inhibitors both reduce de novo lipid synthesis and promote the oxidation of existing fat. This dual effect on lipid metabolism raises the possibility that ACC inhibitors will be substantially more effective in reducing excess fat than other mechanisms. Furthermore, ACC inhibitors will impact insulin sensitivity, plasma and tissue triglycerides, and fasting plasma glucose as a consequence of whole-body and tissue-specific fat mass reduction without the need for poly-pharmacy.

ACC inhibitors need only access the liver and muscle in the peripheral compartment. Avoiding the CNS will address many of side effects associated with the late-stage obesity programs targeting CNS receptors. ACC inhibitors are also expected to have superior safety profiles to existing metabolic disease agents. For example, it is unlikely that an ACC inhibitor will precipitate life-threatening hypoglycemia as is often seen with insulin mimetics, insulin secretagogues, and insulin degradation inhibitors. Also, since ACC inhibitors will reduce whole-body fat mass, they will be superior to the glitazones that increase whole-body fat mass as part of their mechanism of action.

A peripherally acting agent that causes significant weight loss and improves other metabolic endpoints fits well within the US FDA's requirements for approval of a new obesity agent. However, if an approval for obesity continues to be challenging in 5-7 years, ACC inhibitors could be approved for familial combined hyperlipidemia and non-alcoholic steatohepatitis (NASH). There are currently no marketed ACC inhibitors, so an isozyme-nonselective ACC inhibitor would represent first-in-class therapy for treating obesity and metabolic syndrome.

The activity of a provided compound as an inhibitor of ACC or treatment for obesity or metabolic syndrome, may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses ACC. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabeling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of ACC are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

A provided compound or composition thereof may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, a provided compound or composition thereof may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, a provided compound or composition thereof may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance.

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with a provided compound or composition thereof include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with a provided compound or composition thereof include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with a provided compound or composition thereof include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK 84072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-HT$_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), PYY$_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide. SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB 1 receptor antagonists or inverse agonists, ghrelin agonists or antagonists, oxyntomodulin and analogs thereof, monoamine uptake inhibitors (e.g. tesofensine), and combination agents (e.g. buproprion plus zonisamide (Empatic), pramlintide plus metreleptin, buproprion plus naltrexone (Contrave), phentermine plus topiramate (Qsymia).

In some embodiments, the anti-obesity agents used in combination with a provided compound or composition thereof are selected from gut-selective MTP inhibitors (e.g. dirlotapide, mitratapide, implitapide, R56918), CCK-A agonists, 5-HT$_2$c agonists (e.g. lorcaserin/Belviq), MCR4 agonists, lipase inhibitors (e.g. Cetilistat), PYY$_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, a provided compound or composition, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, a provided compound or composition, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, a provided compound or composition, according to the method of the present invention, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

A provided compound finds special utility in triple negative breast cancer, as the tumor suppressor protein BRCA1 binds and stabilizes the inactive form of ACC, thus upregulating de novo lipid synthesis, resulting in cancer cell proliferation Brunet et al. "BRCA1 and acetyl-CoA carboxylase: the metabolic syndrome of breast cancer" Mol. Carcinog. (2008) 47(2), 157-163.

In some embodiments, a provided compound or composition, according to the method of the present invention, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, a provided compound or composition, according to the method of the present invention, may be administered using any amount and any route of administration effective for treating or lessening the severity of a liver disease. In some embodiments, the liver disease is selected from hepatitis C, hepatocellular carcinoma, familial combined hyperlipidemia and non-alcoholic steatohepatitis (NASH), liver cancer, cholangiocarcinoma, angiosarcoma, hemangiosarcoma, and progressive familial intrahepatic cholestasis.

In some embodiments, a provided compound or composition, according to the method of the present invention, may be administered using any amount and any route of administration effective for treating or lessening the severity of a bacterial infection or inhibiting the growth of bacteria.

In some embodiments, a provided compound or composition, according to the method of the present invention, may be administered using any amount and any route of administration effective for treating or lessening the severity of a fungal infection or inhibiting the growth of fungal cells (Shen et al. "A Mechanism for the Potent Inhibition of Eukaryotic Acetyl-Coenzyme A Carboxylase by Soraphen A, a Macrocyclic Polyketide Natural Product" Molecular Cell (2004) 16, 881-891).

In some embodiments, a provided compound inhibits one or more species of fungi at an MIC of 2 μg/mL or less. In some embodiments, a compound of the present invention inhibits at least one of *C. albicans, C. krusei*, and *C. parapsilosis* at a concentration of 2 μg/mL or less. In some embodiments, a compound of the present invention inhibits at least one of *C. albicans, C. krusei*, and *C. parapsilosis* at a concentration of 1 μg/mL or less. In some embodiments, a compound of the present invention inhibits at least two of *C. albicans, C. krusei*, and *C. parapsilosis* at a concentration of 2 μg/mL or less. In some embodiments, a compound of the present invention inhibits at least two of *C. albicans, C. krusei*, and *C. parapsilosis* at a concentration of 1 μg/mL or less. In some embodiments, a compound of the present invention inhibits each of *C. albicans, C. krusei*, and *C. parapsilosis* at a concentration of 2 μg/mL or less. In some embodiments, a compound of the present invention inhibits each of *C. albicans, C. krusei*, and *C. parapsilosis* at a concentration of 1 μg/mL In some embodiments, a provided compound inhibits at least one of *Botrtyis cinerea, Collectotrichum graminicola, Diplodia mavdis, Fusarium moniliforme, Fusarium virguliforme, Phytophthora capsici, Rhizoctonia solani*, and *Septoria* at a concentration of 2 μg/mL or less. In some embodiments, a provided compound inhibits at least one of *Botrtyis cinerea, Collectotrichum graminicola, Diplodia maydis, Fusarium moniliforme, Fusarium virguliforme, Phytophthora capsici, Rhizoctonia solani*, and *Septoria* at a concentration of 1 μg/mL or less. In some embodiments, a compound of the present invention inhibits at least two of *Botrtyis cinerea, Collectotrichum graminicola, Diplodia maydis, Fusarium moniliforme, Fusarium virguliforme, Phytophthora capsici, Rhizoctonia solani*, and *Septoria* at a concentration of 2 μg/mL or less. In some embodiments, a compound of the present invention inhibits at least two of *Botrtyis cinerea, Collectotrichum graminicola, Diplodia maydis, Fusarium monihforme, Fusarium virguliforme, Phytophthora capsici, Rhizoctonia solani*, and *Septoria* at a concentration of 1 μg/mL or less. In some embodiments, a compound of the present invention inhibits at least three of *Botrtyis cinerea, Collectotrichum graminicola, Diplodia maydis, Fusarium moniliforme, Fusarium virguliforme, Phytophthora capsici, Rhizoctonia solani*, and *Septoria* at a concentration of 2 μg/mL or less. In some embodiments, a compound of the present invention inhibits at least three of *Botrtyis cinerea, Collectotrichum graminicola, Diplodia maydis, Fusarium moniliforme, Fusarium virguliforme, Phytophthora capsici, Rhizoctonia solani*, and *Septoria* at a concentration of 1 μg/mL or less.

In some embodiments, a provided compound or composition, according to the method of the present invention, may be administered using any amount and any route of administration effective for treating or lessening the severity of a bacterial infection (Tong, L. et al. J. Cell. Biochem. (2006) 99, 1476-1488).

In some embodiments, a provided compound or composition, according to the method of the present invention, may be administered using any amount and any route of administration effective for treating or lessening the severity of a viral infection (Munger et al. Nat. Biotechnol. (2008) 26, 1179-1186). In some embodiments, the viral infection is Hepatitis C.

In some embodiments, a provided compound or composition, according to the method of the present invention, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2:S16; Baranano et al. Curr. Treat. Opin. Neurol. (2008) 10, 410-419).

In some embodiments, a provided compound or composition, according to the method of the present invention, may be administered using any amount and any route of administration effective for treating or lessening the severity of a parasitic infection or inhibiting the growth of parasites (e.g. malaria and *toxoplasma*: Gornicki et al. "Apicoplast fatty acid biosynthesis as a target for medical intervention in apicomplexan parasites" International Journal of Parasitology (2003) 33, 885-896; Zuther et al. "Growth of *Toxoplasma gondii* is inhibited by aryloxyphenoxypropionate herbicides targeting acetyl-CoA carboxylase" PNAS (1999) 96 (23) 13387-13392).

In some embodiments, a provided compound or composition, according to the method of the present invention, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation via ACC inhibition (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

In certain embodiments, a provided compound or composition, according to the method of the present invention, may be used as herbicides. In some embodiments, the present invention provides a method to inhibit the growth or viability of plants comprising treating plants with compounds of the present invention. In some embodiments of the present invention, a provided compound or composition can be used to inhibit the growth or viability of plants by inhibiting ACC. In some embodiments, the method of the present invention comprises using a provided compound or composition to inhibit fatty acid production in or increase fatty acid oxidation in plants.

The exact amount required will vary from subject to subject, depending on the species, age, and general condition of the subject, the severity of the infection, the particular agent, its mode of administration, and the like. A provided compound or composition of the invention is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

A pharmaceutically acceptable composition of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, a provided compound of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

A provided compound can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting ACC in a biological sample comprising the step of contacting said biological sample with a provided compound, or a composition comprising said compound.

In certain embodiments, the invention relates to a method of modulating fatty acid levels in a biological sample comprising the step of contacting said biological sample with a provided compound, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting ACC in a patient comprising the step of administering to said patient a provided compound, or a composition comprising said compound.

According to another embodiment, the invention relates to a method of inhibiting fatty acid production, stimulating fatty acid oxidation, or both, in a patient comprising the step of administering to said patient a provided compound, or a composition comprising said compound. According to certain embodiments, the invention relates to a method of inhibiting fatty acid production, stimulating fatty acid oxidation, or both in a patient, leading to decreasing obesity or alleviating symptoms of metabolic syndrome, comprising the step of administering to said patient a provided compound, or a composition comprising said compound. In other embodiments, the present invention provides a method for treating a disorder mediated by ACC, in a patient in need thereof, comprising the step of administering to said patient a provided compound or pharmaceutically acceptable composition thereof. Such disorders are described in detail herein.

In some embodiments, a provided compound or composition thereof may be used in a method of treating obesity or another metabolic disorder. In certain embodiments, a provided compound or composition thereof may be used to treat obesity or other metabolic disorder in a mammal. In certain, embodiments the mammal is a human patient. In certain embodiments, a provided compound or composition thereof may be used to treat obesity or other metabolic disorder in a human patient.

In some embodiments, the present invention provides a method of treating obesity or another metabolic disorder, comprising administering a provided compound or composition thereof to a patient with obesity or another metabolic disorder. In certain embodiments, the method of treating obesity or another metabolic disorder comprises administering a provided compound or composition thereof to a mammal. In certain embodiments, the mammal is a human. In some embodiments, the metabolic disorder is dyslipidemia or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfonylureas, thiazolidinediones, antipsychotics, antidepressants, steroids, anticonvulsants (including phenytoin and valproate), pizotifen, or hormonal contraceptives.

In certain embodiments, the present invention provides a method of treating cancer or another proliferative disorder, comprising administering a provided compound or composition thereof to a patient with cancer or another proliferative disorder. In certain embodiments, the method of treating cancer or another proliferative disorder comprises administering a provided compound or composition thereof to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the a provided compound or composition thereof described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by a provided compound or composition thereof is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments, the cancer to be treated by a provided compound or composition thereof is one bearing an activated MAPK pathway. In some embodiments, the cancer bearing an activated MAPK pathway is a melanoma. In certain preferred embodiments, the cancer treated by a provided compound or composition thereof is one associated with BRCA1 mutation. In an especially preferred embodiment, the cancer treated by a provided compound or composition thereof is a triple negative breast cancer.

In certain embodiments, the diseases which can be treated by a provided compound or composition thereof are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, glioma or Huntington's Disease.

In certain embodiments, the disease which can be treated by a provided compound or composition thereof is an infectious disease. In some embodiments, the infectious disease is a viral infection. In some embodiments the viral infection is cytomegalovirus infection or influenza infection. In some embodiments, the infectious disease is a fungal infection. In some embodiments, the infectious disease is a bacterial infection.

Depending upon the particular condition, or disease, to be treated, additional therapeutic agents, which are normally administered to treat that condition, may be administered in combination with a provided compound or composition thereof. As used herein, additional therapeutic agents that are normally administered to treat a particular disease, or condition, are known as "appropriate for the disease, or condition, being treated".

In certain embodiments, a provided compound or composition thereof is administered in combination with one or more additional antifungal (antimycotic) agents for the treatment of a fungal infection. In some embodiments, the one or more additional antifungal (antimycotic) agents are selected from polyene antifungals (including but not limited to amphotericin B (as amphotericin B deoxycholate, amphotericin B lipid complex, or liposomal amphotericin B), candicidin, filipin, hamycin, natamycin, nystatin, and rimocidin), azole antifungals (including but not limited to abafungin, albaconazole, bifonazole, butoconazole, clotrimazole, econazole, efinaconazole, epoxiconazole, fenticonazole, fluconazole, isavuconazole, isoconazole, itraconazole, ketoconazole, luliconazole, miconazole, omoconazole, oxiconazole, posaconazole, propiconazole, ravuconazole, sertaconazole, sulconazole, terconazole, tioconazole, and voriconazole), allylamines (including but not limited to amorolfin, butenafine, naftifine, and terbinafine), echinocandins (including but not limited to anidulafungin, caspofungin, and micafungin), benzoic acid, ciclopirox, flucytosine, griseofulvin, haloprogin, tolnaftate, undecylenic acid, and crystal violet.

In certain embodiments, a provided compound or composition thereof is administered in combination with another inhibitor of ACC or antiobesity agent. In some embodiments, a provided compound or composition thereof is administered in combination with one or more other therapeutic agents. Such therapeutic agents include, but are not limited to agents such as orlistat (Xenical), CNS stimulants, Qsymia, or Belviq.

In certain embodiments, a provided compound or a composition thereof is administered in combination with another anti-cancer, cytotoxin, or chemotherapeutic agent, to a patient in need thereof.

In certain embodiments, the anti-cancer or chemotherapeutic agents used in combination with a provided compound or composition thereof include, but are not limited to, metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia M. DTIC, DTIC-Dome®, Duralone®, Efudex®, Eligard™, Ellence™, Eloxatin™, Elspar®, Emcyt @, Epirubicin, Epoetin Alfa, Erbitux, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate. Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra T, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON T, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide. Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, a provided compound may be administered together with a biguanide selected from metformin, phenformin, or buformin, to a patient in need thereof. In certain embodiments, the patient administered a combination of a provided compound and a biguanide is suffering from a cancer, obesity, a liver disease, diabetes or two or more of the above.

In certain embodiments, a combination of 2 or more therapeutic agents may be administered together with a provided compound. In certain embodiments, a combination of 3 or more therapeutic agents may be administered with a provided compound.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, AMPK activators, PCSK9 inhibitors, SREBP site I protease inhibitors, HMG CoA-reductase inhibitors, anti-emetics (e.g. 5-HT$_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids. TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors, agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, a provided compound, or a pharmaceutically acceptable composition thereof, are administered in combination with antisense agents, a monoclonal or polyclonal antibody or a siRNA therapeutic.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of a provided compound can be administered.

In those compositions which comprise an additional therapeutic agent, that additional therapeutic agent and a provided compound may act synergistically. Therefore, the amount of additional therapeutic agent in such compositions will be less than that required in a monotherapy utilizing only that therapeutic agent. In such compositions a dosage of between 0.01-100 gig/kg body weight/day of the additional therapeutic agent can be administered.

The amount of additional therapeutic agent present in a composition comprising a provided compound will be no more than the amount that would normally be administered in a composition comprising that therapeutic agent as the only active agent. Preferably the amount of additional therapeutic agent in a provided composition will range from about 50% to 100% of the amount normally present in a composition comprising that agent as the only therapeutically active agent.

Agricultural Uses

The invention further refers to an agricultural composition comprising at least one provided compound as defined above or an agriculturally acceptable salt thereof and a liquid or solid carrier. Suitable carriers, as well as auxiliaries and further active compounds which may also be contained in the composition of the invention are defined below.

Suitable "agriculturally acceptable salts" include but are not limited to the salts of those cations or the acid addition salts of those acids whose cations and anions, respectively, have no adverse effect on the fungicidal action of a provided compound. Thus, suitable cations are in particular the ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium. Additional agriculturally acceptable salts include phosphonium ions, sulfonium ions, preferably tri($C_1$-$C_4$-alkyl)sulfonium and sulfoxonium ions, preferably tri($C_1$-$C_4$-alkyl)sulfoxonium. Anions of useful acid addition salts are primarily chloride, bromide, fluoride, hydrogen-sulfate, sulfate, dihydrogenphosphate, hydrogenphosphate, phosphate, nitrate, bicarbonate, carbonate, hexafluorosilicate, hexafluorophosphate, benzoate, and also the anions of $C_1$-$C_4$-alkanoic acids, preferably formate, acetate, propionate and butyrate. Such agriculturally acceptable acid addition salts can be formed by reacting a provided compound bearing a basic ionizable group with an acid of the corresponding anion, preferably hydrochloric acid, hydrobromic acid, sulfuric acid, phosphoric acid or nitric acid.

A provided compound or composition thereof is suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

In some embodiments, a provided compound or composition thereof is particularly important in the control of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

In some embodiments, a provided compound or compositions thereof is used for controlling a multitude of fungi on field crops, such as potatoes, sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

In some embodiments, treatment of plant propagation materials with a provided compound or compositions thereof is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants, such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that, by the use of recombinant DNA techniques, are capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryllA(b), CryIIIA, CryIIIB(bi) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or pa-pain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of them are commercially available such as Yield-Gard® (corn cultivars producing the CryiAb toxin), Yield-Gard® Plus (corn cultivars producing Cry1 Ab and Cry3Bbl toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1 Ac toxin), Bollgard® I (cotton cultivars producing the CryiAc toxin), Bollgard® II (cotton cultivars producing CryiAc and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt 1 1 (e.g. Agrisure® CB) and Bt176 from Syngenta Seeds SAS, France, (corn cultivars producing the CryiAb toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bbl toxin), IPC 531 from Monsanto Europe S.A., Belgium (cotton cultivars producing a modified version of the CryiAc toxin) and 1507 from Pioneer Overseas Corporation, Belgium (corn cultivars producing the Cry1 F toxin and PAT enzyme).

Furthermore, plants are also covered that, by the use of recombinant DNA techniques, are capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g., in the publications mentioned above.

Furthermore, plants are also covered that, by the use of recombinant DNA techniques, are capable to synthesize one or more proteins to increase the productivity (e.g. biomass production, grain yield, starch content, oil content or protein content), tolerance to drought, salinity or other growth-limiting environmental factors or tolerance to pests and fungal, bacterial or viral pathogens of those plants.

Furthermore, plants are also covered that, by the use of recombinant DNA techniques, contain a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that, by the use of recombinant DNA techniques, contain a modified amount of substances of content or new substances of content, specifically to improve raw material production, e.g. potatoes that produce increased amounts of amylopectin (e.g. Amflora® potato, BASF SE, Germany).

A provided compound and compositions thereof is particularly suitable for controlling the following plant diseases:

*Albugo* spp. (white rust) on ornamentals, vegetables (e.g. *A. Candida*) and sunflowers (e.g. *A. tragopogonis*); *Alternaria* spp. (*Alternaria* leaf spot) on vegetables, rape (*A. brassicola* or *brassicae*), sugar beets (*A. lenuis*), fruits, rice, soybeans, potatoes (e.g. *A. solani* or *A. alternala*), tomatoes (e.g. *A. solani* or *A. alternata*) and wheat; *Aphanomyces* spp. on sugar beets and vegetables; *Ascochyla* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeaemaydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichmm* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*. Black Foot Disease) and ornamentals; *Demalophora* (teleomorph: *Rosellinia*) *necatrix* (root and stem rot) on soybeans, *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; *Esca* (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fijikuroi*: Bakanae disease), *Glomerella cingulata* on vines, pome fruits and other plants and *G. gossypii* on cotton; Grain-staining complex on rice; *Guignardia bidwellii* (black rot) on vines; *Gynosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, M. *fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Seploria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstediiou* sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner, anamorph: *Phialophora*) on vines; *Puccinia* spp. (rusts) on various plants, e.g. *P. triticina* (brown or leaf rust), *P. striiformnis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *triticirepentis* (tan spot) on wheat or *P. feres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attemnatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn.

*Erysiphe*) necator (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. miliaria*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leplosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. baeicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incamata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. mida* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

A provided compound or compositions thereof is also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Altemaria* spp., *Paecilomyces* spp. and *Zygomycetes* such as *Mucor* spp., and in addition in the protection of stored products and harvest the following yeast fungi are worthy of note: *Candida* spp. and *Saccharomyces cerevisae*.

A provided compound or compositions thereof may be used for improving the health of a plant. The invention also relates to a method for improving plant health by treating a plant, its propagation material and/or the locus where the plant is growing or is to grow with an effective amount of a provided compound or composition thereof.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

A provided compound can be present in different crystal modifications whose biological activity may differ. They are likewise subject matter of the present invention.

A provided compound is employed as such or in form of a composition by treating the fungi or the plants, plant propagation materials, such as seeds, soil, surfaces, materials or rooms to be protected from fungal attack with a fungicidally effective amount of the active substances. The application can be carrnied out both before and after the infection of the plants, plant propagation materials, such as seeds, soil, surfaces, materials or rooms by the fungi.

Plant propagation materials may be treated with a provided compound or composition thereof comprising at least one provided compound prophylactically either at or before planting or transplanting.

The invention also relates to agrochemical compositions comprising a solvent or solid carrier and at least one provided compound and to the use for controlling harmful fungi.

An agrochemical composition comprises a fungicidally effective amount of a provided compound. The term "effective amount" denotes an amount of a provided compound or composition thereof, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound used.

A provided compound or a pharmaceutically acceptable salt thereof can be converted into customary types of agrochemical compositions, e.g. solutions, emulsions, suspensions, dusts, powders, pastes and granules. The composition type depends on the particular intended purpose; in each case, it should ensure a fine and uniform distribution of the provided compound.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, pp. 8-57 et seq., WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and inorganic thickeners, bactericides, anti-freezing agents, anti-foaming agents, if appropriate colorants and tackifiers or binders (e.g. for seed treatment formulations). Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearyl-phenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinyl-amines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and inorganic clays such as Xanthan gum (Kelzan®, CP Kelco, U.S.A.), Rhodopol® 23 (Rhodia, France), Veegum® (RT. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned und the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidones, polyvinylacetates, polyvinyl alcohols and cellulose ethers (Tylose®, Shin-Etsu, Japan).

Powders, materials for spreading and dusts can be prepared by mixing or concomitantly grinding a provided compound and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types include, but are not limited to: 1. Composition types for dilution with water, i) Water-soluble concentrates (SL, LS): 10 parts by weight of a provided compound are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained. ii) Dispersible concentrates (DC): 20 parts by weight of a provided compound are dissolved in 70 parts by weight of cyclohexanone with addition of 10 parts by weight of a dispersant, e.g. polyvinylpyrrolidone. Dilution with water gives a dispersion. The active substance content is 20% by weight. iii) Emulsifiable concentrates (EC): 15 parts by weight of a provided compound are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight. iv) Emulsions (EW, EO, ES): 25 parts by weight of a provided compound are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight. v) Suspensions (SC, OD, FS): In an agitated ball mill, 20 parts by weight of a provided compound are comminuted with addition of 10 parts by weight of dispersants and wetting agents and 70 parts by weight of water or an organic solvent to give a fine active sub-stance suspension. Dilution with water gives a stable suspension of the active substance. The active substance content in the composition is 20% by weight. vi) Water-dispersible granules and water-soluble granules (WG, SG) 50 parts by weight of a provided compound are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight. vii) Water-dispersible powders and water-soluble powders (WP, SP, SS, WS) 75 parts by weight of a provided compound are ground in a rotor-stator mill with addition of 25 parts by weight of dispersants, wetting agents and silica gel. Dilution with water gives a stable dispersion or solution of the active substance. The active substance content of the composition is 75% by weight. viii) Gel (GF): In an agitated ball mill, 20 parts by weight of a provided compound are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition types to be applied undiluted: ix) Dustable powders (DP, DS): 5 parts by weight of a provided compound are ground finely and mixed intimately with 95 parts by weight of finely divided kaolin. This gives a dustable composition having an active substance content of 5% by weight. x) Granules (GR, FG, GG, MG): 0.5 parts by weight of a provided compound are ground finely and associated with 99.5 parts by weight of carriers. Current methods are extrusion, spray-drying or the fluidized bed. This gives granules to be applied undiluted having an active substance content of 0.5% by weight. xi) ULV solutions (UL) 10 parts by weight of a provided compound are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 600/% by weight, preferably from 0.1 to 40% by weight, in the ready-to-use preparations. Application can be carried out before or during sowing. Methods for applying or treating a provided agrochemical compound or composition thereof on to plant propagation material, especially seeds, are known in the art, and include dressing, coating, pelleting, dusting, soaking and in-furrow application methods of the propagation material. In a preferred embodiment, a provided compound or composition thereof is applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30@; EO/PO block polymers, e.g. Pluronic RPE 2035® and Genapol B®; alcohol ethoxylates such as Lutensol XP 80@; and dioctyl sulfosuccinate sodium such as Leophen RA®.

The compositions according to the invention can, in the use form as fungicides, also be present together with other active substances, e.g. with pesticides, growth regulators, fungicides or else with fertilizers, as pre-mix or, if appropriate, not until immediately prior to use (tank mix). The pesticide may be, for example, an insecticide, a fungicide, an herbicide, or an additional nematicide. The composition may also comprise one or more additional active substances, including biological control agents, microbial extracts, natural products, plant growth activators and/or plant defense agents.

Mixing a provided compound or compositions thereof in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds according to the invention can be used, is intended to illustrate the possible combinations but does not limit them:

A) strobilurins azoxystrobin, coumoxystrobin, dimoxystrobin, enestroburin, enoxastrobin, fenaminstrobin, fluoxastrobin, flufenoxystrobin, kresoxim-methyl, mandestrobin, metominostrobin, orysastrobin, picoxystrobin, pyraclostrobin, pyrametostrobin, pyraoxystrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

B) carboxamides and carboxanilides: benalaxyl, benalaxyl-M, benodanil, benzovindiflupyr, bixafen, boscalid, carboxin, fenfuram, fenhexamid, fluindapyr, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, oxathiapiprolin, penflufen, penthiopyrad, pydiflumetofen, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethyl-thiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide; carboxylic morpholides: dimethomorph, flumorph, pyrimorph; benzoic acid amides: flumetover, fluopicolide, fluopyram, zoxamide, N-(3-ethyl-3,5,5-trimethyl-cyclohexyl)-3-formylamino-2-hydroxy-benzamide; other carboxamides: carpropamid, dicyclomet, mandiproamid, oxytetracyclin, silthiofam and N-(6-methoxy-pyridin-3-yl) cyclopropanecarboxylic acid amide;

C) azoles and triazoles: ametoctradin, azaconazole, bitertanol, bromuconazole, cyproconazole, difenoconazole, diniconazole, diniconazole-M, epoxiconazole, fenbuconazole, fluquinconazole, flusilazole, flutriafol, flutriazole, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol; imidazoles: cyazofamid, imazalil, pefurazoate, prochloraz, triflumizol; benzimidazoles: benomyl, carbendazim, fuberidazole, thiabendazole; —others: ethaboxam, etridiazole, hymexazole and 2-(4-chloro-phenyl)-N-[4-(3,4-dimethoxy-phenyl)-i soxazol-5-yl]-2-prop-2-ynyloxy-acetamide;

D) heterocyclic compounds pyridines: fluazinam, pyrifenox, triclopyricarb, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetrachloro-4-methanesulfonyl-pyridine, 3,4,5-trichloropyridine-2,6-di-carbonitrile, N-(1-(5-bromo-3-chloro-pyridin-2-yl)-ethyl)-2,4-dichioronicotinamide, N-[(5-bromo-3-chloro-pyri din-2-yl)-methyl]-2,4-dichloro-nicotinamide; pyrimidines: bupirimate, cyprodinil, diflumetorim, fenarimol, ferimzone, mepanipyrim, nitrapyrin, nuarimol, pyrimethanil; piperazines: triforine; pyrroles: fenpiclonil, fludioxonil; morpholines: aldimorph, dodemorph, dodemorph-acetate, fenpropimorph, tridemorph; piperidines: fenpropidin; —dicarboximides: fluoroimid, iprodione, procymidone, vinclozolin; -non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester; others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzimidazole, 5-chloro-7-(4-methylpiperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E) carbamates thio- and dithiocarbamates: ferbam, mancozeb, maneb, metam, methasulfocarb, methasulphocarb, metiram, propineb, prothiocarb, thiram, zineb, ziram; carbamates: benthiavalicarb, diethofencarb, iprovalicarb, propamocarb, propamocarb hydrochloride, valiphenal and N-(1-(1-(4-cyano-phenyl)ethanesulfonyl)-but-2-yl) carbamic acid-(4-fluorophenyl) ester:

F) other active substances—guanidines: guanidine, dodine, dodine free base, guazatine, guazatine-acetate, iminoctadine, iminoctadine-triacetate, iminoctadine-tris(albesilate); —antibiotics: kasugamycin, kasugamycin hydrochloride-hydrate, streptomycin, polyoxine, validamycin A; nitrophenyl derivates: binapacryl, dinobuton, dinocap, nitrthal-isopropyl, tecnazene, organometal compounds: fentin salts, such as fentin-acetate, fentin chloride or fentin hydroxide; —sulfur-containing heterocyclyl compounds: dithianon, isoprothiolane; organophosphorus compounds: edifenphos, fosetyl, fosetyl-aluminum, iproben-fos, phosphorous acid and its salts, pyrazophos, tolclofos-methyl; organochlorine compounds: chlorothalonil, dichlofluanid, dichlorophen, flusulfamide, hexachlorobenzene, pencycuron, pentachlorphenole and its salts, phthalide, quintozene, thiophanate, thiophanate-methyl, tolylfluanid, N-(4-chloro-2-nitro-phenyl)-N-ethyl-4-methyl-benzenesulfonamide; inorganic active substances: Bordeaux mixture, copper acetate, copper hydroxide, copper oxychloride, basic copper sulfate, sulfur; biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoromethoxy-2,3-difluoro-phenyl)-methyl)-2-phenylacetamide, N'-(4-(4-chloro-3-trifluoromethyl-phenoxy)-2,5-dimethyl-phenyl)-N-ethyl-N-methylformamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N- methylformamidine, N'-(5-difluoromethyl-2-methyl-4-(3-trimethyl silanyl-propoxy)-phenyl)-N-ethyl-N-methylformamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-S-trifluoromethyl-pyrazole-iyO-acetyˆ-piperidinˆ-ylJ-thiazoleˆ-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester.

G) growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid. N-6-benzyladenine, paclobutrazol, prohexadione (prohexadione-calcium), prohydrojasmon, thidiazuron, triapenthenol, tributyl phosphorotrithioate, 2,3,5-triiodobenzoic acid, trinexapac-ethyl and uniconazole;

H) herbicides—acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor; —amino acid derivatives: bilanafos, glyphosate, glufosinate, sulfosate; —aryloxyphenoxypropionates: chlorazifop, clodinafop, clofop, cyhalofop, diclofop, cyhalofop-butyl, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, quizalofop-P-tefuryl, trifop; —Bipyridyls: diquat, paraquat; (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate; —cyclohexanediones: alloxydim, butroxydim, clethodim, cloproxydim, cycloxydim, pinoxaden; profoxydim, sethoxydim, tepraloxydim, tralkoxydim; —dinitroanilines: benfluralin, ethalfluralin, oryzalin, pendimethalin, prodiamine, trifluralin; —diphenyl ethers: acifluorfen, aclonifen, bifenox, diclofop, ethoxyfen, fomesafen, lactofen, oxyfluorfen; —hydroxybenzonitriles: bomoxynil, dichlobenil, ioxynil; —imidazolinones: imazamethabenz, imazamox, imazapic, imazapyr, imazaquin, imazethapyr; —phenoxy acetic acids: clomeprop, 2,4-dichlorophenoxyacetic acid (2,4-D), 2,4-DB, dichlorprop, MCPA, MCPA-thioethyl, MCPB, Mecoprop; pyrazines: chloridazon, flufenpyr-ethyl, fluthiacet, norflurazon, pyridate; —pyridines: aminopyralid, clopyralid, diflufenican, dithiopyr, fluridone, fluroxypyr, picloram, picolinafen, thiazopyr, triclopyr; —sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrmidin-2-yl)urea; —triazines: ametryn, atrazine, cyanazine, dimethametryn, ethiozin, hexazinone, metamitron, metribuzin, prometryn, simazine, terbuthylazine, terbutryn, triaziflam; —ureas: chlorotoluron, daimuron, diuron, fluometuron, isoproturon, linuron, methabenzthiazuron, tebuthiuron; —other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam; —others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal-dimethyl, cinmethylin, clomazone, cumyluron, cyprosulfamide, dicamba, difenzoquat, diflufenzopyr, *Drechslera monoceras*, endothal, ethofumesate, etobenzanid, fentrazamide, flumiclorac-pentyl, flumioxazin, flupoxam, flurochloridone, flurtamone, halauxifen, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxy-ethoxymethyl)-6-trifluoromethyl-pyridine-3-carbonyl]-bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione (trifludimoxazin), 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

I) insecticides and nematicides—organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenamiphos, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon; —carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate; —pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin; —insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat; —nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane; —GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-l1H-pyrazole-3-carbothioic acid amide; macrocyclic lactone insecticides: abamectin, emamectin, milbemectin, lepimectin, spinosad, spinetoram; -mitochondrial electron transport inhibitor (METI) I acaricides: fenazaquin, pyrida-ben, tebufenpyrad, tolfenpyrad, flufenerim; —METI II and III compounds: acequinocyl, fluacyprim, hydramethylnon; —Uncouplers: chlorfenapyr; —oxidative phosphorylation inhibitors: cyhexatin, diafenthiuron, fenbutatin oxide, propargite; —moulting disruptor compounds: cryomazine; mixed function oxidase inhibitors: piperonyl butoxide; sodium channel blockers: indoxacarb, metaflumizone; —others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon; —other insecticides and nematicides: broflanilide, cyclaniliprole, sulfoxaflor, flupyradifurone, amitraz, pyrimidifen, cyantraniliprole, fluazaindolizine, tetraniliprole, and tioxazafen.

J) Biological control agent:—bacteria genus: Actinomycetes, *Agrobacterium, Arthrobacter, Alcaligenes, Aureobacterium, Azobacter, Bacillus, Beyerinckia, Bradyrhizobium, Brevibacillus, Burkholderia, Chromobacterium, Clostridium, Clmavibacter, Comamonas, Corynebacterium, Curtobacterium, Enterobacter, Flavobacterium, Gluconobacter, Hydrogenophage, Klebsiella, Metarhizium, Methylobacteriumr, Paenibacillus, Pasteuria, Photorhabdus, Phyllobacterium, Pseudomonas, Rhizobium, Serratia, Sphingobacterium, Stenotrophomonas, Streptomyces, Variovax,* and *Xenorhabdus*; —fungi genus: *Alternaria, Ampelomyces, Aspergillus, Aureobasidium, Beauveria, Colletotrichum, Coniothyrium, Gliocladium, Metarhizium, Muscodor, Paecilomyces, Penicillium, Trichoderma, Typhula, Ulocladium,* and *Verticillium*; —plant growth activators or plant defense agents: harpin, *Reynoutria sachalinensis*, jasmonate, lipochitooligosaccharides, salicylic acid, and isoflavones.

The present invention furthermore relates to agrochemical compositions comprising a mixture of at least one provided compound (component 1) and at least one further active substance useful for plant protection, e.g. selected from the groups A) to J) (component 2), in particular one further fungicide, e.g. one or more fungicide from the groups A) to F), as described above, and if desired one suitable solvent or solid carrier. Those mixtures are of particular interest, since many of them at the same application rate show higher efficiencies against harmful fungi. Furthermore, combating harmful fungi with a mixture of a provided compound and at least one fungicide from groups A) to F), as described above, is more efficient than combating those fungi with a provided compound alone or fungicides from groups A) to F) alone. By applying a provided compound together with at least one active substance from groups A) to J) a synergistic effect can be obtained, i.e. more than simple addition of the individual effects is obtained (synergistic mixtures).

According to this invention, applying a provided compound together with at least one further active substance is to be understood to denote that at least one provided compound and at least one further active substance occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in a fungicidally effective amount. This can be obtained by applying a provided compound and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one provided compound (component 1) and one further active substance (component 2), e.g. one active substance from groups A) to J), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising a provided compound (component 1) and a first further active substance (component 2) and a second further active substance (component 3), e.g. two active substances from groups A) to J), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. For example, kits may include one or more fungicide component(s) and/or an adjuvant component and/or an insecticide component and/or a growth regulator component and/or an herbicide. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. In some embodiments, 50 to 500 liters of the ready-to-use spray liquor are applied per hectare of agricultural useful area. In some embodiments 100 to 400 liters of the ready-to-use spray liquor are applied per hectare. In some embodiments, the invention provides a kit for greenhouse application of a ready-to-use composition of the invention.

According to one embodiment, individual components of the composition according to the invention such as parts of a kit or parts of a binary or ternary mixture may be mixed by the user himself in a spray tank and further auxiliaries may be added, if appropriate (tank mix). In a further embodiment, either individual components of the composition according to the invention or partially premixed components, e.g. components comprising a provided compound and/or active substances from the groups A) to I), may be mixed by the user in a spray tank and further auxiliaries and additives may be added, if appropriate (tank mix).

In a further embodiment, either individual components of the composition according to the invention or partially premixed components, e.g. components comprising a provided compound and/or active substances from the groups A) to J), can be applied jointly (e.g. after tankmix) or consecutively.

In some embodiments, the invention provides a mixture comprising a provided compound (component 1) and at least one active substance selected from the strobilurins of group A) (component 2) and particularly selected from azoxystrobin, dimoxystrobin, fluoxastrobin, kresoxim-methyl, orysastrobin, picoxystrobin, pyraclostrobin and trifloxystrobin.

In some embodiments the invention provides a mixture comprising a provided compound (component 1) and at least one active substance selected from the carboxamides of group B) (component 2). In some embodiments, the carboxamide is selected from the group consisting of bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid and N-(3',4',5'-trifluorobiphenyl-2-yl)-3-difluoromethyl-1-methyl-1H-pyrazole-4-carboxamide.

In some embodiments, the invention provides a mixture comprising a provided compound (component 1) and at least one active substance selected from the azoles of group C) (component 2). In some embodiments, the azole is selected from the group consisting of cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

In some embodiments, the invention provides a mixture comprising a provided compound (component 1) and at least one active substance selected from the heterocyclic compounds of group D) (component 2). In some embodiments, the heterocyclic compounds of group D) are selected from the group consisting of fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen and 5-ethyl-6-octyl-[1,2,4]triazolo[1,5-a]pyrimidine-7-ylamine.

In some embodiments, the invention provides a mixture comprising a provided compound (component 1) and at least one active substance selected from the carbamates of group E) (component 2). In some embodiments, the carbamates are selected from the group consisting of mancozeb, metiram, propineb, thiram, iprovalicarb, benthiavalicarb and propamocarb.

In some embodiments the invention provides a mixture comprising a provided compound (component 1) and at least one active substance selected from the fungicides given in group F) (component 2). In some embodiments, the fungicides of group F) are selected from the group consisting of dithianon, fentin salts, such as fentin acetate, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone and spiroxamine.

In some embodiments the invention provides a mixture comprising a provided compound (component 1) and at least one active substance selected from the herbicides given in group H) (component 2). In some embodiments, the herbicides of group H) are selected from the group consisting of acetochlor, clethodim, dicamba, 1,5-dimethyl-6-thioxo-3-(2, 2,7-trifluoro-3,4-dihydro-3-oxo-4-prop-2-ynyl-2H-1,4-benzoxazin-6-yl)-1,3,5-triazinane-2,4-dione (trifludimoxazin), ethyl 2-((3-(2-chloro-4-fluoro-5-(3-methyl-2,6-dioxo-4-(trifluoromethyl)-2,3-dihydropyrimidin-1 (6H)-yl)phenoxy) pyridin-2-yl)oxy)acetate, flumioxazin, fomesafen, glyphosate, glufosinate, halauxifen, isoxaflutole, mesotrione, metolachlor, quizalofop, saflufenacil, sulcotrione, tembotrione, topramezone, and 2,4-D. In some embodiments, the herbicides of group H) are selected from the group consisting of chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, and pinoxaden.

In some embodiments the invention provides a mixture comprising a provided compound (component 1) and at least one active substance selected from the insecticides and nematicides given in group I) (component 2). In some embodiments, the insecticides and nematicides of group I) are selected from the group consisting of abamectin, aldicarb, aldoxycarb, bifenthrin, broflanilide, carbofuran, chlorantraniliprole, clothianidin, cyantraniliprole, cyclaniliprole, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, 3-phenyl-5-(2-thienyl)-1,2,4-oxadiazole, nitenpyram, oxamyl, permethrin, spinetoram, spinosad, spirodichlofen, spirotetramat, tefluthrin, tetraniliprole, thiacloprid, thiamethoxam, thiodicarb, and tioxazafen.

In some embodiments the invention provides a mixture comprising a provided compound (component 1) and at least one active substance selected from the biological control agents given in group J) (component 2). In some embodiments, the bacteria of biological control agents of group J) are selected from the group consisting of *Bacillus amyloliquefaciens, Bacillus cereus, Bacillus firmus, Bacillus, lichenformis, Bacillus pumilus, Bacillus sphaericus, Bacillus sublilis, Bacillus thuringiensis, Bradyrhizobium japonicum, Chromobacterium subtsugae, Metarhizium anisopliae, Pasteuria nishizawae, Pasteuria penetrans, Pasteuria usage, Pseudomonas fluorescens*, and *Streptomyces lydicus*. In some embodiments, the fungi of biological control agents of group J) are selected from the group consisting of *Beauveria bassiana, Coniothyrium minitans, Gliocladium virens, Muscodor albus, Paecilomyces lilacimis, Trichoderma polysporum*, and *Trichoderma virens*.

The active substances referred to as component 2, their preparation and their activity against harmful fungi is known in the art. In some embodiments these substances are commercially available. The compounds described by IUPAC nomenclature, their preparation and their fungicidal activity are also known in the art (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/1 1853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624; WO 12/030887).

The mixtures of active substances can be prepared as compositions comprising besides the active ingredients at least one inert ingredient by usual means, e.g. by the means given for a provided compound or composition thereof.

Concerning usual ingredients of such compositions reference is made to the explanations given for the compositions containing a provided compound.

The mixtures of active substances according to the present invention are suitable as fungicides, as is a provided compound. In some embodiments the mixtures and compositions of the present invention are useful for the protection of plants against a broad spectrum of phytopathogenic fungi. In some embodiments, the phytopathogenic fungi are from the classes of the Ascomycetes, Basidiomycetes, Deuteromycetes and Peronosporomycetes (syn. Oomycetes).

Antimycotic Uses

A provided compound or composition thereof is also suitable for treating diseases in men and animals, especially as antimycotics, for treating cancer and for treating virus infections. The term "antimycotic", as distinguished from the term "fungicide", refers to a medicament for combating zoopathogenic or humanpathogenic fungi, i.e. for combating fungi in animals, especially in mammals (including humans) and birds.

In some embodiments, the present invention provides a medicament comprising at least one provided compound or composition thereof and a pharmaceutically acceptable carrier.

In some embodiments, the invention relates to the use of a provided compound or composition thereof for preparing an antimycotic medicament; i.e. for preparing a medicament for the treatment and/or prophylaxis of infections with humanpathogenic and/or zoopathogenic fungi.

A provided compound or compositions thereof has fungicidal activity against organisms, including but not limited to, dermatophytes, including for example, *Trichophyton rubrum*, *Trichophyton interdigitale*, *Trichophyton verrucosum*, *Trichophyton mentagrophytes*, *Trichophyton megninii*, *Trichophyton tonsurans*, *Trichophyton schoenleinii*, *Trichophyton soudanense*, *Trichophyton violaceum*, *Fpidermophyton floccosum*, *Microsporum audouini*, *Microsporum canis*, *Microsporum distortum*, *Microsporum gypseum*; nondermatophyte molds including, for example, *Scopulariopsis* spp. including, for example, *Scolnlariopsis brevicaulis*, *Fusarium* spp including, for example, *Fusarium solani*, *Aspergillus* spp. including, for example, *Aspergillus flavus*, *Acremonium* spp. including, for example, *Acremonium hyalinum*, *Alternaria*, *Scytalidinum dimidiatum*, and *Scytalidinium hyalinum*; *Candida* spp. including, for example, *Candida albicans*, and *Candida parapsilosis*; *Malassezia* spp. including, for example, *Malassezia fürfür*; *Cryptococcus*; *Blastomyces*; *Histoplasma*; and *Sporothrix schenckii*.

In some embodiments, the present invention provides a method of treating a microbial infection in a subject, comprising: topically administering to a subject in need thereof a therapeutically effective amount of a provided compound or composition thereof useful in treating a microbial infection.

In some embodiments, administration of a provided compound or composition thereof reduces the number of microbes, preferably pathogenic microbes, in or on the mammal to which it is administered. The microbes that can be acted on by the present compositions are selected from the group consisting of fungi, molds, yeast and combinations thereof.

In some embodiments, the presently described subject matter relates to a method for treating a condition, disease or disorder in a subject, wherein the condition, disease or disorder is a fungal infection. In certain embodiments, the fungal infection is a fungal infection of the skin. In certain embodiments, the fungal infection is a fungal infection of the nail. In certain embodiments, the fungal infection is a fungal infection of the hair follicle.

In some embodiments, the presently described subject matter relates to the use of a provided compound or a composition thereof to treat a microbial infection in a subject by topically administering the compound or composition to the subject in need thereof.

In some embodiments, the presently described subject matter relates to the use of a provided compound or composition thereof to treat a fungal infection in a subject by topically administering the compound or composition to the subject in need thereof.

In some embodiments, the presently described subject matter relates to the use of an antifungal agent or a pharmaceutically salt thereof in the manufacture of a medicament for the treatment of a fungal infection.

In some embodiments, the presently described subject matter relates to the use of a provided compound or composition thereof in the manufacture of a medicament for the treatment of a fungal infection.

In some embodiments, conditions treated by administration of a provided compound or composition thereof include superficial fungal infections of the skin that appear on the outer layer of skin and can cause Tinea cruris (jock itch), Tinea corporis (ringworm), Tinea pedis, interdigital Tinea pedis, moccasin-type Tinea pedis, Tinea manuum, Tinea versicolor (piyriasis), Tinea nigra, cutaneous candidiasis, Tinea faciei (facial ringworm), and white and black *piedra*.

Tinea corporis (body ringworm), Tinea cruris (jock itch), and Tinea faciei (facial ringworm), may be caused by *Epidermophyton floccosum*, *Microsporum canis*, *Trichophyton mentagrophytes*, *T rubrum*. *T. tonsurans*, *T. verrucosum*, and/or *T. violaceum*, and are treatable by the administration of a provided compound or composition thereof.

Tinea pedis (athlete's foot) or Tinea manuum (fungal infection of the hand), which may be caused *Epidermophylon floccosum*, *Microsporum canis*, *Trichophylon mentagrophytes*, *T. rubrum*, *T. tonsurans*, *T. verrucosum*, and/or *T. violaceum*, are treatable by the administration of a provided compound or composition thereof.

Cutaneous candidiasis, which may be caused by *Candida albicans*, may also be treatable by the administration of a provided compound or composition thereof.

A provided compound or composition thereof has fungicidal activity against multiple organisms. Accordingly, the administration of the present compositions may treat, for example, superficial fungal infections of the skin related to or caused by *Epidermophyton floccosum, Microsporum canis, Microsporum gvpseum, Trichophyton mentagrophvtes, T. interdigitale, T. rubrum, T. soudanense, T. tolasurans, T. verrucosum, T. violaceum*, and *Candida albicans*.

In some embodiments, the present subject matter also relates to a method of treating and/or preventing a fungal infection of the hair follicle, including for example, one or more of Tinea capitis, Tinea favosa, and Tinea barbae, in a mammal comprising administering to a mammal in need thereof an effective amount a provided compound or composition thereof.

In some embodiments, conditions treated by administration of a provided compound or composition include Tinea capitis and/or Tinea favosa and/or Tinea barbae.

Tinea capitis and/or Tinea favosa and/or Tinea barbae are treatable by the administration of a provided compound or composition thereof.

Tinea capitis is a superficial fungal infection (dermatophytosis) of the skin of the scalp, eyebrows, and eyelashes that attacks the hair shaft and follicles. The disease is primarily caused by dermatophytes in the *Trichophyton* and *Microsporum* genera, including for example, *Microsporum audouini, Microsporum canis. Microsporum distortum, Aiicrosporum gypseum, Trichophyton megninii, Trichophyton mentagrophytes, Trichophyton rubrum, Trichophyton schoenleinii, Trichophyton tonsurans*, and *Trichophyton verrucosum*. The clinical presentation is typically a single or multiple patches of hair loss, sometimes with a 'black dot' pattern (often with broken-off hairs), that may be accompanied by inflammation, scaling, pustules, and itching. Tinea favosa can be considered a variety of Tinea capitis because it involves the scalp. Tinea favosa is primarily caused by dermatophytes in the *Trichophyton* and *Microsporum* genera, including for example, *Microsporum gpseum* and *Trichophylon schoenleinii*. Tinea barbae is a superficial dermatophytosis that is limited to the bearded areas of the face and neck and occurs almost exclusively in older adolescent and adult males. The clinical presentation of Tinea barbae includes inflammatory, deep, kerion-like plaques and non-inflammatory superficial patches resembling Tinea corporis or bacterial folliculitis. The mechanism that causes Tinea barbae is similar to that of Tinea capitis, and is frequently the result of a *Trichophyton rubrum* (*T. rubrum*) infection but may also be the result of *Trichophyton mentagrophytes* var *granulosum* and *Trichophylon verrucasum*. Finally *Microsporum canis* and *Trichophyton mentagrophytes* var *erinacei* have been known to cause Tinea barbae but are relatively rare.

Tinea capitis which may be caused by one or more of *Microsporum audoumni, Microsporum canis, Microsporum distortum, Microsporum gypseum, Trichophylon megninii, Trichophyton mentagrophytes, Trichophyton rubrum, Trichophyton schoenleinii, Trichophyton tonsurans*, and/or *Trichophyton verrucosum*, and Tinea favosa which may be caused by one or more of *Microsporum gypseum* and/or *Trichophyton schoenleinii*, and Tinea barbae which may be caused by one of more of *Trichophyton rubrum* (*T. rubrum*), *Trichophyton menlagrophytes* var *granulosum, Trichophyton verrucosum, Microsporum canis* and *Trichophyton mentagrophytes* var *erinacei*, are treatable by the administration of a provided compound or composition thereof.

A provided compound or a pharmaceutically acceptable salt thereof has fungicidal activity against multiple organisms. Accordingly, the administration of the present compositions may treat, for example, conditions related to or caused by *Microsporumr audouini, Microsporum canis, Microsporum distortum*, AMicrosporum *gypseum, Trichophyton megninii, Trichophyton mentagrophytes* var *granulosum, Trichophyton mentagrophytes* var *erinacei, Trichophyton rubrum, Trichophyton schoenleinii, Trichophyton tonsurans*, and/or *Trichophyton verrucosum*.

In some embodiments, the present subject matter relates to a method of treating and/or preventing onychomycosis in a subject comprising administering to a subject in need thereof an effective amount a provided compound or composition thereof.

Non-limiting conditions that are treated by the administration of a provided compound or composition thereof, include onychomycosis including onychomycosis caused by one or more of dermatophytes, yeasts (candidal onychomycosis), and non-dermatophyte molds.

Onychomycosis is treatable by the administration of a provided compound or composition thereof.

Onychomycosis is a fungal infection of the nail bed, matrix, and/or or nail plate. It is caused by 3 main classes of fungi: dermatophytes, yeasts (candidal onychomycosis), and nondermatophyte molds. Dermatophytes are the most common cause of onychomycosis, but onychomycosis caused by non-dermatophyte molds is becoming more common worldwide. Onychomycosis due to *Candida* is less common. Dermatophytes that can cause onychomycosis include one or more of *Trichophyton rubrum, Trichophyton interdigitale, Epidermophyton floccosum, Trichophyton violaceum, Microsporum gjseum, Trichophyton tonsurans, Trichophyton soudanense*, and *Trichophyton verrucosum*, and dermatophyte associated onychomycosis is often also referred to as tinea ungium. Candidal onychomycosis include cutaneous candidisis and mucocutaneous candidiasis that are caused by one or more *Candida* species, including for example, *Candida albicans* and *Candida parapsilosis*. Non-dermatophyte molds that can cause onychomycosis can include one or more of, for example, *Scopulariopsis brevicaulis, Fusarium* spp., *Aspergillus* spp., *Alternaria, Acremonium, Scytalidinum dimidiatum*, and *Scytalidinium hyalinum*.

There are four classic types of onychomycosis including the following: distal subungual onychomycosis (DLSO) that is the most common form of onychomycosis, and is usually caused by *Trichophyton rubrum* and/or *Trichophyton interdigitale*, which invades the nail bed and the underside of the nail plate; white superficial onychomycosis (WSO) is caused by fungal (e.g., *T. mentagrophytes*) invasion of the superficial layers of the nail plate to form "white islands" on the plate, nondermatophyte molds cause deep white superficial onychomycosis; proximal subungual onychomycosis (PSO) is fungal penetration of the newly formed nail plate through the proximal nail fold and it is the least common form of onychomycosis in healthy people, but is found more commonly when the patient is immunocompromised; endonyx onychomycosis (EO), and candidal onychomycosis (CO) which is *Candida* species invasion of the fingernails.

A provided compound or composition thereof has fungicidal activity against multiple organisms. Accordingly, the administration of a provided compound or composition may treat, for example, conditions, including for example, onychomycosis, related to or caused by one or more dermatophytes, including for example, *Trichophyton rubrum, Trichophyton interdigitale, Fpidermophyton floccosum, Trichophyton violaceum, Microsporum gypseum, Trichophyton tonsurans, Trichophyton soudanense*, and *Trichophyton verrucosum*; caused by one or more *Candida* species, including for example, *Candida albicans* and *Candida parapsilosis*; and/or caused by one or more molds, including for example, *Scopulariopsis brevicaulis*, a *Fusarium* spp., a *Aspergillus* spp., *Alternaria, Acremonium, Scytalidinum dimidiatum*, and *Scytalidinium hyalinm*.

In some embodiments, the present invention provides a provided compound or composition thereof, wherein the composition is combined with a physical/mechanical penetration enhancer that, for example, acts by increasing permeability by reversibly damaging or altering the physicochemical nature of the stratum corneum or nail surface to reduce its diffusional resistance. Such mechanical enhancement can include those known in the art such as manual and electrical nail abrasion, acid etching, ablation by laser, microporation, iontophoresis, or application of low-frequency ultrasound, heat or electric currents on/through the nail or skin to make the diffusion of topical moieties more efficient.

A provided compound or compositions thereof can be topically administered in any formulation, including a gel. A sufficient amount of the topical preparation can be gently rubbed onto the affected area and surrounding skin, for example, in an amount sufficient to cover an affected area plus a margin of healthy skin or tissue surrounding the affected area, for example, a margin of about 0.5 inches. A provided composition can be applied to any body surface, including for example, a skin surface, scalp, eyebrows, eyelashes, bearded areas, nail surface, nail bed, nail matrix, and nail fold, as well as to the mouth, vagina, eye, nose, or other mucous membranes.

For most superficial fungal infections of the skin, a provided compound or composition thereof can be applied in a single, one-time application, once a week, once a bi-week, once a month, or from one to four times daily, for a period of time sufficient to alleviate symptoms or clear the fungal infection, for example, for a period of time of one week, from 1 to 12 weeks or more, from 1 to 10 weeks, from 1 to 8 weeks, from 2 to 12 weeks, from 2 to 10 weeks, from 2 to 8 weeks, from 2 to 6 weeks, from 2 to 4 weeks, from 4 to 12 weeks, from 4 to 10 weeks, from 4 to 8 weeks, from 4 to 6 weeks. A provided compound or composition thereof can be administered, for example, at a frequency of once per day or twice per day. A provided compound or composition thereof can be topically administered once per day for a period of time from 1 week to 8 weeks, from 1 week to 4 weeks, for 1 week, for 2 weeks, for 3 weeks, for 4 weeks, for 5 weeks, for 6 weeks, for 7 weeks, or for 8 weeks.

A provided compound or compositions thereof can be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24 hour period), can include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In certain severe cases, for example, of Tinea pedis and/or Tinea cruris, a maximum per application, per affected area, dose of 8 grams of the presently described composition can be applied to an affected area, for example, once or twice daily.

For example, generally for Tinea corporis or Tinea cruris or Tinea faciei, the present composition can be applied, for example once or twice daily, for example, morning and evening, for about 2-4 weeks. Generally for Tinea pedis application the present composition can be applied once daily, for 2 weeks or longer. For example, a provided compound or composition thereof can be topically applied in an amount sufficient to cover an affected area plus a margin of healthy skin or tissue surrounding the affected area, for example, a margin of about 0.5 inches, at a frequency, for example, of once a day, for a time period, for example of about two weeks.

If desired, other therapeutic agents can be employed in conjunction with a provided compound or composition thereof. The amount of pharmaceutically active ingredients that may be combined with the carrier materials to produce a single dosage form will vary depending upon the host treated, the nature of the disease, disorder, or condition, and the nature of the active ingredients.

In some embodiments, a provided compound or pharmaceutical composition thereof is given in a single or multiple doses per time period, for example, daily, weekly, bi-weekly, or monthly. For example, in some embodiments, a provided compound or pharmaceutical composition thereof is given from one to four times per period.

In some embodiments, for superficial fungal infections of the skin, a provided compound or composition thereof is given once per week, for a period of from one to six weeks, for example for one week, for two weeks, for three weeks, for four weeks, five weeks, or for six weeks.

In some embodiments, for onychomycosis infections, a provided compound or composition thereof is applied at a frequency of from one to four times daily, including for example, once daily, twice daily, three times daily, or four times daily, one a daily or weekly basis, or on a monthly or every other month schedule, for a period of time sufficient to alleviate symptoms or clear the fungal infection, for example, for a period of time from 1 to 52 weeks, from 1 to 26 weeks, from 26 to 52 weeks, from 13 to 39 weeks, from 20 to 40 weeks, from 20 to 48 weeks, from 5 to 50 weeks, from 10 to 45 weeks, from 15 to 40 weeks, from 20 to 35 weeks, from 25 to 30 weeks, for about 30 weeks; from 28 weeks to 50 weeks, from 30 week to 48 weeks, from 32 to 46 weeks, from 34 to 44 weeks, from 36 to 42 weeks, from 38 to 40 weeks, from 2 to 24 weeks, from 2 to 22 weeks, from 2 to 20 weeks, from 2 to 18 weeks, from 2 to 16 weeks, from 2 to 14 weeks, from 2 to 12 weeks, from 2 to 10 weeks, from 2 to 8 weeks, from 2 to 6 weeks, from 2 to 4 weeks, from 10 to 48 weeks, from 12 to 48 weeks, from 14 to 48 weeks, from 16 to 48 weeks, from 18 to 48 weeks, from 20 to 48 weeks, from 22 weeks to 48 weeks, from 24 week to 48 weeks, from 26 to 48 weeks, from 28 to 48 weeks, from 30 to 48 weeks, from 32 to 48 weeks, from 34 to 48 weeks, from 34 to 48 weeks, from 36 to 48 weeks, from 38 to 48 weeks, from 40 to 48 weeks, from 42 to 48 weeks, from 44 to 48 weeks, from 46 to 48 weeks, for 1 weeks, for 2 weeks, for 4 weeks, for 6 weeks, for 8 weeks, for 10 weeks, for 12 weeks, for 24 weeks, for 26 weeks, for 28 weeks, for 30 weeks, for 32 weeks, for 34 weeks, for 36 weeks, for 38 weeks, for 40 weeks, for 42 weeks, for 44 weeks, for 46 weeks, for 48 weeks, for 50 weeks, for 50 weeks, or for 52 weeks. For example, the present compositions can be topically administered, at a frequency of once per day for a period of time from 1 week to 52 weeks, for example for about from 24 weeks to 48 weeks.

In some embodiments, for onychomycosis infections the presently described compositions are applied in a therapeutically effective amount, for example, an amount sufficient to cover an affected area plus a margin of healthy skin and/or nail surrounding the affected area, for example, a margin of about 0.1 to about 0.5 inches. Suitable amounts, for example, per application per affected area or cumulative daily dosage per affected area (one or more nails and, for example, one or two applications in a 24 hour period), can include, for example, from about 0.1 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In certain onychomycosis cases, a maximum per application, per affected area, dose of 8 grams of a provided compound or composition thereof is applied to an affected area (all nails), for example, once or twice daily. In some embodiments, a provided compound or composition thereof is applied, for example once or twice daily, for example, morning and/or evening, for about 1-52 weeks. For example, in some embodiments, a provided compound or composition thereof is topically applied in an amount sufficient to cover an affected area plus a margin of healthy skin and/or nail surrounding the affected area, for example, a margin of about 0.1 to about 0.5 inches, at a frequency, for example, of once a day, for a time period, for example of about 24 to about 48 weeks.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

EXPERIMENTAL PROCEDURES

Example 1: Synthesis of (R)-2-(I-(2-(5-fluoro-2-methoxyphenyl)-2-isopropoxyethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-1

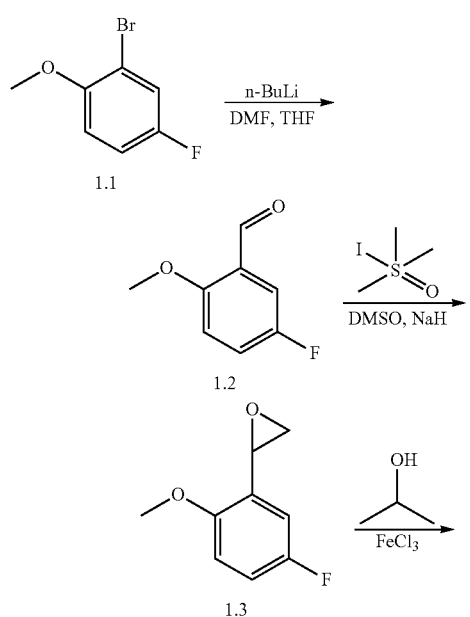

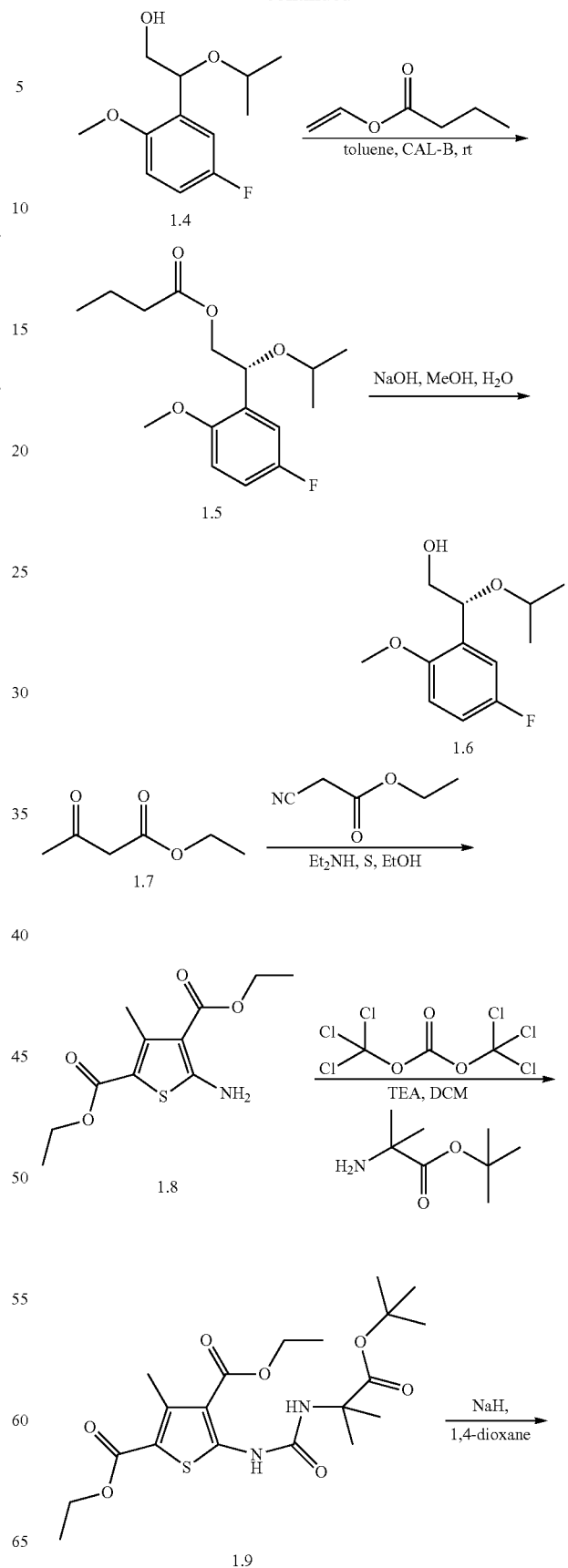

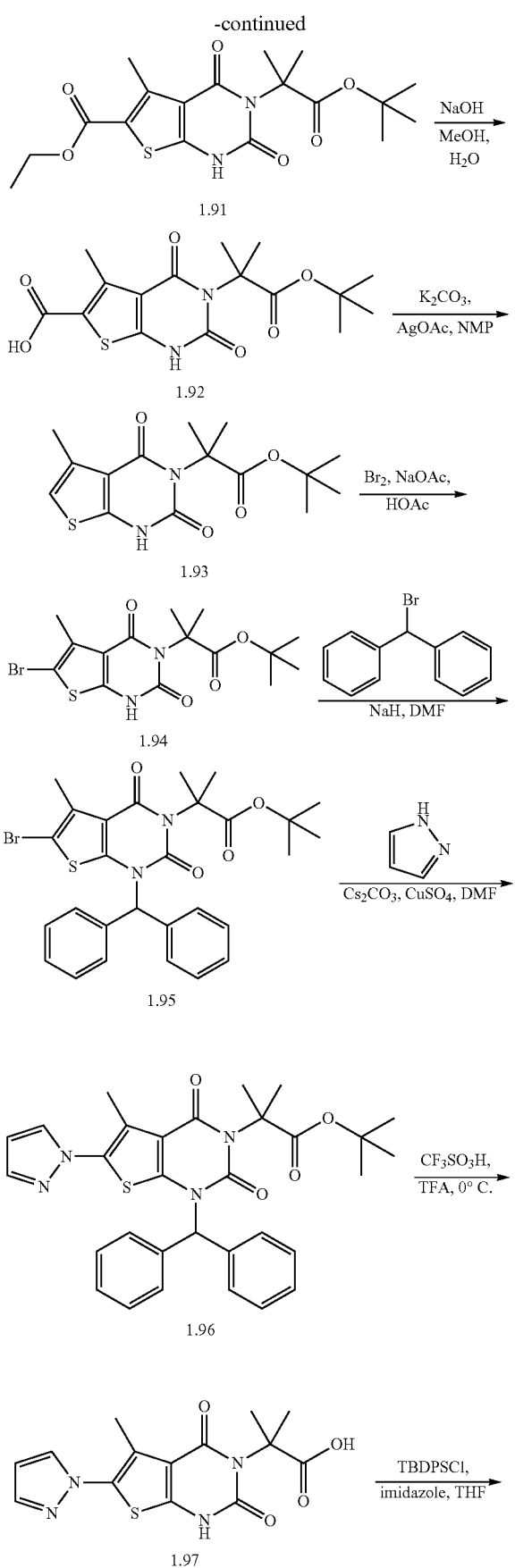
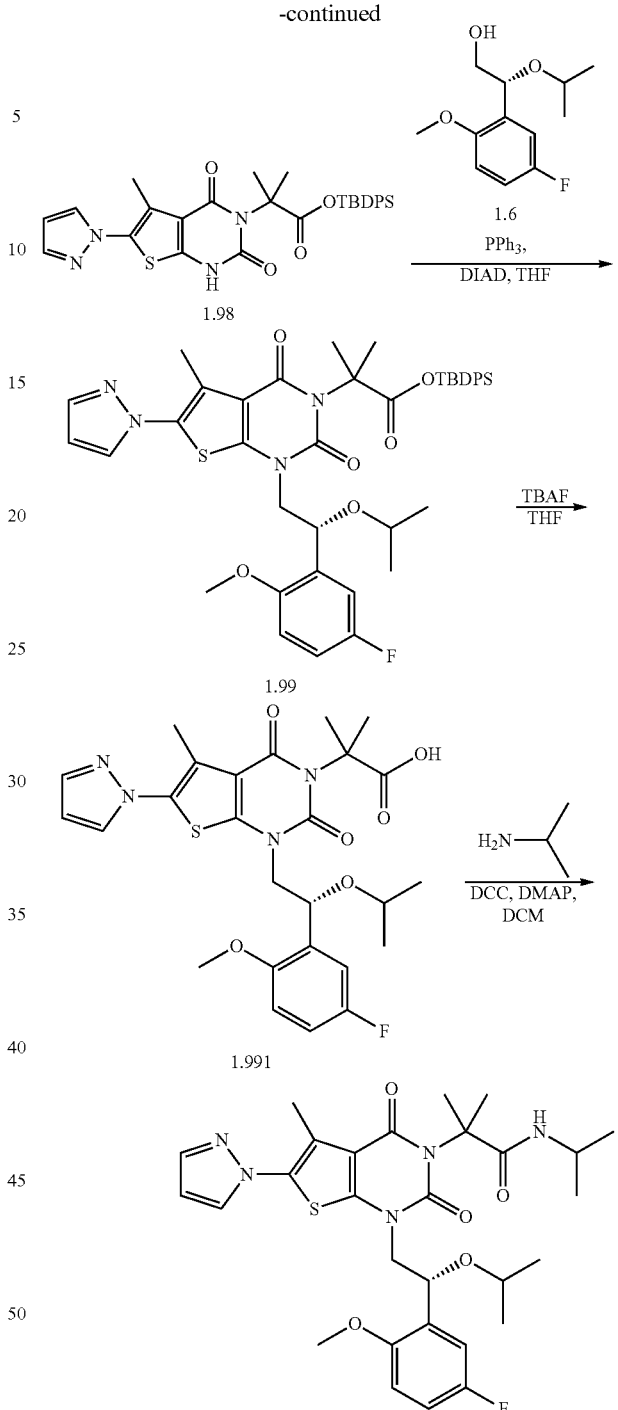

Synthesis of Compound 1.2.

Into a 3000-mL 3-necked round-bottomed flask under nitrogen, was placed 1.1 (100 g, 487.75 mmol, 1.00 equiv), THF (1.5 L). This was followed by the addition of n-BuLi (215.6 mL) dropwise with stirring at −78° C. The resulting solution was stirred for 1 hour at −78° C. To this was added DMF (71.54 g, 978.79 mmol, 2.01 equiv) dropwise with stirring at −78° C. The reaction was stirred for 1 h at room temperature, and then quenched by the addition of 800 mL of NH₄Cl (aq.). The resulting solution was extracted with 500 mL of ethyl acetate, organic layers combined and concentrated under vacuum. The crude was purified by column chromatography to furnish 65.7 g (87%) of 1.2 as a light yellow solid.

Synthesis of Compound 1.3.

Into a 2000-mL 3-necked round-bottomed flask under nitrogen, was placed DMSO (700 mL), NaH (20.48 g, 512.00 mmol, 1.20 equiv, 60%). The reaction was stirred for 1 h at 40° C. This was followed by the addition of S,S-dimethylmethanesulfinyl iodide (112.64 g, 511.83 mmol, 1.20 equiv) in several batches. To this was added 1.2 (65.7 g, 426.24 mmol, 1.00 equiv) dropwise with stirring at 15° C. The reaction was stirred for 1 h at room temperature, then quenched by the addition of 600 mL of $NH_4Cl$ (aq.). The resulting solution was extracted with 600 mL of ethyl acetate and the organic layers combined. The resulting mixture was washed with 2×400 mL of water, 500 mL of brine, dried and concentrated to provide 40 g (56%) of 1.3 as light brown oil.

Synthesis of Compound 1.4.

Into a 1000-mL 3-necked round-bottomed flask, was placed $FeCl_3$ (11.978 g, 73.85 mmol, 0.10 equiv), propan-2-ol (223.2 g, 3.71 mol, 5.00 equiv). This was followed by the addition of 1.3 (125 g, 743.32 mmol, 1.00 equiv) dropwise with stirring at 0° C. The reaction was stirred for 2 h at room temperature, then quenched by the addition of 400 mL of water. The resulting solution was extracted with 2×300 mL of EtOAc, organic layers combined and concentrated under vacuum. The crude was purified by column chromatography to furnish 48 g (28%) of 1.4 as colorless oil.

Synthesis of Compound 1.5.

Into a 500-mL 3-necked round-bottomed flask, was placed 1.4 (48 g, 210.29 mmol, 1.00 equiv), toluene (250 mL), ethenyl butanoate (14.478 g, 126.84 mmol, 0.60 equiv), CAL-B (720 mg). The resulting solution was stirred for 3 h at room temperature. The solids were filtered out. The resulting mixture was concentrated under vacuum. The crude was purified by column chromatography to furnish 28.5 g (45%) of 1.5 as colorless oil.

Synthesis of Compound 1.6.

Into a 500-mL 3-necked round-bottomed flask, was placed 1.5 (21.8 g, 73.07 mmol, 1.00 equiv), methanol (300 mL), water (150 mL), NaOH (5.84 g, 146.01 mmol, 2.00 equiv). The reaction was stirred for 30 min at room temperature. The pH value of the solution was adjusted to 7 with AcOH. The resulting mixture was concentrated under vacuum, extracted with 3×100 mL of EtOAc and the organic layers were combined. The crude was purified by column chromatography to furnish 16 g (96%) of 1.6 as colorless oil Synthesis of Compound 1.8.

Into a 2000-mL round-bottomed flask was placed a solution of 1.7 (320 g, 2.46 mol, 1.00 equiv) in ethanol (600 mL), sulfur (80 g, 1.00 equiv), and ethyl 2-cyanoacetate (280 g, 2.48 mol, 1.00 equiv). This was followed by the addition of morpholine (235 g, 1.00 equiv) dropwise with stirring at 45° C. in 30 min. The reaction was stirred for 5 h at 60° C. The solids were filtered out. The solution was diluted with 3000 mL of $H_2O$. The solids were collected by filtration and the filter cake was washed with 1 L of EtOH (30%) to provide 380 g (60%) of 1.8 as a yellow solid.

Synthesis of Compound 1.9.

Into a 2000-mL 3-necked round-bottomed flask purged and maintained with an inert atmosphere of nitrogen, was placed 1.8 (200 g, 777.28 mmol, 1.00 equiv), $CH_2Cl_2$ (1000 mL). This was followed by the addition of ditrichloromethyl carbonate (76.9 g, 259.14 mmol, 0.33 equiv) with stirring at 0° C. This was followed by the addition of $Et_3N$ (314 g, 3.10 mol, 3.99 equiv) dropwise with stirring at 0° C. in 2 h. The resulting solution was stirred for 3 h at 0° C. To this was added tert-butyl 2-amino-2-methylpropanoate (152 g, 776.70 mmol, 1.00 equiv) at 0° C. The reaction was stirred overnight at room temperature, then quenched by the addition of 1 L of water. The resulting mixture was concentrated under vacuum. The crude product was re-crystallized to provide 105 g (31%) of 1.9 as a yellow solid.

Synthesis of Compound 1.91.

Into a 1-L 3-necked round-bottomed flask under nitrogen nitrogen, was placed 1.9 (42 g, 94.91 mmol, 1.00 equiv), 1,4-dioxane (400 mL). This was followed by the addition of NaH (5.7 g, 142.50 mmol, 1.50 equiv) at 10° C. The reaction was stirred for 2 h at 110° C., then quenched by the addition of 500 mL of NH4Cl (aq.). The resulting solution was extracted with 3×200 mL of EtOAc and the organic layers combined and concentrated under vacuum. The crude product was re-crystallized to provide 24.4 g (65%) of 1.91 as a white solid.

Synthesis of Compound 1.92.

Into a 500-mL 3-necked round-bottomed flask, was placed 1.91 (24.4 g, 61.54 mmol, 1.00 equiv), NaOH (12.2 g, 305.00 mmol, 4.96 equiv), water (20 mL), methanol (250 mL). The resulting solution was stirred for 4 h at 50° C. The resulting mixture was concentrated under vacuum. The pH value of the solution was adjusted to 2 with HCl (10%). The reaction was extracted with 3×300 mL of EtOAc, organic layers were combined and dried over anhydrous sodium sulfate and concentrated under vacuum to provide 19.4 g (86%) of 1.92 as a white solid.

Synthesis of Compound 1.93.

Into a 1-L 3-necked round-bottomed flask, was placed 1.92 (19.4 g, 52.66 mmol, 1.00 equiv), $K_2CO_3$ (8.7 g, 62.95 mmol, 1.20 equiv), $CH_3COOAg$ (10.5 g) and NMP (400 mL). The reaction was stirred for 2 h at 110° C. The reaction was then quenched by the addition of 1 L of water. The resulting solution was extracted with 5×200 mL of EtOAc, organic layers combined and concentrated under vacuum. The crude was purified by column chromatography to furnish 15.3 g (90%) of 1.93 as a white solid.

Synthesis of Compound 1.94.

Into a 1000-mL 3-necked round-bottomed flask, was placed 1.93 (15.3 g, 47.16 mmol, 1.00 equiv), $CH_3COONa$ (8.5 g, 103.66 mmol, 2.20 equiv), acetic acid (300 ml). This was followed by the addition of $Br_2$ (8.3 g, 51.94 mmol, 1.10 equiv) dropwise with stirring. The reaction was stirred for 1 h at room temperature. The resulting mixture was washed with 500 mL of $H_2O$ and concentrated under vacuum to provide 17 g (89%) of 1.94 as a white solid.

Synthesis of Compound 1.95.

Into a 500-mL 3-necked round-bottomed flask purged and maintained with an inert atmosphere of nitrogen, was placed 1.94 (13 g, 32.23 mmol, 1.00 equiv), DMF (200 mL). This was followed by the addition of NaH (1.52 g, 1.18 equiv, 60%) dropwise with stirring in 1 h. To this was added [bromo(phenyl)-methyl]benzene (9.348 g, 37.83 mmol, 1.17 equiv). The reaction was stirred overnight at room temperature, then quenched by the addition of saturated aqueous $NH_4Cl$, extracted with 2×200 mL of EtOAc. Organic layers were combined and concentrated under vacuum. The crude was purified by column chromatography to furnish 17 g (93%) of 1.95 as a yellow solid.

Synthesis of Compound 1.96.

Into a 100-mL round-bottom flask under nitrogen, was placed 1.95 (2 g, 3.51 mmol, 1.00 equiv), 1H-pyrazole (10 g, 146.89 mmol, 41.83 equiv), $CuSO_4$ (2 g), $Cs_2CO_3$ (4 g, 12.28 mmol, 3.50 equiv), DMF (40 mL), 2-pyridinecarboxylic acid (1 g). The reaction was stirred overnight at 130° C. in an oil bath. The resulting mixture was diluted with 200 mL of $H_2O$, extracted with 2×200 ml of EtOAc and the organic layers combined and concentrated under vacuum. The crude was purified by column chromatography to furnish 500 mg (26%) of 1.96 as a yellow solid.

Synthesis of Compound 1.97.

Into a 100-mL round-bottomed flask, was placed a solution of 1.96 (500 mg, 0.90 mmol, 1.00 equiv) in trifluoroacetic acid (5 mL). This was followed by the addition of trifluoromethanesulfonic acid (384 mg, 2.56 mmol, 1.00 equiv). The resulting solution was stirred for 3 h at room temperature. The reaction was then quenched by the addition of 50 mL of water, and then extracted with 2×50 mL of EtOAc. The organic layers were combined and concentrated under vacuum to provide 1 g (crude) of 1.97 as a white solid.

Synthesis of Compound 1.98.

Into a 50-mL round-bottomed flask, was placed 1.97 (1 g, 2.99 mmol, 1.00 equiv), THF (10 mL), TBDPSCl (1.64 g, 2.00 equiv), imidazole (407 mg, 2.00 equiv). The reaction was stirred for 2 h at room temperature. The resulting mixture was concentrated under vacuum. The crude was purified by column chromatography to furnish 650 mg (38%) of 1.98 as a white solid.

Synthesis of Compound 1.99.

Into a 50-mL 3-necked round-bottomed flask under nitrogen, was placed 1.98 (650 mg, 1.13 mmol, 1.00 equiv), THF (10 mL), 1.6 (310 mg, 1.36 mmol, 1.2 equiv), DIAD (458 mg, 2.26 mmol, 2.00 equiv), and PPh$_3$ (594 mg, 2.26 mmol, 2.00 equiv). The reaction was stirred overnight at room temperature. The resulting mixture was concentrated under vacuum. The crude was purified by column chromatography to furnish 500 mg (57%) of 1.99 as a white solid.

Synthesis of Compound 1.991.

Into a 50-mL round-bottomed flask, was placed 1.99 (500 mg, crude), TBAF (500 mg) and THF (20 mL). The reaction was stirred overnight at room temperature. The resulting mixture was concentrated under vacuum. The crude was purified by column chromatography to furnish 200 mg of 1.991 as a white solid.

Synthesis of Compound I-1.

Into a 50-mL round-bottomed flask, was placed 1.991 (200 mg, 0.37 mmol, 1.00 equiv), propan-2-amine (44 mg, 0.74 mmol, 2.03 equiv), DCC (228 mg, 1.11 mmol, 3.01 equiv), 4-dimethylaminopyridine (90 mg, 0.74 mmol, 2.01 equiv), and CH$_2$Cl$_2$ (10 mL). The reaction was stirred overnight at 50° C. The resulting mixture was concentrated under vacuum. The crude was purified by column chromatography to furnish 101.5 mg (47%) of I-1 as a white solid. LC-MS (ES, m/z): [M-C$_4$NOH$_8$]$^+$ 527, [M+Na]$^+$ 608; $^1$H NMR (300 MHz, DMSO-d$_6$): δ 0.96-1.03 (m, 12H), 1.61-1.64 (d, 6H), 2.30 (s, 3H), 3.40-3.48 (m, 1H), 3.70 (s, 3H), 3.75-4.00 (m, 3H), 5.12-5.16 (t, 1H), 6.56 (t, 1H), 6.93-7.00 (m, 1H), 7.06-7.27 (m, 3H), δ 7.80 (s, 1H), 8.10 (s, 1H).

Example 2: Synthesis of (R)-1-(2-(5-fluoro-2-methoxyphenyl)-2-isopropoxyethyl)-5-methyl-3-(2-methyl-1-oxo-1-(piperidin-1-yl)propan-2-yl)-6-(1H-pyrazol-1-yl)thieno[2,3-d]pyrimidine-2,4(1H,3H)-dione, I-2

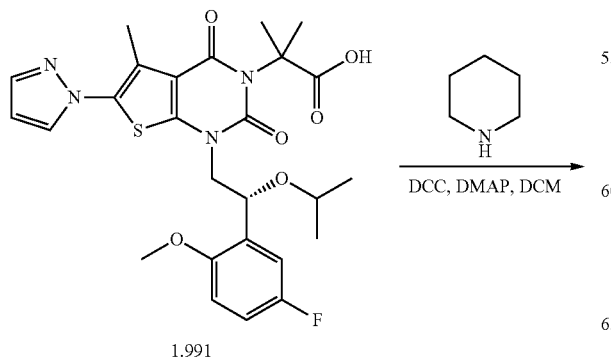

1.991

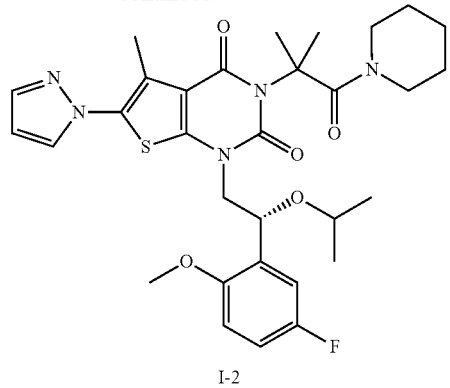

I-2

Into a 50-mL round-bottomed flask, was placed 1.991 (200 mg, 0.37 mmol, 1.00 equiv), DCC (151.5 mg, 0.73 mmol, 2.00 equiv), 4-dimethylaminopyridine (90 mg, 0.74 mmol, 2.01 equiv), piperidine (60 mg, 0.70 mmol, 1.92 equiv), and CH$_2$Cl$_2$ (20 mL). The reaction was stirred for 5 h at 50° C. The resulting mixture was concentrated under vacuum. The crude was purified by column chromatography to furnish 49 mg (22%) of I-2 as a white solid. LC-MS-PH (ES, m/z) [M-C$_5$NH$_{10}$]$^+$ 527, [M+Na]$^+$ 634; $^1$H NMR (400 MHz, DMSO-d$_6$): δ 0.99-1.03 (m, 6H), 1.30-1.80 (m, 12H), 2.35 (s, 3H), 3.10-3.35 (m, 4H), 3.48-3.53 (m, 1H), 3.79 (s, 3H), 3.90-4.30 (m, 2H), 5.20 (t, 1H), 6.60 (s, 1H), 6.98-7.05 (m, 1H), 7.12-7.28 (m, 2H), 7.82 (s, 1H), 8.19 (s, 1H).

Example 3: Synthesis of (R)-1-(2-(5-fluoro-2-methoxyphenyl)-2-isopropoxyethyl)-5-methyl-3-(2-methyl-1-morpholino-1-oxopropan-2-yl)-6-(1H-pyrazol-1-yl)thieno[2,3-d]pyrimidine-2,4(1H,3H)-dione, I-3

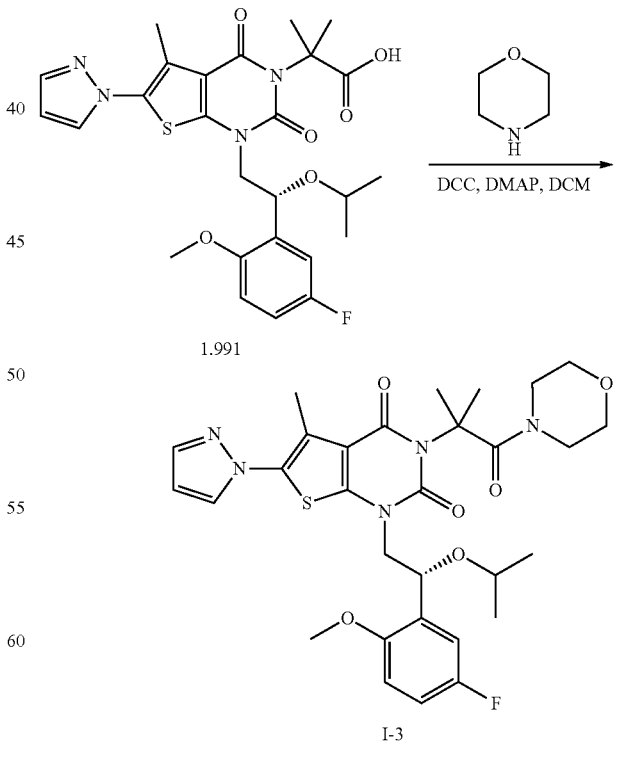

I-3

Compound I-3 was prepared from compound 1.991 and morpholine in 46% yield using similar procedure as described in Example 2. LC-MS (ES, m/z): [M+Na]+636; ¹H NMR (400 MHz, DMSO-$d_6$): δ 0.98-1.03 (m, 6H), 1.60-1.80 (d, 6H), 2.36 (s, 3H), 3.15-3.40 (m, 4H), 3.48-3.60 (m, 5H), 3.78 (s, 3H), 3.90-4.30 (m, 2H), 5.20 (t, 1H), 6.60 (s, 1H), 7.03-7.05 (m, 1H), 7.12-7.25 (m, 2H), 7.82 (s, 1H), 8.20 (s, 1H).

Example 4: Synthesis of (R)-2-(1-(2-(5-fluoro-2-methoxyphenyl)-2-((tetrahydro-2H-pyran-4-yl)oxy)ethyl)-5-methyl-2,4-dioxo-6-(1H-pyrazol-1-yl)-1,4-dihydrothieno[2,3-d]pyrimidin-3(2H)-yl)-2-methylpropanamide, I-4

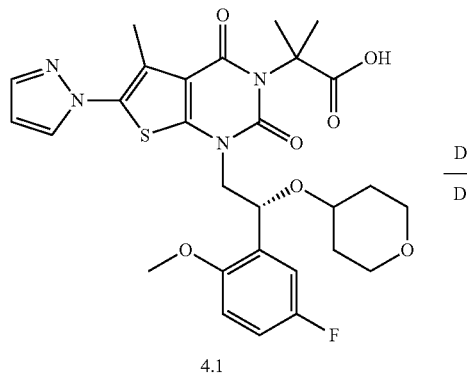

Compound I-4 was prepared in 65.4% yield from compound 4.1 and NH₄Cl using the procedure described in Example 2. LC-MS (ES, m/z): [M+Na]⁺ 608; ¹H NMR (300 MHz, DMSO-$d_6$): δ 8.13 (s, 1H), 7.80 (d, 1H), 7.22-7.18 (m, 1H), 7.15-7.11 (m, 1H), 7.09-6.97 (m, 1H), 6.90-6.60 (brs, 1H), 6.59-6.56 (t, 1H), 5.26-5.22 (m, 1H), 4.02-3.80 (m, 2H), 3.74 (s, 3H), 3.62-3.55 (m, 2H), 3.40-3.37 (m, 1H), 3.31-3.22 (m, 2H), 2.32 (s, 3H), 1.66-1.65 (m, 8H), 1.35-1.24 (m, 2H).

Example 5: Synthesis of 2-(1-((R)-2-(5-fluoro-2-methoxyphenyl)-2-(((s,4S)-4-hydroxycyclohexyl)oxy)ethyl)-5-methyl-2,4-dioxo-6-(1H-pyrazol-1-yl)-1,4-dihydro-thieno[2,3-d]pyrimidin-3(2H)-yl)-2-methylpropanamide, I-5

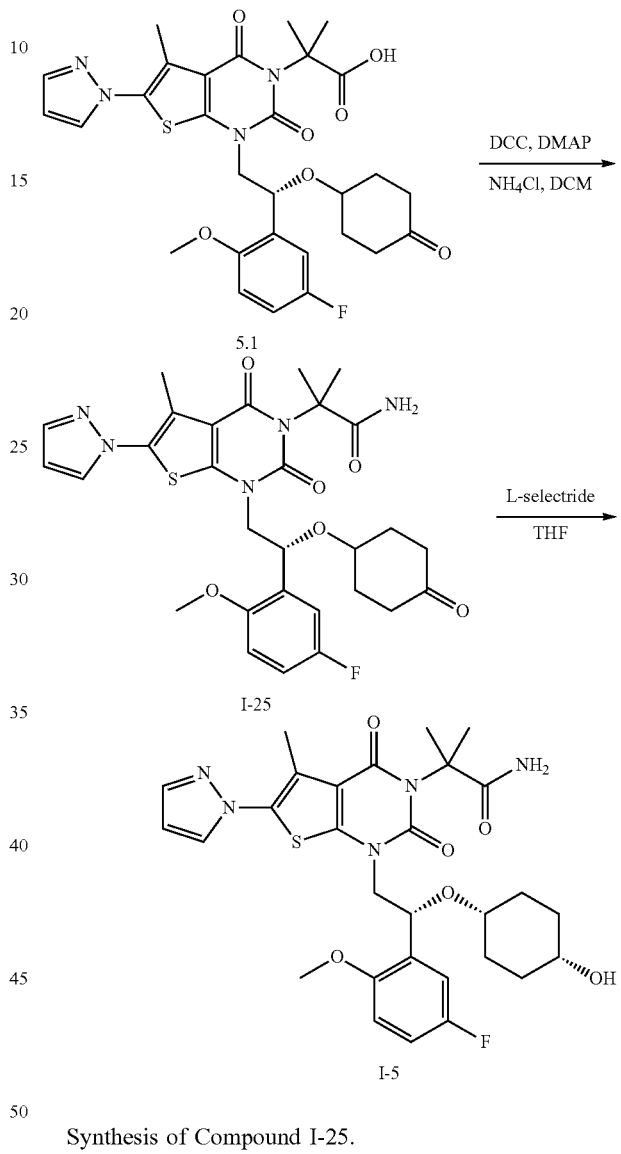

Synthesis of Compound I-25.

Into a 100-mL round-bottomed flask, was placed 5.1 (700 mg, 1.17 mmol, 1.00 equiv), DCC (485 mg, 2.35 mmol, 2.01 equiv), DMAP (285 mg, 2.33 mmol, 2.00 equiv), NH₄Cl (125 mg, 2.34 mmol, 2.00 equiv) and CH₂Cl₂ (20 mL). The reaction was stirred for 4 h at 50° C. The resulting mixture was concentrated under vacuum. The crude was purified by column chromatography to furnish 600 mg (86%) of I-25 as a white solid.

Synthesis of Compound I-5.

Into a 100-mL 3-necked round-bottomed flask under nitrogen, was placed I-25 (600 mg, 1.00 mmol, 1.00 equiv), THF (20 mL). This was followed by the addition of L-selectride (3 mL, 1M) at −78° C. The reaction was stirred for 1 h at −78° C., then quenched by the addition of 20 mL of NH₄Cl (aq.). The resulting solution was extracted with 3×30 mL of CH₂Cl₂ and the organic layers combined and concentrated under vacuum. The crude product was purified by Prep-HPLC to provide 241.8 mg (40%) of I-5 as a white solid. LC-MS (ES, m/z) [M-NH$_2$] 583, [M+H]$^+$ 600, [M+Na]$^+$ 622; $^1$H NMR (400 MHz, DMSO-d): 1.23-1.40 (m, 6H), 1.48-1.60 (m, 2H), 1.62-1.70 (d, 6H), 2.31 (s, 3H), 3.18-3.23 (m, 1H), 3.38-3.48 (m, 1H), 3.75 (s, 3H), 3.82-4.10 (m, 2H), 4.36-4.37 (d, 1H), 5.20-5.23 (t, 1H), 6.59 (s, 1H), 6.60-6.80 (brs, 1H), 6.98-7.03 (m, 1H), 7.07-7.15 (m, 1H), 7.19-7.22 (m, 1H), 7.79 (s, 1H), 8.13 (s, 1H).

Example 6: Synthesis of (R)-2-(1-(2-(5-fluoro-2-methoxyphenyl)-2-((tetrahydro-2H-pyran-4-yl)oxy)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide. I-6

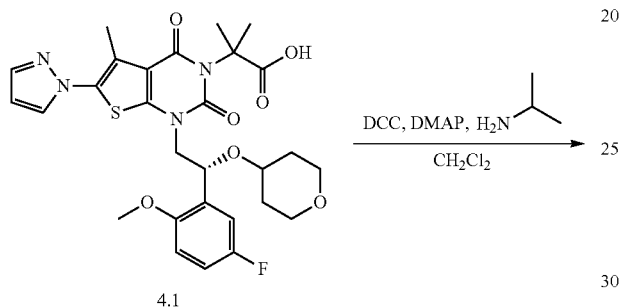

Into a 8-mL microwave vial was placed 4.1 (200 mg, 0.34 mmol, 1.00 equiv), DCC (210 mg, 1.02 mmol, 3.00 equiv). 4-dimethylaminopyridine (83 mg, 0.68 mmol, 2.00 equiv), propan-2-amine (40 mg, 0.68 mmol, 2.00 equiv), and CH$_2$Cl$_2$ (2 mL). The reaction was stirred for 8 h at 50° C. in an oil bath. The mixture was concentrated under vacumm. The crude was purified by column chromatography and preparative HPLC to furnish 58.2 mg (27%) of I-6 as a white solid. LC-MS (ES, m/z): [M-C$_3$H$_8$N]$^+$ 569; $^1$H NMR (300 MHz, DMSO-d): δ1.00-1.02 (m, 6H), 1.24-1.31 (m, 2H), 1.61-1.70 (m, 8H), 2.31 (s, 3H), 3.26-3.29 (m, 2H), 3.30-3.32 (m, 1H), 3.54-3.58 (m, 2H), 3.73 (s, 3H), 3.83-3.88 (m, 2H), 3.99-4.10 (m, 1H), 5.21-5.25 (t, 1H), 6.57 (s, 1H), 7.00-7.05 (m, 1H), 7.07-7.17 (m, 1H), 7.18-7.27 (m, 2H), 7.78 (s, 1H), 8.13 (s, 1H).

Example 7: Synthesis of (R)-1-(2-(5-fluoro-2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-7

Compound I-7 was prepared in 30% yield from compound 4.1 and pyrrolidine using the procedure described in Example 6. LC-MS (ES, mm/z): [M-C4H8N]$^+$ 569; $^1$H NMR (300 MHz, DMSO-d$_6$): δ1.15-1.46 (m, 2H), 1.64-1.96 (m, 12H), 2.31 (s, 3H), 3.00-3.20 (m, 2H), 3.21-3.30 (m, 5H), 3.31-3.41 (m, 1H), 3.56-3.69 (m, 2H), 3.77 (s, 3H), 3.89-4.10 (m, 1H), 5.21-5.25 (t, 1H), 6.57 (s, 1H), 6.90-7.20 (m, 3H), 7.79 (s, 1H), 8.17 (s, 1H).

Example 8: Synthesis of (R)-1-(2-(5-fluoro-2-methoxyphenyl)-2-((tetrahydro-2H-pyran-4-yl)oxy)ethyl)-5-methyl-3-(2-methyl-1-oxo-1-(piperidin-1-yl)propan-2-yl)-6-(1H-pyrazol-1-yl)thieno[2,3-d]pyrimidine-2,4(1H,3H)-dione, I-8

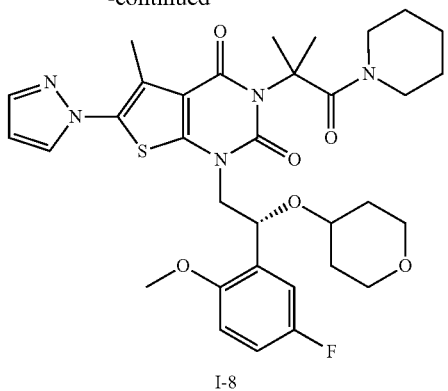

I-8

Compound I-8 was prepared in 34% yield by compound 4.1 and piperidine using the procedure described in Example 6. LC-MS (ES, m/z): [M-C$_5$H$_{10}$N]$^+$ 569; $^1$H NMR (300 MHz, DMSO-d$_6$): δ1.19-1.57 (m, 8H), 1.58-1.83 (m, 8H), 2.28 (s, 3H), δ3.09-3.33 (m, 5H), 3.34-3.43 (m, 3H), 3.57-3.69 (m, 2H), 3.77 (s, 3H), 3.89-4.10 (m, 1H), 5.21-5.25 (t, 1H), 6.57 (s, 1H), 6.90-7.20 (m, 3H), 7.79 (s, 1H), 8.17 (s, 1H).

Example 9: Synthesis of (R)-1-(2-(5-fluoro-2-methoxyphenyl)-2-((tetrahydro-2H-pyran-4-yl)oxy)ethyl)-3-(1-(3-hydroxyazetidin-1-yl)-2-methyl-1-oxopropan-2-yl)-5-methyl-6-(1H-pyrazol-1-yl)thieno[2,3-d]pyrimidine-2,4(1H,3H)-dione, I-9

Into a 8-mL round-bottomed flask was placed 4.1 (200 mg, 0.34 mmol, 1.00 equiv), CH$_2$Cl$_2$ (2 mL), EDCI (98 mg, 0.51 mmol, 1.50 equiv), HOBt (46 mg, 0.34 mmol, 1.00 equiv), DIEA (131.6 mg, 1.02 mmol, 2.99 equiv) and azetidin-3-ol hydrochloride (75 mg, 0.68 mmol, 2.01 equiv). The reaction was stirred for 8 h at 25° C. The resulting mixture was washed with 2 mL H$_2$O. The crude product was purified by preparative HPLC to afford 53.1 mg (24%) of 1-9 as a white solid. LC-MS (ES, m/z): [M-C$_3$H$_6$NO]$^+$ 569; $^1$H NMR (400 MHz, CD$_3$OD): δ 1.45-1.55 (m, 2H), 1.75-1.80 (m, 7H), 1.81-1.85 (m, 1H), 2.37 (s, 3H), 3.37-3.45 (m, 2H), 3.46-3.52 (m, 1H), 3.73-3.83 (m, 7H), 4.15-4.54 (m, 4H), 4.87-4.91 (t, 1H), 5.39-5.43 (t, 1H), 6.59 (s, 1H), 6.95-6.99 (m, 1H), 7.00-7.12 (m, 1H), 7.20-7.25 (m, 1H), 7.80 (d, 1H), 7.95-7.96 (d, 1H).

Example 10: Synthesis of (R)-2-(1-(2-(2-methoxyphenyl)-2-((tetrahydro-2H-pyran-4-yl)oxy)ethyl)-5-methyl-2,4-dioxo-6-(1H-pyrazol-1-yl)-1,4-dihydrothieno[2,3-d]pyrimidin-3(2H)-yl)-2-methylpropanamide, I-10

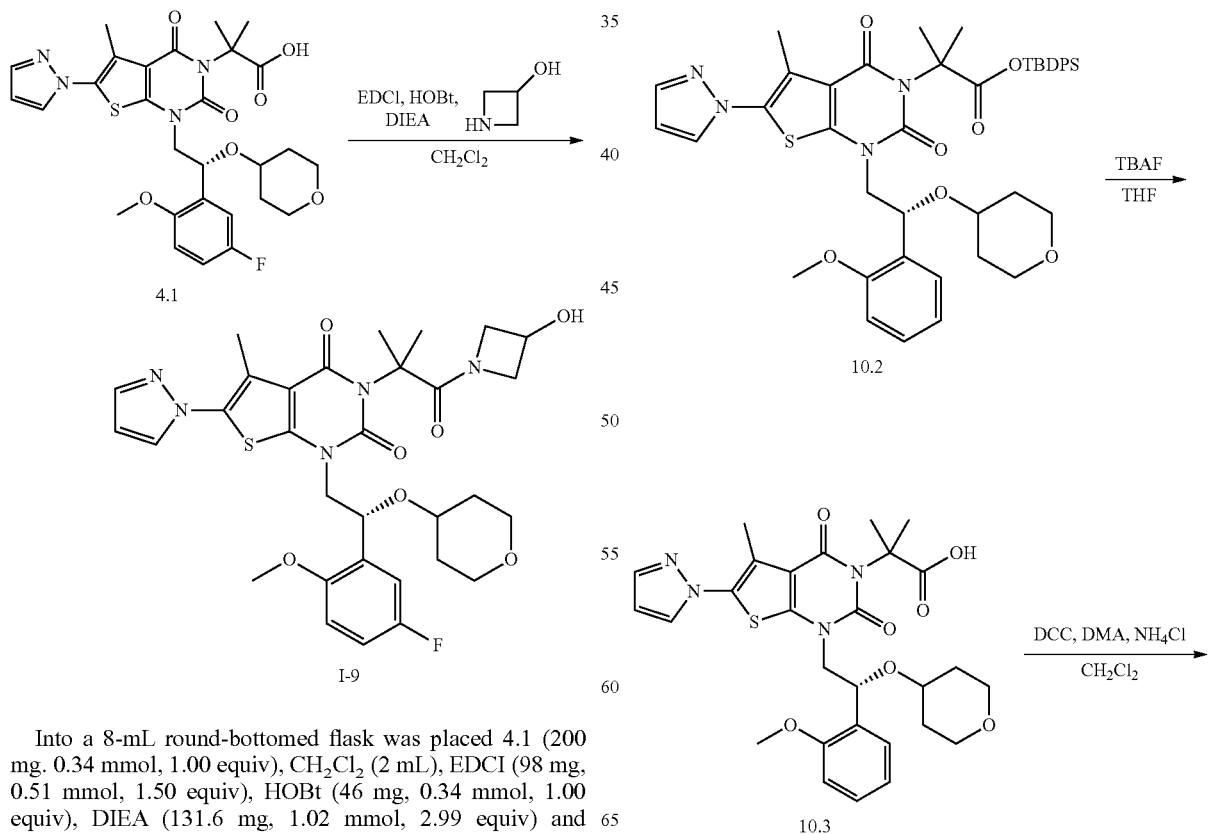

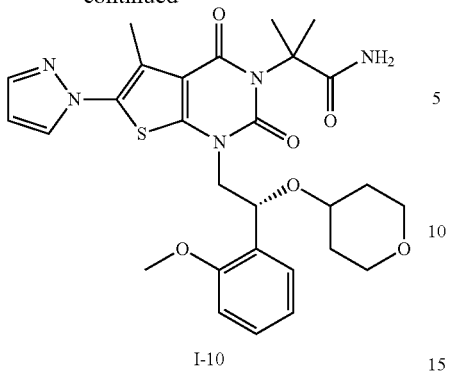

I-10

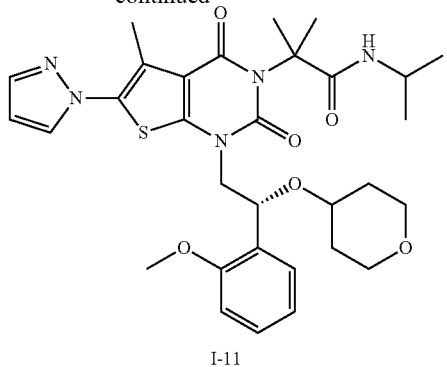

I-11

Synthesis of Compound 10.2.

Into a 25-mL round-bottomed flask was placed 1.98 (500 mg, 0.87 mmol, 1.00 equiv), THF (5 mL), 10.1 (276 mg, 1.09 mmol, 1.25 equiv), DIAD (251 mg, 1.24 mmol, 1.42 equiv), and PPh$_3$ (340 mg, 1.30 mmol, 1.48 equiv). The reaction was stirred for 12 h at 50° C. in an oil bath. The crude product was purified by column chromatography to furnish 600 mg (85%) of 10.2 as a white solid.

Synthesis of Compound 10.3.

Into a 50-mL round-bottomed flask was placed 10.2 (1.2 g, 1.49 mmol, 1.00 equiv), TBAF (1.23 g, 3.73 mmol, 2.51 equiv), and THF (12 mL). The reaction was stirred for 12 h at 25° C. The resulting mixture was concentrated under vacuum, then diluted with EtOAc. The resulting mixture was washed with H$_2$O and concentrated under vacuum. The crude product was purified by column chromatography to furnish 400 mg (47%) of 10.3 as a white solid.

Synthesis of Compound I-10.

Into a 8-mL round-bottomed flask was placed 10.3 (200 mg, 0.35 mmol, 1.00 equiv), CH$_2$Cl$_2$ (2 mL), DCC (217 mg, 1.05 mmol, 3.00 equiv), DMAP (85.4 mg, 0.70 mmol, 2.00 equiv) and NH$_4$Cl (36 mg, 0.67 mmol, 3.00 equiv). The reaction was stirred for 8 h at 50° C. in an oil bath. The crude product was purified by column chromatography to furnish 51.1 mg (26%) of I-10 as a white solid. LC-MS (ES, m/z): [M-NH$_2$]$^+$ 551; $^1$H NMR (400 MHz, DMSO-d$_6$): δ 1.24-1.34 (m, 2H), 1.62-1.68 (m, 8H), 2.33 (s, 3H), 3.23-3.30 (m, 2H), 3.53-3.60 (m, 2H), 3.76 (s, 3H), 3.80-3.95 (m, 1H), 3.96-4.10 (m, 1H), 5.25-5.29 (t, 1H), 6.57-6.58 (t, 1H), 6.66-6.80 (brs, 1H), 6.98-7.05 (m, 2H), 7.06-7.15 (brs, 1H), 7.28-7.32 (t, 1H), 7.45-7.47 (d, 1H), 7.78-7.79 (d, 1H), 8.13-8.14 (d, 1H).

Example 11: Synthesis of (R)—N-isopropyl-2-(1-(2-(2-methoxyphenyl)-2-((tetrahydro-2H-pyran-4-yl)oxy)ethyl)-5-methyl-2,4-dioxo-6-(1H-pyrazol-1-yl)-1,4-dihydrothieno[2,3-d]pyrimidin-3(2H)-yl)-2-methylpropanamide, I-11

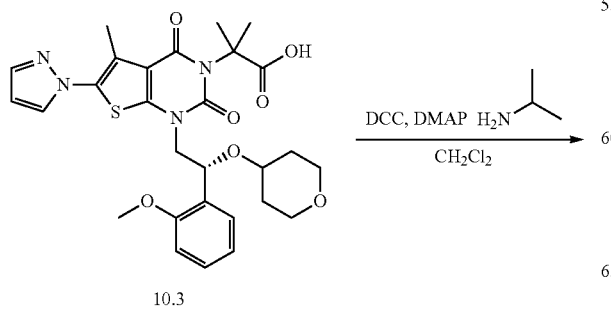

10.3

Into a 8-mL round-bottomed flask was placed 10.3 (200 mg, 0.35 mmol, 1.00 equiv), DCC (217 mg, 1.05 mmol, 2.99 equiv), DMAP (85.4 mg, 0.70 mmol, 1.99 equiv), propan-2-amine (41.3 mg, 0.70 mmol, 1.99 equiv), and CH$_2$Cl$_2$ (2 mL). The reaction was stirred for 12 h at 50° C. The crude product was purified by column chromatography and preparative HPLC to furnish 50.2 mg (23%) of I-11 as a white solid. LC-MS (ES, m/z): [M-C$_3$H$_8$N]$^+$ 551;

$^1$H NMR (400 MHz, DMSO-d$_6$): δ1.01-1.03 (m, 6H), 1.24-1.29 (m, 2H), 1.62-1.68 (m, 8H), 2.33 (s, 3H), 3.23-3.29 (m, 2H), 3.31-3.38 (m, 1H), 3.53-3.60 (m, 2H), 3.76 (s, 3H), 3.80-3.92 (m, 2H), 3.97-4.10 (m, 1H), 5.25-5.29 (t, 1H), 6.57 (s, 1H), 6.97-7.03 (m, 2H), 7.26-7.32 (m, 2H), 7.45-7.47 (d, 1H), 7.78-7.79 (d, 1H), 8.13-8.14 (d, 1H).

Example 12: Synthesis of (R)-1-(2-(2-methoxyphenyl)-2-((tetrahydro-2H-pyran-4-yl)oxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-12

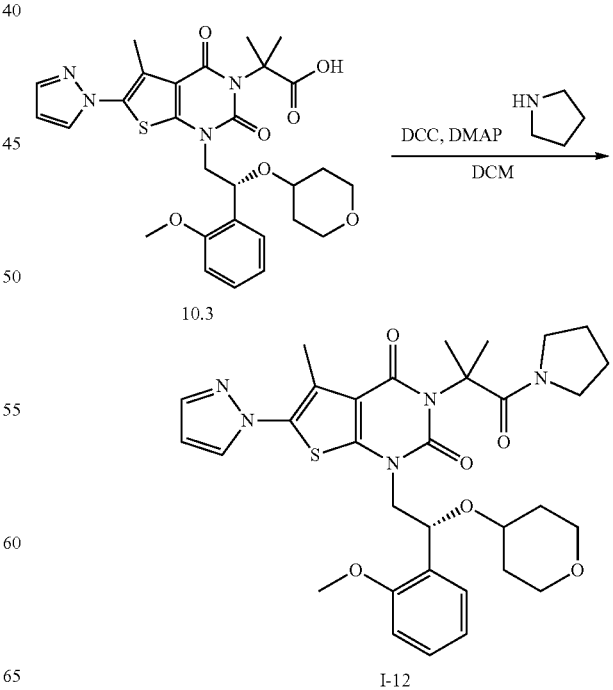

Compound I-12 was prepared from pyrrolidine and 10.3 in 26% yield using the procedure described in Example 11. LC-MS (ES, m/z): [M-C₄H₈N]⁺ 551; ¹H NMR (400 MHz, DMSO-d₆): δ1.18-1.25 (m, 1H), 1.27-1.34 (m, 1H), 1.65-1.72 (m, 12H), 2.33 (s, 3H), 3.12-3.20 (m, 2H), 3.21-3.3.28 (m, 2H), 3.29-3.32 (m, 2H), 3.33-3.38 (m, 1H), 3.57-3.65 (m, 2H), 3.76 (s, 3H), 3.89-4.12 (m, 2H), 5.25-5.29 (t, 1H), 6.57 (s, 1H), 6.97-7.03 (m, 2H), 7.30-7.36 (m, 1H), 7.38-7.45 (m, 1H), 7.78 (d, 1H), 8.17-8.18 (d, 1H).

Example 13: Synthesis of (R)-1-(2-(2-methoxyphenyl)-2-((tetrahydro-2H-pyran-4-yl)oxy)ethyl)-5-methyl-3-(2-methyl-1-oxo-1-(piperidin-1-yl)propan-2-yl)-6-(1H-pyrazol-1-yl)thieno[2,3-d]pyrimidine-2,4(1H,3H)-dione, I-13

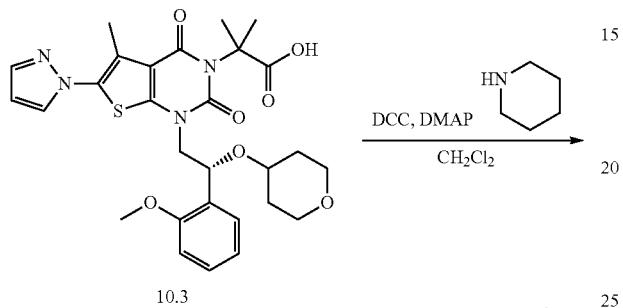

Compound I-13 was prepared in 26% yield from compound 10.3 and piperidine. LC-MS (ES, m/z): [M-C₅H₁₀N]⁺ 551; ¹H NMR (300 MHz, DMSO-d₆): δ1.20-1.55 (m, 8H), 1.56-1.64 (m, 8H), 2.33 (s, 3H), 3.12-3.31 (m, 5H), 3.32-3.38 (m, 3H), 3.57-3.65 (m, 2H), 3.76 (s, 3H), 3.89-4.12 (m, 1H), 5.25-5.29 (t, 1H), 6.57 (s, 1H), 6.97-7.03 (m, 2H), 7.30-7.36 (m, 1H), 7.38-7.45 (m, 1H), 7.78 (s, 1H), 8.14 (s, 1H).

Example 14: Synthesis of 2-(1-((R)-2-(5-fluoro-2-methoxyphenyl)-2-(((1s,4S)-4-hydroxycyclohexyl)oxy)ethyl)-5-methyl-2,4-dioxo-6-(1H-pyrazol-1-yl)-1,4-dihydro-thieno[2,3-d]pyrimidin-3(2H)-yl)-N-isopropyl-2-methylpropanamide, I-14

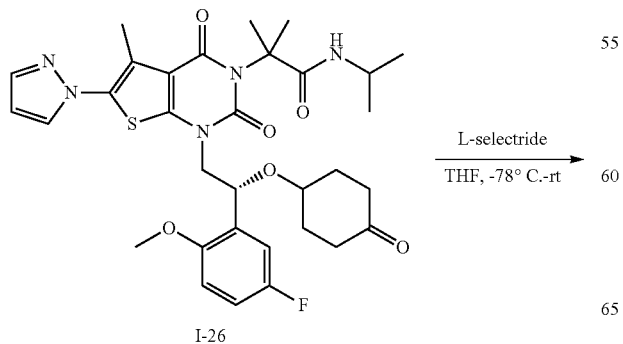

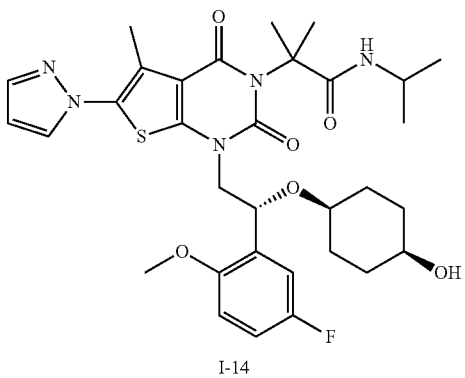

Into a 50-mL 3-necked round-bottomed flask under nitrogen was placed a solution of 1-26 (160 mg, 0.25 mmol, 1.00 equiv) in THF (6 mL). This was followed by the addition of L-selectride (0.75 mL, 0.75 mmol, 3.00 equiv, 1 mol/L) dropwise with stirring at −78° C. The reaction was stirred for 40 min at −78° C. The resulting mixture was quenched with NH₄Cl (aq) and concentrated under vacuum. The crude product was purified by Prep-HPLC to provide 88 mg (55%) of 1-14 as a white solid. LC-MS (ES, m/z): [M+H]⁺ 642, ¹H NMR: (400 MHz, DMSO-d₆): δ8.11 (d, 1H), 7.77 (d, 1H), 7.24-7.17 (m, 2H), 7.13-7.10 (m, 1H), 7.09-6.96 (m, 1H), 6.56 (m, 1H), 5.20-5.17 (m, 1H), 4.35 (d, 1H), 4.05-3.90 (m, 1H), 3.88-3.75 (m, 2H), 3.71 (s, 3H), 3.55-3.35 (m, 1H), 3.20 (m, 1H), 2.28 (s, 3H), 1.61-1.54 (m, 6H), 1.52-1.51 (m, 2H), 1.32-1.20 (m, 6H), 1.01-0.99 (dd, 6H).

Example 15: Synthesis of 1-((R)-2-(5-fluoro-2-methoxyphenyl)-2-(((1s,4S)-4-hydroxycyclohexyl)oxy)ethyl)-5-methyl-3-(2-methyl-1-oxo-1-(pyrrolidin-1-yl)pro-pan-2-yl)-6-(1H-pyrazol-1-yl)thieno[2,3-d]pyrimidine-2,4(1H,3H)-dione, I-15

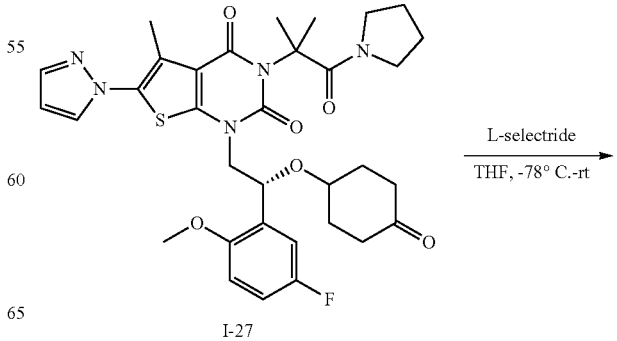

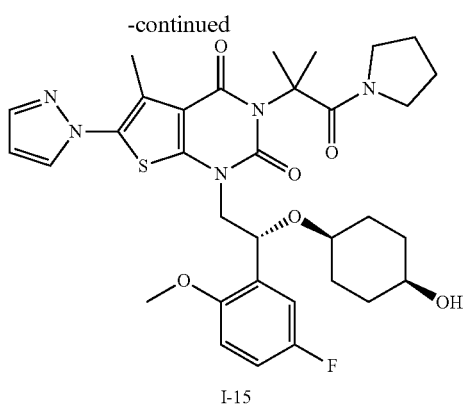

I-15

Into a 25-mL 3-necked round-bottomed flask under nitrogen was placed a solution of 1-27 (190 mg, 0.29 mmol, 1.00 equiv) in THF (5 mL) and L-selectride (0.9 mL, 0.87 mmol, 3.00 equiv, 1 mol/L). The reaction was stirred for 30 min at −78° C. The resulting mixture was quenched with NH₄Cl (aq) and concentrated under vacuum. The crude product was purified by preparative HPLC to furnish 136 mg (71%) of I-15 as a white solid. LC-MS (ES, m/z): [M+H]⁺ 654; ¹H NMR (300 MHz, DMSO-d₆): δ 8.14 (d, 1H), 7.79 (d, 1H), 7.20-7.09 (m, 2H), 7.06-7.00 (m, 1H), 6.57 (m, 1H), 5.21-5.17 (m, 1H), 4.34-4.33 (d, 1H), 4.11-3.80 (m, 2H), 3.77 (s, 3H), 3.50-3.35 (m, 2H), 3.30-3.00 (m, 3H), 2.29 (s, 3H), 1.88-1.60 (m, 10H), 1.60-1.40 (m, 3H), 1.40-1.20 (m, 6H).

Example 16: Synthesis of (R)-2-(1-(2-isopropoxy-2-(2-methoxyphenyl)ethyl)-5-methyl-2,4-dioxo-6-(1H-pyrazol-1-yl)-1,4-dihydrothieno[2,3-d]pyrimidin-3(2H)-yl)-2-methylpropanamide, I-16

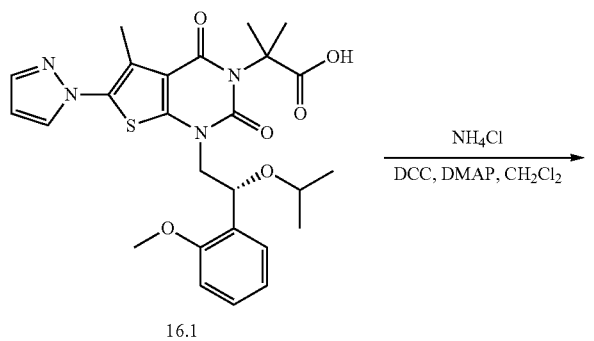

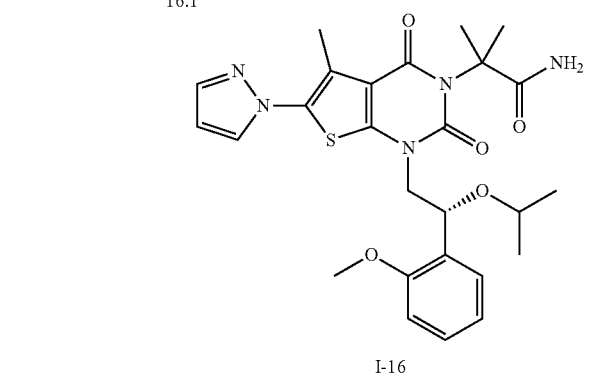

I-16

Into a 6-mL sealed tube was placed 16.1 (150 mg, 0.28 mmol, 1.00 equiv), CH₂Cl₂ (2 mL), DCC (142 mg, 0.69 mmol, 2.42 equiv), 4-DMAP (56 mg, 0.46 mmol, 1.61 equiv), and amine hydrochloride (36.9 mg, 0.69 mmol, 2.42 equiv). The reaction was stirred overnight at 50° C. The resulting mixture was concentrated under vacuum. The crude product was purified by preparative TLC to furnish 69.4 mg (46%) of I-16 as a white solid. LC-MS (ES, m/z): [M-NH₂]⁺ 509, ¹H NMR (400 MHz, DMSO-d₆): δ 0.94-0.98 (dd, 6H), 1.65-1.66 (d, 6H), 2.31 (s, 3H), 3.37-3.43 (m, 1H), 3.73 (s, 3H), 3.93 (s, 2H), 5.16-5.19 (t, 1H), 6.56-6.57 (d, 1H), 6.72 (brs, 1H), 6.94-7.05 (m, 3H), 7.25-7.29 (m, 1H), 7.42-7.44 (m, 1H), 7.77-7.78 (d, 1H), 8.12-8.13 (d, 1H).

Example 17: Synthesis of (R)-2-(1-(2-isopropoxy-2-(2-methoxyphenyl)ethyl)-5-methyl-2,4-dioxo-6-(H-pyrazol-1-yl)-1,4-dihydrothieno[2,3-d]pyrimidin-3(2H)-yl)-N-isopropyl-2-methylpropanamide, I-17

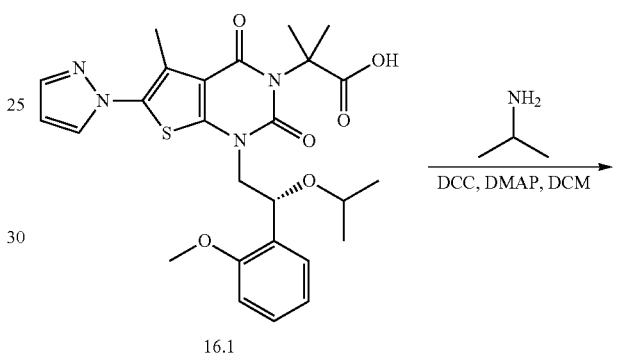

16.1

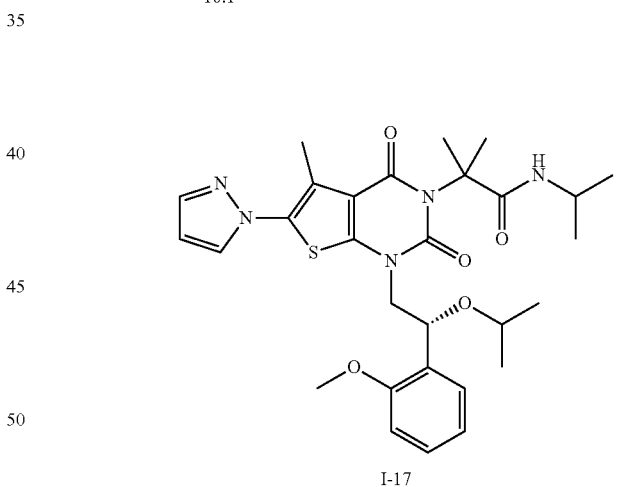

I-17

Into a 6-mL sealed tube was placed 16.1 (150 mg, 0.28 mmol, 1.00 equiv), CH₂Cl₂ (2 mL), DCC (142 mg, 0.69 mmol, 2.42 equiv), DMAP (56 mg, 0.46 mmol, 1.61 equiv) and propan-2-amine (27 mg, 0.46 mmol, 1.60 equiv). The reaction was stirred overnight at 50° C. The resulting mixture was concentrated under vacuum. The crude product was purified by preparative TLC and HPLC to furnish 86.9 mg (54%) of I-17 as a white solid. LC-MS (ES, m/z): [M-C3H8N]⁺ 509; ¹H NMR (400 MHz, DMSO-d₆): δ0.97-1.03 (m, 12H), 1.61-1.65 (d, 6H), 2.31 (s, 3H), 3.39-3.44 (m, 1H), 3.72 (s, 3H), 3.80-3.97 (m, 3H), 5.16-5.19 (t, 1H), 6.56-6.57 (t, 1H), 6.94-7.02 (m, 2H), 7.25-7.29 (m, 2H), 7.42-7.43 (m, 1H), 7.77-7.78 (d, 1H), 8.11-8.12 (d, 1H).

Example 18: Synthesis of (R)-1-(2-isopropoxy-2-(2-methoxyphenyl)ethyl)-5-methyl-3-(2-methyl-1-oxo-2-(pyrrolidin-1-yl)propan-2-yl)-6-(H-pyrazol-1-yl)thieno[2,3-d]pyrimidine-2,4(1H,3H)-dione, I-18

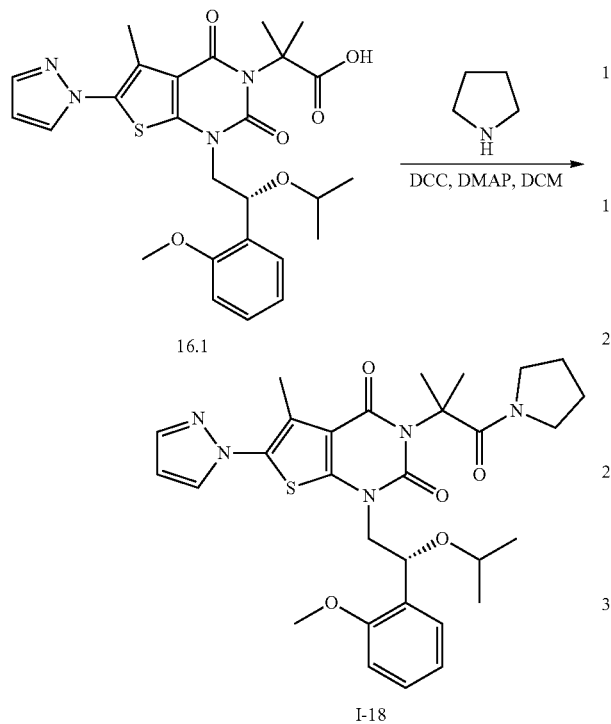

Compound I-18 was prepared in 46% yield from compound 16.1 and pyrrolidine using the procedure described in Example 17. LC-MS (ES, m/z): [M-C4H8N]⁺ 509; ¹H NMR (400 MHz, DMSO-$d_6$): δ 0.93-0.98 (dd, 6H), 1.65-1.72 (m, 10H), 2.31 (s, 3H), 3.05-3.12 (m, 2H), 3.30-3.32 (m, 2H), 3.33-3.43 (m, 1H), 3.77 (s, 3H), 3.95-3.99 (m, 2H), 5.18-5.21 (t, 1H), 6.57-6.58 (t, 1H), 6.98-7.02 (t, 2H), 7.27-7.32 (m, 1H), 5.40-7.42 (d, 1H), 7.79 (d, 1H), 8.16-8.17 (d, 1H).

Example 19: Synthesis of (R)-1-(2-isopropoxy-2-(2-methoxyphenyl)ethyl)-5-methyl-3-(2-methyl-1-oxo-1-(piperidin-1-yl)propan-2-yl)-6-(H-pyrazol-1-yl)thieno[2,3-d]pyrimidine-2,4(1H,3H)-dione, I-19

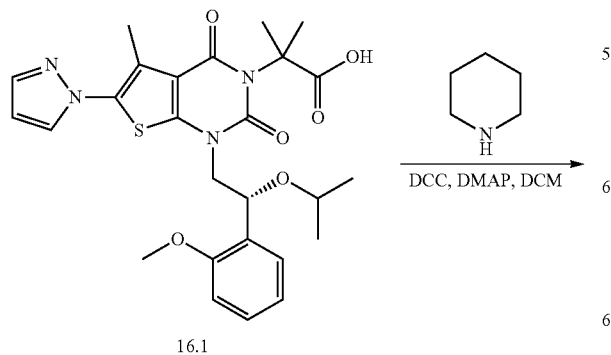

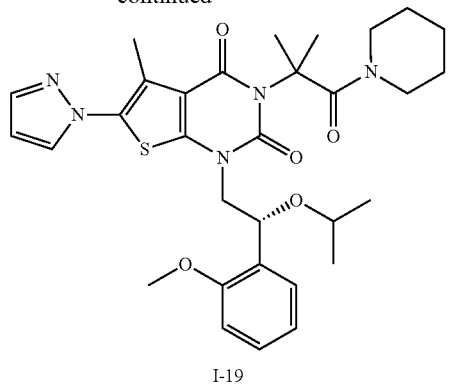

Compound I-19 was prepared in 50% yield from compound 16.1 and piperidine using the procedure described in Example 17. LC-MS (ES, m/z): [M-C₅H₁₀N]⁺ 509; ¹H NMR (400 MHz, DMSO-$d_6$): δ 0.98-0.99 (dd, 6H), 1.36-1.64 (m, 12H), 2.33 (s, 3H), 3.30-3.48 (m, 5H), 3.72-4.23 (m, 5H), 5.21 (m, 1H), 6.57-6.58 (t, 1H), 6.98-7.02 (t, 2H), 7.27-7.32 (m, 1H), 7.40 (m, 1H), 7.79 (s, 1H), 8.17 (s, 1H).

Example 20: Synthesis of (R)-2-(1-(2-isobutoxy-2-(2-methoxyphenyl)ethyl)-5-methyl-2,4-dioxo-6-(1H-pyrazol-1-yl)-1,4-dihydrothieno[2,3-d]pyrimidin-3(2H)-yl)-2-methylpropanamide, I-20

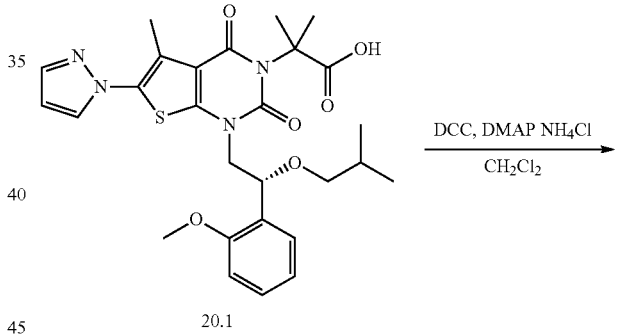

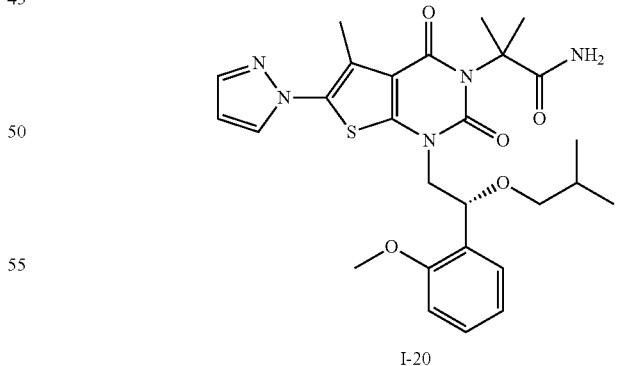

Into a 8-mL round-bottom flask was placed 20.1 (200 mg, 0.37 mmol, 1.00 equiv), DCC (229 mg, 1.11 mmol, 3.00 equiv), DMAP (90.4 mg, 0.74 mmol, 2.00 equiv), NH₄Cl (58.9 mg, 1.10 mmol, 2.98 equiv), and CH₂Cl₂ (2 mL). The reaction was stirred for 12 h at 50° C. in an oil bath. The crude product was purified by column chromatography and preparative HPLC to furnish 83.1 mg (42%) of 1-20 as a white solid. LC-MS (ES, m/z): [M-NH$_2$]$^+$ 523; $^1$H NMR (400 MHz, DMSO-d$_6$): δ 0.69-0.77 (dd, 6H), 1.65-1.71 (m, 7H), 2.32 (s, 3H), 2.93-2.97 (m, 1H), 3.05-3.09 (m, 1H), 3.74 (s, 3H), 3.92-4.03 (m, 2H), 5.07-5.11 (t, 1H), 6.56-6.57 (t, 1H), 6.71 (brs, 1H), 6.96-7.03 (m, 3H), 7.27-7.31 (m, 1H), 7.35-7.37 (m, 1H), 7.78 (d, 1H), 8.11 (d, 1H).

Example 21: Synthesis of (R)-2-(1-(2-isobutoxy-2-(2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-21

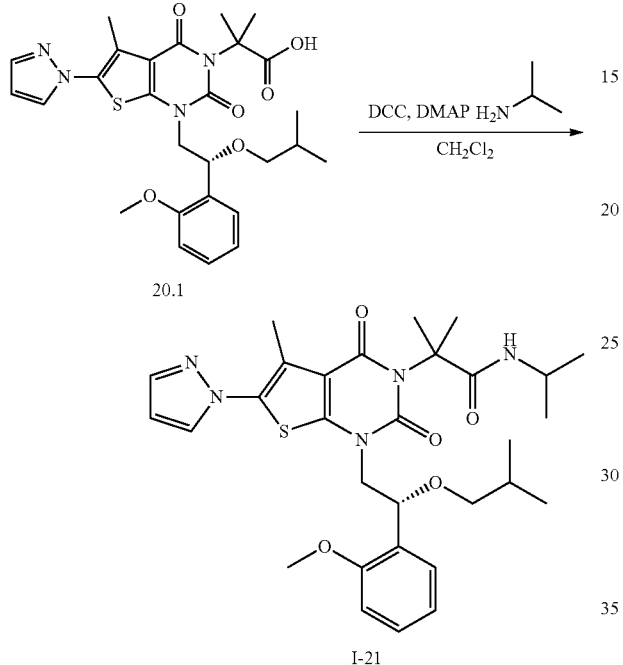

Compound I-21 was prepared in 53% yield from compound 20.1 and propan-2-amine using the procedure described in Example 20. LC-MS (ES, m/z): [M-C$_3$H$_8$N]$^+$ 523; $^1$H NMR (400 MHz, DMSO-d): δ 0.73-0.75 (dd, 6H), 0.99-1.02 (t, 6H), 1.61-1.70 (m, 7H), 2.30 (s, 3H), 2.93-3.00 (m, 1H), 3.01-3.07 (m, 1H), 3.73 (s, 3H), 3.92-4.03 (m, 3H), 5.07-5.11 (t, 1H), 6.56-6.57 (t, 1H), 6.96-7.03 (m, 2H), 7.26-7.32 (m, 2H), 7.33-7.37 (m, 1H), 7.78 (d, 1H), 8.11 (d, 1H).

Example 22: Synthesis of (R)-1-(2-isobutoxy-2-(2-methoxyphenyl)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-22

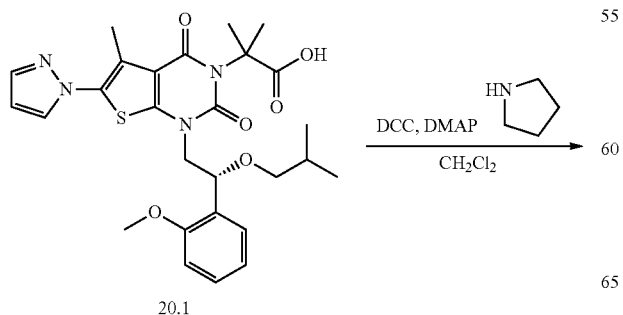

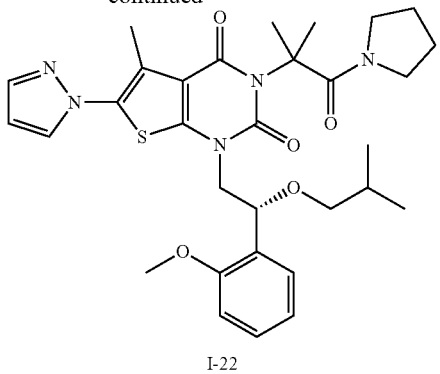

Compound I-22 was prepared in 39% yield from compound 20.1 and pyrrolidine using the procedure described in Example 20. LC-MS (ES, m/z): [M-C$_4$H$_8$N]$^+$ 523; $^1$H NMR (400 MHz, DMSO-d$_6$): δ 0.73-0.75 (dd, 6H), 1.64-1.73 (m, 11H), 2.31 (s, 3H), 2.90-3.14 (m, 4H), 3.33 (s, 2H), 3.78 (s, 3H), 4.01-4.15 (m, 2H), 5.07-5.11 (t, 1H), 6.57-6.58 (t, 1H), 7.01-7.03 (m, 2H), 7.26-7.37 (m, 2H), 7.79 (d, 1H), 8.14-8.15 (d, 1H).

Example 23: Synthesis of (R)-1-(2-isobutoxy-2-(2-methoxyphenyl)ethyl)-5-methyl-3-(2-methyl-1-oxo-1-(piperidin-1-yl)propan-2-yl)-6-(1H-pyrazol-1-yl)thieno[2,3-d]pyrimidine-2,4(1H,3H)-dione, I-23

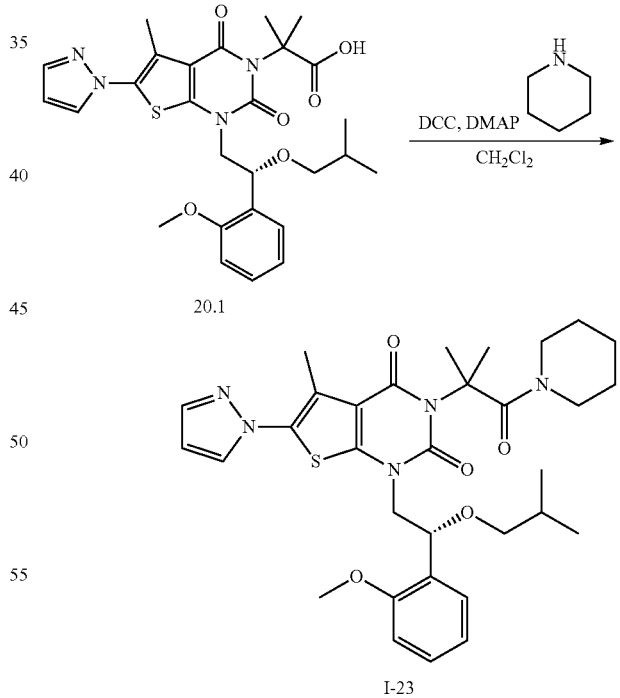

Compound I-23 was prepared in 31% yield from compound 20.1 and piperidine using procedure described in Example 20. LC-MS (ES, m/z): [M-C$_5$H$_{10}$N]$^+$ 523; $^1$H NMR (400 MHz, DMSO-d$_6$): δ 0.73-0.75 (dd, 6H), 1.35-1.68 (m, 13H), 2.32 (s, 3H), 2.88-3.00 (m, 1H), 3.01-3.10 (m, 1H), 3.28-3.30 (m, 2H), 3.31-3.33 (m, 2H), 3.78 (s, 3H), 3.87-4.17 (m, 2H), 5.07-5.11 (t, 1H), 6.57-6.58 (t, 1H), 6.96-7.03 (m, 2H), 7.26-7.37 (m, 2H), 7.79 (d, 1H), 8.15 (s, 1H).

Example 24: Synthesis of (R)-1-(2-(5-fluoro-2-methoxyphenyl)-2-isopropoxyethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-24

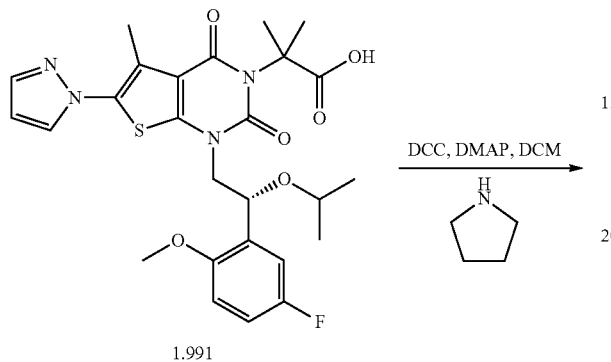

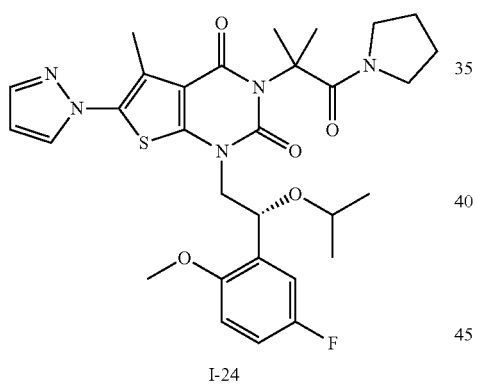

Into a 50-mL round-bottomed flask was placed 1.991 (350 mg, 0.64 mmol, 1.00 equiv), DCC (265 mg, 1.28 mmol, 2.00 equiv), DMAP (157 mg, 1.29 mmol, 2.00 equiv), $CH_2Cl_2$ (10 mL) and pyrrolidine (92 mg, 1.29 mmol, 2.01 equiv). The reaction was stirred overnight at 50° C. The crude product was purified by column chromatography to provide 75.2 mg (20%) of 1-24 as a white solid. LC-MS (ES, m % z): $[M-C_4NH_8]^+$ 527; $^1H$ NMR (400 MHz, DMSO-$d_6$): δ 0.96-1.00 (d, 6H), 1.64-1.80 (m, 10H), 2.31 (s, 3H), 3.05-3.20 (m, 2H), 3.21-3.25 (m, 2H), 3.50-3.55 (m, 1H), 3.76 (s, 3H), 3.85-4.20 (m, 2H), 5.14-5.17 (t, 1H), 6.57 (s, 1H), 6.99-7.03 (m, 1H), 7.10-7.17 (m, 2H), 7.79 (s, 1H), 8.16 (s, 1H).

Example 25: Synthesis of (R)-2-(1-(2-(5-fluoro-2-methoxyphenyl)-2-((4-oxocyclo-hexyl)oxy)ethyl)-5-methyl-2,4-dioxo-6-(1H-pyrazol-1-yl)-1,4-dihydro-thieno[2,3-d]pyrimidin-3(2H)-yl)-2-methylpropanamide, I-25

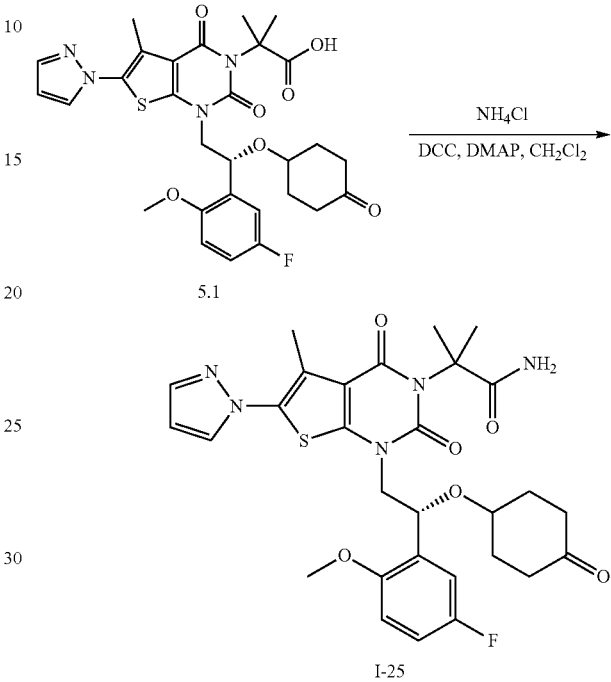

Compound I-25 was prepared from compound 5.1 as described in Example 5. LC-MS (ES, m/z): $[M+H]^+$ 598; $^1H$ NMR (400 MHz, DMSO-$d_6$): δ 8.12-8.11 (d, 1H), 7.78 (d, 1H), 7.27~7.24 (m, 1H), 7.17~7.00 (m, 3H), 6.57 (brs, 1H), 6.56 (s, 1H), 5.30~5.27 (t, 1H), 4.15~3.86 (m, 2H), 3.76 (s, 3H), 3.59~3.57 (m, 1H), 2.29~2.15 (m, 4H), 2.15~2.07 (m, 3H), 1.81~1.76 (m, 4H), 1.64 (m, 6H).

Example 26: Synthesis of (R)-2-(1-(2-(5-fluoro-2-methoxyphenyl)-2-((4-oxocyclo-hexyl)oxy)ethyl)-5-methyl-2,4-dioxo-6-(1H-pyrazol-1-yl)-1,4-dihydro-thieno[2,3-d]pyrimidin-3(2H)-yl)-N-isopropyl-2-methylpropanamide, I-26

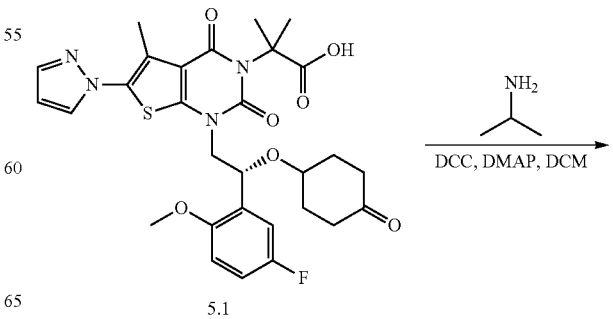

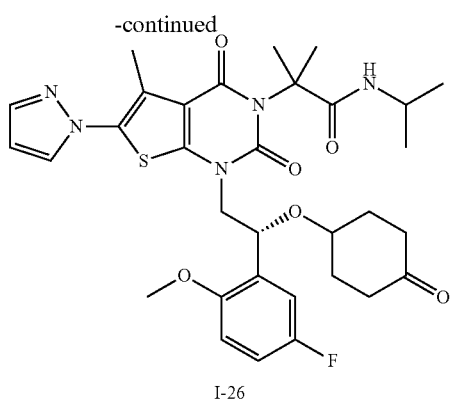

I-26

Into a 25-mL round-bottomed flask, purged and maintained with an inert atmosphere of nitrogen, was placed a solution of 5.1 (400 mg, 0.67 mmol, 1.00 equiv) in CH$_2$Cl$_2$ (4 mL), propan-2-amine (79 mg, 1.34 mmol, 2.00 equiv), DCC (275.6 mg, 1.34 mmol, 2.00 equiv), and DMAP (163 mg, 1.33 mmol, 2.00 equiv). The reaction was stirred for 16 h at 50° C. The crude product was purified by column chromatography and preparative HPLC to furnish 53.6 mg of I-26 as a white solid. LC-MS (ES, m/z): [M+H]$^+$ 640; $^1$H NMR (400 MHz, DMSO-d): δ8.11-8.10 (d, 1H), 7.78-7.77 (d, 1H), 7.27-7.24 (m, 2H), 7.17-7.11 (m, 1H), 7.03-7.00 (m, 1H), 6.57 (s, 1H), 5.30-5.27 (m, 1H), 4.15-3.86 (m, 2H), 3.86-3.81 (m, 1H), 3.74 (s, 3H), 3.59-3.57 (m, 1H), 2.29-2.20 (m, 4H), 2.20-2.07 (m, 3H), 1.81-1.76 (m, 4H), 1.63-1.59 (dd, 6H), 1.01-0.99 (dd, 6H).

Example 27: Synthesis of (R)-1-(2-(5-fluoro-2-methoxyphenyl)-2-((4-oxocyclohexyl)oxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-27

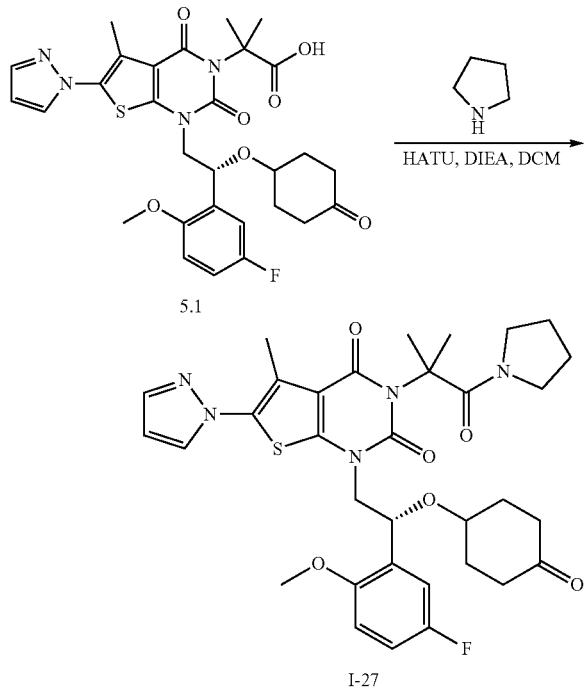

Into a 50-mL round-bottomed flask under nitrogen was placed a solution of 5.1 (400 mg, 0.67 mmol, 1.00 equiv) in CH$_2$Cl$_2$ (20 mL), pyrrolidine (100 mg, 1.41 mmol, 2.00 equiv), HATU (508 mg, 1.34 mmol, 2.00 equiv), and DIEA (175 mg, 1.35 mmol, 2.00 equiv). The resulting solution was stirred for 16 h at 25° C. The resulting mixture was concentrated under vacuum. The crude product was purified by preparative HPLC to furnish 260 mg (60%) of I-27 as a white solid. LC-MS (ES, m/z): [M+H]$^+$ 652; $^1$H-NMR: (400 MHz, DMSO-d$_6$): δ8.14 (s, 1H), 7.78 (s, 1H), 7.25~7.23 (m, 1H), 7.17~7.13 (m, 1H), 7.05~7.03 (m, 1H), 6.57 (s, 1H), 5.28 (m, 1H), 4.10 (m, 2H), 3.92 (s, 3H), 3.60 (m, 1H), 3.30 (m, 1H), 3.06 (m, 2H), 2.29~2.20 (m, 4H), 2.20~2.05 (m, 3H), 1.91~1.50 (m, 15H).

Example 28: Synthesis of (R)-1-(2-(5-fluoro-2-methoxyphenyl)-2-isopropoxyethyl)-5-methyl-3-(2-oxo-2-(pyrrolidin-1-yl)ethyl)-6-(1H-pyrazol-1-yl)thieno[2,3-d]pyrimidine-2,4(1H,3H)-dione, I-28

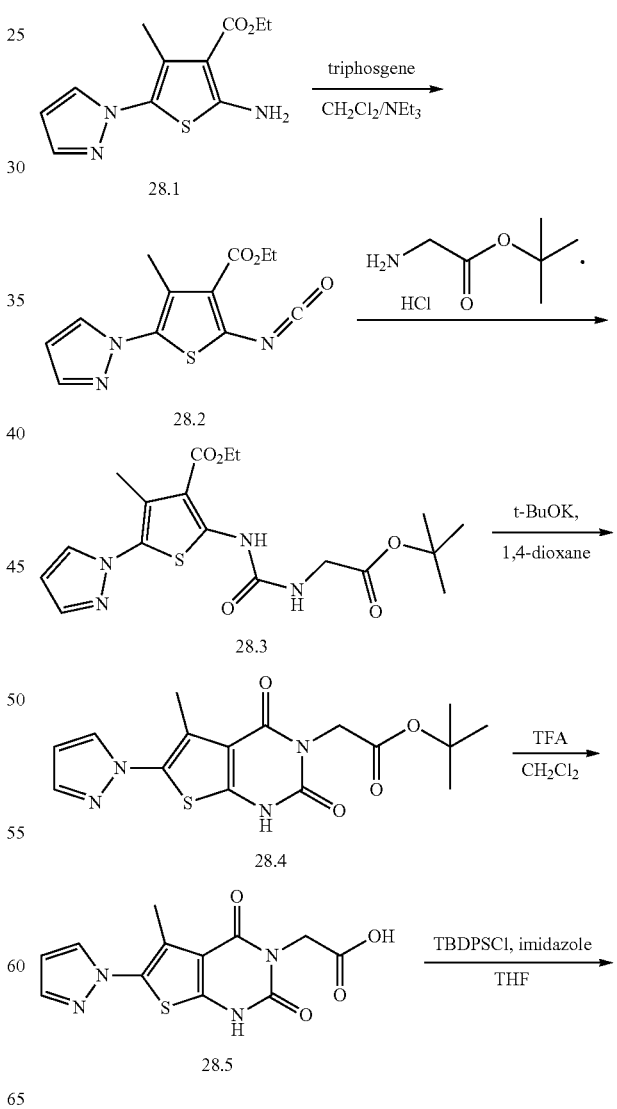

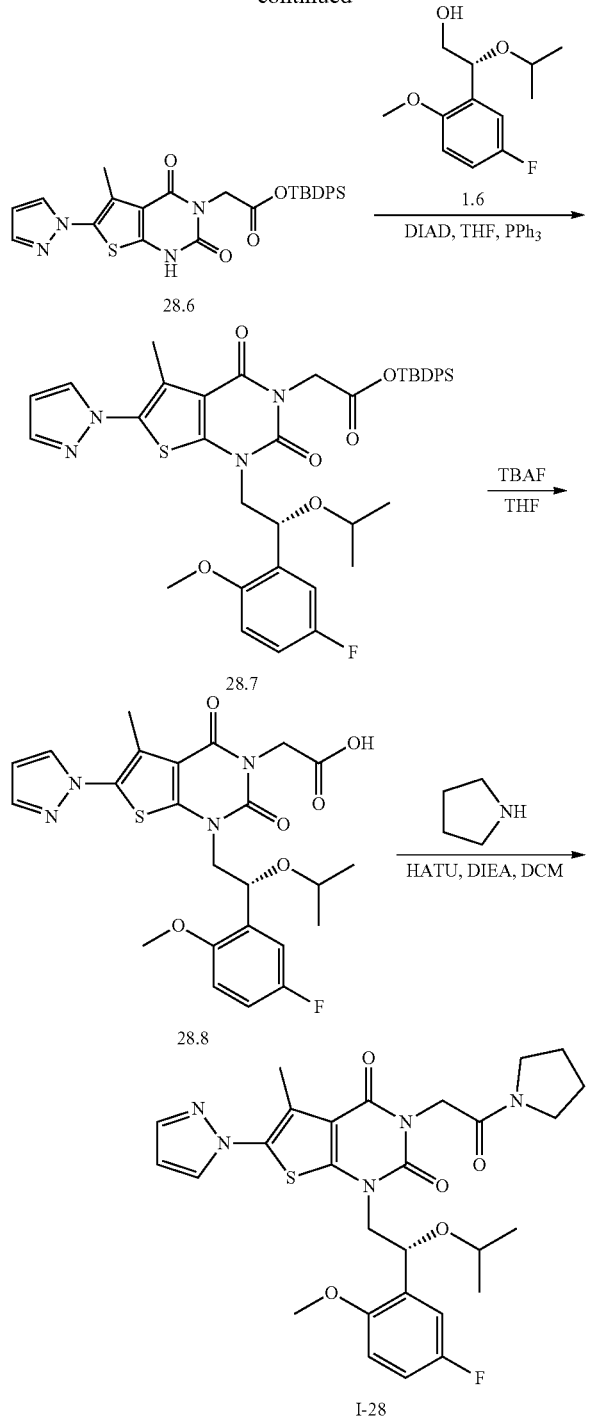

Synthesis of Compound 28.2.

Into a 100-mL 3-necked round-bottomed flask was placed 28.1 (5 g, 19.90 mmol, 1.00 equiv), CH$_2$Cl$_2$ (50 mL), triphosgene (2.34 g, 0.40 equiv), and Et$_3$N (8 g, 79.06 mmol, 4.00 equiv). The resulting solution was stirred for 2 h at room temperature. The crude product was used in the next step directly without further purification.

Synthesis of Compound 28.3.

Into a 100-mL 3-necked round-bottomed flask was placed 28.2 (5.5 g, 19.83 mmol, 1.00 equiv), CH$_2$Cl$_2$ (50 mL), and 2-[(2-aminoacetyl)oxy]-2-methylpropyl hydrochloride (3.3 g, 19.80 mmol, 1.00 equiv). The reaction was stirred for 2 h at room temperature. The reaction was then quenched by the addition of 10 mL of water. The resulting solution was extracted with 3×20 mL of ethyl acetate and the organic layers combined and concentrated under vacuum to provide 6.4 g (79%) of 28.3 as an off-white solid.

Synthesis of Compound 28.4.

Into a 250-mL round-bottomed flask was placed 28.3 (6.4 g, 15.67 mmol, 1.00 equiv), 1,4-dioxane (65 mL), and (tert-butoxy)potassium (3.5 g, 31.19 mmol, 2.00 equiv). The reaction was stirred for 3 h at room temperature, then quenched by the addition of NH$_4$Cl (aq). The resulting solution was extracted with 3×20 mL of EtOAc, the organic layers were combined and concentrated under vacuum to provide 2 g (35%) of 28.4 as a light yellow solid.

Synthesis of Compound 28.5.

Into a 50-mL round-bottomed flask was placed 28.4 (2 g, 5.52 mmol, 1.00 equiv), CH$_2$Cl$_2$ (20 mL), and 2,2,2-trifluoroacetaldehyde (0.5 mL). The reaction was stirred for 2 h at room temperature. The resulting mixture was concentrated under vacuum to provide 1.6 g (95%) of 28.5 as a yellow solid.

Synthesis of Compound 28.6.

Into a 50-mL round-bottomed flask was placed 28.5 (1.6 g, 5.22 mmol, 1.00 equiv), THF (16 mL), 1H-imidazole (750 mg, 11.02 mmol, 2.00 equiv), and tert-butyl(chloro)diphenylsilane (3 g, 10.91 mmol, 2.00 equiv). The reaction was stirred for 2 h at room temperature. The crude product was purified by column chromatography to furnish 1.5 g (53%) of 28.6 as a light yellow solid.

Synthesis of Compound 28.7.

Into a 50-mL 3-necked round-bottomed flask, purged and maintained with an inert atmosphere of nitrogen, was placed 28.6 (1.5 g, 2.75 mmol, 1.00 equiv), 1.6 (753 mg, 3.30 mmol, 1.20 equiv), THF (15 mL), DIAD (834 mg, 6.37 mmol, 1.50 equiv), and PPh$_3$ (1.08 g, 4.12 mmol, 1.50 equiv). The resulting solution was stirred for 10 h at room temperature. The crude product was purified by column chromatography to furnish 1.8 g (crude) of 28.7 as a yellow solid.

Synthesis of Compound 28.8.

Into a 100-mL round-bottomed flask was placed 28.7 (1.8 g, 2.38 mmol, 1.00 equiv), THF (18 mL) and TBAF (2.5 g, 9.58 mmol, 4.00 equiv). The reaction was stirred for 10 hours at room temperature. The crude was purified by column chromatography to furnish 500 mg (41%) of 28.8 as a white solid.

Synthesis of Compound I-28.

Into a 8-mL round-bottomed flask was placed 28.8 (500 mg, 0.97 mmol, 1.00 equiv), CH$_2$Cl$_2$ (5 mL), DIEA (260 mg, 2.01 mmol, 2.00 equiv), HATU (760 mg, 2.00 mmol, 2.00 equiv) and pyrrolidine (142 mg, 2.00 mmol, 2.00 equiv). The reaction was stirred for 10 h at room temperature. The crude product was purified by column chromatography and preparative HPLC to furnish 195.1 mg (35%0) of I-28 as a white solid. LC-MS (ES, m/z): [M+H]$^+$ 570; $^1$H NMR (300 MHz, DMSO-d$_6$): 0.91-0.98 (m, 6H), 1.78-1.83 (m, 2H), 1.93-1.97 (m, 2H), 2.37 (s, 3H), 3.29-3.34 (m, 2H), 3.40-3.44 (m, 1H), 3.53-3.57 (t, 2H), δ 3.75 (s, 3H), 4.86-4.12 (m, 2H), 4.68 (s, 2H), 5.12-5.16 (m, 1H), 6.57-6.59 (t, 1H), 7.00-7.02 (m, 1H), 7.12-7.19 (m, 1H), 7.21-7.23 (m, 1H), 7.78-7.99 (d, 1H), 8.16-8.17 (d, 1H).

Example 29: Synthesis of 2-(1-((R)-2-(5-fluoro-2-methoxyphenyl)-2-isopropoxy-ethyl)-5-methyl-2,4-dioxo-6-(1H-pyrazol-1-yl)-1,4-dihydrothieno[2,3-d]pyrimidin-3(2H)-yl)-N-isopropylpropanamide, I-29

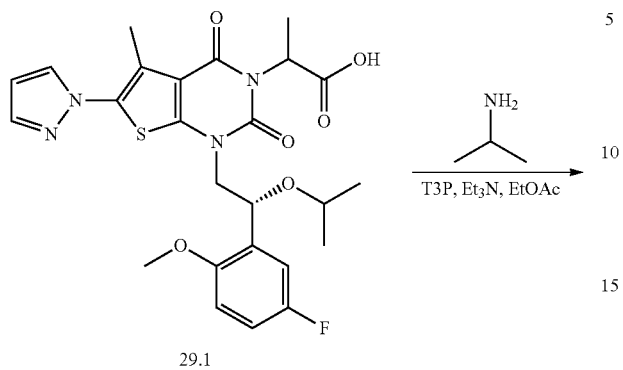

29.1

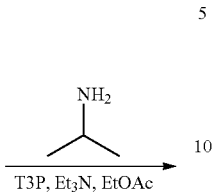

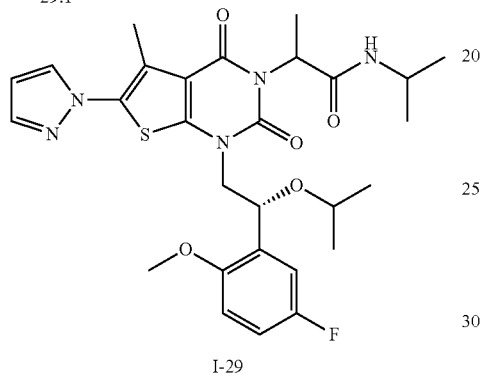

I-29

Into a 5-mL round-bottom flask was placed 29.1 (110 mg, 0.21 mmol, 1.00 equiv), T3P (198 mg), Et₃N (63 mg, 0.62 mmol, 3.00 equiv), EtOAc (2 mL) and propan-2-amine (25 mL). The reaction was stirred for 1 h at room temperature. The resulting mixture was concentrated under vacuum. The crude was purified by column chromatography to furnish 68.1 mg (57%) of 1-29 as a white solid. LC-MS (ES, m/z): [M+H]⁺ 572; ¹H NMR (300 MHz, DMSO-d₆): δ 0.92-1.05 (m, 12H), 1.38-1.41 (m, 3H), 2.37 (s, 3H), 3.41-3.44 (m, 1H), 3.72-3.75 (m, 3H), 3.88-4.12 (m, 3H), 5.16-5.25 (m, 2H), 6.58 (t, 1H), 7.00-7.03 (m, 1H), 7.10-7.20 (m, 2H), 7.44-7.51 (m, 1H), 7.79 (d, 1H), 8.17 (t, 1H).

Example 30: Synthesis of (R)-2-(1-((R)-2-(5-fluoro-2-methoxyphenyl)-2-isopropoxyethyl)-5-methyl-2,4-dioxo-6-(1H-pyrazol-1-yl)-1,4-dihydrothieno[2,3-d]pyrimidin-3(2H)-yl)-N-isopropylpropanamide, I-30

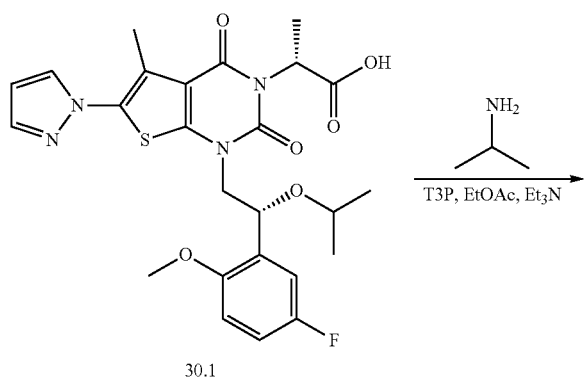

30.1

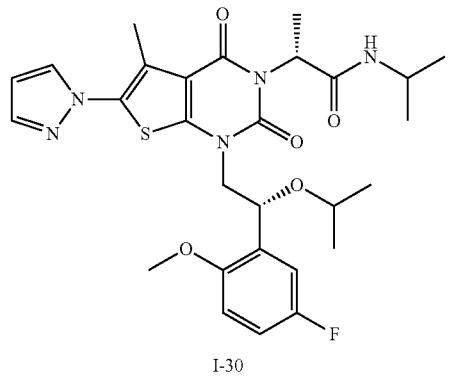

I-30

Into a 6-mL sealed tube was placed 30.1 (100 mg, 0.19 mmol, 1.00 equiv), ethyl acetate (1.5 mL), T3P (90.3 mg), Et₃N (57.3 mg, 0.57 mmol, 3.00 equiv) and propan-2-amine (22.3 mg, 0.38 mmol, 2.00 equiv). The reaction was stirred for 3 hours at room temperature. The resulting mixture was concentrated under vacuum. The crude product was purified by preparative TLC and HPLC to furnish 33.1 mg (31%) of 1-30 as a white solid.

LC-MS (ES, m/z): [M+H]⁺ 572; ¹H NMR (400 MHz, DMSO-d₆): δ0.92-1.05 (m, 12H), 1.38-1.41 (t, 3H), 2.37 (s, 3H), 3.41-3.44 (m, 1H), 3.72-3.75 (d, 3H), 3.88-4.01 (m, 3H), 5.15-5.25 (m, 2H), 6.58-6.59 (t, 1H), 6.99-7.03 (m, 1H), 7.10-7.20 (m, 2H), 7.44-7.51 (m, 1H), 7.79-7.80 (d, 1H), 8.17-8.18 (t, 1H).

Example 31: Synthesis of 1-((R)-2-(5-fluoro-2-methoxyphenyl)-2-isopropoxyethyl)-5-methyl-3-((S)-1-oxo-1-(pyrrolidin-1-yl)propan-2-yl)-6-(1H-pyrazol-1-yl)thieno[2,3-d]pyrimidine-2,4(1H,3H)-dione, I-31

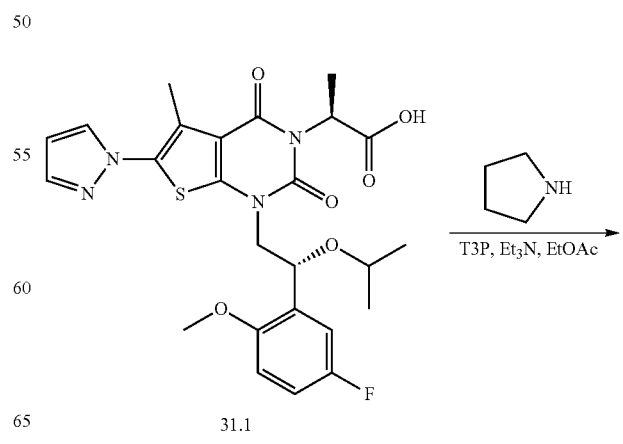

31.1

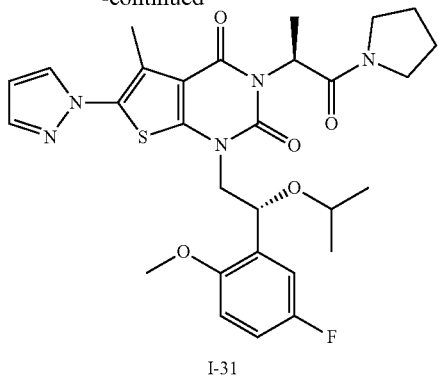

I-31

Into a 5-mL round-bottom flask was placed 31.1 (110 mg, 0.21 mmol, 1.00 equiv), T3P (198 mg), Et₃N (63 mg, 0.62 mmol, 3.00 equiv), EtOAc (2 mL) and pyrrolidine (25 mg, 0.35 mmol, 1.70 equiv). The reaction was stirred for 1 hour at room temperature. The crude product was purified by column chromatography to furnish 76.6 mg (63%) of I-31 as a white solid. LC-MS (ES, m/z): [M+H]⁺ 584; ¹H NMR (300 MHz, DMSO-d₆): δ 0.90-0.93 (m, 3H), 0.95-0.99 (m, 3H), 1.32-1.37 (m, 3H), 1.55-1.59 (m, 1H), 1.72-1.78 (m, 3H), 2.27 (s, 3H), 2.73-2.80 (m, 1H), 3.19-3.25 (m, 2H), 3.31-3.41 (m, 2H), 3.76-3.78 (m, 3H), 3.89-4.10 (m, 2H), 5.17-5.21 (m, 1H), 5.40-5.43 (m, 1H), 6.59 (s, 1H), 7.01-7.05 (m, 1H), 7.10-7.19 (m, 2H), 7.80 (d, 1H), 8.19 (d, 1H).

Example 32: Synthesis of 1-((R)-2-(5-fluoro-2-methoxyphenyl)-2-isopropoxyethyl)-5-methyl-3-(1-oxo-1-(pyrrolidin-1-yl)propan-2-yl)-6-(1H-pyrazol-1-yl)thieno[2,3-d]pyrimidine-2,4(1H,3H)-dione, I-32

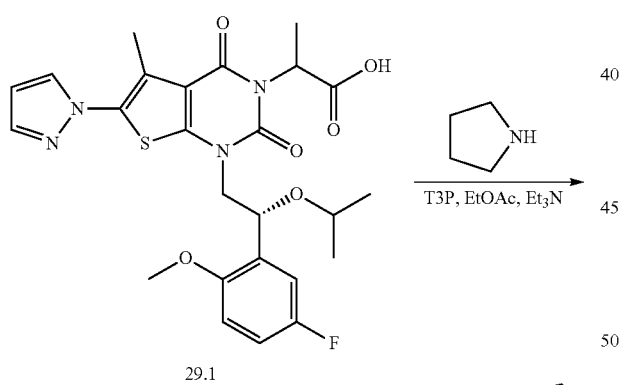

Compound I-32 was prepared from compound 29.1 and pyrrolidine using procedure described in Example 29. LC-MS (ES, m/z): [M+H]⁺ 584; ¹H NMR (400 MHz, DMSO-d₆): δ 0.90 (d, 3H), 0.91 (d, 3H), 1.32-1.37 (m, 3H), 1.61 (m, 1H), δ 1.78 (m, 3H), 2.39 (s, 3H), 2.77-2.79 (m, 1H), 3.22-3.31 (m, 2H), 3.33-3.41 (m, 2H), 3.76-3.78 (d, 3H), 3.81-4.17 (m, 2H), 5.18-5.21 (m, 1H), 5.40-5.43 (m, 1H), 6.58-6.59 (t, 1H), 7.01-7.04 (m, 1H), 7.11-7.20 (m, 2H), 7.80 (d, 1H), 8.19-8.21 (t, 1H).

Example 33: Synthesis of (R)-2-(1-(2-ethoxy-2-(5-fluoro-2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-33

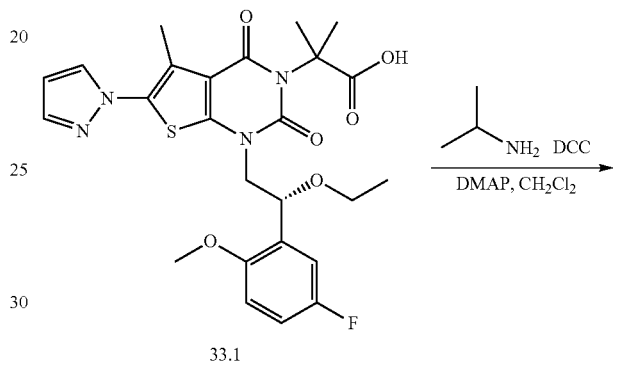

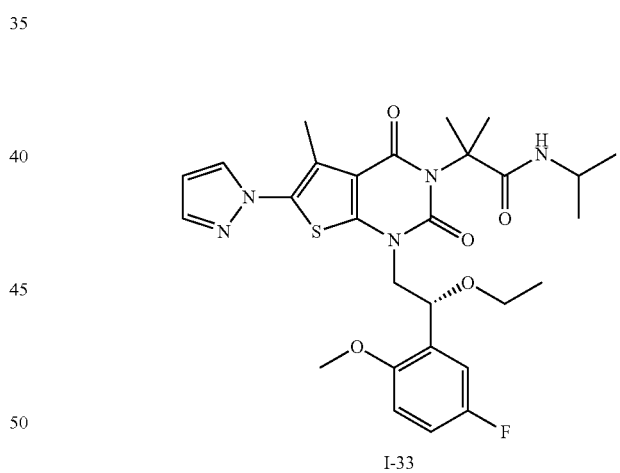

Into a 6-mL sealed tube was placed 33.1 (300 mg, 0.57 mmol, 1.00 equiv), CH₂Cl₂ (2 mL), propan-2-amine (66.8 mg, 1.13 mmol, 2.00 equiv), DMAP (138.1 mg, 1.13 mmol, 2.00 equiv) and DCC (349.8 mg, 12.93 mmol, 22.88 equiv). The reaction was stirred overnight at 50° C. in an oil bath. The resulting mixture was concentrated under vacuum. The crude product was purified by preparative TLC and HPLC to furnish 110.1 mg (34%) of I-33 as a white solid. LC-MS (ES, m/z): [M-C3H8N]⁺ 513; ¹H NMR (400 MHz, DMSO-d₆): δ 1.01-1.06 (m, 9H), 1.59-1.63 (d, 6H), 2.29 (s, 3H), 3.37-3.39 (m, 2H), 3.67 (s, 3H), 3.81-3.87 (m, 1H), 3.96-3.99 (m, 2H), 5.03-5.06 (t, 1H), 6.56-6.57 (t, 1H), 6.94-6.97 (m, 1H), 7.07-7.16 (m, 2H), 7.28-7.30 (d, 1H), 7.77 (d, 1H), 8.10 (d, 1H).

Example 34: Synthesis of (R)-1-(2-ethoxy-2-(5-fluoro-2-methoxyphenyl)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-34

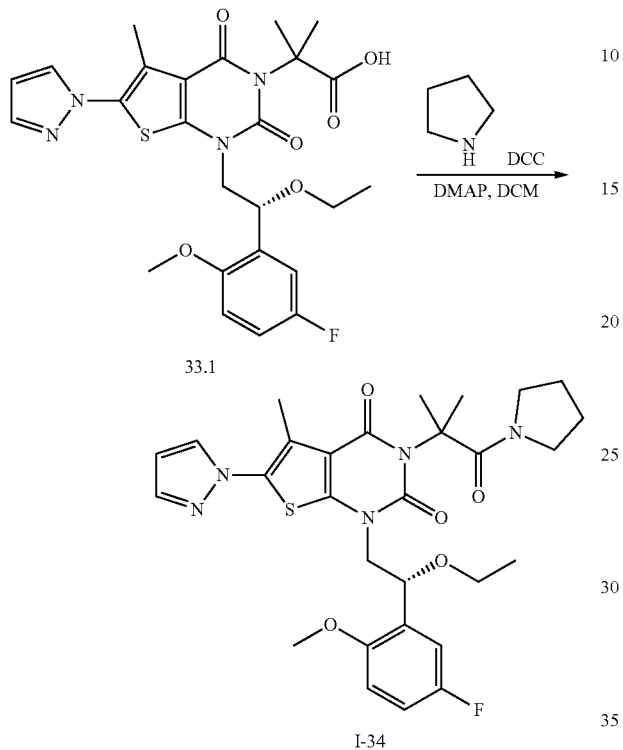

Compound I-34 was prepared from compound 33.1 and pyrrolidine using procedure described in Example 33. LC-MS (ES, m/z): [M-C$_5$H$_8$N]$^+$ 513; $^1$H NMR (400 MHz, DMSO-d$_6$): δ1.02-1.06 (t, 3H), 1.61-1.73 (m, 10H), 2.30 (s, 3H), 2.90-3.00 (m, 1H), 3.13-3.14 (m, 1H), 3.30 (m, 2H), 3.32-3.40 (m, 2H), 3.74 (s, 3H), 4.01 (m, 2H), 5.05-5.07 (t, 1H), 6.57-6.58 (t, 1H), 6.99-7.00 (m, 1H), 7.10-7.15 (m, 2H), 7.79 (d, 1H), 8.15 (d, 1H).

Example 35: Synthesis of (R)-2-(1-(2-(5-fluoro-2-methoxyphenyl)-2-(2-hydroxy-ethoxy)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-35

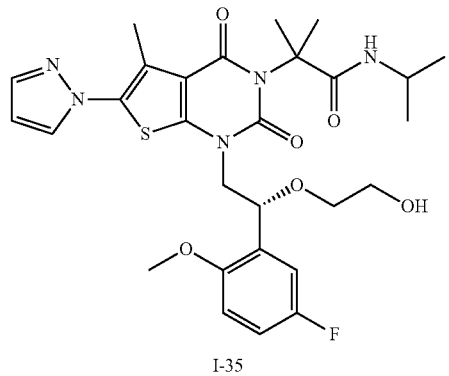

Into a 25-mL round-bottom flask was placed 35.1 (100 mg, 0.18 mmol, 1.00 equiv), EtOAc (10 mL), propan-2-amine (20 mg, 0.34 mmol, 1.85 equiv), Et$_3$N (55 mg, 0.54 mmol, 2.97 equiv), T3P (87 mg, 0.27 mmol, 1.50 equiv). The reaction was stirred for 12 hours at 25° C. The resulting mixture was concentrated under vacuum. The crude product was purified by column chromatography and preparative HPLC to provide 3.0 mg (3%) of I-35 as a white solid. LC-MS (ES, m/z): [M+H]$^+$ 588, [M+Na]$^+$ 610; $^1$H NMR (300 MHz, DMSO-d$_6$): δ 0.98-1.02 (t, 6H), 1.59-1.62 (d, 6H), 2.27-2.29 (m, 2H), 3.32 (s, 3H), 3.37-3.44 (m, 2H), 3.66 (s, 3H), 3.82-3.98 (m, 1H), 3.97-4.00 (m, 2H), 4.60 (t, 1H), 5.07-5.10 (m, 1H), 6.56-6.57 (m, 1H), 6.91-6.97 (m, 1H), 7.07-7.10 (m, 1H), 7.2-7.28 (m, 2H), 7.78 (d, 1H), 8.09 (s, 1H).

Example 36: Synthesis of (R)-1-(2-(5-fluoro-2-methoxyphenyl)-2-(2-hydroxy-ethoxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-36

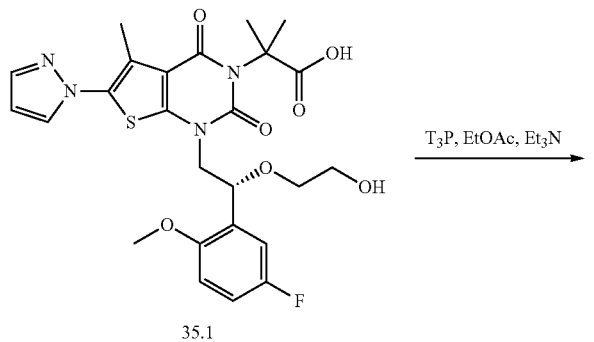

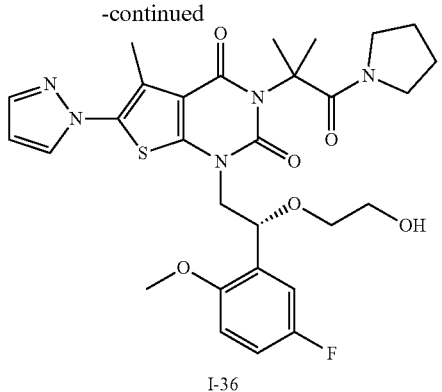

I-36

Compound I-36 was prepared from compound 35.1 and pyrrolidine using the procedure described in example 35. LC-MS (ES, m/z): [M-C$_4$H$_8$N]+529, [M+H]$^+$ 600; $^1$H NMR (300 MHz, DMSO-d$_6$): δ1.52-1.78 (m, 10H), 2.29 (s, 3H), 3.30-3.40 (m, 7H), 3.40-3.45 (m, 2H), 3.72 (s, 3H), 3.92-4.01 (m, 1H), 4.55-4.65 (m, 1H), 5.08-5.12 (m, 1H), 6.5-6.58 (m, 1H), 6.92-6.99 (m, 1H), 7.05-7.10 (m, 1H), 7.11-7.21 (m, 1H), 7.79-7.90 (d, 1H), 8.11-8.15 (d, 1H).

Example 37: Synthesis of 1-((R)-2-(5-fluoro-2-methoxyphenyl)-2-((R)-2-hydroxy-propoxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-37

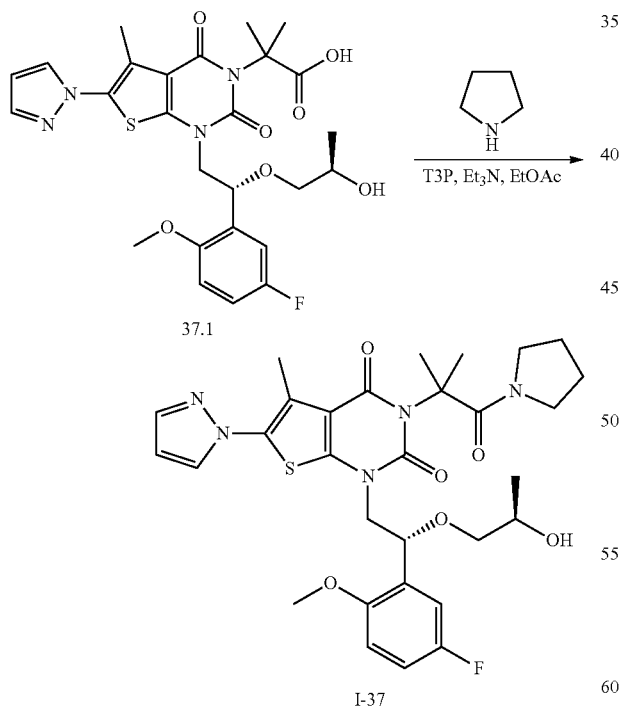

Into a 8-mL vial, was placed 37.1 (80 mg, 0.14 mmol, 1.00 equiv), EtOAc (2 mL), T$_3$P (181 mg), Et$_3$N (43 mg, 0.42 mmol, 2.98 equiv) and pyrrolidine (20 mg, 0.28 mmol, 1.97 equiv). The reaction was stirred overnight at room temperature. The resulting mixture was washed with 1×3 mL of H$_2$O. The resulting mixture was concentrated under vacuum. The crude was purified by column chromatography to furnish 58.7 mg (67%) of I-37 as a white solid. LC-MS (ES, m/z): [M+H]$^+$ 614; $^1$H NMR (300 MHz, DMSO-d$_6$): δ 0.94-0.96 (d, 3H), 1.61-1.72 (m, 10H), 2.30 (s, 3H), 2.95-3.10 (m, 1H), 3.13-3.14 (d, 3H), 3.29-3.31 (m, 2H), 3.57-3.63 (m, 1H), 3.74 (s, 3H), 4.06-4.19 (m, 2H), 4.50-4.52 (d, 1H), 5.09-5.13 (t, 1H), 6.56-6.57 (t, 1H), 6.98-7.03 (m, 1H), 7.09-7.16 (m, 1H), 7.78-7.79 (d, 1H), 8.13-8.14 (d, 1H).

Example 38: Synthesis of 2-(1-((R)-2-(5-fluoro-2-methoxyphenyl)-2-((S)-2-hydroxy-propoxy)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-38

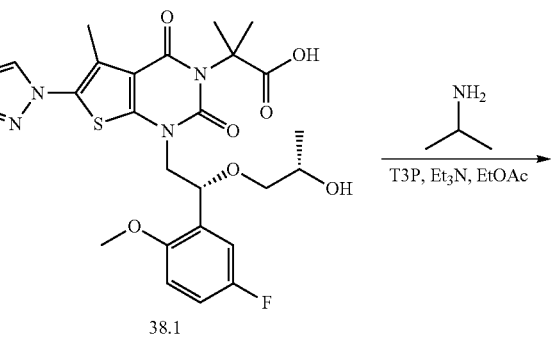

38.1

I-38

Compound I-38 was prepared in 30% yield from compound 38.1 and propan-2-amine using procedure described in Example 37. LC-MS (ES, m/z): [M+Na]$^+$ 624; $^1$H NMR (300 MHz, DMSO-d$_6$): δ 0.95-0.98 (d, 3H), 1.02-1.14 (t, 6H), 1.60-1.62 (d, 6H), 2.29 (s, 3H), 3.04-3.09 (m, 1H), 3.18-3.23 (m, 1H), 3.61-3.68 (m, 4H), 3.78-3.87 (m, 1H), 3.89-3.99 (m, 2H), 4.55-4.56 (d, 1H), 5.06-5.10 (t, 1H), 6.56-6.57 (t, 1H), 6.93-6.97 (m, 1H), 7.06-7.13 (m, 1H), 7.20-7.26 (m, 2H), 7.77 (d, 1H), 8.09 (d, 1H).

Example 39: Synthesis of 2-(1-((R)-2-(5-fluoro-2-methoxyphenyl)-2-((R)-2-hydroxy-propoxy)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-39

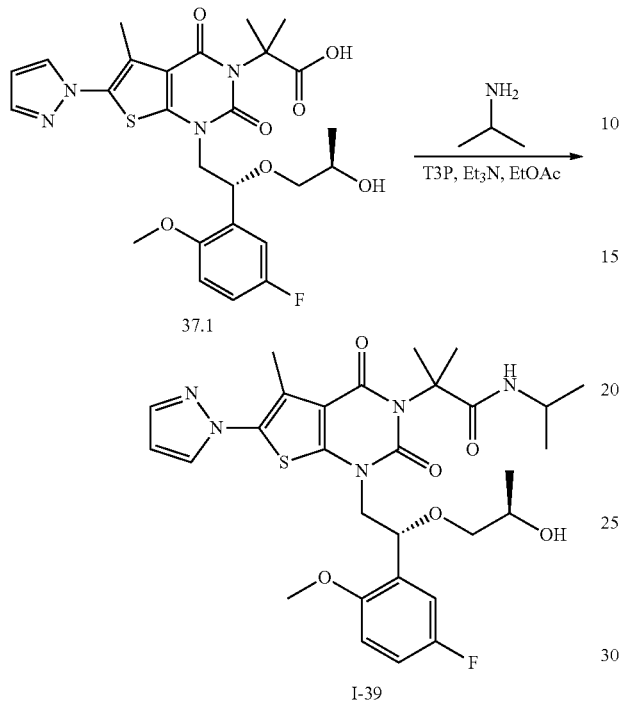

Into a 8-mL vial was placed 37.1 (80 mg, 0.14 mmol, 1.00 equiv), EtOAc (2 mL), Et₃N (43 mg, 0.42 mmol, 2.98 equiv), propan-2-amine (20 mg, 0.34 mmol, 2.37 equiv) and T3P (181 mg, 0.28 mmol, 1.99 equiv). The reaction was stirred overnight at room temperature. The resulting mixture was washed with 1×3 mL of H₂O, and then concentrated under vacuum. The crude product was purified by preparative TLC to afford 23.9 mg (28%) of 1-39 as a white solid. LC-MS (ES, m/z): [M+Na]⁺ 624; ¹H NMR (400 MHz, DMSO-d₆): δ 0.95-0.97 (d, 3H), 0.99-1.02 (t, 6H), 1.60-1.63 (d, 6H), 2.33 (s, 3H), 3.13-3.15 (d, 2H), 3.59-3.65 (m, 1H), 3.69 (s, 3H), 3.80-3.87 (m, 1H), 4.04-4.14 (m, 2H), 4.51-4.53 (d, 1H), 5.08-5.12 (t, 1H), 6.57 (s, 1H), 6.95-6.98 (m, 1H), 7.08-7.14 (m, 1H), 7.14-7.19 (m, 1H), 7.25-7.27 (m, 1H), 7.78 (s, 1H), 8.10 (s, 1H).

Example 40: Synthesis of 1-((R)-2-(5-fluoro-2-methoxyphenyl)-2-((S)-2-hydroxy-propoxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-40

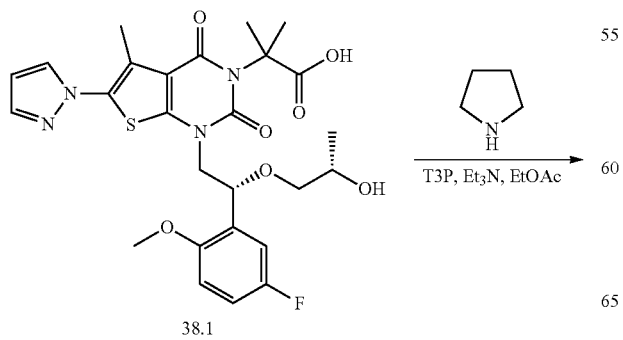

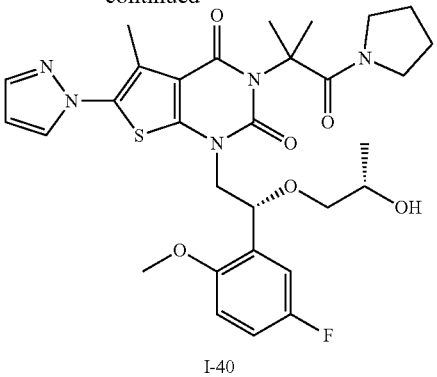

Compound I-40 was prepared in 65% yield from compound 38.1 and pyrrolidine using the procedure developed in Example 37. LC-MS (ES, m/z): [M+H]⁺ 614 [M+Na]⁺ 636; ¹H NMR (400 MHz, DMSO-d₆): δ 0.94-0.96 (d, 3H), 1.62-1.73 (m, 10H), 2.30 (s, 3H), 2.90-3.11 (m, 2H), 3.12-3.19 (m, 1H), 3.20-3.23 (m, 1H), 3.30-3.33 (m, 2H), 3.62-3.68 (m, 1H), 3.74 (s, 3H), 3.95-4.17 (m, 2H), 4.56-4.57 (d, 1H), 5.08-5.11 (t, 1H), 6.57-6.58 (t, 1H), 6.99-7.01 (m, 1H), 7.02-7.15 (m, 1H), 7.19-7.21 (m, 1H), 7.79-7.80 (d, 1H), 8.14-8.15 (d, 1H).

Example 41: Synthesis of (R)-2-(1-(2-(5-fluoro-2-methoxyphenyl)-2-(2-hydroxy-2-methylpropoxy)ethyl)-5-methyl-2,4-dioxo-6-(1H-pyrazol-1-yl)-1,4-dihydro-thieno[2,3-d] pyrimidin-3(2H)-yl)-N-isopropyl-2-methylpropanamide, I-41

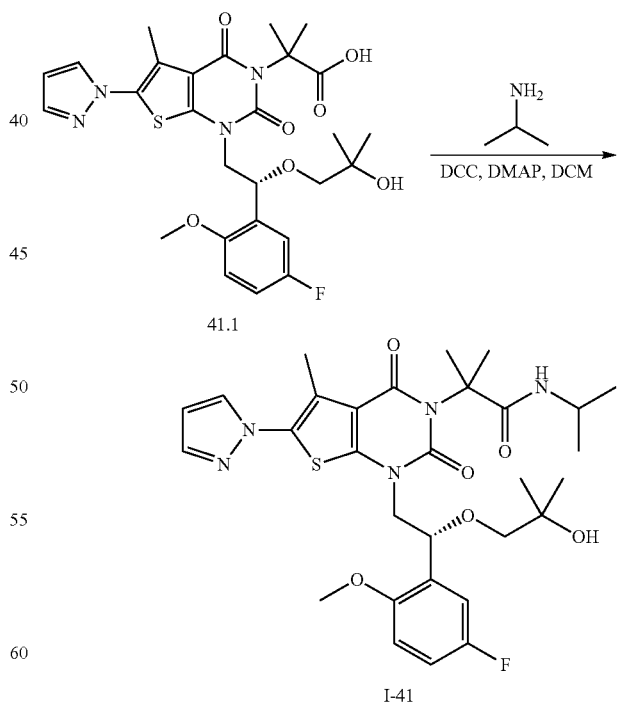

Into a 8-mL vial was placed 41.1 (160 mg, 0.28 mmol, 1.00 equiv), DCC (114 mg, 0.55 mmol, 1.98 equiv), DMAP (68 mg, 0.56 mmol, 2.00 equiv), CH₂Cl₂ (2 mL) and propan-2-amine (34 mg, 0.58 mmol, 2.07 equiv). The reaction was stirred overnight at 50° C. The resulting mixture was concentrated under vacuum. The crude product was purified by preparative TLC to furnish 134.5 mg (78%) of 1-41 as an off-white solid. LC-MS (ES, m/z): [M+H]+ 616 [M+Na]+ 638; ¹H NMR (300 MHz, DMSO-d): δ 0.93-1.03 (m, 12H), 1.60-1.63 (d, 6H), 2.50 (s, 3H), 2.92-2.95 (d, 1H), 3.08-3.11 (d, 1H), 3.72 (s, 3H), 3.78-3.89 (m, 1H), 3.98-4.00 (m, 2H), 4.27 (s, 1H), 5.09-5.13 (t, 1H), 6.56-6.57 (t, 3H), 6.97-7.01 (m, 1H), 7.08-7.24 (m, 3H), 7.77-7.78 (d, 1H), 8.09-8.10 (d, 1H).

Example 42: Synthesis of (R)-1-(2-(5-fluoro-2-methoxyphenyl)-2-(2-hydroxy-2-methylpropoxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-42

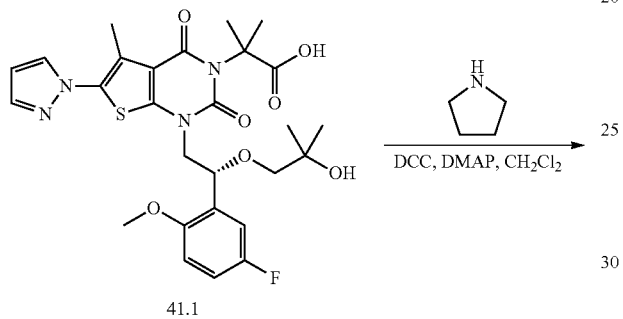

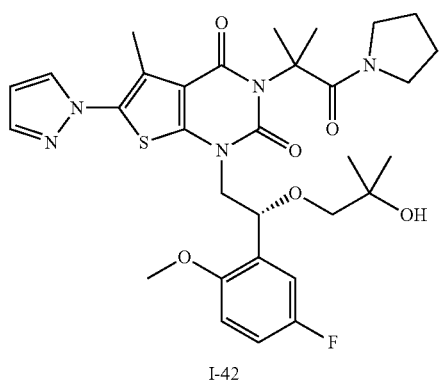

I-42

Compound I-42 was prepared from 41.1 and pyrollidine in 76% yield using the procedure described in Example 41. LC-MS (ES, m/z): [M+H]+ 628 [M+Na]+ 650; ¹H NMR (300 MHz, DMSO-d₆): δ 0.93-1.00 (m, 6H), 1.64-1.80 (m, 10H), 2.30 (s, 3H), 2.90-3.24 (m, 6H), 3.76 (s, 1H), 4.00-4.08 (m, 2H), 4.27 (s, 1H), 5.08-5.12 (t, 1H), 6.56-6.58 (t, 1H), 7.00-7.05 (m, 1H), 7.10-7.17 (m, 2H), 7.78-7.79 (d, 1H), 8.12-8.13 (d, 1H).

Example 43: Synthesis of (R)-2-(I-(2-(5-fluoro-2-methoxyphenyl)-2-(2-methoxy-ethoxy)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-43

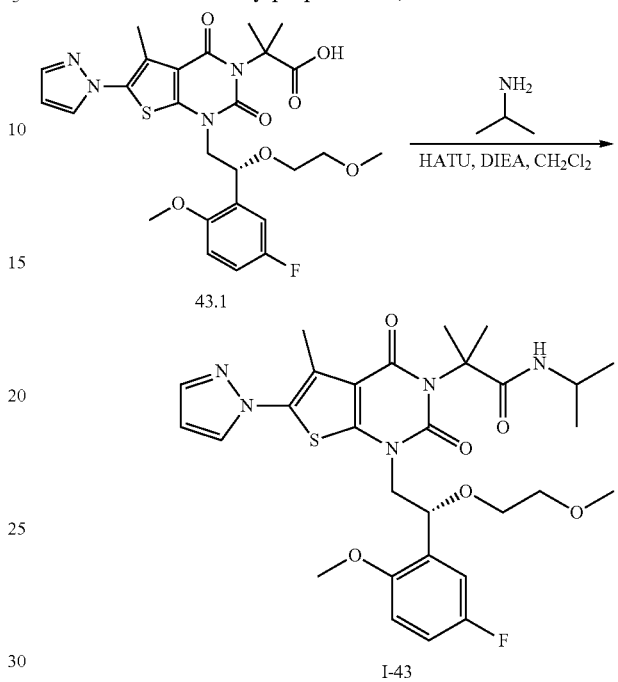

Into a 10-mL round-bottom flask was placed a solution of 43.1 (200 mg, 0.36 mmol, 1.00 equiv) in CH₂Cl₂ (1.5 mL), HATU (274 mg, 0.72 mmol, 2.00 equiv), DIEA (92 mg, 0.71 mmol, 2.00 equiv) and propan-2-amine (42 mg, 0.73 mmol, 2.00 equiv). The reaction was stirred for 1 h at room temperature. The resulting solution was diluted with CH₂Cl₂, and washed with H₂O. The resulting mixture was concentrated under vacuum. The crude product was purified by preparative HPLC to furnish 126.6 mg (59%) of 1-43 as a white solid. LC-MS (ES, m/z): [M+Na]+ 624; ¹H NMR (400 MHz, DMSO-d): δ 8.11-8.10 (d, 1H), 7.78 (d, 1H), 7.26-7.24 (d, 1H), 7.18-7.10 (m, 2H), 6.98-6.94 (m, 1H), 6.57-6.56 (m, 1H), 5.12-5.09 (m, 1H), 4.00-3.93 (m, 2H), 3.90-3.75 (m, 1H), 3.68 (s, 3H), 3.50-3.43 (m, 1H), 3.39-3.32 (m, 3H), 3.12 (s, 3H), 2.30 (s, 3H), 1.63-1.60 (d, 6H), 1.02-0.99 (dd, 6H).

Example 44: Synthesis of (R)-1-(2-(5-fluoro-2-methoxyphenyl)-2-(2-methoxy-ethoxy)ethyl)-5-methyl-3-(2-methyl-1-oxo-1-(pyrrolidin-1-yl)propan-2-yl)-6-(1H-pyrazol-1-yl)thieno[2,3-d]pyrimidine-2,4(1H,3H)-dione, I-44

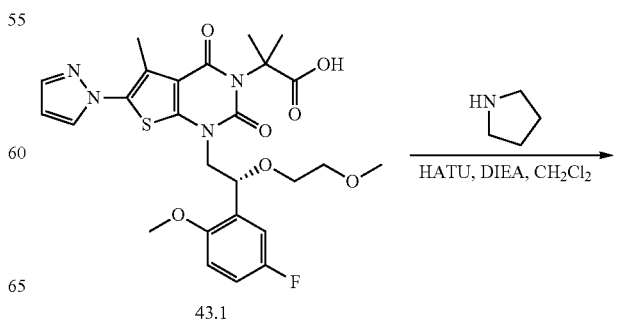

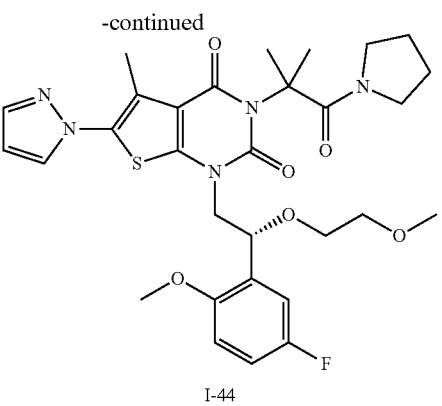

I-44

Compound I-44 was prepared from compound 43.1 and pyrrolidine in 55% yield using the procedure described in Example 43. LC-MS (ES, m/z): [M+H]+ 614; ¹H NMR (400 MHz, CD₃OD-d₄): δ 7.94 (d, 1H), 7.78 (d, 1H), 7.19-7.16 (d, 1H), 7.06-7.00 (m, 1H), 6.98-6.95 (m, 1H), 6.59-6.57 (m, 1H), 5.26-5.23 (m, 1H), 4.50-3.93 (m, 2H), 3.83 (s, 3H), 3.59-3.51 (m, 1H), 3.50-3.42 (m, 5H), 3.33-3.25 (m, 1H), 3.24 (s, 3H), 3.29-3.12 (m, 1H), 2.32 (s, 3H), 1.88-1.60 (m, 10H).

Example 45: Synthesis of (R)-3-(1-(2,5-dihydro-1H-pyrrol-1-yl)-2-methyl-1-oxopropan-2-yl)-1-(2-(5-fluoro-2-methoxyphenyl)-2-((tetrahydro-2H-pyran-4-yl)oxy)ethyl)-5-methyl-6-(1H-pyrazol-1-yl)thieno[2,3-d]pyrimidine-2,4(1H,3H)-dione, I-45

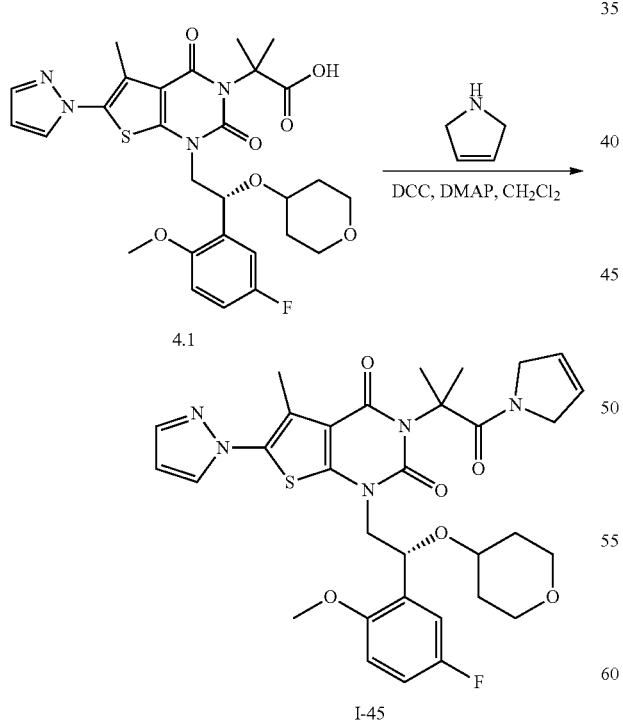

Into a 8-mL round-bottom flask was placed compound 4.1 (200 mg, 0.34 mmol, 1.00 equiv), CH₂Cl₂ (2 mL), DCC (210 mg, 1.02 mmol, 2.99 equiv), 4-DMAP (83.3 mg, 0.68 mmol, 2.00 equiv) and 2,5-dihydro-1H-pyrrole (47 mg, 0.68 mmol, 1.99 equiv). The reaction was stirred overnight at room temperature. The resulting mixture was concentrated under vacuum. The crude product was purified by preparative HPLC to furnish 85.0 mg (39%9/) of 1-45 as a white solid. LC-MS (ES, m/z): [M-C₄H₆N]+ 569 [M+Na]+ 660; ¹H NMR (400 MHz, DMSO-d₆): δ1.13-1.48 (m, 2H), 1.54-1.80 (m, 8H), 2.32 (s, 3H), 3.23-3.26 (m, 2H), 3.39-3.41 (m, 1H), 3.60-3.70 (m, 2H), 3.79 (s, 3H), 3.95-4.12 (m, 6H), 5.25 (m, 1H), 5.76-5.90 (m, 2H), 6.58-6.59 (t, 1H), 7.02-7.05 (m, 1H), 7.13-7.21 (m, 2H), 7.79-7.80 (d, 1H), 8.17-8.18 (d, 1H).

Example 46. Synthesis of (R)—N-cyclohexyl-2-(1-(2-(5-fluoro-2-methoxyphenyl)-2-(2-methoxyethoxy)ethyl)-5-methyl-2,4-dioxo-6-(1H-pyrazol-1-yl)-1,4-dihydrothieno[2,3-d]pyrimidin-3(2H)-yl)-2-methylpropanamide, I-46

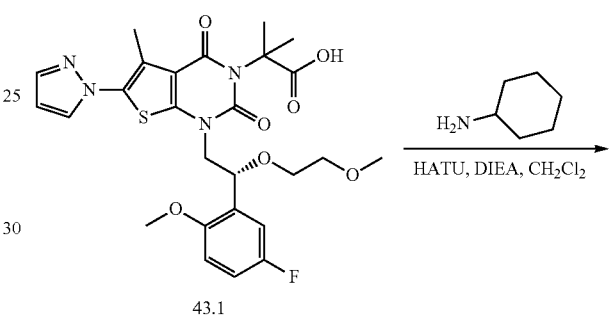

I-46

Compound I-46 was prepared from compound 43.1 and cyclohexanamine using procedure described in Example 43. LC-MS: (ES, m/z): [M+H]+ 642; ¹H NMR (400 MHz, DMSO-d₆): δ8.10 (d, 1H), 7.78 (d, 1H), 7.25-7.22 (d, 1H), 7.18-7.09 (m, 2H), 6.98-6.94 (m, 1H), 6.58-6.56 (m, 1H), 5.12-5.08 (m, 1H), 3.99-3.93 (m, 2H), 3.68 (s, 3H), 3.50-3.43 (m, 2H), 3.39-3.34 (m, 3H), 3.12 (s, 3H), 2.29 (s, 3H), 1.75-1.53 (m, 10H), 1.25-1.18 (m, 2H), 1.17-0.99 (m, 3H).

Example 47. Synthesis of (R)—N-cyclobutyl-2-(1-(2-(5-fluoro-2-methoxyphenyl)-2-(2-methoxyethoxy)ethyl)-5-methyl-2,4-dioxo-6-(1H-pyrazol-1-yl)-1,4-dihydrothieno[2,3-d]pyrimidin-3(2H)-yl)-2-methylpropanamide, I-47

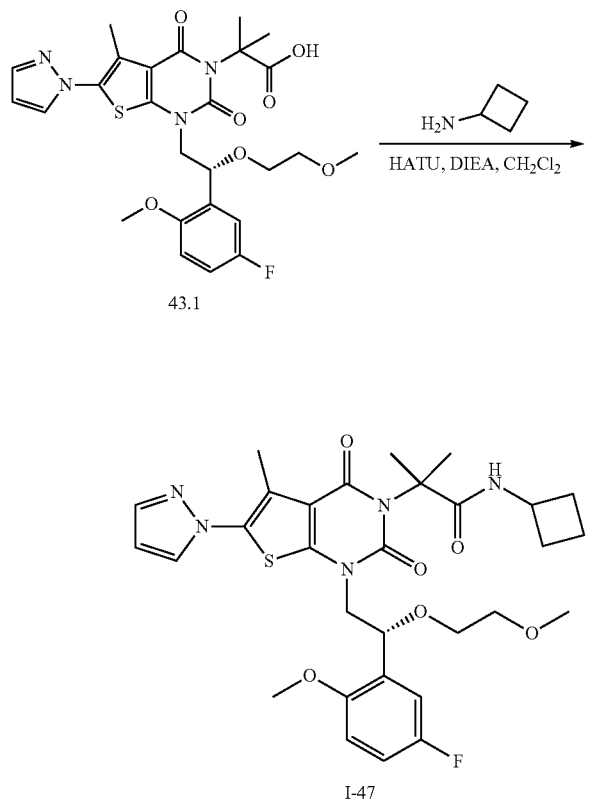

Compound I-47 was prepared from compound 43.1 and cyclobutanamine using procedure described in Example 43. LC-MS (ES, m/z): [M+H]+ 614; ¹H NMR (400 MHz, DMSO-d₆): δ 8.11 (d, 1H), 7.78 (d, 1H), 7.63-7.61 (d, 1H), 7.18-7.09 (m, 2H), 6.98-6.95 (m, 1H), 6.58-6.56 (m, 1H), 5.12-5.08 (m, 1H), 4.15-4.12 (m, 1H), 4.02-3.93 (m, 2H), 3.69 (s, 3H), 3.47-3.40 (m, 1H), 3.39-3.34 (m, 3H), 3.12 (s, 3H), 2.30 (s, 3H), 2.10-2.05 (m, 2H), 1.90-1.82 (m, 2H), 1.62 (s, 3H), 1.60 (s, 3H), 1.60-1.55 (m, 2H).

Example 54. Synthesis of 1-((R)-2-(5-fluoro-2-methoxyphenyl)-2-(2-methoxyethoxy)ethyl)-5-methyl-3-(1-oxo-1-(pyrrolidin-1-yl)propan-2-yl)-6-(1H-pyrazol-1-yl)thieno[2,3-d]pyrimidine-2,4(1H,3H)-dione, I-54

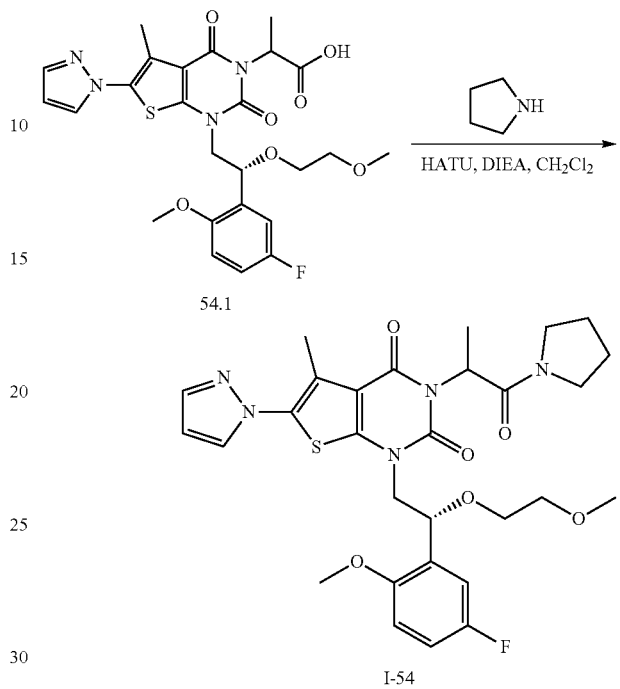

A 25-mL round-bottom flask purged under nitrogen, was charged with 54.1 (500 mg, 0.91 mmol, 1.00 equiv), CH₂Cl₂ (10.0 mL), DIEA (235 mg, 1.82 mmol, 2.00 equiv), pyrrolidine (129 mg, 1.81 mmol, 2.00 equiv) and HATU (416 mg, 1.09 mmol, 1.20 equiv). The reaction was stirred overnight at room temperature. Upon completion resulting mixture was washed with NaCl (aq) then extracted with EtOAc. Organic layers were combined and concentrated under vacuum. The crude was purified by column chromatography to provide 395 mg (72.0%) of I-54 as a white solid. LC-MS: (ES, m/z): [M+H]+ 600, ¹H NMR (300 MHz, DMSO-d): δ 8.16-8.18 (t, 1H), 7.79-7.80 (d, 1H), 7.11-7.17 (m, 2H), 7.03-7.05 (m, 1H), 6.57-6.59 (t, 1H), 5.37-5.40 (m, 1H), 5.12-5.14 (m, 1H), 4.04-4.12 (m, 2H), 3.74-3.76 (m, 3H), 3.43-3.50 (m, 5H), 3.20-3.29 (m, 2H), 3.07 (s, 3H), 2.73-2.81 (m, 1H), 2.38 (s, 3H), 1.74-1.81 (m, 3H), 1.55-1.63 (m, 1H), 1.32-1.36 (m, 3H).

Example 73. Synthesis of (S)-2-(1-((R)-2-(5-fluoro-2-methoxyphenyl)-2-(2-methoxy-ethoxy)ethyl)-5-methyl-2,4-dioxo-6-(1H-pyrazol-1-yl)-1,4-dihydrothieno[2,3-d]pyrimidin-3(2H)-yl)-N-isopropylpropanamide, I-73

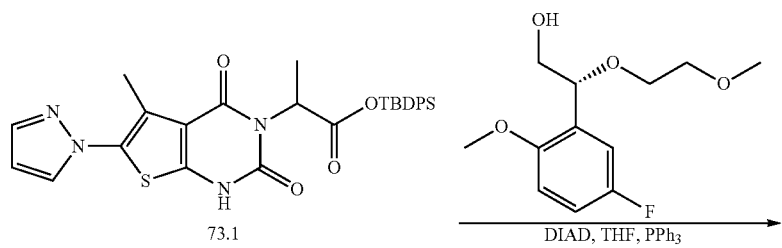

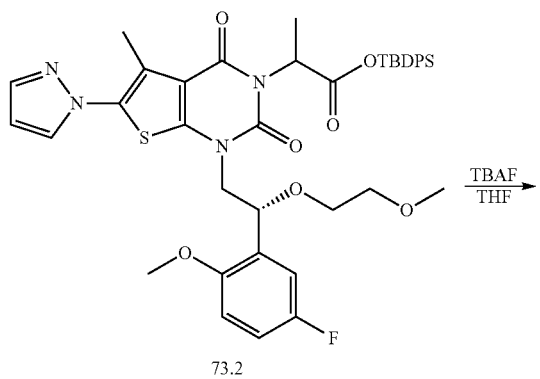

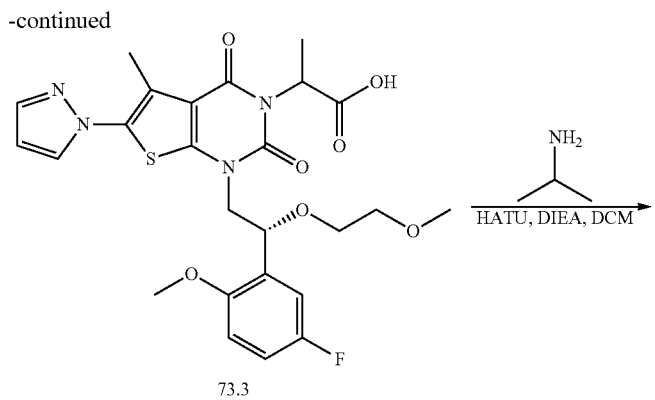

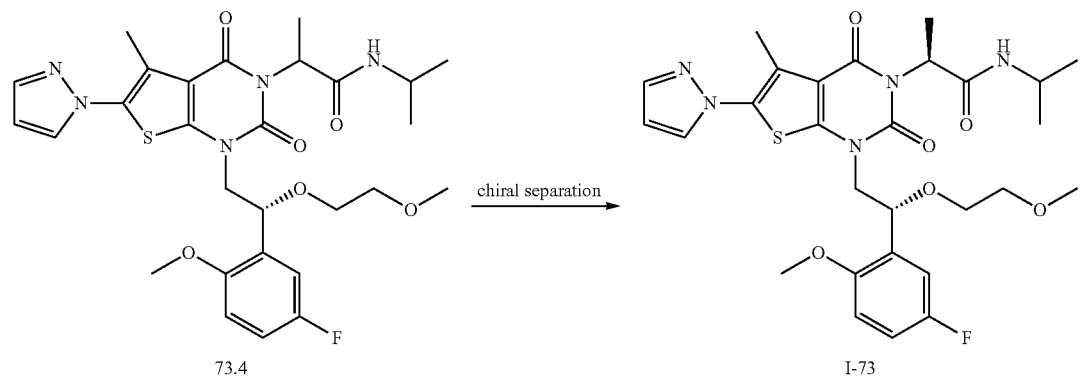

Synthesis of Compound 73.2.

A 100-mL round-bottom flask under nitrogen, was charged with 73.1 (3.0 g, 5.37 mmol, 1.00 equiv), THF (30 mL), DIAD (1.62 g, 8.01 mmol, 1.50 equiv) and (2R)-2-(5-fluoro-2-methoxyphenyl)-2-(2-methoxyethoxy)ethan-1-ol (1.57 g, 6.43 mmol, 1.20 equiv), followed by the addition of PPh$_3$ (1.68 g, 6.41 mmol, 1.20 equiv) in portions. The reaction was stirred for 10 hours at room temperature. Upon completion mixture was concentrated under vacuum and the crude was purified by column chromatography to furnish 4.0 g (crude) of 73.2 as a white solid.

Synthesis of Compound 73.3.

Into a 100-mL round-bottom flask under nitrogen, was placed 73.2 (4 g, 5.10 mmol, 1.00 equiv), THF (40 mL), H$_2$O (8.0 mL) and TBAF (5.73 g, 21.92 mmol, 3.00 equiv). The reaction was stirred overnight at room temperature, then quenched by the addition of water. The resulting solution was extracted with EtOAc, organic layers were combined and concentrated under vacuum. The crude was purified by column chromatography to provide 1.1 g (39.0%) of 73.3 as a white solid.

Synthesis of Compound 73.4.

A 50-mL round-bottom flask under nitrogen, was charged with 73.3 (1.1 g, 2.01 mmol, 1.00 equiv), CH$_2$Cl$_2$ (15.0 mL), DIEA (510 mg, 3.95 mmol, 2.00 equiv), propan-2-amine (270 mg, 4.57 mmol, 2.00 equiv), HATU (910 mg, 2.39 mmol, 1.20 equiv). The reaction was stirred overnight at room temperature, and then washed with NaCl (aq). Mixture was extracted with EtOAc, organic layers were combined and concentrated under vacuum. The crude was purified by column chromatography to furnish 400 mg (34.0%) of 73.4 as a white solid.

Synthesis of Compound I-73.

The crude 73.4 was purified by chiral separation to provide 1-73. LC-MS (ES, min): [M+H]$^+$ 588; $^1$H NMR (300 MHz, DMSO-d$_6$): δ 0.94-1.0 (dd, 6H), 1.35-1.37 (d, 3H), 2.33 (s, 3H), 3.05 (s, 3H), 3.27-3.33 (m, 1H), 3.39-3.45 (m, 3H), 3.69 (s, 3H), 3.85-4.02 (m, 3H), 5.04-5.08 (t, 1H), 5.18-5.20 (q, 1H), 6.53-6.55 (t, 1H), 6.94-6.99 (m, 1H), 7.05-7.15 (m, 2H), 7.40-7.43 (d, 1H), 7.74-7.75 (d, 1H), 8.10-8.11 (d, 1H).

Example 74. Synthesis of (R)-2-(1-((R)-2-(5-fluoro-2-methoxyphenyl)-2-(2-methoxy-ethoxy)ethyl)-5-methyl-2,4-dioxo-6-(1H-pyrazol-1-yl)-1,4-dihydrothieno[2,3-d]pyrimidin-3(2H)-yl)-N-isopropylpropanamide, I-74

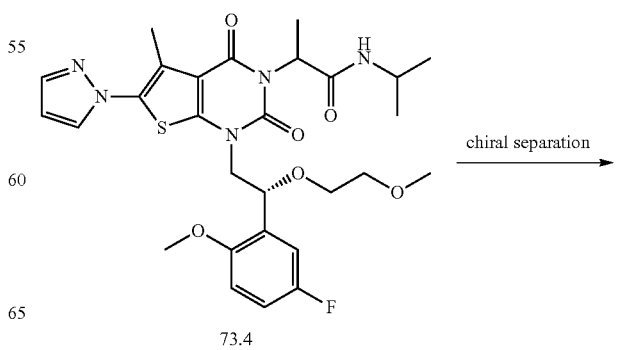

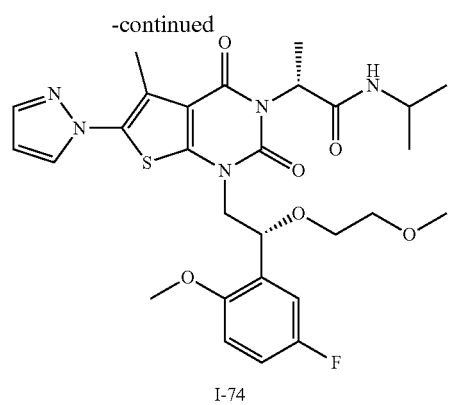

I-74

Compound I-74 was prepared by chiral separation of compound 73.4. LC-MS: (ES, m/z): [M+H]$^+$ 588; $^1$H NMR (300 MHz, DMSO-d$_6$): δ 0.93-1.01 (dd, 6H), 1.33-1.35 (d, 3H), 2.32 (s, 3H), 3.05 (s, 3H), 3.27-3.29 (m, 1H), 3.29-3.35 (m, 2H), 3.42-3.46 (m, 1H), 3.70 (s, 3H), 3.84-4.06 (m, 3H), 5.09-5.17 (m, 2H), 6.53-6.55 (t, 1H), 6.93-6.97 (m, 1H), 7.05-7.14 (m, 2H), 7.37-7.40 (m, 1H), 7.74-7.75 (d, 1H), 8.10-8.11 (d, 1H).

Example 75. Synthesis of 1-((R)-2-(5-fluoro-2-methoxyphenyl)-2-(2-methoxyethoxy)ethyl)-5-methyl-3-((S)-1-oxo-1-(pyrrolidin-1-yl)propan-2-yl)-6-(1H-pyrazol-1-yl)thieno[2,3-d]pyrimidine-2,4(1H,3H)-dione, I-75

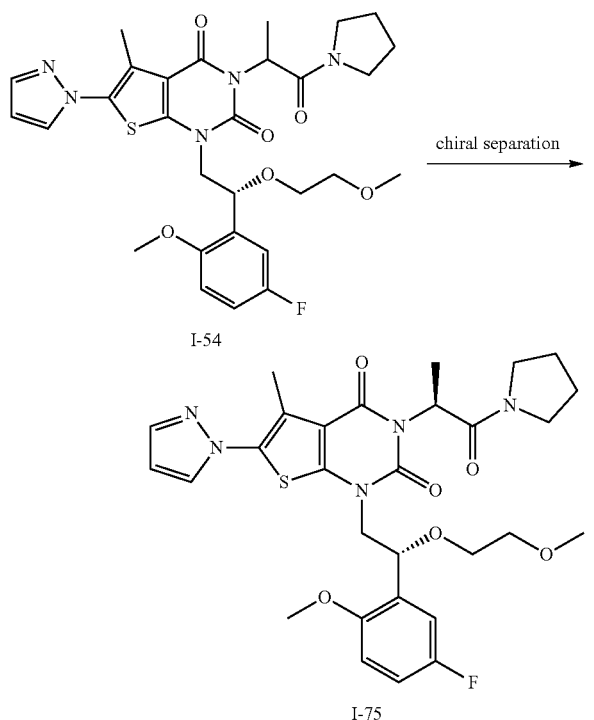

Compound I-75 was prepared by chiral separation of compound I-54. LC-MS: (ES, m/z): [M+H]$^+$ 600; $^1$H NMR (300 MHz, DMSO-d$_6$): δ1.30-1.32 (d, 3H), 1.51-1.73 (m, 4H), 2.33 (s, 3H), 2.74-2.79 (m, 1H), 3.03 (s, 3H), 3.19-3.23 (m, 4H), δ3.23-3.30 (m, 2H), 3.33-3.45 (m, 1H), 3.72 (s, 3H), δ 3.96-4.10 (m, 2H), 5.05-5.10 (t, 1H), 5.31-5.37 (m, 1H), 6.53-6.55 (t, 1H), 6.96-7.12 (m, 3H), 7.75-7.76 (d, 1H), 8.12-8.13 (d, 1H).

Example 76. Synthesis of 1-((R)-2-(5-fluoro-2-methoxyphenyl)-2-(2-methoxyethoxy)ethyl)-5-methyl-3-((R)-1-oxo-1-(pyrrolidin-1-yl)propan-2-yl)-6-(1H-pyrazol-1-yl)thieno[2,3-d]pyrimidine-2,4(1H,3H)-dione, I-76

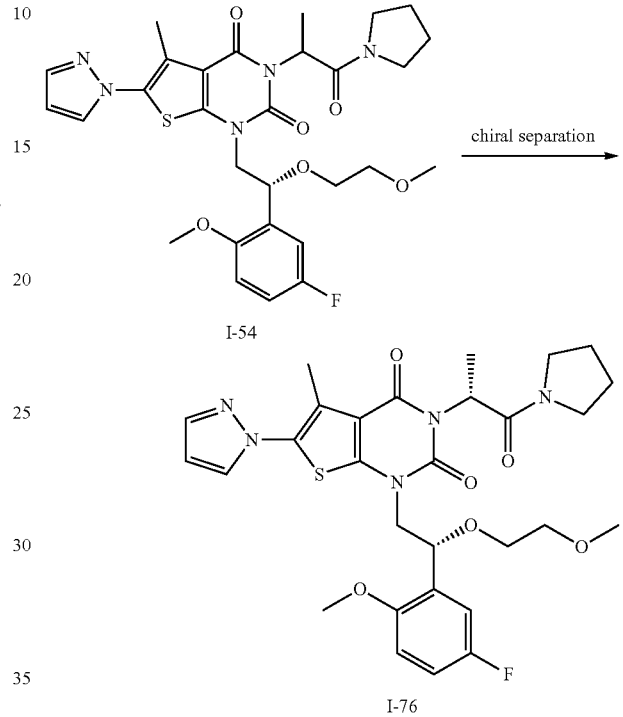

Compound I-76 was prepared by chiral purification of compound I-54. LC-MS [M+H]$^+$ 600; $^1$H NMR (300 MHz, DMSO-d$_6$): δ 1.27-1.30 (d, 3H), 1.52-1.55 (m, 1H), 1.56-1.73 (m, 3H), 2.33 (s, 3H), 2.74-2.79 (m, 1H), 3.03 (s, 3H), 3.18-3.24 (m, 4H), 3.24-3.29 (m, 2H), 3.42-3.45 (m, 1H), 3.70 (s, 3H), 3.97-4.11 (m, 2H), 5.08-5.12 (t, 1H), 5.31-5.36 (m, 1H), 6.54-6.55 (t, 1H), 6.96-7.14 (m, 3H), 7.75-7.76 (d, 1H), 8.12-8.13 (d, 1H).

Example 77. Synthesis of (R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3(2H)-yl)-2-methylpropanamide, I-77

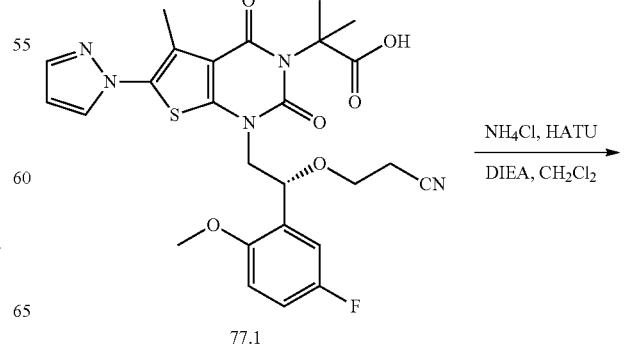

-continued

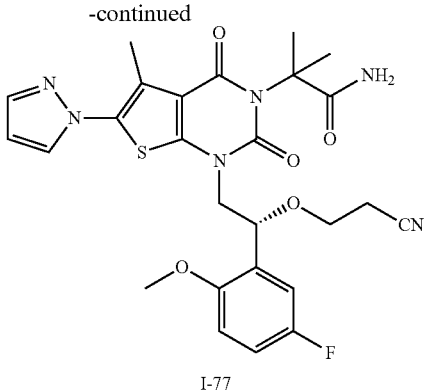

I-77

Compound I-77 was prepared from compound 77.1 and NH₄Cl using procedure described in Example 43. LC-MS (ES, m/z): [M-NH₂] 538, [M+H]⁺ 555; ¹H NMR (400 MHz, DMSO-d₆): δ 1.64-1.65 (d, 6H), 2.30 (s, 3H), 2.69-2.72 (t, 2H), 3.47-3.56 (m, 2H), 3.72 (s, 3H), 3.96-4.01 (m, 1H), 4.08-4.12 (m, 1H), 5.12-5.16 (t, 1H), 6.57-6.58 (d, 1H), 6.61-6.80 (brs, 1H), 6.95-7.02 (m, 2H), 7.12-7.16 (m, 1H), 7.20-7.23 (m, 1H), 7.77-7.78 (d, 1H), 8.09-8.10 (d, 1H).

Example 78. Synthesis of (R)-2-(1-(2-(2-cyanoethoxy)-2-(5-fluoro-2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-78

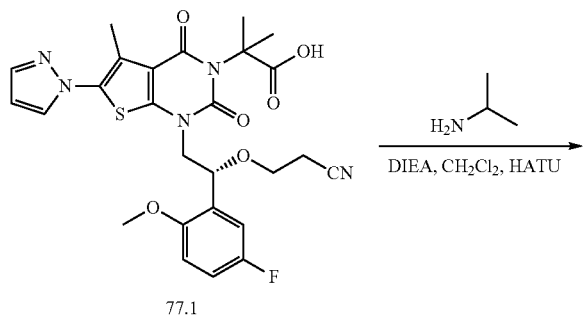

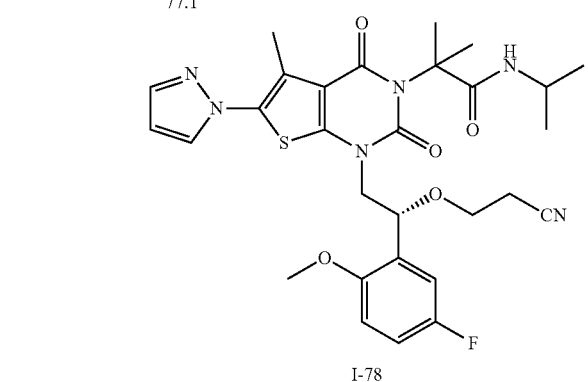

I-78

Compound I-78 was prepared from compound 77.1 and propan-2-amine using procedure described in Example 43. LC-MS (ES, m/z): [M-C₃H₈N]⁺ 538, [M+H]⁺ 597; ¹H NMR (400 MHz, DMSO-d₆): δ 1.00-1.03 (t, 6H), 1.61-1.64 (d, 6H), 2.29 (s, 3H), 2.68-2.7 (t, 2H), 3.46-3.56 (m, 2H), 3.79 (s, 3H), 3.81-3.90 (m, 1H), 4.02-4.06 (m, 2H), 5.12-5.16 (t, 1H), 6.57-6.58 (d, 1H), 6.98-7.02 (m, 1H), 7.08-7.21 (m, 3H), 7.78 (d, 1H), 8.09 (d, 1H).

Example 80. Synthesis of (R)-2-(1-(2-(2-cyanoethoxy)-2-(2-methoxyphenyl)ethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-80

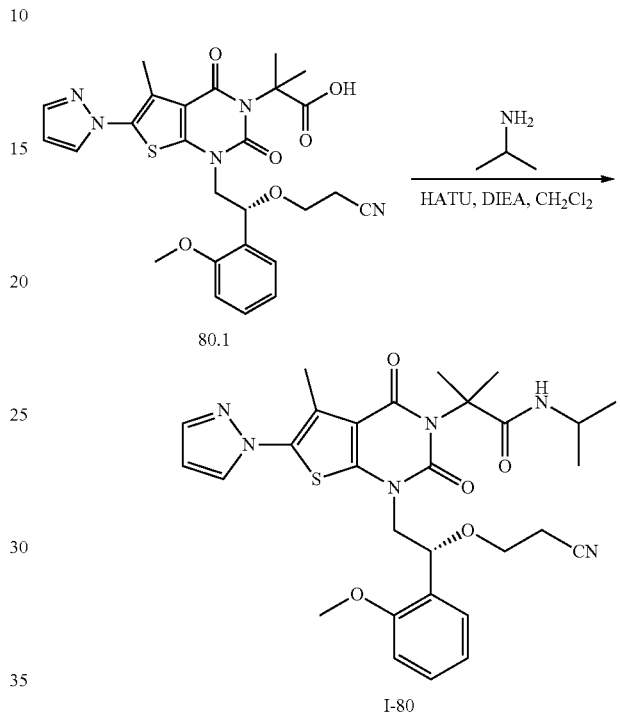

I-80

Compound I-80 was prepared from compound 80.1 and propan-2-amine using procedure described in Example 43. LC-MS [M+H]⁺ 579; ¹H NMR (300 MHz, DMSO-d₆): δ 0.99-1.03 (dd, 6H), 1.61-1.64 (d, 6H), 2.29 (s, 3H), 2.64-2.69 (m, 2H), 3.42-3.52 (m, 2H), 3.73 (s, 3H), 3.78-3.88 (m, 1H), 3.99-4.02 (m, 2H), 5.15-5.17 (t, 1H), 6.55-6.57 (t, 1H), 6.97-7.04 (m, 2H), 7.14-7.17 (d, 1H), 7.29-7.31 (m, 1H), 7.40-7.43 (m, 1H), 7.76-7.77 (d, 1H), 8.08-8.09 (d, 1H).

Example 81. Synthesis of (R)-3-(1-(5-fluoro-2-methoxyphenyl)-2-(5-methyl-3-(2-methyl-1-oxo-1-(pyrrolidin-1-yl)propan-2-yl)-2,4-dioxo-6-(1H-pyrazol-1-yl)-3,4-dihydrothieno[2,3-d]pyrimidin-(2H)-yl)ethoxy)propanenitrile, I-81

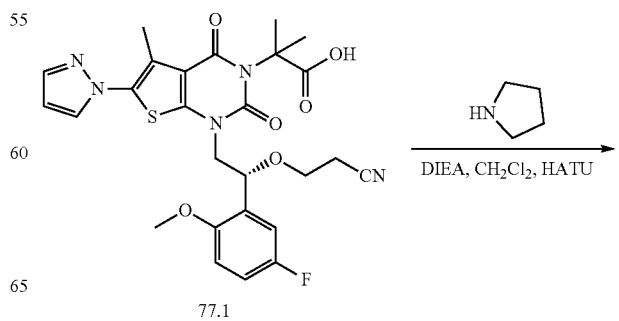

77.1

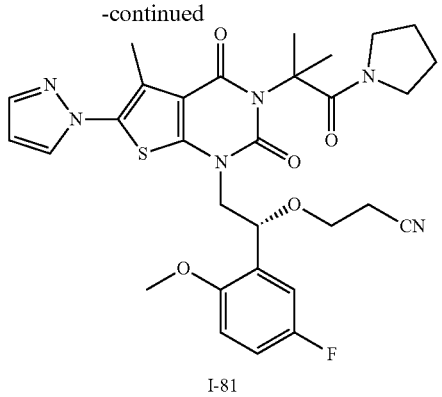

I-81

Compound I-81 was prepared from compound 77.1 and pyrrolidine using procedure described in Example 43. LC-MS (ES, m/z): [M-C$_4$H$_8$N]+538, [M+H]$^+$ 609; $^1$H NMR (400 MHz, DMSO-d$_6$): δ1.59-1.62 (m, 8H), 1.62-1.76 (m, 2H), 2.29 (s, 3H), 2.74 (s, 4H), 2.94-3.13 (m, 2H), 3.44-3.53 (m, 2H), 3.75 (s, 3H), 4.01-4.09 (m, 2H), 5.02-5.06 (t, 1H), 6.56-6.58 (t, 1H), 7.01-7.05 (m, 1H), δ7.13-7.19 (m, 2H), 7.78-7.79 (d, 1H), 8.12 (d, 1H).

Example 84. Synthesis of (R)-3-(I-(2-methoxyphenyl)-2-(5-methyl-3-(2-methyl-1-oxo-1-(pyrrolidin-1-yl)propan-2-yl)-2,4-dioxo-6-(1H-pyrazol-1-yl)-3,4-dihydrothieno[2,3-d]pyrimidin-1(2H)-yl)ethoxy) propanenitrile, I-84

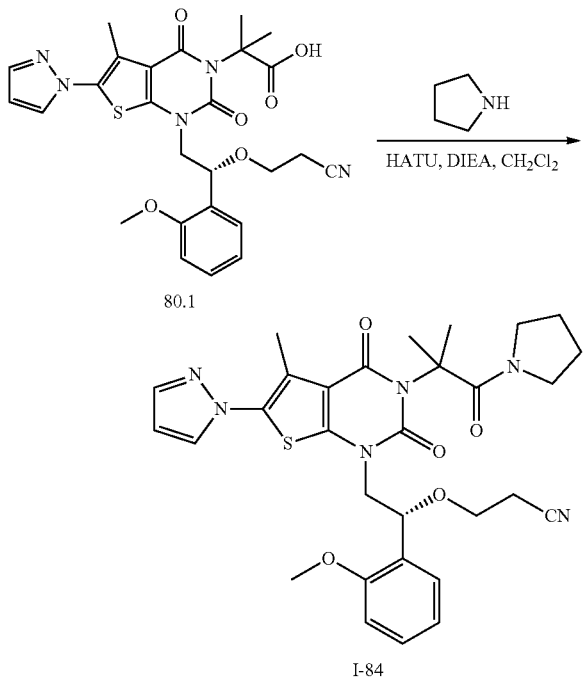

Compound I-84 was prepared from compound 80.1 and pyrrolidine using procedure described in Example 43. LC-MS-PH-NAM-2342-0: (ES, m/z): [M-C$_4$H$_8$N]$^+$ 520: $^1$H NMR (300 MHz, DMSO-d$_6$): δ1.62-1.80 (m, 10H), 2.29 (s, 3H), 2.64-2.68 (m, 3H), 2.95-3.18 (m, 2H), 3.32-3.33 (m, 1H), 3.33-3.42 (m, 2H), 3.76 (s, 3H), 4.01-4.18 (m, 2H), 5.12-5.17 (t, 1H), 6.55-6.57 (m, 1H), 6.98-7.03 (m, 2H), 7.29-7.40 (m, 2H), 7.77-7.78 (d, 1H), 8.10-8.11 (d, 1H).

Example 86. Synthesis of (R)-2-(1-(2-(5-fluoro-2-methoxyphenyl)-2-hydroxyethyl)-5-methyl-2,4-dioxo-6-(1H-pyrazol-1-yl)-1,4-dihydrothieno[2,3-d]pyrimidin-3(2H)-yl)-N-isopropyl-2-methylpropanamide, I-86

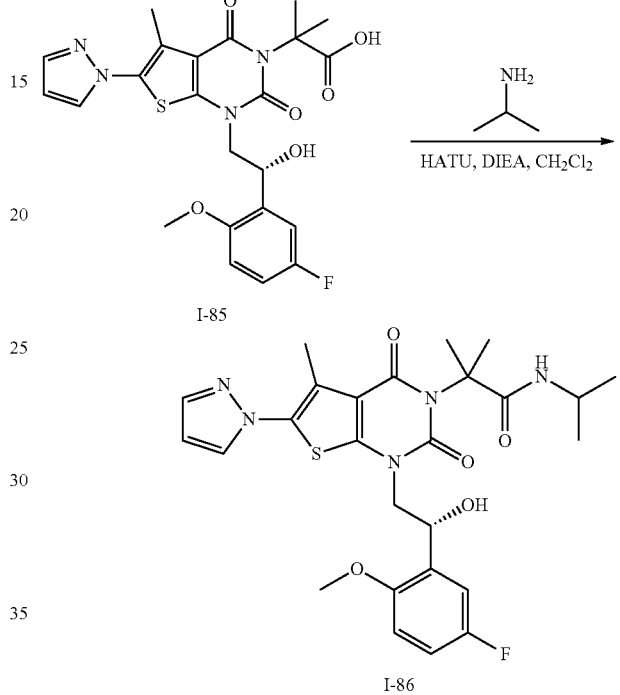

Compound I-86 was prepared from compound I-85 using procedure described in Example 43. LC-MS (ES, m/z): [M-C$_3$H$_8$N]$^+$ 485; $^1$H NMR (300 MHz, DMSO-d$_6$): δ 0.98-1.01 (d, 6H), 1.62 (s, 6H), 2.30 (s, 3H), 3.69 (s, 3H), 3.80-3.87 (m, 2H), 3.93-4.0 (m, 1H), 5.30-5.33 (m, 1H), 5.78-5.80 (d, 1H), 6.56-6.58 (t, 1H), 6.90-6.95 (m, 1H), 7.03-7.10 (m, 1H), 7.22-7.26 (m, 2H), 7.77-7.78 (d, 1H), 8.11-8.12 (d, 1H).

Example 114

In Vitro Acetyl-CoA Carboxylase (ACC) Inhibition Assay

An exemplary procedure for the in vitro ACC inhibition assay, which can be used to determine the inhibitory action of compounds of the invention toward either human (hACC2) or fungal (fACC2) ACC2, follows. The ADP-Glo™ Kinase Assay kit from Promega was used. The ADP-Glo™ Kinase Assay is a luminescent ADP detection assay to measure enzymatic activity by quantifying the amount of ADP produced during an enzyme reaction. The assay is performed in two steps; first, after the enzyme reaction, an equal volume of ADP-Glo™ Reagent is added to terminate the reaction and deplete the remaining ATP. Second, the Kinase Detection Reagent is added to simultaneously convert ADP to ATP and allow the newly synthesized ATP to be measured using a luciferase/luciferin reaction. Luminescence can be correlated to ADP concentrations by using an ATP-to-ADP conversion curve. The detailed procedure is as follows. 50 µL of the compound being tested (600 µM in DMSO) was added to a 384-well dilution plate. The compound was diluted 1:3 in succession in DMSO for each row for 11 wells. 0.5 µL ACC2 working solution was added to 384-well white Optiplate assay plate. 0.5 µL diluted compound solution in each column from step 2 was added to assay plate, each row containing 2 replicates. For the last 2 rows, 0.5 µL negative control (DMSO) was added in one row and 0.5 µL positive control (compound I-97) in the other. The plates were incubated at room temperature for 15 minutes. 5 µL substrate working solution was added to each well to initiate reaction. Final ACC2 reaction concentrations consist of: 5 nM ACC2, 20 µM ATP, 20 µM acetyl-CoA, 12 mM NaHCO$_3$, 0.01% Brij35, 2 mM DTT, 5% DMSO, test compound concentrations: 30 µM, 10 µM, 3.33 µM, 1.11 µM, 0.37 µM, 0.123 µM, 0.0411 µM, 0.0137 µM, 0.00457 µM, 0.00152 µM, and 0.00051 µM. Plates were incubated at room temperature for 60 minutes. 10 µL ADP glo reagent was added. Plates were incubated at room temperature for 40 minutes. 20 µL kinase detection reagent was added. Plates were incubated at room temperature for 40 minutes, and then read on a Perkin Elmer EnVision 2104 plate reader for luminescence as Relative Light Units (RLU).

Data for each concentration, as well as the positive and negative controls were averaged, and the standard deviation calculated. Percent inhibition was calculated by the formula: 100×(average negative control−compound)/(average negative control−average positive control). The IC$_{50}$ for each compound was calculated by fitting the data with a non-linear regression equation: Y=Bottom+(Top-Bottom)/(1+10^((Log IC$_{50}$−X)*Hill Slope)), where X is the log of compound concentration and Y is percent inhibition.

The results of the in vitro ACC2 inhibition assays are set forth in Table 2. The compound numbers correspond to the compound numbers in Table 1. Compounds having an activity designated as "AA" provided an IC$_{50}$ 0.0006-0.003 µM; provided an "A" provided an IC$_{50}$ 0.003-0.01 µM; compounds having an activity designated as "B" provided an IC$_{50}$ 0.01-0.04 µM; and compounds having an activity designated as "C" provided an IC$_{50}$>0.04 µM IC$_{50}$. "NA" stands for "not assayed."

TABLE 2

Results of in vitro ACC2 Inhibition Assay

| Compound | hACC2 | fACC2 |
| --- | --- | --- |
| I-1 | B | AA |
| I-2 | B | AA |
| I-3 | B | NA |
| I-4 | B | NA |
| I-5 | A | NA |
| I-6 | B | NA |
| I-7 | A | NA |
| I-8 | B | NA |
| I-9 | B | NA |
| I-10 | A | NA |
| I-11 | B | NA |
| I-12 | A | NA |
| I-13 | B | AA |
| I-14 | A | NA |
| I-15 | A | NA |
| I-16 | B | NA |
| I-17 | A | NA |
| I-18 | A | AA |
| I-19 | B | NA |
| I-20 | A | NA |
| I-21 | B | NA |
| I-22 | A | NA |
| I-23 | B | NA |
| I-24 | A | AA |
| I-25 | A | NA |
| I-26 | A | AA |
| I-27 | B | NA |
| I-28 | B | AA |
| I-29 | B | AA |
| I-30 | A | AA |
| I-31 | A | AA |
| I-32 | A | AA |
| I-33 | B | AA |
| I-34 | B | AA |
| I-35 | B | AA |
| I-36 | A | AA |
| I-37 | A | AA |
| I-38 | B | AA |
| I-39 | A | AA |
| I-40 | B | AA |
| I-41 | A | AA |
| I-42 | A | AA |
| I-43 | B | AA |
| I-44 | C | A |
| I-45 | B | AA |
| I-46 | C | AA |
| I-47 | B | AA |
| I-48 | A | AA |
| I-49 | A | AA |
| I-50 | A | AA |
| I-51 | A | AA |
| I-52 | A | AA |
| I-53 | A | AA |
| I-54 | B | AA |
| I-55 | A | AA |
| I-56 | C | B |
| I-57 | B | B |
| I-58 | A | AA |
| I-59 | A | AA |
| I-60 | A | AA |
| I-61 | B | AA |
| I-62 | A | AA |
| I-63 | A | AA |
| I-64 | A | AA |
| I-65 | B | A |
| I-66 | B | AA |
| I-67 | B | AA |
| I-68 | B | AA |
| I-69 | B | AA |
| I-70 | B | AA |
| I-71 | B | AA |
| I-72 | A | AA |
| I-73 | A | AA |
| I-74 | C | B |
| I-75 | A | AA |
| I-76 | C | A |
| I-77 | C | AA |
| I-78 | B | AA |
| I-79 | A | AA |
| I-80 | B | A |
| I-81 | A | AA |
| I-82 | B | AA |
| I-83 | B | A |
| I-84 | B | AA |
| I-85 | B | AA |
| I-86 | A | NA |

Example 115

Thermal Shift Assay

Compounds of the present invention are evaluated in a thermal shift assay using methods substantially similar to those described by Vedadi et al. "Chemical screening methods to identify ligands that promote protein stability, protein crystallization, and structure determination." PNAS (2006) vol. 103, 43, 15835-15840, the entirety of which is incorporated herein by reference.

Example 116

[$^{14}$C] Acetate Incorporation Assay

Compounds of the present invention are evaluated in a [$^{14}$C] Acetate Incorporation Assay. An exemplary procedure for the assay, which measures the incorporation of isotopically labeled acetate into fatty acids, follows. HepG2 cells are maintained in T-75 flasks containing DMEM supplemented with 2 mM 1-glutamine, penicillin G (100 units/mL), streptomycin 100 µg/mL with 10% FBS and incubated in a humidified incubator with 5% $CO_2$ at 37° C. Cells were fed every 2-3 days. On Day 1 cells are seeded in 24 well plates at a density of 1.2×10$^5$ cells/ml/well with the growth medium. On Day 3 the medium is replaced with fresh medium containing 10% FBS. On Day 4 the medium is replaced with 0.5 ml of fresh medium containing test compound (in DMSO; final [DMSO] is 0.5%) and the cells are incubated at 37° C. for 1 hour. To one copy of plate, 4 ul of [2-$^{14}$C] acetate (56 mCi/mmol; 1 mCi/ml; PerkinElmer) is added and the cells are incubated at 37° C., 5% $CO_2$ for 5 hrs. To a second copy of plate, 4 ul of cold acetate are added and the cells are incubated at 37° C., 5% $CO_2$ for 5 hrs. This plate is used for protein concentration measurement. Medium is removed and placed in a 15 ml centrifuge tube (BD, Falcon/352096). Cells are rinsed with 1 mL PBS, then aspirated, and the rinse and aspiration steps are repeated. 0.5 ml of 0.1N NaOH are added to each well and let sit at RT to dissolve cell monolayer. The remaining cell suspension is pooled with medium. For the protein determination plate, an aliquot is removed for protein determination (25 ul). 1.0 mL of EtOH and 0.17 mL 50% KOH are added to tubes containing medium and cell suspensions. Cells are incubated at 90° C. for 1 hr, then cooled to room temperature. 5 ml petroleum ether is added per tube, shaken vigorously, centrifuged at 1000 rpm for 5 min, and 500 uL of the petroleum ether layer is transferred to tubes for Microbeta reading, then 2 ml Aquasol-2 are added to each tube, and the tubes are shaken and counted with a Microbeta Liquid Scintillation Counter (Perkin Elmer).

The remaining petroleum ether layer is discarded and the aqueous phase reserved for fatty acid extractions. The aqueous phase was acidified with 1 ml of concentrated HCl, checking pH of one or two extracts to make sure pH was below 1.5 ml of petroleum ether is added per tube, shaken vigorously, centrifuged at 1000 rpm for 5 min, and 4 ml of the petroleum ether layer is transferred to a new glass tube (10*18 mm). 5 ml of petroleum ether was added per tube, shaken vigorously, centrifuged at 1000 rpm for 5 min, and 5 ml of the petroleum ether layer is transferred to the glass tube, and the extraction repeated again. The petroleum ether extracts are pooled and evaporated to dryness overnight. On Day 5 the residue from the petroleum ether fractions is resuspended in 120 uL of chloroform-hexane (1:1) containing 200 ug of linoleic acid as a carrier. 5 uL of this is spotted onto silica gel sheets, and the plates are developed using heptane-diethyl ether-acetic acid (90:30:1) as eluent. The fatty acid band is visualized with iodine vapor and the corresponding bands are cut out into scintillation vials. 2 ml of Aquasol-2 is added to each vial, and the vials are shaken and counted on a scintillation counter.

Example 117

Compounds of the present invention were evaluated in an Anti-Fungal Activity Assay. An exemplary procedure for the assay, which measures the susceptibility of various *Candida* species to anti-fungal compounds, follows. Compounds to be tested (including fluconazole and amphotericin B) were dissolved in DMSO to obtain a solution having a concentration of 1 mg/mL. These stock solutions were sterile filtered using a 0.22 um nylon syringe filter, then diluted in sterile water to achieve a final concentration of 128 µg/mL.

All species were grown from frozen stock by directly plating on to freshly prepared Sabouraud Dextrose agar (BD, Difco) and incubated overnight in ambient air at 35° C. for 24 h. A direct suspension was prepared in RPMI 1640+ MOPS (Lonza, Biowhittaker) by taking individual colonies from the overnight cultures using sterile swabs soaked in sterile saline. The concentration of the suspension was determined using pre-determined standard curves. These suspensions were then diluted down to 5×10$^3$ CFU/mL to achieve a final concentration of 2.5×10$^3$ CFU/mL once added to the microtiter plate as per CLSI guidelines (M27-A3, Vol. 28 No. 14).

Broth microtiter MIC challenge plates were prepared following CLSI guidelines (M27-A3, Vol. 28 No. 14). The original CLSI guidelines focused on reading *Candida* MICs after 48 h of incubation. As reading after only 24 h offers a clear advantage of patient care, QC limits are being established for all drugs at 24 h. That being said there are no known interpretive breakpoints for amphotericin B at 24 h and the current fluconazole interpretive breakpoints are based on a 48 h reading. The MIC for the test compounds were recorded at 48 h. All MIC determinations were achieved by visually comparing the growth found in the antibiotic challenged wells to that of the growth control. The first well found in the dilution scheme that showed no growth (or complete inhibition) was recorded as the MIC.

The results of the Anti-Fungal Activity Assay are shown in Table 3. Compounds having an activity designated as "AA" provided an MIC of 0.08-0.24 pig/mL; "A" provided an MIC of 0.25-1.0 µg/mL; compounds having an activity designated as "B" provided an MIC of 1.1-2.0 µg/mL; compounds having an activity designated as "C" provided an MIC of 2.1-4.0 µg/mL; and compounds having an activity designated as "D" provided an MIC of >4.1 µg/mL.

TABLE 3

Exemplary Anti-Fungal (*Candida*) Activity Assay Results

| | *Candida* Species (MIC, µg/mL, 3 replicates) | | |
|---|---|---|---|
| Compound Number | *C. albicans* ATCC 90028 | *C. krusei* ATCC 6258 | *C. parapsilosis* ATCC 22019 |
| I-1 | C | A | C |
| I-2 | A | A | B |
| I-3 | D | C | D |
| I-4 | D | C | D |
| I-5 | B | B | C |
| I-6 | A | A | B |
| I-7 | B | A | B |
| I-8 | A | A | A |
| I-11 | D | D | D |
| I-12 | C | C | D |
| I-13 | A | A | B |
| I-14 | A | B | A |
| I-15 | A | B | A |
| I-17 | A | A | A |
| I-18 | B | C | C |
| I-19 | D | C | D |
| I-21 | A | A | A |
| I-22 | A | A | B |
| I-23 | A | A | B |
| I-24 | D | C | D |

TABLE 3-continued

Exemplary Anti-Fungal (*Candida*) Activity Assay Results

| Compound Number | *Candida* Species (MIC, µg/mL, 3 replicates) | | |
|---|---|---|---|
| | *C. albicans* ATCC 90028 | *C. krusei* ATCC 6258 | *C. parapsilosis* ATCC 22019 |
| I-25 | B | A | B |
| I-26 | B | A | B |
| I-27 | B | B | B |
| I-28 | A | A | A |
| I-29 | B | C | D |
| I-30 | A | A | A |
| I-31 | B | C | C |
| I-32 | C | C | D |
| I-33 | D | D | D |
| I-34 | D | D | D |
| I-36 | C | B | C |
| I-37 | C | B | C |
| I-38 | D | C | D |
| I-39 | D | C | D |
| I-40 | D | A | C |
| I-41 | D | D | D |
| I-42 | C | C | D |
| I-43 | B | A | C |
| I-45 | C | A | C |
| I-46 | D | D | D |
| I-47 | A | A | A |
| I-48 | D | D | D |
| I-49 | D | B | D |
| I-50 | D | D | D |
| I-51 | B | A | C |
| I-52 | C | B | B |
| I-53 | D | B | C |
| I-54 | D | D | D |
| I-55 | C | C | C |
| I-56 | D | D | D |
| I-57 | D | D | D |
| I-58 | D | C | D |
| I-59 | D | D | D |
| I-60 | D | D | D |
| I-61 | D | D | D |
| I-62 | D | D | D |
| I-63 | D | D | D |
| I-64 | D | D | D |
| I-65 | D | D | D |
| I-66 | D | D | D |
| I-67 | D | D | D |
| I-68 | D | D | D |
| I-69 | D | D | D |
| I-70 | D | D | D |
| I-71 | D | D | D |
| I-72 | D | D | D |
| I-73 | C | D | C |
| I-74 | D | D | D |
| I-75 | NA | NA | NA |
| I-76 | D | D | D |
| I-77 | D | D | D |
| I-78 | NA | NA | NA |
| I-79 | NA | NA | NA |
| I-80 | D | D | D |
| I-81 | D | D | D |
| I-82 | D | D | D |
| I-83 | D | D | D |
| I-84 | D | D | D |
| I-85 | C | A | A |
| I-86 | B | B | A |

Compounds of the present invention were evaluated in a growth inhibition assay to determine the ability to control the growth of fungal pathogens, such as *Botrtyis cinerea* (Bc), *Collectotrichum graminicola* (Cg). *Diplodia maydis* (Dm), *Fusarium moniliforme* (Fm), *Fusarium virguliforme* (Fv), *Phytophthora capsici* (Pc), *Rhizoctonia solani* (Rs), and *Septoria tritici* (St).

Compounds to be tested were dissolved in DMSO at 2.5 mg/ml to produce compound stock solutions ("stocks"). Stocks were diluted with DMSO by a five-fold dilution in a 96-well stock plate, and two sets of final concentrations of 50, 10, and 2 ppm or 2, 0.4, and 0.08 ppm were obtained in vitro. A set of positive controls was also prepared, with various concentrations of Soraphen (2, 0.4, and 0.08 ppm), Metalaxyl (1.1, 0.22, and 0.04 ppm), and Metconazole (2, 0.4, and 0.08 ppm or 0.2, 0.04, and 0.008 ppm) after the five-fold dilutions. Negative controls on each plate included 2% DMSO, water, and a blank (media+2% DMSO).

Fungal spores were isolated from previously sub-cultured plates of *Botrtyis cinerea* (Bc). *Collectotrichum graminicola* (Cg). *Diplodia maydis* (Dm), *Fusarium moniliforme* (Fm), *Fusarium virguliforme* (Fv), *Phytophthora capsici* (Pc), and *Septoria tritici* (St). The isolated spores were diluted to individual concentrations with a 17% V8 liquid media. For *Rhizoctonia solani* (Rs) and *Pythium irregulare*, 1.5 mm mycelial plugs were used in place of spores and ¼ Potato Dextrose Broth (PDB) was used for dilution. The spore concentrations and plug sizes were based on growth curves generated at 48 hours for each pathogen.

In a second 96-well plate, the spores or mycelial plugs, media, diluted compound solutions, and controls were combined. Once the compound was added, a true final concentration of compound in each well was measured by an OD600 reading, which adjusted for any compound precipitation that might have occurred in the well. Plate readings were repeated at both 24 and 48 hours. The blank negative control was used as a background subtraction. Additional visual ratings were performed at both 24 and 48 hours for checking on precipitation and confirming efficacy. Visual and OD600 ratings of the compounds at 48 hours were compared to the 2% DMSO negative control, and the percent of pathogen growth inhibition was determined based on those values.

The results of the growth inhibition assay are shown in Table 4a and 4b. Compounds having an activity designated as "AA" provided a compound concentration of 0.08 ppm at 90% inhibition of fungal pathogens; compounds having an activity designated as "A" provided a compound concentration of 0.4 ppm at 90% inhibition of fungal pathogens; compounds having an activity designated as "B" provided a compound concentration of 2.0 ppm at 90% inhibition of fungal pathogens; compounds having an activity designated as "C" provided a compound concentration of 10.0 ppm at 90% inhibition of fungal pathogens; and compounds having an activity designated as "D" provided a compound concentration of >50 ppm at 90% inhibition of fungal pathogens.

TABLE 4a

Exemplary Anti-Fungal Activity Assay Results

| Compound Number | Concentration at 90% Inhibition | | | | | | | |
|---|---|---|---|---|---|---|---|---|
| | Bc | Cg | Dm | Fm | Fv | Pc | Rs | St |
| I-1 | A | B | B | AA | A | D | B | D |
| I-2 | A | B | A | AA | A | D | A | D |
| I-3 | D | D | D | B | B | D | D | D |
| I-4 | B | D | D | B | D | D | D | D |
| I-5 | B | D | D | B | D | D | D | D |
| I-6 | B | C | C | A | B | D | D | D |
| I-7 | B | A | C | AA | D | D | B | D |
| I-8 | B | B | C | AA | B | D | D | D |
| I-11 | D | D | D | B | D | D | D | D |
| I-12 | D | C | D | A | D | D | B | D |
| I-13 | B | D | D | A | D | D | D | D |
| I-14 | A | D | B | AA | B | D | B | D |
| I-15 | B | D | D | A | B | D | D | D |
| I-17 | B | D | B | A | A | D | D | D |

TABLE 4a-continued

Exemplary Anti-Fungal Activity Assay Results

| Compound Number | Concentration at 90% Inhibition | | | | | | | |
|---|---|---|---|---|---|---|---|---|
| | Bc | Cg | Dm | Fm | Fv | Pc | Rs | St |
| I-18 | B | B | B | AA | A | D | A | D |
| I-19 | A | C | B | AA | A | D | B | D |
| I-21 | B | D | C | A | D | D | B | D |
| I-22 | B | B | B | B | D | D | B | D |
| I-23 | B | D | C | A | D | D | D | D |
| I-24 | A | A | B | AA | A | D | A | D |
| I-25 | D | D | D | C | D | D | D | D |
| I-26 | A | D | B | AA | B | D | B | D |
| I-27 | B | C | D | A | C | D | B | D |
| I-28 | B | D | D | A | B | D | C | D |
| I-29 | B | B | B | A | B | D | B | D |
| I-30 | B | B | B | A | A | D | B | D |
| I-31 | A | A | A | AA | A | D | B | D |
| I-32 | A | A | B | AA | A | D | B | D |
| I-33 | B | C | D | A | A | D | C | D |
| I-34 | A | B | C | AA | A | D | B | D |
| I-35 | B | B | D | A | B | D | B | D |
| I-36 | D | D | D | B | B | D | D | D |
| I-37 | B | D | D | A | B | D | C | D |
| I-38 | B | D | D | A | B | D | C | D |
| I-39 | B | A | C | A | D | D | A | D |
| I-40 | D | D | D | B | D | D | C | D |
| I-41 | B | B | C | A | A | D | C | D |
| I-42 | D | D | D | A | D | D | C | D |
| I-43 | D | D | D | B | B | D | D | D |
| I-45 | D | B | D | B | D | D | B | D |

Bc = *Botrtyis cinerea*;
Cg = *Collectotrichum graminicola*;
Dm = *Diplodia maydis*;
Fm = *Fusarium moniliforme*;
Fv = *Fusarium virguliforme*;
Pc = *Phytophthora capsici*;
Rs = *Rhizoctonia solani*;
St = *Septoria*

TABLE 4b

Exemplary Anti-Fungal Activity Assay Results

| Compound Number | Concentration at 90% Inhibition | | | | | | | |
|---|---|---|---|---|---|---|---|---|
| | Bc | Cg | Dm | Fm | Fv | Pc | Rs | St |
| I-1 | A | B | B | AA | A | D | B | D |
| I-2 | A | B | A | AA | A | D | A | D |
| I-3 | C | D | C | B | B | D | D | D |
| I-4 | B | C | D | B | D | D | D | D |
| I-5 | B | D | C | B | C | D | C | D |
| I-6 | B | B | B | A | B | D | C | D |
| I-7 | B | A | B | AA | C | D | B | D |
| I-8 | B | B | B | AA | B | D | C | D |
| I-9 | D | D | D | D | D | D | D | D |
| I-10 | D | D | D | C | D | D | D | D |
| I-11 | C | C | C | B | C | D | D | D |
| I-12 | C | B | C | A | C | D | B | D |
| I-13 | B | C | C | A | C | D | C | D |
| I-14 | A | D | B | AA | B | D | B | D |
| I-15 | B | C | C | A | B | D | C | D |
| I-16 | D | D | D | D | D | D | C | D |
| I-17 | B | C | B | A | A | D | D | D |
| I-18 | B | B | B | AA | A | D | A | D |
| I-19 | A | B | B | AA | A | D | B | D |
| I-20 | C | D | C | C | D | D | D | D |
| I-21 | B | C | B | A | C | D | B | D |
| I-22 | B | B | B | A | C | D | B | D |
| I-23 | B | C | B | A | D | D | D | D |
| I-24 | A | A | B | AA | A | D | A | D |
| I-25 | C | D | D | B | D | D | D | D |
| I-26 | A | C | B | AA | B | D | B | D |
| I-27 | B | B | C | A | B | D | B | D |
| I-28 | B | C | D | A | B | D | B | D |

TABLE 4b-continued

Exemplary Anti-Fungal Activity Assay Results

| Compound Number | Concentration at 90% Inhibition | | | | | | | |
|---|---|---|---|---|---|---|---|---|
| | Bc | Cg | Dm | Fm | Fv | Pc | Rs | St |
| I-29 | B | B | B | A | B | D | B | D |
| I-30 | B | B | B | A | A | D | B | D |
| I-31 | A | A | A | AA | A | D | B | D |
| I-32 | A | A | B | AA | A | D | B | D |
| I-33 | B | B | D | A | A | D | B | D |
| I-34 | A | B | B | AA | A | D | B | D |
| I-35 | B | B | C | A | B | D | B | D |
| I-36 | C | C | D | B | B | D | C | D |
| I-37 | B | C | C | A | B | D | B | D |
| I-38 | B | C | C | A | B | D | B | D |
| I-39 | B | A | B | A | B | C | A | C |
| I-40 | C | C | D | B | C | D | B | D |
| I-41 | B | B | B | A | A | D | B | C |
| I-42 | C | C | C | A | C | D | B | D |
| I-43 | C | D | C | B | B | D | C | D |
| I-44 | D | D | D | C | C | D | D | D |
| I-45 | C | B | C | B | C | D | B | D |
| I-46 | C | D | D | B | D | D | D | D |
| I-47 | B | C | D | A | B | D | D | D |
| I-75 | B | B | B | AA | A | D | AA | D |
| I-76 | D | D | D | B | D | D | D | D |
| I-77 | D | D | D | B | C | D | D | D |
| I-78 | C | D | D | C | D | D | C | D |
| I-79 | A | A | A | AA | A | D | AA | C |
| I-81 | A | B | B | AA | A | D | AA | D |
| I-82 | C | D | D | B | C | D | C | D |
| I-85 | D | D | D | C | D | D | C | D |
| I-86 | B | B | C | A | A | D | A | D |

Bc = *Botrtyis cinerea*;
Cg = *Collectotrichum graminicola*;
Dm = *Diplodia maydis*;
Fm = *Fusarium moniliforme*;
Fv = *Fusarium virguliforme*;
Pc = *Phytophthora capsici*;
Rs = *Rhizoctonia solani*;
St = *Septoria*

The results of the Anti-Fungal (*Candida*) activity assay indicate that many compounds of the invention inhibit each of *C. albicans, C. krusei*, and *C. parapsilosis* at a concentration of less than 2 µg/mL, and some compounds inhibit each of those organisms at a concentration of less than 1 µg/mL.

Example 118

Compounds of the invention are also assayed in a Cancer Cell Viability Assay as described by Beckers et al. "Chemical Inhibition of Acetyl-CoA Carboxylase Induces Growth Arrest and Cytotoxicity Selectively in Cancer Cells" Cancer Res. (2007) 67, 8180-8187. An exemplary procedure for the assay, which measures the percentage of cancer cells surviving following administration of inhibitor compounds, follows.

LNCaP (prostate cancer cell line) cells plated at $4 \times 10^5$ per 6 cm dish are incubated at 37° C., and the following day they are treated with increasing concentrations of inhibitor compounds and incubated. Viable cells and the percentage of dead cells is counted and calculated every day for 5 days from day 0, using trypan blue staining.

Example 119

Compounds of the present invention are also assayed in an In Vivo Fatty Acid Synthesis Study as described by Harwood et al. "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals" Journal of Biological Chemistry (2008) 278, 37099-37111. An exemplary procedure for the assay, which measures the amount of radioactive [$C^{14}$]-acetate incorporated into rat liver tissue, follows.

Animals given food ad water ad libitum are treated orally at a volume of 1.0 mL/200 g body weight (rat) with either an aqueous solution containing 0.5% methylcellulose (vehicle), or an aqueous solution containing 0.5% methylcellulose plus test compound. One to four hours after compound administration, animals receive an intraperitoneal injection of 0.5 mL of [$C^{14}$]-acetate (64 uCi/mL; 56 uCi/mL). One hour after radiolabeled acetate administration, animals are sacrificed by $CO_2$ asphyxiation and two 0.75 g liver pieces are removed and saponified at 70 degrees C. for 120 minutes in 1.5 mL of 2.5M NaOH. After saponification, 2.5 mL of absolute ethanol are added to each sample and the solutions are mixed and allowed to stand overnight. Petroleum ether (4.8 mL) is then added to each sample, and the mixtures are first shaken vigorously for 2 minutes and then centrifuged at 1000×g in a benchtop Sorvall for 5 minutes. The resultant petroleum ether layers, which contain non-saponifiable lipids, are removed and discarded. The remaining aqueous layer is acidified to pH<2 by the addition of 12M HCl and extracted two times with 4.8 mL of petroleum ether. The pooled organic fractions are transferred to liquid scintillation vials, dried under nitrogen, dissolved in 7 mL of Aquasol liquid scintillation fluid, and assessed for radioactivity using a Beckman 6500 liquid scintillation counter. Results are recorded as disintigrations per minute (DPM) per milligram of tissue.

Example 120

Compounds of the present invention are also assayed in a Respiratory Quotient Measurement Assay, as described by Harwood et al. "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals" Journal of Biological Chemistry (2008) 278, 37099-37111. An exemplary procedure for the assay, which measures the ratio of carbon dioxide production to oxygen consumption in rats, follows.

Male Sprague-Dawley rats (350-400 g) housed under standard laboratory conditions, either fed chow, fasted, or fasted and refed a diet high in sucrose for 2 days prior to experimentation are removed from their home cages, weighed, and placed into sealed chambers (43"43"10 cm) of the calorimeter (one rat per chamber). The chambers are placed in activity monitors. The calorimeter is calibrated before each use, air flow rate is adjusted to 1.6 liters/min, and the system settling and sampling times are set to 60 and 15 s, respectively. Base-line oxygen consumption, $CO_2$ production, and ambulatory activity are measured every 10 min for up to 3 h before treatment. After collecting base-line data, the chambers are opened and rats are given a 1.0-ml oral bolus of either an aqueous 0.5% methylcellulose solution (vehicle control) or an aqueous 0.5% methylcellulose solution containing test compound and then returned to the Oxymax chambers. Measurements are made every 30 min for an additional 3-6 h after dose. Fed vehicle controls are used to assess effects produced by vehicle administration and by drift in the RQ measurement during the course of the experimentation (if any). Overnight-fasted, vehicle-treated controls are used to determine maximal potential RQ reduction. Results are plotted as their absolute RQ value (±SEM) over time.

Example 121

Compounds of the present invention are also assayed in a propidium iodide (PI) cell death assay, based on the procedure described by van Engeland et al. "A novel assay to measure loss of plasma membrane asymmetry during apoptosis of adherent cells in culture" Cytometry (1996) 24 (2), 131-139. An exemplary procedure for the assay, which measures the number of intact mitotic cells following drug application follows.

Hepatocellular carcinoma cells (such as HepG2 or Hep3B) are seeded in a 24-well plate at a density of 1.106/ml in 0.5 ml of culture medium, and incubated for 3 hours to allow time for cells to adhere. Cells are treated with experimental compounds, 1 uM doxorubicin (1,2) or vehicle (DMSO) control for 120 hours after treatment: a. First culture supernatant is removed into 2 mL polypropylene tube and place on ice; b. Then wells are washed with 0.5 mL PBS, transferring the wash volume to the 2 mL tube containing culture supernatant (floating cells). The cells are kept on ice. Harvesting is accomplished by adding into the wells 200 uL of accutase for 5 min. The accutase is then inactivated with 300 uL media. The misture is pipetted up and down and the trypsinized cells are transferred from the well into the 2 mL tube with the floating cells (total volume: 1.5 mL). The cells are kept on ice. The cells are spun at 0.6 rcf for 10 min at 4 degrees C. Following centrifugation the medium is aspirated, and the cells are resuspended in 500 uL of media by vortexing in pulses for about 15 seconds. The cells are kept on ice.

For cell counting: 20 uL of cells are added to a plate after vortexing in pulses for 15 s, and the plate was kept on ice. Then 20 uL trypan blue is added immediately before counting. Cells are counted with a TC10 Biorad cell counter. The cells are spun at 0.6 rcf for 10 min at 4 degrees C. The medium is aspirated carefully and the cells are resuspended in 500 uL of annexin binding buffer 1× by vortexing. The cell suspension is transferred to a 5 ml FACS tube then 5 ul of Propidium Iodide are added. The cells are gently mixed and incubated for 15 min at room temperature in the dark.

For the flow cytometric analysis, unstained/untreated samples are used at each time point as a negative control, and doxorubicin treated samples are used at each time point as a positive control. A FACScan flow cytometer is used, and FL2-A histograms are analyzed with FlowJo software.

Example 122

Compounds of the present invention are also assayed in high fat diet induced obesity (DIO) studies. A representative protocol for the assay follows.

The compounds of the present invention are readily adapted to clinical use as anti-obesity agents, insulin sensitizing agents, hyperinsulinemia-reversing agents, and hepatic steatosis-reversing agents. Such activity was determined by assessing the amount of test compound that reduces body weight and percentage body fat, reduces plasma insulin levels, blunts the rise and/or accelerates the reduction in plasma insulin and glucose levels in response to an oral glucose challenge, and reduces hepatic lipid content relative to a control vehicle without test compound in mammals. Sprague Dawley rats were fed either chow, a diet high in sucrose (for example AIN76A rodent diet; Research diets Inc. Cat #10001) or a diet high in fat (for example Research diets Inc. Cat #12451), for from 3-8 weeks prior to and during test compound administration.

The anti-obesity, insulin sensitizing, hyperinsulinemia-reversing, and hepatic steatosis-reversing potential of compounds of the present invention is demonstrated by evaluating modifications to a variety of parameters of lipid and carbohydrate metabolism using methods based on standard procedures known to those skilled in the art. For example, after a 3-8 week period of ad libitum feeding of either a chow, high-fat, or high-sucrose diet, animals that continued to receive the diet are treated for 1-8 weeks with test compound administered either by oral gavage in water or saline or water or saline containing 0.5% methylcelulose using a Q.D., B.I.D, or T.I.D. dosing regimen. At various times during study and at sacrifice (by $CO_2$ asphyxiation), blood is collected either from the tail vein of an unanesthesized rat or from the vena cava of animals at sacrifice into heparin or EDTA containing tubes for centrifugal separation to prepare plasma. Plasma levels of parameters of lipid and carbohydrate metabolism known by those skilled in the art to be altered coincident with anti-obesity, insulin sensitizing, hyperinsulinemia-reversing, and hepatic steatosis-reversing actions, including but not limited to cholesterol and triglycerides, glucose, insulin, leptin, adiponectin, ketone bodies, free fatty acids, and glycerol, are measured using methods known to those skilled in the art.

The anti-obesity potential of compounds of the present invention can also be demonstrated by evaluating their potential to produce a reduction in body weight, a reduction in percentage body fat (measured by for example dual-energy x-ray absorptiometry (DEXA) analysis), and a reduction in plasma leptin levels. The anti-obesity and hepatic steatosis-reversing potential of compounds of the present invention can also be demonstrated by evaluating their potential to reduce the concentration of triglycerides in the liver, using extraction and quantitation procedures known to those skilled in the art. The insulin sensitizing and hyperinsulinemia-reversing potential of compounds of the present invention can also be demonstrated by evaluating their potential to blunt the rise and/or accelerate the reduction in plasma insulin and glucose levels in response to an oral glucose challenge, using procedures known to those skilled in the art.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula:

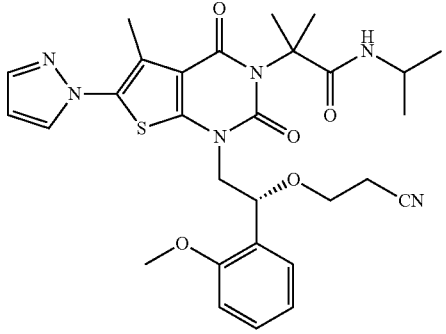 [SMILES: COc1ccccc1[C@H](Cn1c(=O)n(C(C)(C)C(=O)NC(C)C)c(=O)c2c(C)c(-n3cccn3)sc21)OCCC#N]

or a pharmaceutically acceptable salt or agriculturally acceptable salt thereof.

* * * * *